Figure 1:
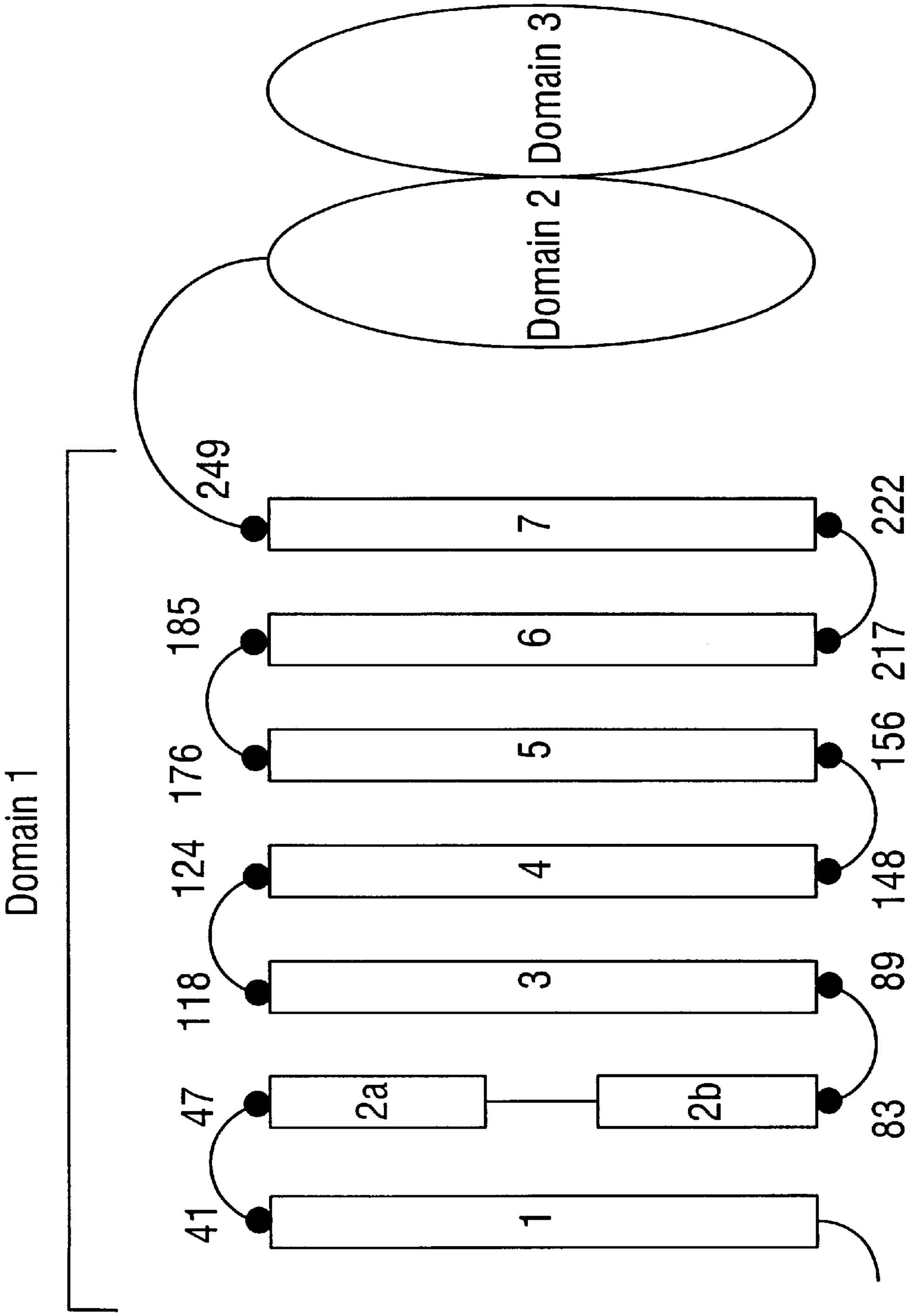

US005914318A

United States Patent [19]

Baum et al.

[11] Patent Number: 5,914,318

[45] Date of Patent: Jun. 22, 1999

[54] TRANSGENIC PLANTS EXPRESSING LEPIDOPTERAN-ACTIVE δ-ENDOTOXINS

[75] Inventors: James A. Baum, Doylestown; Amy Jelen Gilmer, Langhorne; Anne-Marie Light Mettus, Feasterville, all of Pa.

[73] Assignee: Ecogen, Inc., Langhorne, Pa.

[21] Appl. No.: 08/980,071

[22] Filed: Nov. 26, 1997

Related U.S. Application Data

[63] Continuation-in-part of application No. 08/757,536, Nov. 27, 1996.

[51] Int. Cl.[6] .................................................. C07K 14/325

[52] U.S. Cl. ........................ 514/12; 530/350; 435/252.31

[58] Field of Search .............................. 514/12; 530/350; 435/252.31

[56] References Cited

U.S. PATENT DOCUMENTS

| | | | |
|---|---|---|---|
| 4,448,885 | 5/1984 | Schnepf et al. | 435/253 |
| 4,467,036 | 8/1984 | Schnepf et al. | 435/317 |
| 4,766,203 | 8/1988 | Krieg et al. | 530/370 |
| 4,797,279 | 1/1989 | Karamata et al. | 424/93 |
| 4,910,016 | 3/1990 | Gaertner et al. | 424/93 |
| 5,024,837 | 6/1991 | Donovan et al. | 424/93 |
| 5,126,133 | 6/1992 | Payne et al. | 424/93 |
| 5,188,960 | 2/1993 | Payne et al. | 435/252.3 |
| 5,322,687 | 6/1994 | Donovan et al. | 424/93 |
| 5,441,884 | 8/1995 | Baum | 435/252.31 |
| 5,500,365 | 3/1996 | Fischhoff et al. | 435/240.4 |
| 5,567,600 | 10/1996 | Adang et al. | 536/23.71 |
| 5,567,862 | 10/1996 | Adang et al. | 800/205 |
| 5,573,766 | 11/1996 | Blenk et al. | 424/93.461 |
| 5,589,382 | 12/1996 | Payne et al. | 435/252.5 |
| 5,659,123 | 8/1997 | Van Rie et al. | 800/205 |

FOREIGN PATENT DOCUMENTS

| | | |
|---|---|---|
| 0193259 | 3/1986 | European Pat. Off. . |
| 0295156B1 | 12/1988 | European Pat. Off. . |
| 0405810 | 1/1991 | European Pat. Off. . |
| 0408403 | 1/1991 | European Pat. Off. . |
| WO88/09812 | 12/1988 | WIPO . |
| WO91/16433 | 10/1991 | WIPO . |
| WO93/03154 | 2/1993 | WIPO . |
| WO95/02058 | 1/1995 | WIPO . |
| WO95/06730 | 3/1995 | WIPO . |

OTHER PUBLICATIONS

Dean et al., "Probing the mechanism of action of *Bacillus thuringiensis* insecticidal proteins by site–directed mutagenesis—a minireview," *Gene,* 179:111–117, 1996.

International Search Report dated Apr. 21, 1998 (PCT/US97/22181)(MECO:206P).

Nakamura et al., "Insecticidal activity and processing in larval gut juices of genetically engineered 130–kDa proteins of *Bacillus thuringiensis* subsp. *aizawai," Biosci. Biotech. Biochem.,* 56(1):1–7, 1992.

Kalman et al., "Cloning of a novel CryIC–type gene from a strain of *Bacillus thuringiensis* subsp. *galleriae," Applied and Environmental Microbiology,* 59(4):1131–1137, 1993.

Li et al., "Crystal structure of insecticidal δ–endotoxin from *Bacillus thuringiensis* at 2.5 Å resolution," *Nature,* 353:815–821, 1991.

Schnepf and Whiteley, "Cloning and expression of the *Bacillus thuringiensis* crystal protein gene in *Escherichia coli," Proc. Natl. Acad. Sci. USA,* 78(5):2893–2897, 1981.

Schnepf et al., "The amino acid sequence of a crystal protein from *Bacillus thruingiensis* deduced from the DNA base sequence," *J. Biol. Chem.,* 260(10):6264–6272, 1985.

Walters et al., "Ion channel activity of n–terminal fragments from CryIA(c) delta–endotoxin," *Biochem. Biophy. Res. Comm.,* 196(2):921–926, 1993.

Almond and Dean, "Suppression of Protein Structure Destabilizing Mutations in *Bacillus thuringiensis* Delta Endotoxins by Second Site Mutations," *Biochemistry,* 32:1040–1046, 1993.

Angsuthanasombat et al., "Effects on Toxicity of Eliminating a Cleavage Site in a Predicted Interhelical Loop in *Bacillus thuringiensis* CryIVB δ–Endotoxin," *FEMS Microbiol. Lett.,* 111:255–262, 1993.

Aronson et al., "Mutagenesis of Specificity and Toxicity Regions of a *Bacillus thuringiensis* Protoxin Gene," *Journal of Bacteriology,* 177(14):4059–4065, Jul. 1995.

Baum, "TnpI Recombinase: Identification of Sites within Tn5401 Required for TnpI Binding and Site–Specific Recombination," *Journal of Bacteriology,* 177(14):4036–4042, Jul. 1995.

Baum et al., "Novel Cloning Vectors for *Bacillus thuringiensis," Applied and Environmental Microbiology,* 56(11):3420–3428, Nov. 1990.

Caramori et al., "In vivo Generation of Hybrids Between Two *Bacillus thuringiensis* Insect–Toxin–Encoding Genes," *Gene,* 98:37–44, 1991.

Chambers et al., "Isolation and Characterization of a Novel Insecticidal Crystal Protein Gene from *Bacillus thuringiensis* subsp. *Aizawai," Journal of Bacteriology,* 173(13):3966–3976, Jul. 1991.

(List continued on next page.)

*Primary Examiner*—Karen Cochrane Carlson
*Attorney, Agent, or Firm*—Arnold, White & Durkee

[57] ABSTRACT

Disclosed are novel synthetically-modified *B. thuringiensis* nucleic acid segments encoding δ-endotoxins having insecticidal activity against lepidopteran insects. Also disclosed are synthetic crystal proteins encoded by these novel nucleic acid sequences. Methods of making and using these genes and proteins are disclosed as well as methods for the recombinant expression, and transformation of suitable host cells. Transformed host cells and transgenic plants expressing the modified endotoxin are also aspects of the invention. Also disclosed are methods for modifying, altering, and mutagenizing specific loop regions between the α helices in domain 1 of these crystal proteins, including Cry1C, to produce genetically-engineered recombinant cry* genes, and the proteins they encode which have improved insecticidal activity. In preferred embodiments, novel Cry1C* amino acid segments and the modified cry1C* nucleic acid sequences which encode them are disclosed.

9 Claims, 13 Drawing Sheets

OTHER PUBLICATIONS

Chen et al., "Site–directed Mutations in a Highly Conserved Region of *Bacillus thuringiensis* Delta–endotoxin Affect Inhibition of Short–circuit Current Across *Bombyx mori* Midguts," *Proc. Natl. Acad. Sci.,* 90:9041–9045, Oct. 1993.

Chen et al., "Mutations in Domain I of *Bacillus thuringiensis* δ–Endotoxin CryIAb Reduce the Irreversible Binding of Toxin to *Manduca sexta* Brush Border Membrane Vesicles," *J. Biol. Chem.,* 270(11):6412–6419, Mar. 1995.

De Maagd et al., "Domain III Substitution in *Bacillus thuringiensis* Dekta–Endotoxin CryIA(b) Results in Superior Toxicity for *Spodoptera exigua* and Altered Membrane Protein Recognition" *Applied and Environmental Microbiology,* 62(5):1537–1543, May 1996.

Donovan et al., "Amiono Acid Sequence and Entomocidal Activity of the P2 Crystal Protein" *J. Biol. Chem.,* 263(1):561–567, Jan. 1988.

English and Slatin, "Mode of Action of Delta–Endotoxins from *Bacillus thuringiensis:* A Comparison with Other Bacterial Toxins" *Insect Biochem. Molec. Biol.,* 22(1):1–7, 1992.

Gazit and Shai, "Structural and Functional Characterization of the α5 Segment of *Bacillus thuringiensis* δ–Endotoxin," *Biochemistry,* 32(13):3429–3436, 1993.

Gazit and Shai, "The Assembly and Organization of the α5 and α7 Helices from the Pore–forming Domain of *Bacillus thuringiensis* δ–Endotoxin," *J. Biol. Chem.,* 270(6):2571–2578, Feb. 1995.

Ge et al., "Functinal Domains of *Bacillus thuringiensis* Insecticidal Crystal Proteins," *J. Biol. Chem.,* 266(27):17954–17958, Sep. 1991.

Grochulski et al., "*Bacillus thuringiensis* CryIA(a) Insecticidal Toxin: Crystal Structure and Channel Formation," *J. Mol. Biol.,* 254:447–464, 1995.

Hofte and Whiteley, "Insecticidal Crystal Proteins of *Bacillus thuringiensis,*" *Microbioligical Review,* 53(2):242–255, Jun. 1989.

Honée et al., "Nucleotide sequence of crystal isolated from *B.thuringiensis* subspecies *entomocidus* 60.5 coding for a toxin highly active against *Spodoptera* species," *Nucleic Acids Research,* 16(13):6240, 1988.

Krieg et al., "*Bacillus thurigiensis* var. *Tenebrionis*: ein neuer, gegenüber Larven von Coleopteren wirksamer Pathotyp," *Z. ang. Ent.,* 96:500–508, 1983.

Kwak et al., "Exploration of Receptor Binding of *Bacillus thuringiensis* Toxins," *Mem Inst. Oswaldo,* 90(1):75–79, Jan./Feb. 1995.

Lambert et al., "A *Bacillus thuringiensis* Insecticidal Crystal Protein with a High Activity against Members of the Family Noctuidae," *Applied and Environmental Microbiology,* 62(1):80–86, Jan. 1996.

Lee et al., "Location of a *Bombyx mori* Receptor Binding Region on a *Bacillus thuringiensis* δ–Endotoxin," *J. Biol. Chem.,* 267(5):3115–3121, Feb. 1992.

Lee et al., "Domain III Exchanges of *Bacillus thuringiensis* CryIA Toxins Affect Binding to Different Gypsy Moth Midgut Receptors," *Biochemical And Biophysical Research Communications,* 216(1):306–312, Nov. 1995.

Lu et al., "Identification of Amino Acid Residues of *Bacillus thuringiensis* δ–Endotoxin CryIAa Associated with Membrane Binding and Toxicity to *Bombyx mori,*" *J. of Bacteriology,* 176(17):5554–5559, Sep. 1994.

Mettus and Macaluso, "Expression of *Bacillus thuringiensis* δ–Endotoxin Genes during Vegetative Growth," *Applied and Environmental Microbiology,* 56(4):1128–1134, Apr. 1990.

Rajamohan et al., "Single Amino Acid Changes in Domain II of *Bacillus thuringiensis* CryIAb δ–Endotoxin Affect Irreversible Binding to *Manduca sexta* Midgut Membrane Vesicles" *J. of Bacteriology,* 177(9):2276–2282, May 1995.

Rajamohan et al., "Role of Domain II, Loop 2 Residues of *Bacillus thuringiensis* CryIAb δ–Endotoxin in Reversible and Irreversible Binding to *Manduca sexta* and *Heliothis virescens,*" *J. of Biological Chemistry,* 271(5):2390–2396, Feb. 1996.

Sanchis et al., "Multiplicity of δ–endotoxin genes with different insecticidal specificities in *Bacillus thuringiensis aizawai* 7.29," *Molecular Microbiology,* 2(3):393–404, 1988.

Sanchis et al., "Nucleotide sequence and analysis of the N–terminal coding region of the Spodoptera–active δ–endotoxin gene of *Bacillus thuringiensis aizawai* 7.29," *Molecular Microbiology,* 3(2):229–238, 1989.

Smedley and Ellar, "Mutagenesis of three surface–exposed loops of a *Bacillus thuringiensis* insecticidical toxin reveals residues important for toxicity, receptor recognition and possibly membrane insertion," *Microbiology,* 142:1617–1624, 1996.

Smith et al., "Mosquitocidal Activity of the CryIC δ–Endotoxin from *Bacillus thuringiensis* subsp. *aizawai,*" *Applied and Environmental Microbiology,* 62(2):680–684, Feb. 1996.

Smith and Ellar, "Mutagenesis of two surface–exposed loops of the *Bacillus thuringiensis* CryIC δ–endotoxin affects insecticidal specificity," *Biochem. J.,* 302:611–616, 1994.

von Tersch et al., "Membrane–Permeabilizing Activities of *Bacillus thuringiensis,* Coleopteran–Active Toxin CryIIIB2 and CryIIIB2 Domain I Peptide," *Applied and Environmental Microbiology,* 60(10):3711–3717, Oct. 1994.

Wolfersberger et al., "Site–Directed Mutation in the Third Domain of *Bacillus thuringiensis* δ–Endotoxin CryIAa Affect Its Ability to Increase the Permeability of *Bombyx mori* Midgut Brush Border Membrane Vesicles," *Applied and Environmental Microbiology,* 62(1):279–282, Jan. 1996.

Wu and Aronson, "Localized Mutagenesis Defines Regions of the *Bacillus thuringiensis* δ–Endotoxin Involved in Toxicity and Specificity," *J. of Biol. Chem.,* 267(4):2311–2317, Feb. 1992.

Wu and Dean, "Functional Significance of Loops in The Receptor Binding Domain of *Bacillus thuringiensis* CryIIIA δ–Endotoxin," *J. Mol. Biol.,* 255:628–640, 1996.

Figure 4A:
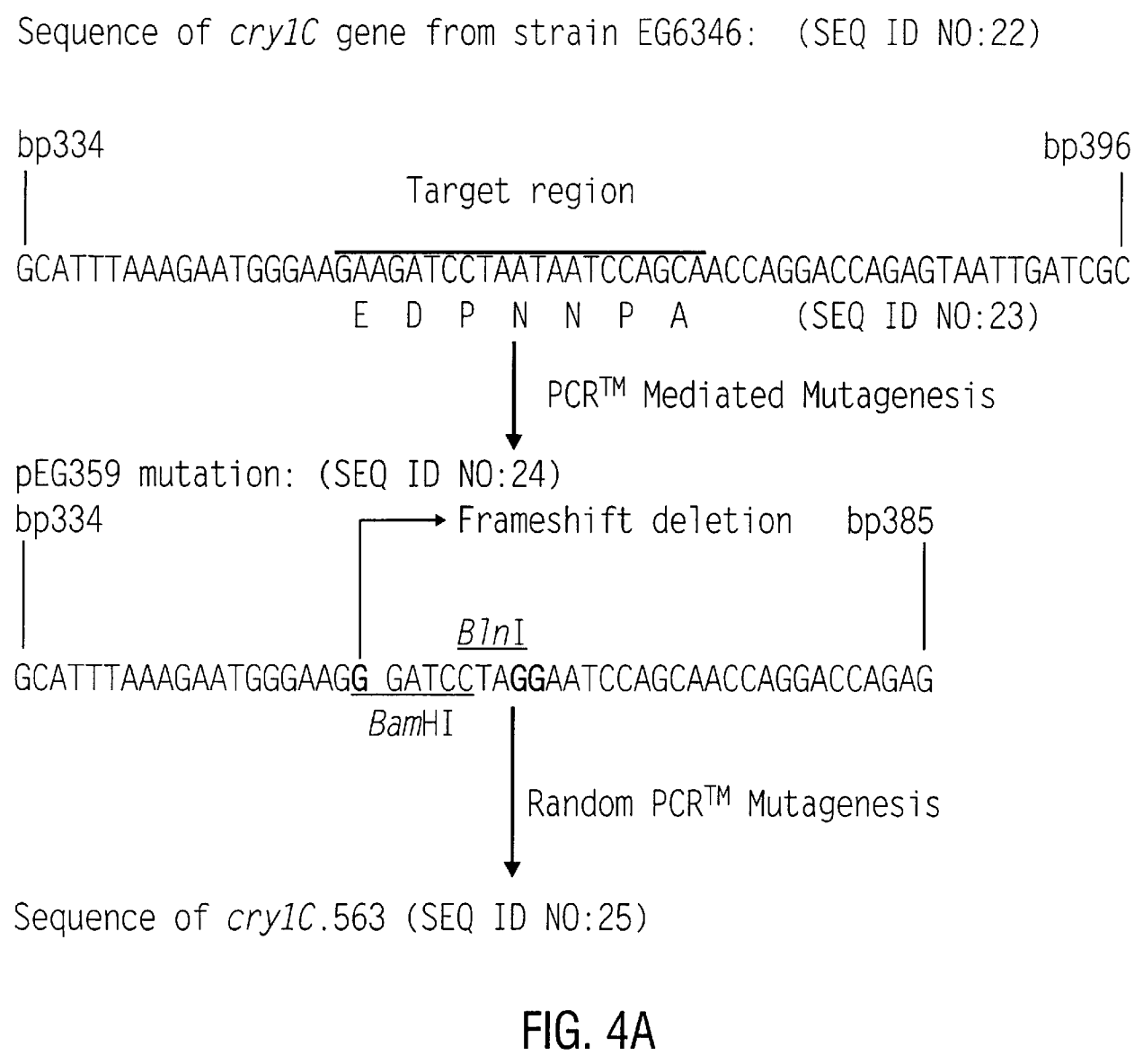

Sequence of *cry1C* gene from strain EG6346: (SEQ ID NO:22)

bp334 bp396

Target region

GCATTTAAAGAATGGGAAGAAGATCCTAATAATCCAGCAACCAGGACCAGAGTAATTGATCGC

E D P N N P A (SEQ ID NO:23)

PCR™ Mediated Mutagenesis pEG359 mutation: (SEQ ID NO:24)

bp334 Frameshift deletion bp385

*BlnI*

GCATTTAAAGAATGGGAAGG GATCCTAGGAATCCAGCAACCAGGACCAGAG

*Bam*HI

Random PCR™ Mutagenesis

Sequence of *cry1C*.563 (SEQ ID NO:25)

FIG. 4A bp334 — Target region — bp396

GCATTTAAAGAATGGGAAGATGATCCTCATAATCCCACAACCAGGACCAGAGTAATTGATCGC

D D P H N P T (SEQ ID NO:26)

Sequence of *cry1C*.579 (SEQ ID NO:54)

bp334 — Target region — bp396

GCATTTAAAGAATGGGAAGTAGATCCTAATAATCCTGGAACCAGGACCAGAGTAATTGATCGC

V D P N N P G (SEQ ID NO:55)

Sequence of *cry1C*.499 (SEQ ID NO:56)

bp334 — Target region — bp396

GCATTTAAAGAATGGGAAGAAGATCCCCATAATCCAGCAACCAGGACCAGAGTAATTGATCGC

E D P H N P A (SEQ ID NO:57)

FIG. 4B

```
CRYIAa  TNPALREEMRIQFNDMNSALTTAIPLLAVQNYQVPLLSVYVQAANLHLSV  171  SEQ ID NO:28
CRYIAd  TNPALTEEMRIQFNDMNSALTTAIPLFTVQNYQVPLLSVYVQAANLHLSV  171  SEQ ID NO:29
CRYIAb  TNPALREEMRIQFNDMNSALTTAIPLFAVQNYQVPLLSVYVQAANLHLSV  171  SEQ ID NO:30
CRYIAe  TNPALREEMRIQFNDMNSALTTAIPLFTVQNYQVPLLSVYVQAVNLHLSV  171  SEQ ID NO:31
CRYIAc  TNPALREEMRIQFNDMNSALTTAIPLFAVQNYQVPLLSVYVQAANLHLSV  171  SEQ ID NO:32
CRYIFa  NNAQLREDVRIRFANTDDALITAINNFTLTSFEIPLLSVYVQAANLHLSL  169  SEQ ID NO:33
CRYIFb  NNAQLREDVRIRFANTDDALITAINNFTLTSFEIPLLSVYVQAANLHLSL  169  SEQ ID NO:34
CRYIGa  NNPASQERVRTRFRLTDDAIVTGLPTLAIRNLEVVNLSVYTQAANLHLSL  169  SEQ ID NO:35
CRYICa  NNPETRTRVIDRFRILDGLLERDIPSFRISGFEVPLLSVYAQAANLHLAI  170  SEQ ID NO:36

                                 R148

CRYICb  DNPVTRTRVVDRFRILDGLLERDIPSFRIAGFEVPLLSVYAQAANLHLAI  170  SEQ ID NO:37
CRYIEa  TNPALKEEMRTQFNDMNSILVTAIPLFSVQNYQVPFLSVYVQAANLHLSV  169  SEQ ID NO:38
CRYIEb  TNPALREEMRIQFNDMNSALTTAIPLFSVQGYEIPLLSVYVQAANLHLSV  168  SEQ ID NO:39
CRYIDa  TNPALREEMRIQFNDMNSALITAIPLFRVQNYEVALLSVYVQAANLHLSI  170  SEQ ID NO:40
CRYIDb  SNPALREEMRTQFNVMNSALIAAIPLLRVRNYEVALLSVYVQAANLHLSV  170  SEQ ID NO:41
CRYIHa  NNEALQQDVRNRFSNTDNALITAIPILREQGFEIPLLSVYVQAANLHLSL  173  SEQ ID NO:42
```

FIG. 6A

| | | | |
|---|---|---|---|
| CRYIHb | NNESLQQDVRNRFSNTDNALITAIPILREQGFEIPLLTVYVQAANLHLSL | 172 | SEQ ID NO:43 |
| CRYIJa | DNEAAKSRVIDRFRILDGLIEANIPSFRIIGFEVPLLSVYVQAANLHLAL | 170 | SEQ ID NO:44 |
| CRYIJb | DNTAARSRVTERFRIIDAQIEANIPSFRIPGFEVPLLSVYAQAANLHLAL | 170 | SEQ ID NO:45 |
| CRYIBa | DDARTRSVLYTQYIALELDFLNAMPLFAIRNQEVPLLMVYAQAANLHLLL | 190 | SEQ ID NO:46 |
| CRYIBb | NDARSRSIILERYVALELDITTAIPLFRIRNEEVPLLMVYAQAANLHLLL | 195 | SEQ ID NO:47 |
| CRYIBc | NDARSRSIILERYVALELDITTAIPLFRIRNEEVPLLMVYAQAANLHLLL | 195 | SEQ ID NO:48 |
| CRYIKa | NDARSRSIIRERYIALELDITTAIPLFSIRNEEVPLLMVYAQAANLHLLL | 196 | SEQ ID NO:49 |
| CRYIIa | NNTRARSVVKSQYIALELMFVQKLPSFAVSGEEVPLLPIYAQAANLHLLL | 199 | SEQ ID NO:50 |
| CRYIIb | NNTRARSVVKNQYIALELMFVQKLPSFAVSGEEVPLLPIYAQAANLHLLL | 199 | SEQ ID NO:51 |

FIG. 6B

```
SEQUENCE LISTING

(1) GENERAL INFORMATION:

   (iii) NUMBER OF SEQUENCES: 76

(2) INFORMATION FOR SEQ ID NO:1:

     (i) SEQUENCE CHARACTERISTICS:
          (A) LENGTH: 3567 base pairs
          (B) TYPE: nucleic acid
          (C) STRANDEDNESS: single
          (D) TOPOLOGY: linear

    (ix) FEATURE:
          (A) NAME/KEY: CDS
          (B) LOCATION: 1..3567

    (xi) SEQUENCE DESCRIPTION: SEQ ID NO:1:
```

-continued

```
ATG GAG GAA AAT AAT CAA AAT CAA TGC ATA CCT TAC AAT TGT TTA AGT         48
Met Glu Glu Asn Asn Gln Asn Gln Cys Ile Pro Tyr Asn Cys Leu Ser
 1               5                  10                  15

AAT CCT GAA GAA GTA CTT TTG GAT GGA GAA CGG ATA TCA ACT GGT AAT         96
Asn Pro Glu Glu Val Leu Leu Asp Gly Glu Arg Ile Ser Thr Gly Asn
            20                  25                  30

TCA TCA ATT GAT ATT TCT CTG TCA CTT GTT CAG TTT CTG GTA TCT AAC        144
Ser Ser Ile Asp Ile Ser Leu Ser Leu Val Gln Phe Leu Val Ser Asn
        35                  40                  45

TTT GTA CCA GGG GGA GGA TTT TTA GTT GGA TTA ATA GAT TTT GTA TGG        192
Phe Val Pro Gly Gly Gly Phe Leu Val Gly Leu Ile Asp Phe Val Trp
    50                  55                  60

GGA ATA GTT GGC CCT TCT CAA TGG GAT GCA TTT CTA GTA CAA ATT GAA        240
Gly Ile Val Gly Pro Ser Gln Trp Asp Ala Phe Leu Val Gln Ile Glu
65                  70                  75                  80

CAA TTA ATT AAT GAA AGA ATA GCT GAA TTT GCT AGG AAT GCT GCT ATT        288
Gln Leu Ile Asn Glu Arg Ile Ala Glu Phe Ala Arg Asn Ala Ala Ile
                85                  90                  95

GCT AAT TTA GAA GGA TTA GGA AAC AAT TTC AAT ATA TAT GTG GAA GCA        336
Ala Asn Leu Glu Gly Leu Gly Asn Asn Phe Asn Ile Tyr Val Glu Ala
            100                 105                 110

TTT AAA GAA TGG GAA GAA GAT CCT AAT AAT CCA GCA ACC AGG ACC AGA        384
Phe Lys Glu Trp Glu Glu Asp Pro Asn Asn Pro Ala Thr Arg Thr Arg
        115                 120                 125

GTA ATT GAT CGC TTT CGT ATA CTT GAT GGG CTA CTT GAA AGG GAC ATT        432
Val Ile Asp Arg Phe Arg Ile Leu Asp Gly Leu Leu Glu Arg Asp Ile
    130                 135                 140

CCT TCG TTT GCA ATT TCT GGA TTT GAA GTA CCC CTT TTA TCC GTT TAT        480
Pro Ser Phe Ala Ile Ser Gly Phe Glu Val Pro Leu Leu Ser Val Tyr
145                 150                 155                 160

GCT CAA GCG GCC AAT CTG CAT CTA GCT ATA TTA AGA GAT TCT GTA ATT        528
Ala Gln Ala Ala Asn Leu His Leu Ala Ile Leu Arg Asp Ser Val Ile
                165                 170                 175

TTT GGA GAA AGA TGG GGA TTG ACA ACG ATA AAT GTC AAT GAA AAC TAT        576
Phe Gly Glu Arg Trp Gly Leu Thr Thr Ile Asn Val Asn Glu Asn Tyr
            180                 185                 190

AAT AGA CTA ATT AGG CAT ATT GAT GAA TAT GCT GAT CAC TGT GCA AAT        624
Asn Arg Leu Ile Arg His Ile Asp Glu Tyr Ala Asp His Cys Ala Asn
        195                 200                 205

ACG TAT AAT CGG GGA TTA AAT AAT TTA CCG AAA TCT ACG TAT CAA GAT        672
Thr Tyr Asn Arg Gly Leu Asn Asn Leu Pro Lys Ser Thr Tyr Gln Asp
    210                 215                 220

TGG ATA ACA TAT AAT CGA TTA CGG AGA GAC TTA ACA TTG ACT GTA TTA        720
Trp Ile Thr Tyr Asn Arg Leu Arg Arg Asp Leu Thr Leu Thr Val Leu
225                 230                 235                 240

GAT ATC GCC GCT TTC TTT CCA AAC TAT GAC AAT AGG AGA TAT CCA ATT        768
Asp Ile Ala Ala Phe Phe Pro Asn Tyr Asp Asn Arg Arg Tyr Pro Ile
                245                 250                 255

CAG CCA GTT GGT CAA CTA ACA AGG GAA GTT TAT ACG GAC CCA TTA ATT        816
Gln Pro Val Gly Gln Leu Thr Arg Glu Val Tyr Thr Asp Pro Leu Ile
            260                 265                 270

AAT TTT AAT CCA CAG TTA CAG TCT GTA GCT CAA TTA CCT ACT TTT AAC        864
Asn Phe Asn Pro Gln Leu Gln Ser Val Ala Gln Leu Pro Thr Phe Asn
        275                 280                 285

GTT ATG GAG AGC AGC GCA ATT AGA AAT CCT CAT TTA TTT GAT ATA TTG        912
Val Met Glu Ser Ser Ala Ile Arg Asn Pro His Leu Phe Asp Ile Leu
    290                 295                 300

AAT AAT CTT ACA ATC TTT ACG GAT TGG TTT AGT GTT GGA CGC AAT TTT        960
Asn Asn Leu Thr Ile Phe Thr Asp Trp Phe Ser Val Gly Arg Asn Phe
305                 310                 315                 320
```

-continued

```
TAT TGG GGA GGA CAT CGA GTA ATA TCT AGC CTT ATA GGA GGT GGT AAC      1008
Tyr Trp Gly Gly His Arg Val Ile Ser Ser Leu Ile Gly Gly Gly Asn
                325                 330                 335

ATA ACA TCT CCT ATA TAT GGA AGA GAG GCG AAC CAG GAG CCT CCA AGA      1056
Ile Thr Ser Pro Ile Tyr Gly Arg Glu Ala Asn Gln Glu Pro Pro Arg
            340                 345                 350

TCC TTT ACT TTT AAT GGA CCG GTA TTT AGG ACT TTA TCA AAT CCT ACT      1104
Ser Phe Thr Phe Asn Gly Pro Val Phe Arg Thr Leu Ser Asn Pro Thr
        355                 360                 365

TTA CGA TTA TTA CAG CAA CCT TGG CCA GCG CCA CCA TTT AAT TTA CGT      1152
Leu Arg Leu Leu Gln Gln Pro Trp Pro Ala Pro Pro Phe Asn Leu Arg
    370                 375                 380

GGT GTT GAA GGA GTA GAA TTT TCT ACA CCT ACA AAT AGC TTT ACG TAT      1200
Gly Val Glu Gly Val Glu Phe Ser Thr Pro Thr Asn Ser Phe Thr Tyr
385                 390                 395                 400

CGA GGA AGA GGT ACG GTT GAT TCT TTA ACT GAA TTA CCG CCT GAG GAT      1248
Arg Gly Arg Gly Thr Val Asp Ser Leu Thr Glu Leu Pro Pro Glu Asp
                405                 410                 415

AAT AGT GTG CCA CCT CGC GAA GGA TAT AGT CAT CGT TTA TGT CAT GCA      1296
Asn Ser Val Pro Pro Arg Glu Gly Tyr Ser His Arg Leu Cys His Ala
            420                 425                 430

ACT TTT GTT CAA AGA TCT GGA ACA CCT TTT TTA ACA ACT GGT GTA GTA      1344
Thr Phe Val Gln Arg Ser Gly Thr Pro Phe Leu Thr Thr Gly Val Val
        435                 440                 445

TTT TCT TGG ACG CAT CGT AGT GCA ACT CTT ACA AAT ACA ATT GAT CCA      1392
Phe Ser Trp Thr His Arg Ser Ala Thr Leu Thr Asn Thr Ile Asp Pro
    450                 455                 460

GAG AGA ATT AAT CAA ATA CCT TTA GTG AAA GGA TTT AGA GTT TGG GGG      1440
Glu Arg Ile Asn Gln Ile Pro Leu Val Lys Gly Phe Arg Val Trp Gly
465                 470                 475                 480

GGC ACC TCT GTC ATT ACA GGA CCA GGA TTT ACA GGA GGG GAT ATC CTT      1488
Gly Thr Ser Val Ile Thr Gly Pro Gly Phe Thr Gly Gly Asp Ile Leu
                485                 490                 495

CGA AGA AAT ACC TTT GGT GAT TTT GTA TCT CTA CAA GTC AAT ATT AAT      1536
Arg Arg Asn Thr Phe Gly Asp Phe Val Ser Leu Gln Val Asn Ile Asn
            500                 505                 510

TCA CCA ATT ACC CAA AGA TAC CGT TTA AGA TTT CGT TAC GCT TCC AGT      1584
Ser Pro Ile Thr Gln Arg Tyr Arg Leu Arg Phe Arg Tyr Ala Ser Ser
        515                 520                 525

AGG GAT GCA CGA GTT ATA GTA TTA ACA GGA GCG GCA TCC ACA GGA GTG      1632
Arg Asp Ala Arg Val Ile Val Leu Thr Gly Ala Ala Ser Thr Gly Val
    530                 535                 540

GGA GGC CAA GTT AGT GTA AAT ATG CCT CTT CAG AAA ACT ATG GAA ATA      1680
Gly Gly Gln Val Ser Val Asn Met Pro Leu Gln Lys Thr Met Glu Ile
545                 550                 555                 560

GGG GAG AAC TTA ACA TCT AGA ACA TTT AGA TAT ACC GAT TTT AGT AAT      1728
Gly Glu Asn Leu Thr Ser Arg Thr Phe Arg Tyr Thr Asp Phe Ser Asn
                565                 570                 575

CCT TTT TCA TTT AGA GCT AAT CCA GAT ATA ATT GGG ATA AGT GAA CAA      1776
Pro Phe Ser Phe Arg Ala Asn Pro Asp Ile Ile Gly Ile Ser Glu Gln
            580                 585                 590

CCT CTA TTT GGT GCA GGT TCT ATT AGT AGC GGT GAA CTT TAT ATA GAT      1824
Pro Leu Phe Gly Ala Gly Ser Ile Ser Ser Gly Glu Leu Tyr Ile Asp
        595                 600                 605

AAA ATT GAA ATT ATT CTA GCA GAT GCA ACA TTT GAA GCA GAA TCT GAT      1872
Lys Ile Glu Ile Ile Leu Ala Asp Ala Thr Phe Glu Ala Glu Ser Asp
    610                 615                 620

TTA GAA AGA GCA CAA AAG GCG GTG AAT GCC CTG TTT ACT TCT TCC AAT      1920
Leu Glu Arg Ala Gln Lys Ala Val Asn Ala Leu Phe Thr Ser Ser Asn
625                 630                 635                 640
```

-continued

```
CAA ATC GGG TTA AAA ACC GAT GTG ACG GAT TAT CAT ATT GAT CAA GTA      1968
Gln Ile Gly Leu Lys Thr Asp Val Thr Asp Tyr His Ile Asp Gln Val
                645                 650                 655

TCC AAT TTA GTG GAT TGT TTA TCA GAT GAA TTT TGT CTG GAT GAA AAG      2016
Ser Asn Leu Val Asp Cys Leu Ser Asp Glu Phe Cys Leu Asp Glu Lys
            660                 665                 670

CGA GAA TTG TCC GAG AAA GTC AAA CAT GCG AAG CGA CTC AGT GAT GAG      2064
Arg Glu Leu Ser Glu Lys Val Lys His Ala Lys Arg Leu Ser Asp Glu
        675                 680                 685

CGG AAT TTA CTT CAA GAT CCA AAC TTC AGA GGG ATC AAT AGA CAA CCA      2112
Arg Asn Leu Leu Gln Asp Pro Asn Phe Arg Gly Ile Asn Arg Gln Pro
    690                 695                 700

GAC CGT GGC TGG AGA GGA AGT ACA GAT ATT ACC ATC CAA GGA GGA GAT      2160
Asp Arg Gly Trp Arg Gly Ser Thr Asp Ile Thr Ile Gln Gly Gly Asp
705                 710                 715                 720

GAC GTA TTC AAA GAG AAT TAC GTC ACA CTA CCG GGT ACC GTT GAT GAG      2208
Asp Val Phe Lys Glu Asn Tyr Val Thr Leu Pro Gly Thr Val Asp Glu
                725                 730                 735

TGC TAT CCA ACG TAT TTA TAT CAG AAA ATA GAT GAG TCG AAA TTA AAA      2256
Cys Tyr Pro Thr Tyr Leu Tyr Gln Lys Ile Asp Glu Ser Lys Leu Lys
            740                 745                 750

GCT TAT ACC CGT TAT GAA TTA AGA GGG TAT ATC GAA GAT AGT CAA GAC      2304
Ala Tyr Thr Arg Tyr Glu Leu Arg Gly Tyr Ile Glu Asp Ser Gln Asp
        755                 760                 765

TTA GAA ATC TAT TTG ATC CGT TAC AAT GCA AAA CAC GAA ATA GTA AAT      2352
Leu Glu Ile Tyr Leu Ile Arg Tyr Asn Ala Lys His Glu Ile Val Asn
    770                 775                 780

GTG CCA GGC ACG GGT TCC TTA TGG CCG CTT TCA GCC CAA AGT CCA ATC      2400
Val Pro Gly Thr Gly Ser Leu Trp Pro Leu Ser Ala Gln Ser Pro Ile
785                 790                 795                 800

GGA AAG TGT GGA GAA CCG AAT CGA TGC GCG CCA CAC CTT GAA TGG AAT      2448
Gly Lys Cys Gly Glu Pro Asn Arg Cys Ala Pro His Leu Glu Trp Asn
                805                 810                 815

CCT GAT CTA GAT TGT TCC TGC AGA GAC GGG GAA AAA TGT GCA CAT CAT      2496
Pro Asp Leu Asp Cys Ser Cys Arg Asp Gly Glu Lys Cys Ala His His
            820                 825                 830

TCC CAT CAT TTC ACC TTG GAT ATT GAT GTT GGA TGT ACA GAC TTA AAT      2544
Ser His His Phe Thr Leu Asp Ile Asp Val Gly Cys Thr Asp Leu Asn
        835                 840                 845

GAG GAC TTA GGT GTA TGG GTG ATA TTC AAG ATT AAG ACG CAA GAT GGC      2592
Glu Asp Leu Gly Val Trp Val Ile Phe Lys Ile Lys Thr Gln Asp Gly
    850                 855                 860

CAT GCA AGA CTA GGG AAT CTA GAG TTT CTC GAA GAG AAA CCA TTA TTA      2640
His Ala Arg Leu Gly Asn Leu Glu Phe Leu Glu Glu Lys Pro Leu Leu
865                 870                 875                 880

GGG GAA GCA CTA GCT CGT GTG AAA AGA GCG GAG AAG AAG TGG AGA GAC      2688
Gly Glu Ala Leu Ala Arg Val Lys Arg Ala Glu Lys Lys Trp Arg Asp
                885                 890                 895

AAA CGA GAG AAA CTG CAG TTG GAA ACA AAT ATT GTT TAT AAA GAG GCA      2736
Lys Arg Glu Lys Leu Gln Leu Glu Thr Asn Ile Val Tyr Lys Glu Ala
            900                 905                 910

AAA GAA TCT GTA GAT GCT TTA TTT GTA AAC TCT CAA TAT GAT AGA TTA      2784
Lys Glu Ser Val Asp Ala Leu Phe Val Asn Ser Gln Tyr Asp Arg Leu
        915                 920                 925

CAA GTG GAT ACG AAC ATC GCA ATG ATT CAT GCG GCA GAT AAA CGC GTT      2832
Gln Val Asp Thr Asn Ile Ala Met Ile His Ala Ala Asp Lys Arg Val
    930                 935                 940

CAT AGA ATC CGG GAA GCG TAT CTG CCA GAG TTG TCT GTG ATT CCA GGT      2880
His Arg Ile Arg Glu Ala Tyr Leu Pro Glu Leu Ser Val Ile Pro Gly
945                 950                 955                 960
```

```
GTC AAT GCG GCC ATT TTC GAA GAA TTA GAG GGA CGT ATT TTT ACA GCG     2928
Val Asn Ala Ala Ile Phe Glu Glu Leu Glu Gly Arg Ile Phe Thr Ala
                965                 970                 975

TAT TCC TTA TAT GAT GCG AGA AAT GTC ATT AAA AAT GGC GAT TTC AAT     2976
Tyr Ser Leu Tyr Asp Ala Arg Asn Val Ile Lys Asn Gly Asp Phe Asn
            980                 985                 990

AAT GGC TTA TTA TGC TGG AAC GTG AAA GGT CAT GTA GAT GTA GAA GAG     3024
Asn Gly Leu Leu Cys Trp Asn Val Lys Gly His Val Asp Val Glu Glu
        995                1000                1005

CAA AAC AAC CAC CGT TCG GTC CTT GTT ATC CCA GAA TGG GAG GCA GAA     3072
Gln Asn Asn His Arg Ser Val Leu Val Ile Pro Glu Trp Glu Ala Glu
    1010                1015                1020

GTG TCA CAA GAG GTT CGT GTC TGT CCA GGT CGT GGC TAT ATC CTT CGT     3120
Val Ser Gln Glu Val Arg Val Cys Pro Gly Arg Gly Tyr Ile Leu Arg
1025                1030                1035                1040

GTC ACA GCA TAT AAA GAG GGA TAT GGA GAG GGC TGC GTA ACG ATC CAT     3168
Val Thr Ala Tyr Lys Glu Gly Tyr Gly Glu Gly Cys Val Thr Ile His
                1045                1050                1055

GAG ATC GAA GAC AAT ACA GAC GAA CTG AAA TTC AGC AAC TGT GTA GAA     3216
Glu Ile Glu Asp Asn Thr Asp Glu Leu Lys Phe Ser Asn Cys Val Glu
            1060                1065                1070

GAG GAA GTA TAT CCA AAC AAC ACA GTA ACG TGT AAT AAT TAT ACT GGG     3264
Glu Glu Val Tyr Pro Asn Asn Thr Val Thr Cys Asn Asn Tyr Thr Gly
        1075                1080                1085

ACT CAA GAA GAA TAT GAG GGT ACG TAC ACT TCT CGT AAT CAA GGA TAT     3312
Thr Gln Glu Glu Tyr Glu Gly Thr Tyr Thr Ser Arg Asn Gln Gly Tyr
    1090                1095                1100

GAC GAA GCC TAT GGT AAT AAC CCT TCC GTA CCA GCT GAT TAC GCT TCA     3360
Asp Glu Ala Tyr Gly Asn Asn Pro Ser Val Pro Ala Asp Tyr Ala Ser
1105                1110                1115                1120

GTC TAT GAA GAA AAA TCG TAT ACA GAT GGA CGA AGA GAG AAT CCT TGT     3408
Val Tyr Glu Glu Lys Ser Tyr Thr Asp Gly Arg Arg Glu Asn Pro Cys
                1125                1130                1135

GAA TCT AAC AGA GGC TAT GGG GAT TAC ACA CCA CTA CCG GCT GGT TAT     3456
Glu Ser Asn Arg Gly Tyr Gly Asp Tyr Thr Pro Leu Pro Ala Gly Tyr
            1140                1145                1150

GTA ACA AAG GAT TTA GAG TAC TTC CCA GAG ACC GAT AAG GTA TGG ATT     3504
Val Thr Lys Asp Leu Glu Tyr Phe Pro Glu Thr Asp Lys Val Trp Ile
        1155                1160                1165

GAG ATC GGA GAA ACA GAA GGA ACA TTC ATC GTG GAT AGC GTG GAA TTA     3552
Glu Ile Gly Glu Thr Glu Gly Thr Phe Ile Val Asp Ser Val Glu Leu
    1170                1175                1180

CTC CTT ATG GAG GAA                                                 3567
Leu Leu Met Glu Glu
1185
```

(2) INFORMATION FOR SEQ ID NO:2:

(i) SEQUENCE CHARACTERISTICS:
(A) LENGTH: 1189 amino acids
(B) TYPE: amino acid
(D) TOPOLOGY: linear (ii) MOLECULE TYPE: protein (xi) SEQUENCE DESCRIPTION: SEQ ID NO:2:

```
Met Glu Glu Asn Asn Gln Asn Gln Cys Ile Pro Tyr Asn Cys Leu Ser
  1               5                  10                  15

Asn Pro Glu Glu Val Leu Leu Asp Gly Glu Arg Ile Ser Thr Gly Asn
             20                  25                  30

Ser Ser Ile Asp Ile Ser Leu Ser Leu Val Gln Phe Leu Val Ser Asn
        35                  40                  45
```

```
Phe Val Pro Gly Gly Gly Phe Leu Val Gly Leu Ile Asp Phe Val Trp
     50                  55                  60

Gly Ile Val Gly Pro Ser Gln Trp Asp Ala Phe Leu Val Gln Ile Glu
 65                  70                  75                  80

Gln Leu Ile Asn Glu Arg Ile Ala Glu Phe Ala Arg Asn Ala Ala Ile
                 85                  90                  95

Ala Asn Leu Glu Gly Leu Gly Asn Asn Phe Asn Ile Tyr Val Glu Ala
            100                 105                 110

Phe Lys Glu Trp Glu Glu Asp Pro Asn Asn Pro Ala Thr Arg Thr Arg
        115                 120                 125

Val Ile Asp Arg Phe Arg Ile Leu Asp Gly Leu Leu Glu Arg Asp Ile
    130                 135                 140

Pro Ser Phe Ala Ile Ser Gly Phe Glu Val Pro Leu Leu Ser Val Tyr
145                 150                 155                 160

Ala Gln Ala Ala Asn Leu His Leu Ala Ile Leu Arg Asp Ser Val Ile
                165                 170                 175

Phe Gly Glu Arg Trp Gly Leu Thr Thr Ile Asn Val Asn Glu Asn Tyr
            180                 185                 190

Asn Arg Leu Ile Arg His Ile Asp Glu Tyr Ala Asp His Cys Ala Asn
        195                 200                 205

Thr Tyr Asn Arg Gly Leu Asn Asn Leu Pro Lys Ser Thr Tyr Gln Asp
    210                 215                 220

Trp Ile Thr Tyr Asn Arg Leu Arg Arg Asp Leu Thr Leu Thr Val Leu
225                 230                 235                 240

Asp Ile Ala Ala Phe Phe Pro Asn Tyr Asp Asn Arg Arg Tyr Pro Ile
                245                 250                 255

Gln Pro Val Gly Gln Leu Thr Arg Glu Val Tyr Thr Asp Pro Leu Ile
            260                 265                 270

Asn Phe Asn Pro Gln Leu Gln Ser Val Ala Gln Leu Pro Thr Phe Asn
        275                 280                 285

Val Met Glu Ser Ser Ala Ile Arg Asn Pro His Leu Phe Asp Ile Leu
    290                 295                 300

Asn Asn Leu Thr Ile Phe Thr Asp Trp Phe Ser Val Gly Arg Asn Phe
305                 310                 315                 320

Tyr Trp Gly Gly His Arg Val Ile Ser Ser Leu Ile Gly Gly Gly Asn
                325                 330                 335

Ile Thr Ser Pro Ile Tyr Gly Arg Glu Ala Asn Gln Glu Pro Pro Arg
            340                 345                 350

Ser Phe Thr Phe Asn Gly Pro Val Phe Arg Thr Leu Ser Asn Pro Thr
        355                 360                 365

Leu Arg Leu Leu Gln Gln Pro Trp Pro Ala Pro Pro Phe Asn Leu Arg
    370                 375                 380

Gly Val Glu Gly Val Glu Phe Ser Thr Pro Thr Asn Ser Phe Thr Tyr
385                 390                 395                 400

Arg Gly Arg Gly Thr Val Asp Ser Leu Thr Glu Leu Pro Pro Glu Asp
                405                 410                 415

Asn Ser Val Pro Pro Arg Glu Gly Tyr Ser His Arg Leu Cys His Ala
            420                 425                 430

Thr Phe Val Gln Arg Ser Gly Thr Pro Phe Leu Thr Thr Gly Val Val
        435                 440                 445

Phe Ser Trp Thr His Arg Ser Ala Thr Leu Thr Asn Thr Ile Asp Pro
    450                 455                 460

Glu Arg Ile Asn Gln Ile Pro Leu Val Lys Gly Phe Arg Val Trp Gly
```

-continued

```
465                 470                 475                 480

Gly Thr Ser Val Ile Thr Gly Pro Gly Phe Thr Gly Gly Asp Ile Leu
                485                 490                 495

Arg Arg Asn Thr Phe Gly Asp Phe Val Ser Leu Gln Val Asn Ile Asn
            500                 505                 510

Ser Pro Ile Thr Gln Arg Tyr Arg Leu Arg Phe Arg Tyr Ala Ser Ser
        515                 520                 525

Arg Asp Ala Arg Val Ile Val Leu Thr Gly Ala Ala Ser Thr Gly Val
    530                 535                 540

Gly Gly Gln Val Ser Val Asn Met Pro Leu Gln Lys Thr Met Glu Ile
545                 550                 555                 560

Gly Glu Asn Leu Thr Ser Arg Thr Phe Arg Tyr Thr Asp Phe Ser Asn
                565                 570                 575

Pro Phe Ser Phe Arg Ala Asn Pro Asp Ile Ile Gly Ile Ser Glu Gln
            580                 585                 590

Pro Leu Phe Gly Ala Gly Ser Ile Ser Ser Gly Glu Leu Tyr Ile Asp
        595                 600                 605

Lys Ile Glu Ile Ile Leu Ala Asp Ala Thr Phe Glu Ala Glu Ser Asp
    610                 615                 620

Leu Glu Arg Ala Gln Lys Ala Val Asn Ala Leu Phe Thr Ser Ser Asn
625                 630                 635                 640

Gln Ile Gly Leu Lys Thr Asp Val Thr Asp Tyr His Ile Asp Gln Val
                645                 650                 655

Ser Asn Leu Val Asp Cys Leu Ser Asp Glu Phe Cys Leu Asp Glu Lys
            660                 665                 670

Arg Glu Leu Ser Glu Lys Val Lys His Ala Lys Arg Leu Ser Asp Glu
        675                 680                 685

Arg Asn Leu Leu Gln Asp Pro Asn Phe Arg Gly Ile Asn Arg Gln Pro
    690                 695                 700

Asp Arg Gly Trp Arg Gly Ser Thr Asp Ile Thr Ile Gln Gly Gly Asp
705                 710                 715                 720

Asp Val Phe Lys Glu Asn Tyr Val Thr Leu Pro Gly Thr Val Asp Glu
                725                 730                 735

Cys Tyr Pro Thr Tyr Leu Tyr Gln Lys Ile Asp Glu Ser Lys Leu Lys
            740                 745                 750

Ala Tyr Thr Arg Tyr Glu Leu Arg Gly Tyr Ile Glu Asp Ser Gln Asp
        755                 760                 765

Leu Glu Ile Tyr Leu Ile Arg Tyr Asn Ala Lys His Glu Ile Val Asn
    770                 775                 780

Val Pro Gly Thr Gly Ser Leu Trp Pro Leu Ser Ala Gln Ser Pro Ile
785                 790                 795                 800

Gly Lys Cys Gly Glu Pro Asn Arg Cys Ala Pro His Leu Glu Trp Asn
                805                 810                 815

Pro Asp Leu Asp Cys Ser Cys Arg Asp Gly Glu Lys Cys Ala His His
            820                 825                 830

Ser His His Phe Thr Leu Asp Ile Asp Val Gly Cys Thr Asp Leu Asn
        835                 840                 845

Glu Asp Leu Gly Val Trp Val Ile Phe Lys Ile Lys Thr Gln Asp Gly
    850                 855                 860

His Ala Arg Leu Gly Asn Leu Glu Phe Leu Glu Glu Lys Pro Leu Leu
865                 870                 875                 880

Gly Glu Ala Leu Ala Arg Val Lys Arg Ala Glu Lys Lys Trp Arg Asp
                885                 890                 895
```

```
Lys Arg Glu Lys Leu Gln Leu Glu Thr Asn Ile Val Tyr Lys Glu Ala
            900                 905                 910

Lys Glu Ser Val Asp Ala Leu Phe Val Asn Ser Gln Tyr Asp Arg Leu
        915                 920                 925

Gln Val Asp Thr Asn Ile Ala Met Ile His Ala Ala Asp Lys Arg Val
    930                 935                 940

His Arg Ile Arg Glu Ala Tyr Leu Pro Glu Leu Ser Val Ile Pro Gly
945                 950                 955                 960

Val Asn Ala Ala Ile Phe Glu Glu Leu Glu Gly Arg Ile Phe Thr Ala
                965                 970                 975

Tyr Ser Leu Tyr Asp Ala Arg Asn Val Ile Lys Asn Gly Asp Phe Asn
            980                 985                 990

Asn Gly Leu Leu Cys Trp Asn Val Lys Gly His Val Asp Val Glu Glu
        995                 1000                1005

Gln Asn Asn His Arg Ser Val Leu Val Ile Pro Glu Trp Glu Ala Glu
    1010                1015                1020

Val Ser Gln Glu Val Arg Val Cys Pro Gly Arg Gly Tyr Ile Leu Arg
1025                1030                1035                1040

Val Thr Ala Tyr Lys Glu Gly Tyr Gly Glu Gly Cys Val Thr Ile His
                1045                1050                1055

Glu Ile Glu Asp Asn Thr Asp Glu Leu Lys Phe Ser Asn Cys Val Glu
            1060                1065                1070

Glu Glu Val Tyr Pro Asn Asn Thr Val Thr Cys Asn Asn Tyr Thr Gly
        1075                1080                1085

Thr Gln Glu Glu Tyr Glu Gly Thr Tyr Thr Ser Arg Asn Gln Gly Tyr
    1090                1095                1100

Asp Glu Ala Tyr Gly Asn Asn Pro Ser Val Pro Ala Asp Tyr Ala Ser
1105                1110                1115                1120

Val Tyr Glu Glu Lys Ser Tyr Thr Asp Gly Arg Arg Glu Asn Pro Cys
                1125                1130                1135

Glu Ser Asn Arg Gly Tyr Gly Asp Tyr Thr Pro Leu Pro Ala Gly Tyr
            1140                1145                1150

Val Thr Lys Asp Leu Glu Tyr Phe Pro Glu Thr Asp Lys Val Trp Ile
        1155                1160                1165

Glu Ile Gly Glu Thr Glu Gly Thr Phe Ile Val Asp Ser Val Glu Leu
    1170                1175                1180

Leu Leu Met Glu Glu
1185
```

(2) INFORMATION FOR SEQ ID NO:3:

(i) SEQUENCE CHARACTERISTICS:
(A) LENGTH: 3567 base pairs
(B) TYPE: nucleic acid
(C) STRANDEDNESS: single
(D) TOPOLOGY: linear (ix) FEATURE:
(A) NAME/KEY: CDS
(B) LOCATION: 1..3567

(xi) SEQUENCE DESCRIPTION: SEQ ID NO:3:

```
ATG GAG GAA AAT AAT CAA AAT CAA TGC ATA CCT TAC AAT TGT TTA AGT        48
Met Glu Glu Asn Asn Gln Asn Gln Cys Ile Pro Tyr Asn Cys Leu Ser
  1               5                  10                  15

AAT CCT GAA GAA GTA CTT TTG GAT GGA GAA CGG ATA TCA ACT GGT AAT        96
Asn Pro Glu Glu Val Leu Leu Asp Gly Glu Arg Ile Ser Thr Gly Asn
             20                  25                  30
```

-continued

```
TCA TCA ATT GAT ATT TCT CTG TCA CTT GTT CAG TTT CTG GTA TCT AAC       144
Ser Ser Ile Asp Ile Ser Leu Ser Leu Val Gln Phe Leu Val Ser Asn
         35                  40                  45

TTT GTA CCA GGG GGA GGA TTT TTA GTT GGA TTA ATA GAT TTT GTA TGG       192
Phe Val Pro Gly Gly Gly Phe Leu Val Gly Leu Ile Asp Phe Val Trp
     50                  55                  60

GGA ATA GTT GGC CCT TCT CAA TGG GAT GCA TTT CTA GTA CAA ATT GAA       240
Gly Ile Val Gly Pro Ser Gln Trp Asp Ala Phe Leu Val Gln Ile Glu
 65                  70                  75                  80

CAA TTA ATT AAT GAA AGA ATA GCT GAA TTT GCT AGG AAT GCT GCT ATT       288
Gln Leu Ile Asn Glu Arg Ile Ala Glu Phe Ala Arg Asn Ala Ala Ile
                 85                  90                  95

GCT AAT TTA GAA GGA TTA GGA AAC AAT TTC AAT ATA TAT GTG GAA GCA       336
Ala Asn Leu Glu Gly Leu Gly Asn Asn Phe Asn Ile Tyr Val Glu Ala
            100                 105                 110

TTT AAA GAA TGG GAA GAA GAT CCT AAT AAT CCA GCA ACC AGG ACC AGA       384
Phe Lys Glu Trp Glu Glu Asp Pro Asn Asn Pro Ala Thr Arg Thr Arg
        115                 120                 125

GTA ATT GAT CGC TTT CGT ATA CTT GAT GGG CTA CTT GAA AGG GAC ATT       432
Val Ile Asp Arg Phe Arg Ile Leu Asp Gly Leu Leu Glu Arg Asp Ile
    130                 135                 140

CCT TCG TTT GAC ATT TCT GGA TTT GAA GTA CCC CTT TTA TCC GTT TAT       480
Pro Ser Phe Asp Ile Ser Gly Phe Glu Val Pro Leu Leu Ser Val Tyr
145                 150                 155                 160

GCT CAA GCG GCC AAT CTG CAT CTA GCT ATA TTA AGA GAT TCT GTA ATT       528
Ala Gln Ala Ala Asn Leu His Leu Ala Ile Leu Arg Asp Ser Val Ile
                165                 170                 175

TTT GGA GAA AGA TGG GGA TTG ACA ACG ATA AAT GTC AAT GAA AAC TAT       576
Phe Gly Glu Arg Trp Gly Leu Thr Thr Ile Asn Val Asn Glu Asn Tyr
            180                 185                 190

AAT AGA CTA ATT AGG CAT ATT GAT GAA TAT GCT GAT CAC TGT GCA AAT       624
Asn Arg Leu Ile Arg His Ile Asp Glu Tyr Ala Asp His Cys Ala Asn
        195                 200                 205

ACG TAT AAT CGG GGA TTA AAT AAT TTA CCG AAA TCT ACG TAT CAA GAT       672
Thr Tyr Asn Arg Gly Leu Asn Asn Leu Pro Lys Ser Thr Tyr Gln Asp
    210                 215                 220

TGG ATA ACA TAT AAT CGA TTA CGG AGA GAC TTA ACA TTG ACT GTA TTA       720
Trp Ile Thr Tyr Asn Arg Leu Arg Arg Asp Leu Thr Leu Thr Val Leu
225                 230                 235                 240

GAT ATC GCC GCT TTC TTT CCA AAC TAT GAC AAT AGG AGA TAT CCA ATT       768
Asp Ile Ala Ala Phe Phe Pro Asn Tyr Asp Asn Arg Arg Tyr Pro Ile
                245                 250                 255

CAG CCA GTT GGT CAA CTA ACA AGG GAA GTT TAT ACG GAC CCA TTA ATT       816
Gln Pro Val Gly Gln Leu Thr Arg Glu Val Tyr Thr Asp Pro Leu Ile
            260                 265                 270

AAT TTT AAT CCA CAG TTA CAG TCT GTA GCT CAA TTA CCT ACT TTT AAC       864
Asn Phe Asn Pro Gln Leu Gln Ser Val Ala Gln Leu Pro Thr Phe Asn
        275                 280                 285

GTT ATG GAG AGC AGC GCA ATT AGA AAT CCT CAT TTA TTT GAT ATA TTG       912
Val Met Glu Ser Ser Ala Ile Arg Asn Pro His Leu Phe Asp Ile Leu
    290                 295                 300

AAT AAT CTT ACA ATC TTT ACG GAT TGG TTT AGT GTT GGA CGC AAT TTT       960
Asn Asn Leu Thr Ile Phe Thr Asp Trp Phe Ser Val Gly Arg Asn Phe
305                 310                 315                 320

TAT TGG GGA GGA CAT CGA GTA ATA TCT AGC CTT ATA GGA GGT GGT AAC      1008
Tyr Trp Gly Gly His Arg Val Ile Ser Ser Leu Ile Gly Gly Gly Asn
                325                 330                 335

ATA ACA TCT CCT ATA TAT GGA AGA GAG GCG AAC CAG GAG CCT CCA AGA      1056
Ile Thr Ser Pro Ile Tyr Gly Arg Glu Ala Asn Gln Glu Pro Pro Arg
            340                 345                 350
```

-continued

```
TCC TTT ACT TTT AAT GGA CCG GTA TTT AGG ACT TTA TCA AAT CCT ACT     1104
Ser Phe Thr Phe Asn Gly Pro Val Phe Arg Thr Leu Ser Asn Pro Thr
        355                 360                 365

TTA CGA TTA TTA CAG CAA CCT TGG CCA GCG CCA CCA TTT AAT TTA CGT     1152
Leu Arg Leu Leu Gln Gln Pro Trp Pro Ala Pro Pro Phe Asn Leu Arg
    370                 375                 380

GGT GTT GAA GGA GTA GAA TTT TCT ACA CCT ACA AAT AGC TTT ACG TAT     1200
Gly Val Glu Gly Val Glu Phe Ser Thr Pro Thr Asn Ser Phe Thr Tyr
385                 390                 395                 400

CGA GGA AGA GGT ACG GTT GAT TCT TTA ACT GAA TTA CCG CCT GAG GAT     1248
Arg Gly Arg Gly Thr Val Asp Ser Leu Thr Glu Leu Pro Pro Glu Asp
            405                 410                 415

AAT AGT GTG CCA CCT CGC GAA GGA TAT AGT CAT CGT TTA TGT CAT GCA     1296
Asn Ser Val Pro Pro Arg Glu Gly Tyr Ser His Arg Leu Cys His Ala
            420                 425                 430

ACT TTT GTT CAA AGA TCT GGA ACA CCT TTT TTA ACA ACT GGT GTA GTA     1344
Thr Phe Val Gln Arg Ser Gly Thr Pro Phe Leu Thr Thr Gly Val Val
        435                 440                 445

TTT TCT TGG ACG CAT CGT AGT GCA ACT CTT ACA AAT ACA ATT GAT CCA     1392
Phe Ser Trp Thr His Arg Ser Ala Thr Leu Thr Asn Thr Ile Asp Pro
    450                 455                 460

GAG AGA ATT AAT CAA ATA CCT TTA GTG AAA GGA TTT AGA GTT TGG GGG     1440
Glu Arg Ile Asn Gln Ile Pro Leu Val Lys Gly Phe Arg Val Trp Gly
465                 470                 475                 480

GGC ACC TCT GTC ATT ACA GGA CCA GGA TTT ACA GGA GGG GAT ATC CTT     1488
Gly Thr Ser Val Ile Thr Gly Pro Gly Phe Thr Gly Gly Asp Ile Leu
            485                 490                 495

CGA AGA AAT ACC TTT GGT GAT TTT GTA TCT CTA CAA GTC AAT ATT AAT     1536
Arg Arg Asn Thr Phe Gly Asp Phe Val Ser Leu Gln Val Asn Ile Asn
            500                 505                 510

TCA CCA ATT ACC CAA AGA TAC CGT TTA AGA TTT CGT TAC GCT TCC AGT     1584
Ser Pro Ile Thr Gln Arg Tyr Arg Leu Arg Phe Arg Tyr Ala Ser Ser
        515                 520                 525

AGG GAT GCA CGA GTT ATA GTA TTA ACA GGA GCG GCA TCC ACA GGA GTG     1632
Arg Asp Ala Arg Val Ile Val Leu Thr Gly Ala Ala Ser Thr Gly Val
    530                 535                 540

GGA GGC CAA GTT AGT GTA AAT ATG CCT CTT CAG AAA ACT ATG GAA ATA     1680
Gly Gly Gln Val Ser Val Asn Met Pro Leu Gln Lys Thr Met Glu Ile
545                 550                 555                 560

GGG GAG AAC TTA ACA TCT AGA ACA TTT AGA TAT ACC GAT TTT AGT AAT     1728
Gly Glu Asn Leu Thr Ser Arg Thr Phe Arg Tyr Thr Asp Phe Ser Asn
            565                 570                 575

CCT TTT TCA TTT AGA GCT AAT CCA GAT ATA ATT GGG ATA AGT GAA CAA     1776
Pro Phe Ser Phe Arg Ala Asn Pro Asp Ile Ile Gly Ile Ser Glu Gln
            580                 585                 590

CCT CTA TTT GGT GCA GGT TCT ATT AGT AGC GGT GAA CTT TAT ATA GAT     1824
Pro Leu Phe Gly Ala Gly Ser Ile Ser Ser Gly Glu Leu Tyr Ile Asp
        595                 600                 605

AAA ATT GAA ATT ATT CTA GCA GAT GCA ACA TTT GAA GCA GAA TCT GAT     1872
Lys Ile Glu Ile Ile Leu Ala Asp Ala Thr Phe Glu Ala Glu Ser Asp
    610                 615                 620

TTA GAA AGA GCA CAA AAG GCG GTG AAT GCC CTG TTT ACT TCT TCC AAT     1920
Leu Glu Arg Ala Gln Lys Ala Val Asn Ala Leu Phe Thr Ser Ser Asn
625                 630                 635                 640

CAA ATC GGG TTA AAA ACC GAT GTG ACG GAT TAT CAT ATT GAT CAA GTA     1968
Gln Ile Gly Leu Lys Thr Asp Val Thr Asp Tyr His Ile Asp Gln Val
            645                 650                 655

TCC AAT TTA GTG GAT TGT TTA TCA GAT GAA TTT TGT CTG GAT GAA AAG     2016
Ser Asn Leu Val Asp Cys Leu Ser Asp Glu Phe Cys Leu Asp Glu Lys
            660                 665                 670
```

-continued

```
CGA GAA TTG TCC GAG AAA GTC AAA CAT GCG AAG CGA CTC AGT GAT GAG      2064
Arg Glu Leu Ser Glu Lys Val Lys His Ala Lys Arg Leu Ser Asp Glu
        675                 680                 685

CGG AAT TTA CTT CAA GAT CCA AAC TTC AGA GGG ATC AAT AGA CAA CCA      2112
Arg Asn Leu Leu Gln Asp Pro Asn Phe Arg Gly Ile Asn Arg Gln Pro
    690                 695                 700

GAC CGT GGC TGG AGA GGA AGT ACA GAT ATT ACC ATC CAA GGA GGA GAT      2160
Asp Arg Gly Trp Arg Gly Ser Thr Asp Ile Thr Ile Gln Gly Gly Asp
705                 710                 715                 720

GAC GTA TTC AAA GAG AAT TAC GTC ACA CTA CCG GGT ACC GTT GAT GAG      2208
Asp Val Phe Lys Glu Asn Tyr Val Thr Leu Pro Gly Thr Val Asp Glu
                725                 730                 735

TGC TAT CCA ACG TAT TTA TAT CAG AAA ATA GAT GAG TCG AAA TTA AAA      2256
Cys Tyr Pro Thr Tyr Leu Tyr Gln Lys Ile Asp Glu Ser Lys Leu Lys
            740                 745                 750

GCT TAT ACC CGT TAT GAA TTA AGA GGG TAT ATC GAA GAT AGT CAA GAC      2304
Ala Tyr Thr Arg Tyr Glu Leu Arg Gly Tyr Ile Glu Asp Ser Gln Asp
        755                 760                 765

TTA GAA ATC TAT TTG ATC CGT TAC AAT GCA AAA CAC GAA ATA GTA AAT      2352
Leu Glu Ile Tyr Leu Ile Arg Tyr Asn Ala Lys His Glu Ile Val Asn
    770                 775                 780

GTG CCA GGC ACG GGT TCC TTA TGG CCG CTT TCA GCC CAA AGT CCA ATC      2400
Val Pro Gly Thr Gly Ser Leu Trp Pro Leu Ser Ala Gln Ser Pro Ile
785                 790                 795                 800

GGA AAG TGT GGA GAA CCG AAT CGA TGC GCG CCA CAC CTT GAA TGG AAT      2448
Gly Lys Cys Gly Glu Pro Asn Arg Cys Ala Pro His Leu Glu Trp Asn
                805                 810                 815

CCT GAT CTA GAT TGT TCC TGC AGA GAC GGG GAA AAA TGT GCA CAT CAT      2496
Pro Asp Leu Asp Cys Ser Cys Arg Asp Gly Glu Lys Cys Ala His His
            820                 825                 830

TCC CAT CAT TTC ACC TTG GAT ATT GAT GTT GGA TGT ACA GAC TTA AAT      2544
Ser His His Phe Thr Leu Asp Ile Asp Val Gly Cys Thr Asp Leu Asn
        835                 840                 845

GAG GAC TTA GGT GTA TGG GTG ATA TTC AAG ATT AAG ACG CAA GAT GGC      2592
Glu Asp Leu Gly Val Trp Val Ile Phe Lys Ile Lys Thr Gln Asp Gly
    850                 855                 860

CAT GCA AGA CTA GGG AAT CTA GAG TTT CTC GAA GAG AAA CCA TTA TTA      2640
His Ala Arg Leu Gly Asn Leu Glu Phe Leu Glu Glu Lys Pro Leu Leu
865                 870                 875                 880

GGG GAA GCA CTA GCT CGT GTG AAA AGA GCG GAG AAG AAG TGG AGA GAC      2688
Gly Glu Ala Leu Ala Arg Val Lys Arg Ala Glu Lys Lys Trp Arg Asp
                885                 890                 895

AAA CGA GAG AAA CTG CAG TTG GAA ACA AAT ATT GTT TAT AAA GAG GCA      2736
Lys Arg Glu Lys Leu Gln Leu Glu Thr Asn Ile Val Tyr Lys Glu Ala
            900                 905                 910

AAA GAA TCT GTA GAT GCT TTA TTT GTA AAC TCT CAA TAT GAT AGA TTA      2784
Lys Glu Ser Val Asp Ala Leu Phe Val Asn Ser Gln Tyr Asp Arg Leu
        915                 920                 925

CAA GTG GAT ACG AAC ATC GCA ATG ATT CAT GCG GCA GAT AAA CGC GTT      2832
Gln Val Asp Thr Asn Ile Ala Met Ile His Ala Ala Asp Lys Arg Val
    930                 935                 940

CAT AGA ATC CGG GAA GCG TAT CTG CCA GAG TTG TCT GTG ATT CCA GGT      2880
His Arg Ile Arg Glu Ala Tyr Leu Pro Glu Leu Ser Val Ile Pro Gly
945                 950                 955                 960

GTC AAT GCG GCC ATT TTC GAA GAA TTA GAG GGA CGT ATT TTT ACA GCG      2928
Val Asn Ala Ala Ile Phe Glu Glu Leu Glu Gly Arg Ile Phe Thr Ala
                965                 970                 975

TAT TCC TTA TAT GAT GCG AGA AAT GTC ATT AAA AAT GGC GAT TTC AAT      2976
Tyr Ser Leu Tyr Asp Ala Arg Asn Val Ile Lys Asn Gly Asp Phe Asn
            980                 985                 990
```

-continued

```
AAT GGC TTA TTA TGC TGG AAC GTG AAA GGT CAT GTA GAT GTA GAA GAG     3024
Asn Gly Leu Leu Cys Trp Asn Val Lys Gly His Val Asp Val Glu Glu
        995                 1000                1005

CAA AAC AAC CAC CGT TCG GTC CTT GTT ATC CCA GAA TGG GAG GCA GAA     3072
Gln Asn Asn His Arg Ser Val Leu Val Ile Pro Glu Trp Glu Ala Glu
    1010                1015                1020

GTG TCA CAA GAG GTT CGT GTC TGT CCA GGT CGT GGC TAT ATC CTT CGT     3120
Val Ser Gln Glu Val Arg Val Cys Pro Gly Arg Gly Tyr Ile Leu Arg
1025                1030                1035                1040

GTC ACA GCA TAT AAA GAG GGA TAT GGA GAG GGC TGC GTA ACG ATC CAT     3168
Val Thr Ala Tyr Lys Glu Gly Tyr Gly Glu Gly Cys Val Thr Ile His
                1045                1050                1055

GAG ATC GAA GAC AAT ACA GAC GAA CTG AAA TTC AGC AAC TGT GTA GAA     3216
Glu Ile Glu Asp Asn Thr Asp Glu Leu Lys Phe Ser Asn Cys Val Glu
            1060                1065                1070

GAG GAA GTA TAT CCA AAC AAC ACA GTA ACG TGT AAT AAT TAT ACT GGG     3264
Glu Glu Val Tyr Pro Asn Asn Thr Val Thr Cys Asn Asn Tyr Thr Gly
        1075                1080                1085

ACT CAA GAA GAA TAT GAG GGT ACG TAC ACT TCT CGT AAT CAA GGA TAT     3312
Thr Gln Glu Glu Tyr Glu Gly Thr Tyr Thr Ser Arg Asn Gln Gly Tyr
    1090                1095                1100

GAC GAA GCC TAT GGT AAT AAC CCT TCC GTA CCA GCT GAT TAC GCT TCA     3360
Asp Glu Ala Tyr Gly Asn Asn Pro Ser Val Pro Ala Asp Tyr Ala Ser
1105                1110                1115                1120

GTC TAT GAA GAA AAA TCG TAT ACA GAT GGA CGA AGA GAG AAT CCT TGT     3408
Val Tyr Glu Glu Lys Ser Tyr Thr Asp Gly Arg Arg Glu Asn Pro Cys
                1125                1130                1135

GAA TCT AAC AGA GGC TAT GGG GAT TAC ACA CCA CTA CCG GCT GGT TAT     3456
Glu Ser Asn Arg Gly Tyr Gly Asp Tyr Thr Pro Leu Pro Ala Gly Tyr
            1140                1145                1150

GTA ACA AAG GAT TTA GAG TAC TTC CCA GAG ACC GAT AAG GTA TGG ATT     3504
Val Thr Lys Asp Leu Glu Tyr Phe Pro Glu Thr Asp Lys Val Trp Ile
        1155                1160                1165

GAG ATC GGA GAA ACA GAA GGA ACA TTC ATC GTG GAT AGC GTG GAA TTA     3552
Glu Ile Gly Glu Thr Glu Gly Thr Phe Ile Val Asp Ser Val Glu Leu
    1170                1175                1180

CTC CTT ATG GAG GAA                                                 3567
Leu Leu Met Glu Glu
1185
```

(2) INFORMATION FOR SEQ ID NO:4:

(i) SEQUENCE CHARACTERISTICS:
(A) LENGTH: 1189 amino acids
(B) TYPE: amino acid
(D) TOPOLOGY: linear (ii) MOLECULE TYPE: protein (xi) SEQUENCE DESCRIPTION: SEQ ID NO:4:

```
Met Glu Glu Asn Asn Gln Asn Gln Cys Ile Pro Tyr Asn Cys Leu Ser
  1               5                  10                  15

Asn Pro Glu Glu Val Leu Leu Asp Gly Glu Arg Ile Ser Thr Gly Asn
            20                  25                  30

Ser Ser Ile Asp Ile Ser Leu Ser Leu Val Gln Phe Leu Val Ser Asn
        35                  40                  45

Phe Val Pro Gly Gly Gly Phe Leu Val Gly Leu Ile Asp Phe Val Trp
    50                  55                  60

Gly Ile Val Gly Pro Ser Gln Trp Asp Ala Phe Leu Val Gln Ile Glu
 65                  70                  75                  80

Gln Leu Ile Asn Glu Arg Ile Ala Glu Phe Ala Arg Asn Ala Ala Ile
```

-continued

```
                85                  90                  95

Ala Asn Leu Glu Gly Leu Gly Asn Asn Phe Asn Ile Tyr Val Glu Ala
            100                 105                 110

Phe Lys Glu Trp Glu Glu Asp Pro Asn Asn Pro Ala Thr Arg Thr Arg
        115                 120                 125

Val Ile Asp Arg Phe Arg Ile Leu Asp Gly Leu Leu Glu Arg Asp Ile
    130                 135                 140

Pro Ser Phe Asp Ile Ser Gly Phe Glu Val Pro Leu Leu Ser Val Tyr
145                 150                 155                 160

Ala Gln Ala Ala Asn Leu His Leu Ala Ile Leu Arg Asp Ser Val Ile
                165                 170                 175

Phe Gly Glu Arg Trp Gly Leu Thr Thr Ile Asn Val Asn Glu Asn Tyr
            180                 185                 190

Asn Arg Leu Ile Arg His Ile Asp Glu Tyr Ala Asp His Cys Ala Asn
        195                 200                 205

Thr Tyr Asn Arg Gly Leu Asn Asn Leu Pro Lys Ser Thr Tyr Gln Asp
    210                 215                 220

Trp Ile Thr Tyr Asn Arg Leu Arg Arg Asp Leu Thr Leu Thr Val Leu
225                 230                 235                 240

Asp Ile Ala Ala Phe Phe Pro Asn Tyr Asp Asn Arg Arg Tyr Pro Ile
                245                 250                 255

Gln Pro Val Gly Gln Leu Thr Arg Glu Val Tyr Thr Asp Pro Leu Ile
            260                 265                 270

Asn Phe Asn Pro Gln Leu Gln Ser Val Ala Gln Leu Pro Thr Phe Asn
        275                 280                 285

Val Met Glu Ser Ser Ala Ile Arg Asn Pro His Leu Phe Asp Ile Leu
    290                 295                 300

Asn Asn Leu Thr Ile Phe Thr Asp Trp Phe Ser Val Gly Arg Asn Phe
305                 310                 315                 320

Tyr Trp Gly Gly His Arg Val Ile Ser Ser Leu Ile Gly Gly Gly Asn
                325                 330                 335

Ile Thr Ser Pro Ile Tyr Gly Arg Glu Ala Asn Gln Glu Pro Pro Arg
            340                 345                 350

Ser Phe Thr Phe Asn Gly Pro Val Phe Arg Thr Leu Ser Asn Pro Thr
        355                 360                 365

Leu Arg Leu Leu Gln Gln Pro Trp Pro Ala Pro Pro Phe Asn Leu Arg
    370                 375                 380

Gly Val Glu Gly Val Glu Phe Ser Thr Pro Thr Asn Ser Phe Thr Tyr
385                 390                 395                 400

Arg Gly Arg Gly Thr Val Asp Ser Leu Thr Glu Leu Pro Pro Glu Asp
                405                 410                 415

Asn Ser Val Pro Pro Arg Glu Gly Tyr Ser His Arg Leu Cys His Ala
            420                 425                 430

Thr Phe Val Gln Arg Ser Gly Thr Pro Phe Leu Thr Thr Gly Val Val
        435                 440                 445

Phe Ser Trp Thr His Arg Ser Ala Thr Leu Thr Asn Thr Ile Asp Pro
    450                 455                 460

Glu Arg Ile Asn Gln Ile Pro Leu Val Lys Gly Phe Arg Val Trp Gly
465                 470                 475                 480

Gly Thr Ser Val Ile Thr Gly Pro Gly Phe Thr Gly Gly Asp Ile Leu
                485                 490                 495

Arg Arg Asn Thr Phe Gly Asp Phe Val Ser Leu Gln Val Asn Ile Asn
            500                 505                 510
```

```
Ser Pro Ile Thr Gln Arg Tyr Arg Leu Arg Phe Arg Tyr Ala Ser Ser
        515                 520                 525

Arg Asp Ala Arg Val Ile Val Leu Thr Gly Ala Ala Ser Thr Gly Val
    530                 535                 540

Gly Gly Gln Val Ser Val Asn Met Pro Leu Gln Lys Thr Met Glu Ile
545                 550                 555                 560

Gly Glu Asn Leu Thr Ser Arg Thr Phe Arg Tyr Thr Asp Phe Ser Asn
                565                 570                 575

Pro Phe Ser Phe Arg Ala Asn Pro Asp Ile Ile Gly Ile Ser Glu Gln
            580                 585                 590

Pro Leu Phe Gly Ala Gly Ser Ile Ser Ser Gly Glu Leu Tyr Ile Asp
        595                 600                 605

Lys Ile Glu Ile Ile Leu Ala Asp Ala Thr Phe Glu Ala Glu Ser Asp
    610                 615                 620

Leu Glu Arg Ala Gln Lys Ala Val Asn Ala Leu Phe Thr Ser Ser Asn
625                 630                 635                 640

Gln Ile Gly Leu Lys Thr Asp Val Thr Asp Tyr His Ile Asp Gln Val
                645                 650                 655

Ser Asn Leu Val Asp Cys Leu Ser Asp Glu Phe Cys Leu Asp Glu Lys
            660                 665                 670

Arg Glu Leu Ser Glu Lys Val Lys His Ala Lys Arg Leu Ser Asp Glu
        675                 680                 685

Arg Asn Leu Leu Gln Asp Pro Asn Phe Arg Gly Ile Asn Arg Gln Pro
    690                 695                 700

Asp Arg Gly Trp Arg Gly Ser Thr Asp Ile Thr Ile Gln Gly Gly Asp
705                 710                 715                 720

Asp Val Phe Lys Glu Asn Tyr Val Thr Leu Pro Gly Thr Val Asp Glu
                725                 730                 735

Cys Tyr Pro Thr Tyr Leu Tyr Gln Lys Ile Asp Glu Ser Lys Leu Lys
            740                 745                 750

Ala Tyr Thr Arg Tyr Glu Leu Arg Gly Tyr Ile Glu Asp Ser Gln Asp
        755                 760                 765

Leu Glu Ile Tyr Leu Ile Arg Tyr Asn Ala Lys His Glu Ile Val Asn
    770                 775                 780

Val Pro Gly Thr Gly Ser Leu Trp Pro Leu Ser Ala Gln Ser Pro Ile
785                 790                 795                 800

Gly Lys Cys Gly Glu Pro Asn Arg Cys Ala Pro His Leu Glu Trp Asn
                805                 810                 815

Pro Asp Leu Asp Cys Ser Cys Arg Asp Gly Glu Lys Cys Ala His His
            820                 825                 830

Ser His His Phe Thr Leu Asp Ile Asp Val Gly Cys Thr Asp Leu Asn
        835                 840                 845

Glu Asp Leu Gly Val Trp Val Ile Phe Lys Ile Lys Thr Gln Asp Gly
    850                 855                 860

His Ala Arg Leu Gly Asn Leu Glu Phe Leu Glu Glu Lys Pro Leu Leu
865                 870                 875                 880

Gly Glu Ala Leu Ala Arg Val Lys Arg Ala Glu Lys Lys Trp Arg Asp
                885                 890                 895

Lys Arg Glu Lys Leu Gln Leu Glu Thr Asn Ile Val Tyr Lys Glu Ala
            900                 905                 910

Lys Glu Ser Val Asp Ala Leu Phe Val Asn Ser Gln Tyr Asp Arg Leu
        915                 920                 925

Gln Val Asp Thr Asn Ile Ala Met Ile His Ala Ala Asp Lys Arg Val
    930                 935                 940
```

-continued

```
His Arg Ile Arg Glu Ala Tyr Leu Pro Glu Leu Ser Val Ile Pro Gly
945                 950                 955                 960

Val Asn Ala Ala Ile Phe Glu Glu Leu Glu Gly Arg Ile Phe Thr Ala
                965                 970                 975

Tyr Ser Leu Tyr Asp Ala Arg Asn Val Ile Lys Asn Gly Asp Phe Asn
            980                 985                 990

Asn Gly Leu Leu Cys Trp Asn Val Lys Gly His Val Asp Val Glu Glu
        995                 1000                1005

Gln Asn Asn His Arg Ser Val Leu Val Ile Pro Glu Trp Glu Ala Glu
    1010                1015                1020

Val Ser Gln Glu Val Arg Val Cys Pro Gly Arg Gly Tyr Ile Leu Arg
1025                1030                1035                1040

Val Thr Ala Tyr Lys Glu Gly Tyr Gly Glu Gly Cys Val Thr Ile His
                1045                1050                1055

Glu Ile Glu Asp Asn Thr Asp Glu Leu Lys Phe Ser Asn Cys Val Glu
            1060                1065                1070

Glu Glu Val Tyr Pro Asn Asn Thr Val Thr Cys Asn Asn Tyr Thr Gly
        1075                1080                1085

Thr Gln Glu Glu Tyr Glu Gly Thr Tyr Thr Ser Arg Asn Gln Gly Tyr
    1090                1095                1100

Asp Glu Ala Tyr Gly Asn Asn Pro Ser Val Pro Ala Asp Tyr Ala Ser
1105                1110                1115                1120

Val Tyr Glu Glu Lys Ser Tyr Thr Asp Gly Arg Arg Glu Asn Pro Cys
                1125                1130                1135

Glu Ser Asn Arg Gly Tyr Gly Asp Tyr Thr Pro Leu Pro Ala Gly Tyr
            1140                1145                1150

Val Thr Lys Asp Leu Glu Tyr Phe Pro Glu Thr Asp Lys Val Trp Ile
        1155                1160                1165

Glu Ile Gly Glu Thr Glu Gly Thr Phe Ile Val Asp Ser Val Glu Leu
    1170                1175                1180

Leu Leu Met Glu Glu
1185
```

(2) INFORMATION FOR SEQ ID NO:5:

(i) SEQUENCE CHARACTERISTICS:
(A) LENGTH: 3567 base pairs
(B) TYPE: nucleic acid
(C) STRANDEDNESS: single
(D) TOPOLOGY: linear (ix) FEATURE:
(A) NAME/KEY: CDS
(B) LOCATION: 1..3567

(xi) SEQUENCE DESCRIPTION: SEQ ID NO:5:

```
ATG GAG GAA AAT AAT CAA AAT CAA TGC ATA CCT TAC AAT TGT TTA AGT       48
Met Glu Glu Asn Asn Gln Asn Gln Cys Ile Pro Tyr Asn Cys Leu Ser
  1               5                  10                  15

AAT CCT GAA GAA GTA CTT TTG GAT GGA GAA CGG ATA TCA ACT GGT AAT       96
Asn Pro Glu Glu Val Leu Leu Asp Gly Glu Arg Ile Ser Thr Gly Asn
            20                  25                  30

TCA TCA ATT GAT ATT TCT CTG TCA CTT GTT CAG TTT CTG GTA TCT AAC      144
Ser Ser Ile Asp Ile Ser Leu Ser Leu Val Gln Phe Leu Val Ser Asn
        35                  40                  45

TTT GTA CCA GGG GGA GGA TTT TTA GTT GGA TTA ATA GAT TTT GTA TGG      192
Phe Val Pro Gly Gly Gly Phe Leu Val Gly Leu Ile Asp Phe Val Trp
     50                  55                  60
```

-continued

```
GGA ATA GTT GGC CCT TCT CAA TGG GAT GCA TTT CTA GTA CAA ATT GAA       240
Gly Ile Val Gly Pro Ser Gln Trp Asp Ala Phe Leu Val Gln Ile Glu
 65                  70                  75                  80

CAA TTA ATT AAT GAA AGA ATA GCT GAA TTT GCT AGG AAT GCT GCT ATT       288
Gln Leu Ile Asn Glu Arg Ile Ala Glu Phe Ala Arg Asn Ala Ala Ile
                 85                  90                  95

GCT AAT TTA GAA GGA TTA GGA AAC AAT TTC AAT ATA TAT GTG GAA GCA       336
Ala Asn Leu Glu Gly Leu Gly Asn Asn Phe Asn Ile Tyr Val Glu Ala
            100                 105                 110

TTT AAA GAA TGG GAA GAA GAT CCT AAT AAT CCA GCA ACC AGG ACC AGA       384
Phe Lys Glu Trp Glu Glu Asp Pro Asn Asn Pro Ala Thr Arg Thr Arg
        115                 120                 125

GTA ATT GAT CGC TTT CGT ATA CTT GAT GGG CTA CTT GAA AGG GAC ATT       432
Val Ile Asp Arg Phe Arg Ile Leu Asp Gly Leu Leu Glu Arg Asp Ile
    130                 135                 140

CCT TCG TTT CGA ATT TCT GGA TTT GAA GTA CCC CTT TTA TCC GTT TAT       480
Pro Ser Phe Arg Ile Ser Gly Phe Glu Val Pro Leu Leu Ser Val Tyr
145                 150                 155                 160

GCT CAA GCG GCC AAT CTG CAT CTA GCT ATA TTA AGA GAT TCT GTA ATT       528
Ala Gln Ala Ala Asn Leu His Leu Ala Ile Leu Arg Asp Ser Val Ile
                165                 170                 175

TTT GGA GAA GCA TGG GGG TTG ACA ACG ATA AAT GTC AAT GAA AAC TAT       576
Phe Gly Glu Ala Trp Gly Leu Thr Thr Ile Asn Val Asn Glu Asn Tyr
            180                 185                 190

AAT AGA CTA ATT AGG CAT ATT GAT GAA TAT GCT GAT CAC TGT GCA AAT       624
Asn Arg Leu Ile Arg His Ile Asp Glu Tyr Ala Asp His Cys Ala Asn
        195                 200                 205

ACG TAT AAT CGG GGA TTA AAT AAT TTA CCG AAA TCT ACG TAT CAA GAT       672
Thr Tyr Asn Arg Gly Leu Asn Asn Leu Pro Lys Ser Thr Tyr Gln Asp
    210                 215                 220

TGG ATA ACA TAT AAT CGA TTA CGG AGA GAC TTA ACA TTG ACT GTA TTA       720
Trp Ile Thr Tyr Asn Arg Leu Arg Arg Asp Leu Thr Leu Thr Val Leu
225                 230                 235                 240

GAT ATC GCC GCT TTC TTT CCA AAC TAT GAC AAT AGG AGA TAT CCA ATT       768
Asp Ile Ala Ala Phe Phe Pro Asn Tyr Asp Asn Arg Arg Tyr Pro Ile
                245                 250                 255

CAG CCA GTT GGT CAA CTA ACA AGG GAA GTT TAT ACG GAC CCA TTA ATT       816
Gln Pro Val Gly Gln Leu Thr Arg Glu Val Tyr Thr Asp Pro Leu Ile
            260                 265                 270

AAT TTT AAT CCA CAG TTA CAG TCT GTA GCT CAA TTA CCT ACT TTT AAC       864
Asn Phe Asn Pro Gln Leu Gln Ser Val Ala Gln Leu Pro Thr Phe Asn
        275                 280                 285

GTT ATG GAG AGC AGC GCA ATT AGA AAT CCT CAT TTA TTT GAT ATA TTG       912
Val Met Glu Ser Ser Ala Ile Arg Asn Pro His Leu Phe Asp Ile Leu
    290                 295                 300

AAT AAT CTT ACA ATC TTT ACG GAT TGG TTT AGT GTT GGA CGC AAT TTT       960
Asn Asn Leu Thr Ile Phe Thr Asp Trp Phe Ser Val Gly Arg Asn Phe
305                 310                 315                 320

TAT TGG GGA GGA CAT CGA GTA ATA TCT AGC CTT ATA GGA GGT GGT AAC      1008
Tyr Trp Gly Gly His Arg Val Ile Ser Ser Leu Ile Gly Gly Gly Asn
                325                 330                 335

ATA ACA TCT CCT ATA TAT GGA AGA GAG GCG AAC CAG GAG CCT CCA AGA      1056
Ile Thr Ser Pro Ile Tyr Gly Arg Glu Ala Asn Gln Glu Pro Pro Arg
            340                 345                 350

TCC TTT ACT TTT AAT GGA CCG GTA TTT AGG ACT TTA TCA AAT CCT ACT      1104
Ser Phe Thr Phe Asn Gly Pro Val Phe Arg Thr Leu Ser Asn Pro Thr
        355                 360                 365

TTA CGA TTA TTA CAG CAA CCT TGG CCA GCG CCA CCA TTT AAT TTA CGT      1152
Leu Arg Leu Leu Gln Gln Pro Trp Pro Ala Pro Pro Phe Asn Leu Arg
    370                 375                 380
```

```
GGT GTT GAA GGA GTA GAA TTT TCT ACA CCT ACA AAT AGC TTT ACG TAT      1200
Gly Val Glu Gly Val Glu Phe Ser Thr Pro Thr Asn Ser Phe Thr Tyr
385                 390                 395                 400

CGA GGA AGA GGT ACG GTT GAT TCT TTA ACT GAA TTA CCG CCT GAG GAT      1248
Arg Gly Arg Gly Thr Val Asp Ser Leu Thr Glu Leu Pro Pro Glu Asp
                405                 410                 415

AAT AGT GTG CCA CCT CGC GAA GGA TAT AGT CAT CGT TTA TGT CAT GCA      1296
Asn Ser Val Pro Pro Arg Glu Gly Tyr Ser His Arg Leu Cys His Ala
            420                 425                 430

ACT TTT GTT CAA AGA TCT GGA ACA CCT TTT TTA ACA ACT GGT GTA GTA      1344
Thr Phe Val Gln Arg Ser Gly Thr Pro Phe Leu Thr Thr Gly Val Val
        435                 440                 445

TTT TCT TGG ACG CAT CGT AGT GCA ACT CTT ACA AAT ACA ATT GAT CCA      1392
Phe Ser Trp Thr His Arg Ser Ala Thr Leu Thr Asn Thr Ile Asp Pro
    450                 455                 460

GAG AGA ATT AAT CAA ATA CCT TTA GTG AAA GGA TTT AGA GTT TGG GGG      1440
Glu Arg Ile Asn Gln Ile Pro Leu Val Lys Gly Phe Arg Val Trp Gly
465                 470                 475                 480

GGC ACC TCT GTC ATT ACA GGA CCA GGA TTT ACA GGA GGG GAT ATC CTT      1488
Gly Thr Ser Val Ile Thr Gly Pro Gly Phe Thr Gly Gly Asp Ile Leu
                485                 490                 495

CGA AGA AAT ACC TTT GGT GAT TTT GTA TCT CTA CAA GTC AAT ATT AAT      1536
Arg Arg Asn Thr Phe Gly Asp Phe Val Ser Leu Gln Val Asn Ile Asn
            500                 505                 510

TCA CCA ATT ACC CAA AGA TAC CGT TTA AGA TTT CGT TAC GCT TCC AGT      1584
Ser Pro Ile Thr Gln Arg Tyr Arg Leu Arg Phe Arg Tyr Ala Ser Ser
        515                 520                 525

AGG GAT GCA CGA GTT ATA GTA TTA ACA GGA GCG GCA TCC ACA GGA GTG      1632
Arg Asp Ala Arg Val Ile Val Leu Thr Gly Ala Ala Ser Thr Gly Val
    530                 535                 540

GGA GGC CAA GTT AGT GTA AAT ATG CCT CTT CAG AAA ACT ATG GAA ATA      1680
Gly Gly Gln Val Ser Val Asn Met Pro Leu Gln Lys Thr Met Glu Ile
545                 550                 555                 560

GGG GAG AAC TTA ACA TCT AGA ACA TTT AGA TAT ACC GAT TTT AGT AAT      1728
Gly Glu Asn Leu Thr Ser Arg Thr Phe Arg Tyr Thr Asp Phe Ser Asn
                565                 570                 575

CCT TTT TCA TTT AGA GCT AAT CCA GAT ATA ATT GGG ATA AGT GAA CAA      1776
Pro Phe Ser Phe Arg Ala Asn Pro Asp Ile Ile Gly Ile Ser Glu Gln
            580                 585                 590

CCT CTA TTT GGT GCA GGT TCT ATT AGT AGC GGT GAA CTT TAT ATA GAT      1824
Pro Leu Phe Gly Ala Gly Ser Ile Ser Ser Gly Glu Leu Tyr Ile Asp
        595                 600                 605

AAA ATT GAA ATT ATT CTA GCA GAT GCA ACA TTT GAA GCA GAA TCT GAT      1872
Lys Ile Glu Ile Ile Leu Ala Asp Ala Thr Phe Glu Ala Glu Ser Asp
    610                 615                 620

TTA GAA AGA GCA CAA AAG GCG GTG AAT GCC CTG TTT ACT TCT TCC AAT      1920
Leu Glu Arg Ala Gln Lys Ala Val Asn Ala Leu Phe Thr Ser Ser Asn
625                 630                 635                 640

CAA ATC GGG TTA AAA ACC GAT GTG ACG GAT TAT CAT ATT GAT CAA GTA      1968
Gln Ile Gly Leu Lys Thr Asp Val Thr Asp Tyr His Ile Asp Gln Val
                645                 650                 655

TCC AAT TTA GTG GAT TGT TTA TCA GAT GAA TTT TGT CTG GAT GAA AAG      2016
Ser Asn Leu Val Asp Cys Leu Ser Asp Glu Phe Cys Leu Asp Glu Lys
            660                 665                 670

CGA GAA TTG TCC GAG AAA GTC AAA CAT GCG AAG CGA CTC AGT GAT GAG      2064
Arg Glu Leu Ser Glu Lys Val Lys His Ala Lys Arg Leu Ser Asp Glu
        675                 680                 685

CGG AAT TTA CTT CAA GAT CCA AAC TTC AGA GGG ATC AAT AGA CAA CCA      2112
Arg Asn Leu Leu Gln Asp Pro Asn Phe Arg Gly Ile Asn Arg Gln Pro
    690                 695                 700
```

-continued

GAC CGT GGC TGG AGA GGA AGT ACA GAT ATT ACC ATC CAA GGA GGA GAT 2160
Asp Arg Gly Trp Arg Gly Ser Thr Asp Ile Thr Ile Gln Gly Gly Asp
705 710 715 720

GAC GTA TTC AAA GAG AAT TAC GTC ACA CTA CCG GGT ACC GTT GAT GAG 2208
Asp Val Phe Lys Glu Asn Tyr Val Thr Leu Pro Gly Thr Val Asp Glu
725 730 735

TGC TAT CCA ACG TAT TTA TAT CAG AAA ATA GAT GAG TCG AAA TTA AAA 2256
Cys Tyr Pro Thr Tyr Leu Tyr Gln Lys Ile Asp Glu Ser Lys Leu Lys
740 745 750

GCT TAT ACC CGT TAT GAA TTA AGA GGG TAT ATC GAA GAT AGT CAA GAC 2304
Ala Tyr Thr Arg Tyr Glu Leu Arg Gly Tyr Ile Glu Asp Ser Gln Asp
755 760 765

TTA GAA ATC TAT TTG ATC CGT TAC AAT GCA AAA CAC GAA ATA GTA AAT 2352
Leu Glu Ile Tyr Leu Ile Arg Tyr Asn Ala Lys His Glu Ile Val Asn
770 775 780

GTG CCA GGC ACG GGT TCC TTA TGG CCG CTT TCA GCC CAA AGT CCA ATC 2400
Val Pro Gly Thr Gly Ser Leu Trp Pro Leu Ser Ala Gln Ser Pro Ile
785 790 795 800

GGA AAG TGT GGA GAA CCG AAT CGA TGC GCG CCA CAC CTT GAA TGG AAT 2448
Gly Lys Cys Gly Glu Pro Asn Arg Cys Ala Pro His Leu Glu Trp Asn
805 810 815

CCT GAT CTA GAT TGT TCC TGC AGA GAC GGG GAA AAA TGT GCA CAT CAT 2496
Pro Asp Leu Asp Cys Ser Cys Arg Asp Gly Glu Lys Cys Ala His His
820 825 830

TCC CAT CAT TTC ACC TTG GAT ATT GAT GTT GGA TGT ACA GAC TTA AAT 2544
Ser His His Phe Thr Leu Asp Ile Asp Val Gly Cys Thr Asp Leu Asn
835 840 845

GAG GAC TTA GGT GTA TGG GTG ATA TTC AAG ATT AAG ACG CAA GAT GGC 2592
Glu Asp Leu Gly Val Trp Val Ile Phe Lys Ile Lys Thr Gln Asp Gly
850 855 860

CAT GCA AGA CTA GGG AAT CTA GAG TTT CTC GAA GAG AAA CCA TTA TTA 2640
His Ala Arg Leu Gly Asn Leu Glu Phe Leu Glu Glu Lys Pro Leu Leu
865 870 875 880

GGG GAA GCA CTA GCT CGT GTG AAA AGA GCG GAG AAG AAG TGG AGA GAC 2688
Gly Glu Ala Leu Ala Arg Val Lys Arg Ala Glu Lys Lys Trp Arg Asp
885 890 895

AAA CGA GAG AAA CTG CAG TTG GAA ACA AAT ATT GTT TAT AAA GAG GCA 2736
Lys Arg Glu Lys Leu Gln Leu Glu Thr Asn Ile Val Tyr Lys Glu Ala
900 905 910

AAA GAA TCT GTA GAT GCT TTA TTT GTA AAC TCT CAA TAT GAT AGA TTA 2784
Lys Glu Ser Val Asp Ala Leu Phe Val Asn Ser Gln Tyr Asp Arg Leu
915 920 925

CAA GTG GAT ACG AAC ATC GCA ATG ATT CAT GCG GCA GAT AAA CGC GTT 2832
Gln Val Asp Thr Asn Ile Ala Met Ile His Ala Ala Asp Lys Arg Val
930 935 940

CAT AGA ATC CGG GAA GCG TAT CTG CCA GAG TTG TCT GTG ATT CCA GGT 2880
His Arg Ile Arg Glu Ala Tyr Leu Pro Glu Leu Ser Val Ile Pro Gly
945 950 955 960

GTC AAT GCG GCC ATT TTC GAA GAA TTA GAG GGA CGT ATT TTT ACA GCG 2928
Val Asn Ala Ala Ile Phe Glu Glu Leu Glu Gly Arg Ile Phe Thr Ala
965 970 975

TAT TCC TTA TAT GAT GCG AGA AAT GTC ATT AAA AAT GGC GAT TTC AAT 2976
Tyr Ser Leu Tyr Asp Ala Arg Asn Val Ile Lys Asn Gly Asp Phe Asn
980 985 990

AAT GGC TTA TTA TGC TGG AAC GTG AAA GGT CAT GTA GAT GTA GAA GAG 3024
Asn Gly Leu Leu Cys Trp Asn Val Lys Gly His Val Asp Val Glu Glu
995 1000 1005

CAA AAC AAC CAC CGT TCG GTC CTT GTT ATC CCA GAA TGG GAG GCA GAA 3072
Gln Asn Asn His Arg Ser Val Leu Val Ile Pro Glu Trp Glu Ala Glu
1010 1015 1020

-continued

```
GTG TCA CAA GAG GTT CGT GTC TGT CCA GGT CGT GGC TAT ATC CTT CGT      3120
Val Ser Gln Glu Val Arg Val Cys Pro Gly Arg Gly Tyr Ile Leu Arg
1025                1030                1035                1040

GTC ACA GCA TAT AAA GAG GGA TAT GGA GAG GGC TGC GTA ACG ATC CAT      3168
Val Thr Ala Tyr Lys Glu Gly Tyr Gly Glu Gly Cys Val Thr Ile His
                1045                1050                1055

GAG ATC GAA GAC AAT ACA GAC GAA CTG AAA TTC AGC AAC TGT GTA GAA      3216
Glu Ile Glu Asp Asn Thr Asp Glu Leu Lys Phe Ser Asn Cys Val Glu
            1060                1065                1070

GAG GAA GTA TAT CCA AAC AAC ACA GTA ACG TGT AAT AAT TAT ACT GGG      3264
Glu Glu Val Tyr Pro Asn Asn Thr Val Thr Cys Asn Asn Tyr Thr Gly
        1075                1080                1085

ACT CAA GAA GAA TAT GAG GGT ACG TAC ACT TCT CGT AAT CAA GGA TAT      3312
Thr Gln Glu Glu Tyr Glu Gly Thr Tyr Thr Ser Arg Asn Gln Gly Tyr
    1090                1095                1100

GAC GAA GCC TAT GGT AAT AAC CCT TCC GTA CCA GCT GAT TAC GCT TCA      3360
Asp Glu Ala Tyr Gly Asn Asn Pro Ser Val Pro Ala Asp Tyr Ala Ser
1105                1110                1115                1120

GTC TAT GAA GAA AAA TCG TAT ACA GAT GGA CGA AGA GAG AAT CCT TGT      3408
Val Tyr Glu Glu Lys Ser Tyr Thr Asp Gly Arg Arg Glu Asn Pro Cys
                1125                1130                1135

GAA TCT AAC AGA GGC TAT GGG GAT TAC ACA CCA CTA CCG GCT GGT TAT      3456
Glu Ser Asn Arg Gly Tyr Gly Asp Tyr Thr Pro Leu Pro Ala Gly Tyr
            1140                1145                1150

GTA ACA AAG GAT TTA GAG TAC TTC CCA GAG ACC GAT AAG GTA TGG ATT      3504
Val Thr Lys Asp Leu Glu Tyr Phe Pro Glu Thr Asp Lys Val Trp Ile
        1155                1160                1165

GAG ATC GGA GAA ACA GAA GGA ACA TTC ATC GTG GAT AGC GTG GAA TTA      3552
Glu Ile Gly Glu Thr Glu Gly Thr Phe Ile Val Asp Ser Val Glu Leu
    1170                1175                1180

CTC CTT ATG GAG GAA                                                  3567
Leu Leu Met Glu Glu
1185
```

(2) INFORMATION FOR SEQ ID NO:6:

(i) SEQUENCE CHARACTERISTICS:
(A) LENGTH: 1189 amino acids
(B) TYPE: amino acid
(D) TOPOLOGY: linear (ii) MOLECULE TYPE: protein (xi) SEQUENCE DESCRIPTION: SEQ ID NO:6:

```
Met Glu Glu Asn Asn Gln Asn Gln Cys Ile Pro Tyr Asn Cys Leu Ser
  1               5                  10                  15

Asn Pro Glu Glu Val Leu Leu Asp Gly Glu Arg Ile Ser Thr Gly Asn
            20                  25                  30

Ser Ser Ile Asp Ile Ser Leu Ser Leu Val Gln Phe Leu Val Ser Asn
        35                  40                  45

Phe Val Pro Gly Gly Gly Phe Leu Val Gly Leu Ile Asp Phe Val Trp
     50                  55                  60

Gly Ile Val Gly Pro Ser Gln Trp Asp Ala Phe Leu Val Gln Ile Glu
 65                  70                  75                  80

Gln Leu Ile Asn Glu Arg Ile Ala Glu Phe Ala Arg Asn Ala Ala Ile
                 85                  90                  95

Ala Asn Leu Glu Gly Leu Gly Asn Asn Phe Asn Ile Tyr Val Glu Ala
            100                 105                 110

Phe Lys Glu Trp Glu Glu Asp Pro Asn Asn Pro Ala Thr Arg Thr Arg
        115                 120                 125
```

-continued

```
Val Ile Asp Arg Phe Arg Ile Leu Asp Gly Leu Leu Glu Arg Asp Ile
    130                 135                 140

Pro Ser Phe Arg Ile Ser Gly Phe Glu Val Pro Leu Leu Ser Val Tyr
145                 150                 155                 160

Ala Gln Ala Ala Asn Leu His Leu Ala Ile Leu Arg Asp Ser Val Ile
                165                 170                 175

Phe Gly Glu Ala Trp Gly Leu Thr Thr Ile Asn Val Asn Glu Asn Tyr
            180                 185                 190

Asn Arg Leu Ile Arg His Ile Asp Glu Tyr Ala Asp His Cys Ala Asn
        195                 200                 205

Thr Tyr Asn Arg Gly Leu Asn Asn Leu Pro Lys Ser Thr Tyr Gln Asp
    210                 215                 220

Trp Ile Thr Tyr Asn Arg Leu Arg Arg Asp Leu Thr Leu Thr Val Leu
225                 230                 235                 240

Asp Ile Ala Ala Phe Phe Pro Asn Tyr Asp Asn Arg Arg Tyr Pro Ile
                245                 250                 255

Gln Pro Val Gly Gln Leu Thr Arg Glu Val Tyr Thr Asp Pro Leu Ile
            260                 265                 270

Asn Phe Asn Pro Gln Leu Gln Ser Val Ala Gln Leu Pro Thr Phe Asn
        275                 280                 285

Val Met Glu Ser Ser Ala Ile Arg Asn Pro His Leu Phe Asp Ile Leu
    290                 295                 300

Asn Asn Leu Thr Ile Phe Thr Asp Trp Phe Ser Val Gly Arg Asn Phe
305                 310                 315                 320

Tyr Trp Gly Gly His Arg Val Ile Ser Ser Leu Ile Gly Gly Gly Asn
                325                 330                 335

Ile Thr Ser Pro Ile Tyr Gly Arg Glu Ala Asn Gln Glu Pro Pro Arg
            340                 345                 350

Ser Phe Thr Phe Asn Gly Pro Val Phe Arg Thr Leu Ser Asn Pro Thr
        355                 360                 365

Leu Arg Leu Leu Gln Gln Pro Trp Pro Ala Pro Pro Phe Asn Leu Arg
    370                 375                 380

Gly Val Glu Gly Val Glu Phe Ser Thr Pro Thr Asn Ser Phe Thr Tyr
385                 390                 395                 400

Arg Gly Arg Gly Thr Val Asp Ser Leu Thr Glu Leu Pro Pro Glu Asp
                405                 410                 415

Asn Ser Val Pro Pro Arg Glu Gly Tyr Ser His Arg Leu Cys His Ala
            420                 425                 430

Thr Phe Val Gln Arg Ser Gly Thr Pro Phe Leu Thr Thr Gly Val Val
        435                 440                 445

Phe Ser Trp Thr His Arg Ser Ala Thr Leu Thr Asn Thr Ile Asp Pro
    450                 455                 460

Glu Arg Ile Asn Gln Ile Pro Leu Val Lys Gly Phe Arg Val Trp Gly
465                 470                 475                 480

Gly Thr Ser Val Ile Thr Gly Pro Gly Phe Thr Gly Gly Asp Ile Leu
                485                 490                 495

Arg Arg Asn Thr Phe Gly Asp Phe Val Ser Leu Gln Val Asn Ile Asn
            500                 505                 510

Ser Pro Ile Thr Gln Arg Tyr Arg Leu Arg Phe Arg Tyr Ala Ser Ser
        515                 520                 525

Arg Asp Ala Arg Val Ile Val Leu Thr Gly Ala Ala Ser Thr Gly Val
    530                 535                 540

Gly Gly Gln Val Ser Val Asn Met Pro Leu Gln Lys Thr Met Glu Ile
545                 550                 555                 560
```

Gly Glu Asn Leu Thr Ser Arg Thr Phe Arg Tyr Thr Asp Phe Ser Asn
565 570 575

Pro Phe Ser Phe Arg Ala Asn Pro Asp Ile Ile Gly Ile Ser Glu Gln
580 585 590

Pro Leu Phe Gly Ala Gly Ser Ile Ser Ser Gly Glu Leu Tyr Ile Asp
595 600 605

Lys Ile Glu Ile Ile Leu Ala Asp Ala Thr Phe Glu Ala Glu Ser Asp
610 615 620

Leu Glu Arg Ala Gln Lys Ala Val Asn Ala Leu Phe Thr Ser Ser Asn
625 630 635 640

Gln Ile Gly Leu Lys Thr Asp Val Thr Asp Tyr His Ile Asp Gln Val
645 650 655

Ser Asn Leu Val Asp Cys Leu Ser Asp Glu Phe Cys Leu Asp Glu Lys
660 665 670

Arg Glu Leu Ser Glu Lys Val Lys His Ala Lys Arg Leu Ser Asp Glu
675 680 685

Arg Asn Leu Leu Gln Asp Pro Asn Phe Arg Gly Ile Asn Arg Gln Pro
690 695 700

Asp Arg Gly Trp Arg Gly Ser Thr Asp Ile Thr Ile Gln Gly Gly Asp
705 710 715 720

Asp Val Phe Lys Glu Asn Tyr Val Thr Leu Pro Gly Thr Val Asp Glu
725 730 735

Cys Tyr Pro Thr Tyr Leu Tyr Gln Lys Ile Asp Glu Ser Lys Leu Lys
740 745 750

Ala Tyr Thr Arg Tyr Glu Leu Arg Gly Tyr Ile Glu Asp Ser Gln Asp
755 760 765

Leu Glu Ile Tyr Leu Ile Arg Tyr Asn Ala Lys His Glu Ile Val Asn
770 775 780

Val Pro Gly Thr Gly Ser Leu Trp Pro Leu Ser Ala Gln Ser Pro Ile
785 790 795 800

Gly Lys Cys Gly Glu Pro Asn Arg Cys Ala Pro His Leu Glu Trp Asn
805 810 815

Pro Asp Leu Asp Cys Ser Cys Arg Asp Gly Glu Lys Cys Ala His His
820 825 830

Ser His His Phe Thr Leu Asp Ile Asp Val Gly Cys Thr Asp Leu Asn
835 840 845

Glu Asp Leu Gly Val Trp Val Ile Phe Lys Ile Lys Thr Gln Asp Gly
850 855 860

His Ala Arg Leu Gly Asn Leu Glu Phe Leu Glu Glu Lys Pro Leu Leu
865 870 875 880

Gly Glu Ala Leu Ala Arg Val Lys Arg Ala Glu Lys Lys Trp Arg Asp
885 890 895

Lys Arg Glu Lys Leu Gln Leu Glu Thr Asn Ile Val Tyr Lys Glu Ala
900 905 910

Lys Glu Ser Val Asp Ala Leu Phe Val Asn Ser Gln Tyr Asp Arg Leu
915 920 925

Gln Val Asp Thr Asn Ile Ala Met Ile His Ala Ala Asp Lys Arg Val
930 935 940

His Arg Ile Arg Glu Ala Tyr Leu Pro Glu Leu Ser Val Ile Pro Gly
945 950 955 960

Val Asn Ala Ala Ile Phe Glu Glu Leu Glu Gly Arg Ile Phe Thr Ala
965 970 975

Tyr Ser Leu Tyr Asp Ala Arg Asn Val Ile Lys Asn Gly Asp Phe Asn

-continued

```
            980                 985                 990

Asn Gly Leu Leu Cys Trp Asn Val Lys Gly His Val Asp Val Glu Glu
        995                 1000                1005

Gln Asn Asn His Arg Ser Val Leu Val Ile Pro Glu Trp Glu Ala Glu
    1010                1015                1020

Val Ser Gln Glu Val Arg Val Cys Pro Gly Arg Gly Tyr Ile Leu Arg
1025                1030                1035                1040

Val Thr Ala Tyr Lys Glu Gly Tyr Gly Glu Gly Cys Val Thr Ile His
                1045                1050                1055

Glu Ile Glu Asp Asn Thr Asp Glu Leu Lys Phe Ser Asn Cys Val Glu
            1060                1065                1070

Glu Glu Val Tyr Pro Asn Asn Thr Val Thr Cys Asn Asn Tyr Thr Gly
        1075                1080                1085

Thr Gln Glu Glu Tyr Glu Gly Thr Tyr Thr Ser Arg Asn Gln Gly Tyr
    1090                1095                1100

Asp Glu Ala Tyr Gly Asn Asn Pro Ser Val Pro Ala Asp Tyr Ala Ser
1105                1110                1115                1120

Val Tyr Glu Glu Lys Ser Tyr Thr Asp Gly Arg Arg Glu Asn Pro Cys
                1125                1130                1135

Glu Ser Asn Arg Gly Tyr Gly Asp Tyr Thr Pro Leu Pro Ala Gly Tyr
            1140                1145                1150

Val Thr Lys Asp Leu Glu Tyr Phe Pro Glu Thr Asp Lys Val Trp Ile
        1155                1160                1165

Glu Ile Gly Glu Thr Glu Gly Thr Phe Ile Val Asp Ser Val Glu Leu
    1170                1175                1180

Leu Leu Met Glu Glu
1185
```

(2) INFORMATION FOR SEQ ID NO:7:

(i) SEQUENCE CHARACTERISTICS:
(A) LENGTH: 3567 base pairs
(B) TYPE: nucleic acid
(C) STRANDEDNESS: single
(D) TOPOLOGY: linear (ix) FEATURE:
(A) NAME/KEY: CDS
(B) LOCATION: 1..3567

(xi) SEQUENCE DESCRIPTION: SEQ ID NO:7:

```
ATG GAG GAA AAT AAT CAA AAT CAA TGC ATA CCT TAC AAT TGT TTA AGT       48
Met Glu Glu Asn Asn Gln Asn Gln Cys Ile Pro Tyr Asn Cys Leu Ser
  1               5                  10                  15

AAT CCT GAA GAA GTA CTT TTG GAT GGA GAA CGG ATA TCA ACT GGT AAT       96
Asn Pro Glu Glu Val Leu Leu Asp Gly Glu Arg Ile Ser Thr Gly Asn
            20                  25                  30

TCA TCA ATT GAT ATT TCT CTG TCA CTT GTT CAG TTT CTG GTA TCT AAC      144
Ser Ser Ile Asp Ile Ser Leu Ser Leu Val Gln Phe Leu Val Ser Asn
        35                  40                  45

TTT GTA CCA GGG GGA GGA TTT TTA GTT GGA TTA ATA GAT TTT GTA TGG      192
Phe Val Pro Gly Gly Gly Phe Leu Val Gly Leu Ile Asp Phe Val Trp
     50                  55                  60

GGA ATA GTT GGC CCT TCT CAA TGG GAT GCA TTT CTA GTA CAA ATT GAA      240
Gly Ile Val Gly Pro Ser Gln Trp Asp Ala Phe Leu Val Gln Ile Glu
 65                  70                  75                  80

CAA TTA ATT AAT GAA AGA ATA GCT GAA TTT GCT AGG AAT GCT GCT ATT      288
Gln Leu Ile Asn Glu Arg Ile Ala Glu Phe Ala Arg Asn Ala Ala Ile
                 85                  90                  95
```

-continued

```
GCT AAT TTA GAA GGA TTA GGA AAC AAT TTC AAT ATA TAT GTG GAA GCA      336
Ala Asn Leu Glu Gly Leu Gly Asn Asn Phe Asn Ile Tyr Val Glu Ala
            100                 105                 110

TTT AAA GAA TGG GAA GAT GAT CCT CAT AAT CCC ACA ACC AGG ACC AGA      384
Phe Lys Glu Trp Glu Asp Asp Pro His Asn Pro Thr Thr Arg Thr Arg
        115                 120                 125

GTA ATT GAT CGC TTT CGT ATA CTT GAT GGG CTA CTT GAA AGG GAC ATT      432
Val Ile Asp Arg Phe Arg Ile Leu Asp Gly Leu Leu Glu Arg Asp Ile
    130                 135                 140

CCT TCG TTT CGA ATT TCT GGA TTT GAA GTA CCC CTT TTA TCC GTT TAT      480
Pro Ser Phe Arg Ile Ser Gly Phe Glu Val Pro Leu Leu Ser Val Tyr
145                 150                 155                 160

GCT CAA GCG GCC AAT CTG CAT CTA GCT ATA TTA AGA GAT TCT GTA ATT      528
Ala Gln Ala Ala Asn Leu His Leu Ala Ile Leu Arg Asp Ser Val Ile
                165                 170                 175

TTT GGA GAA AGA TGG GGA TTG ACA ACG ATA AAT GTC AAT GAA AAC TAT      576
Phe Gly Glu Arg Trp Gly Leu Thr Thr Ile Asn Val Asn Glu Asn Tyr
            180                 185                 190

AAT AGA CTA ATT AGG CAT ATT GAT GAA TAT GCT GAT CAC TGT GCA AAT      624
Asn Arg Leu Ile Arg His Ile Asp Glu Tyr Ala Asp His Cys Ala Asn
        195                 200                 205

ACG TAT AAT CGG GGA TTA AAT AAT TTA CCG AAA TCT ACG TAT CAA GAT      672
Thr Tyr Asn Arg Gly Leu Asn Asn Leu Pro Lys Ser Thr Tyr Gln Asp
    210                 215                 220

TGG ATA ACA TAT AAT CGA TTA CGG AGA GAC TTA ACA TTG ACT GTA TTA      720
Trp Ile Thr Tyr Asn Arg Leu Arg Arg Asp Leu Thr Leu Thr Val Leu
225                 230                 235                 240

GAT ATC GCC GCT TTC TTT CCA AAC TAT GAC AAT AGG AGA TAT CCA ATT      768
Asp Ile Ala Ala Phe Phe Pro Asn Tyr Asp Asn Arg Arg Tyr Pro Ile
                245                 250                 255

CAG CCA GTT GGT CAA CTA ACA AGG GAA GTT TAT ACG GAC CCA TTA ATT      816
Gln Pro Val Gly Gln Leu Thr Arg Glu Val Tyr Thr Asp Pro Leu Ile
            260                 265                 270

AAT TTT AAT CCA CAG TTA CAG TCT GTA GCT CAA TTA CCT ACT TTT AAC      864
Asn Phe Asn Pro Gln Leu Gln Ser Val Ala Gln Leu Pro Thr Phe Asn
        275                 280                 285

GTT ATG GAG AGC AGC GCA ATT AGA AAT CCT CAT TTA TTT GAT ATA TTG      912
Val Met Glu Ser Ser Ala Ile Arg Asn Pro His Leu Phe Asp Ile Leu
    290                 295                 300

AAT AAT CTT ACA ATC TTT ACG GAT TGG TTT AGT GTT GGA CGC AAT TTT      960
Asn Asn Leu Thr Ile Phe Thr Asp Trp Phe Ser Val Gly Arg Asn Phe
305                 310                 315                 320

TAT TGG GGA GGA CAT CGA GTA ATA TCT AGC CTT ATA GGA GGT GGT AAC     1008
Tyr Trp Gly Gly His Arg Val Ile Ser Ser Leu Ile Gly Gly Gly Asn
                325                 330                 335

ATA ACA TCT CCT ATA TAT GGA AGA GAG GCG AAC CAG GAG CCT CCA AGA     1056
Ile Thr Ser Pro Ile Tyr Gly Arg Glu Ala Asn Gln Glu Pro Pro Arg
            340                 345                 350

TCC TTT ACT TTT AAT GGA CCG GTA TTT AGG ACT TTA TCA AAT CCT ACT     1104
Ser Phe Thr Phe Asn Gly Pro Val Phe Arg Thr Leu Ser Asn Pro Thr
        355                 360                 365

TTA CGA TTA TTA CAG CAA CCT TGG CCA GCG CCA CCA TTT AAT TTA CGT     1152
Leu Arg Leu Leu Gln Gln Pro Trp Pro Ala Pro Pro Phe Asn Leu Arg
    370                 375                 380

GGT GTT GAA GGA GTA GAA TTT TCT ACA CCT ACA AAT AGC TTT ACG TAT     1200
Gly Val Glu Gly Val Glu Phe Ser Thr Pro Thr Asn Ser Phe Thr Tyr
385                 390                 395                 400

CGA GGA AGA GGT ACG GTT GAT TCT TTA ACT GAA TTA CCG CCT GAG GAT     1248
Arg Gly Arg Gly Thr Val Asp Ser Leu Thr Glu Leu Pro Pro Glu Asp
                405                 410                 415
```

-continued

```
AAT AGT GTG CCA CCT CGC GAA GGA TAT AGT CAT CGT TTA TGT CAT GCA      1296
Asn Ser Val Pro Pro Arg Glu Gly Tyr Ser His Arg Leu Cys His Ala
            420                 425                 430

ACT TTT GTT CAA AGA TCT GGA ACA CCT TTT TTA ACA ACT GGT GTA GTA      1344
Thr Phe Val Gln Arg Ser Gly Thr Pro Phe Leu Thr Thr Gly Val Val
        435                 440                 445

TTT TCT TGG ACG CAT CGT AGT GCA ACT CTT ACA AAT ACA ATT GAT CCA      1392
Phe Ser Trp Thr His Arg Ser Ala Thr Leu Thr Asn Thr Ile Asp Pro
    450                 455                 460

GAG AGA ATT AAT CAA ATA CCT TTA GTG AAA GGA TTT AGA GTT TGG GGG      1440
Glu Arg Ile Asn Gln Ile Pro Leu Val Lys Gly Phe Arg Val Trp Gly
465                 470                 475                 480

GGC ACC TCT GTC ATT ACA GGA CCA GGA TTT ACA GGA GGG GAT ATC CTT      1488
Gly Thr Ser Val Ile Thr Gly Pro Gly Phe Thr Gly Gly Asp Ile Leu
                485                 490                 495

CGA AGA AAT ACC TTT GGT GAT TTT GTA TCT CTA CAA GTC AAT ATT AAT      1536
Arg Arg Asn Thr Phe Gly Asp Phe Val Ser Leu Gln Val Asn Ile Asn
            500                 505                 510

TCA CCA ATT ACC CAA AGA TAC CGT TTA AGA TTT CGT TAC GCT TCC AGT      1584
Ser Pro Ile Thr Gln Arg Tyr Arg Leu Arg Phe Arg Tyr Ala Ser Ser
        515                 520                 525

AGG GAT GCA CGA GTT ATA GTA TTA ACA GGA GCG GCA TCC ACA GGA GTG      1632
Arg Asp Ala Arg Val Ile Val Leu Thr Gly Ala Ala Ser Thr Gly Val
    530                 535                 540

GGA GGC CAA GTT AGT GTA AAT ATG CCT CTT CAG AAA ACT ATG GAA ATA      1680
Gly Gly Gln Val Ser Val Asn Met Pro Leu Gln Lys Thr Met Glu Ile
545                 550                 555                 560

GGG GAG AAC TTA ACA TCT AGA ACA TTT AGA TAT ACC GAT TTT AGT AAT      1728
Gly Glu Asn Leu Thr Ser Arg Thr Phe Arg Tyr Thr Asp Phe Ser Asn
                565                 570                 575

CCT TTT TCA TTT AGA GCT AAT CCA GAT ATA ATT GGG ATA AGT GAA CAA      1776
Pro Phe Ser Phe Arg Ala Asn Pro Asp Ile Ile Gly Ile Ser Glu Gln
            580                 585                 590

CCT CTA TTT GGT GCA GGT TCT ATT AGT AGC GGT GAA CTT TAT ATA GAT      1824
Pro Leu Phe Gly Ala Gly Ser Ile Ser Ser Gly Glu Leu Tyr Ile Asp
        595                 600                 605

AAA ATT GAA ATT ATT CTA GCA GAT GCA ACA TTT GAA GCA GAA TCT GAT      1872
Lys Ile Glu Ile Ile Leu Ala Asp Ala Thr Phe Glu Ala Glu Ser Asp
    610                 615                 620

TTA GAA AGA GCA CAA AAG GCG GTG AAT GCC CTG TTT ACT TCT TCC AAT      1920
Leu Glu Arg Ala Gln Lys Ala Val Asn Ala Leu Phe Thr Ser Ser Asn
625                 630                 635                 640

CAA ATC GGG TTA AAA ACC GAT GTG ACG GAT TAT CAT ATT GAT CAA GTA      1968
Gln Ile Gly Leu Lys Thr Asp Val Thr Asp Tyr His Ile Asp Gln Val
                645                 650                 655

TCC AAT TTA GTG GAT TGT TTA TCA GAT GAA TTT TGT CTG GAT GAA AAG      2016
Ser Asn Leu Val Asp Cys Leu Ser Asp Glu Phe Cys Leu Asp Glu Lys
            660                 665                 670

CGA GAA TTG TCC GAG AAA GTC AAA CAT GCG AAG CGA CTC AGT GAT GAG      2064
Arg Glu Leu Ser Glu Lys Val Lys His Ala Lys Arg Leu Ser Asp Glu
        675                 680                 685

CGG AAT TTA CTT CAA GAT CCA AAC TTC AGA GGG ATC AAT AGA CAA CCA      2112
Arg Asn Leu Leu Gln Asp Pro Asn Phe Arg Gly Ile Asn Arg Gln Pro
    690                 695                 700

GAC CGT GGC TGG AGA GGA AGT ACA GAT ATT ACC ATC CAA GGA GGA GAT      2160
Asp Arg Gly Trp Arg Gly Ser Thr Asp Ile Thr Ile Gln Gly Gly Asp
705                 710                 715                 720

GAC GTA TTC AAA GAG AAT TAC GTC ACA CTA CCG GGT ACC GTT GAT GAG      2208
Asp Val Phe Lys Glu Asn Tyr Val Thr Leu Pro Gly Thr Val Asp Glu
                725                 730                 735
```

-continued

TGC TAT CCA ACG TAT TTA TAT CAG AAA ATA GAT GAG TCG AAA TTA AAA 2256
Cys Tyr Pro Thr Tyr Leu Tyr Gln Lys Ile Asp Glu Ser Lys Leu Lys
740 745 750

GCT TAT ACC CGT TAT GAA TTA AGA GGG TAT ATC GAA GAT AGT CAA GAC 2304
Ala Tyr Thr Arg Tyr Glu Leu Arg Gly Tyr Ile Glu Asp Ser Gln Asp
755 760 765

TTA GAA ATC TAT TTG ATC CGT TAC AAT GCA AAA CAC GAA ATA GTA AAT 2352
Leu Glu Ile Tyr Leu Ile Arg Tyr Asn Ala Lys His Glu Ile Val Asn
770 775 780

GTG CCA GGC ACG GGT TCC TTA TGG CCG CTT TCA GCC CAA AGT CCA ATC 2400
Val Pro Gly Thr Gly Ser Leu Trp Pro Leu Ser Ala Gln Ser Pro Ile
785 790 795 800

GGA AAG TGT GGA GAA CCG AAT CGA TGC GCG CCA CAC CTT GAA TGG AAT 2448
Gly Lys Cys Gly Glu Pro Asn Arg Cys Ala Pro His Leu Glu Trp Asn
805 810 815

CCT GAT CTA GAT TGT TCC TGC AGA GAC GGG GAA AAA TGT GCA CAT CAT 2496
Pro Asp Leu Asp Cys Ser Cys Arg Asp Gly Glu Lys Cys Ala His His
820 825 830

TCC CAT CAT TTC ACC TTG GAT ATT GAT GTT GGA TGT ACA GAC TTA AAT 2544
Ser His His Phe Thr Leu Asp Ile Asp Val Gly Cys Thr Asp Leu Asn
835 840 845

GAG GAC TTA GGT GTA TGG GTG ATA TTC AAG ATT AAG ACG CAA GAT GGC 2592
Glu Asp Leu Gly Val Trp Val Ile Phe Lys Ile Lys Thr Gln Asp Gly
850 855 860

CAT GCA AGA CTA GGG AAT CTA GAG TTT CTC GAA GAG AAA CCA TTA TTA 2640
His Ala Arg Leu Gly Asn Leu Glu Phe Leu Glu Glu Lys Pro Leu Leu
865 870 875 880

GGG GAA GCA CTA GCT CGT GTG AAA AGA GCG GAG AAG AAG TGG AGA GAC 2688
Gly Glu Ala Leu Ala Arg Val Lys Arg Ala Glu Lys Lys Trp Arg Asp
885 890 895

AAA CGA GAG AAA CTG CAG TTG GAA ACA AAT ATT GTT TAT AAA GAG GCA 2736
Lys Arg Glu Lys Leu Gln Leu Glu Thr Asn Ile Val Tyr Lys Glu Ala
900 905 910

AAA GAA TCT GTA GAT GCT TTA TTT GTA AAC TCT CAA TAT GAT AGA TTA 2784
Lys Glu Ser Val Asp Ala Leu Phe Val Asn Ser Gln Tyr Asp Arg Leu
915 920 925

CAA GTG GAT ACG AAC ATC GCA ATG ATT CAT GCG GCA GAT AAA CGC GTT 2832
Gln Val Asp Thr Asn Ile Ala Met Ile His Ala Ala Asp Lys Arg Val
930 935 940

CAT AGA ATC CGG GAA GCG TAT CTG CCA GAG TTG TCT GTG ATT CCA GGT 2880
His Arg Ile Arg Glu Ala Tyr Leu Pro Glu Leu Ser Val Ile Pro Gly
945 950 955 960

GTC AAT GCG GCC ATT TTC GAA GAA TTA GAG GGA CGT ATT TTT ACA GCG 2928
Val Asn Ala Ala Ile Phe Glu Glu Leu Glu Gly Arg Ile Phe Thr Ala
965 970 975

TAT TCC TTA TAT GAT GCG AGA AAT GTC ATT AAA AAT GGC GAT TTC AAT 2976
Tyr Ser Leu Tyr Asp Ala Arg Asn Val Ile Lys Asn Gly Asp Phe Asn
980 985 990

AAT GGC TTA TTA TGC TGG AAC GTG AAA GGT CAT GTA GAT GTA GAA GAG 3024
Asn Gly Leu Leu Cys Trp Asn Val Lys Gly His Val Asp Val Glu Glu
995 1000 1005

CAA AAC AAC CAC CGT TCG GTC CTT GTT ATC CCA GAA TGG GAG GCA GAA 3072
Gln Asn Asn His Arg Ser Val Leu Val Ile Pro Glu Trp Glu Ala Glu
1010 1015 1020

GTG TCA CAA GAG GTT CGT GTC TGT CCA GGT CGT GGC TAT ATC CTT CGT 3120
Val Ser Gln Glu Val Arg Val Cys Pro Gly Arg Gly Tyr Ile Leu Arg
1025 1030 1035 1040

GTC ACA GCA TAT AAA GAG GGA TAT GGA GAG GGC TGC GTA ACG ATC CAT 3168
Val Thr Ala Tyr Lys Glu Gly Tyr Gly Glu Gly Cys Val Thr Ile His
1045 1050 1055

```
GAG ATC GAA GAC AAT ACA GAC GAA CTG AAA TTC AGC AAC TGT GTA GAA      3216
Glu Ile Glu Asp Asn Thr Asp Glu Leu Lys Phe Ser Asn Cys Val Glu
            1060                1065                1070

GAG GAA GTA TAT CCA AAC AAC ACA GTA ACG TGT AAT AAT TAT ACT GGG      3264
Glu Glu Val Tyr Pro Asn Asn Thr Val Thr Cys Asn Asn Tyr Thr Gly
        1075                1080                1085

ACT CAA GAA GAA TAT GAG GGT ACG TAC ACT TCT CGT AAT CAA GGA TAT      3312
Thr Gln Glu Glu Tyr Glu Gly Thr Tyr Thr Ser Arg Asn Gln Gly Tyr
    1090                1095                1100

GAC GAA GCC TAT GGT AAT AAC CCT TCC GTA CCA GCT GAT TAC GCT TCA      3360
Asp Glu Ala Tyr Gly Asn Asn Pro Ser Val Pro Ala Asp Tyr Ala Ser
1105                1110                1115                1120

GTC TAT GAA GAA AAA TCG TAT ACA GAT GGA CGA AGA GAG AAT CCT TGT      3408
Val Tyr Glu Glu Lys Ser Tyr Thr Asp Gly Arg Arg Glu Asn Pro Cys
                1125                1130                1135

GAA TCT AAC AGA GGC TAT GGG GAT TAC ACA CCA CTA CCG GCT GGT TAT      3456
Glu Ser Asn Arg Gly Tyr Gly Asp Tyr Thr Pro Leu Pro Ala Gly Tyr
            1140                1145                1150

GTA ACA AAG GAT TTA GAG TAC TTC CCA GAG ACC GAT AAG GTA TGG ATT      3504
Val Thr Lys Asp Leu Glu Tyr Phe Pro Glu Thr Asp Lys Val Trp Ile
        1155                1160                1165

GAG ATC GGA GAA ACA GAA GGA ACA TTC ATC GTG GAT AGC GTG GAA TTA      3552
Glu Ile Gly Glu Thr Glu Gly Thr Phe Ile Val Asp Ser Val Glu Leu
    1170                1175                1180

CTC CTT ATG GAG GAA                                                  3567
Leu Leu Met Glu Glu
1185
```

(2) INFORMATION FOR SEQ ID NO:8:

(i) SEQUENCE CHARACTERISTICS:
(A) LENGTH: 1189 amino acids
(B) TYPE: amino acid
(D) TOPOLOGY: linear (ii) MOLECULE TYPE: protein (xi) SEQUENCE DESCRIPTION: SEQ ID NO:8:

```
Met Glu Glu Asn Asn Gln Asn Gln Cys Ile Pro Tyr Asn Cys Leu Ser
  1               5                  10                  15

Asn Pro Glu Glu Val Leu Leu Asp Gly Glu Arg Ile Ser Thr Gly Asn
             20                  25                  30

Ser Ser Ile Asp Ile Ser Leu Ser Leu Val Gln Phe Leu Val Ser Asn
         35                  40                  45

Phe Val Pro Gly Gly Gly Phe Leu Val Gly Leu Ile Asp Phe Val Trp
     50                  55                  60

Gly Ile Val Gly Pro Ser Gln Trp Asp Ala Phe Leu Val Gln Ile Glu
 65                  70                  75                  80

Gln Leu Ile Asn Glu Arg Ile Ala Glu Phe Ala Arg Asn Ala Ala Ile
                 85                  90                  95

Ala Asn Leu Glu Gly Leu Gly Asn Asn Phe Asn Ile Tyr Val Glu Ala
            100                 105                 110

Phe Lys Glu Trp Glu Asp Asp Pro His Asn Pro Thr Thr Arg Thr Arg
        115                 120                 125

Val Ile Asp Arg Phe Arg Ile Leu Asp Gly Leu Leu Glu Arg Asp Ile
    130                 135                 140

Pro Ser Phe Arg Ile Ser Gly Phe Glu Val Pro Leu Leu Ser Val Tyr
145                 150                 155                 160

Ala Gln Ala Ala Asn Leu His Leu Ala Ile Leu Arg Asp Ser Val Ile
                165                 170                 175
```

-continued

Phe Gly Glu Arg Trp Gly Leu Thr Thr Ile Asn Val Asn Glu Asn Tyr
            180                 185                 190

Asn Arg Leu Ile Arg His Ile Asp Glu Tyr Ala Asp His Cys Ala Asn
        195                 200                 205

Thr Tyr Asn Arg Gly Leu Asn Asn Leu Pro Lys Ser Thr Tyr Gln Asp
    210                 215                 220

Trp Ile Thr Tyr Asn Arg Leu Arg Arg Asp Leu Thr Leu Thr Val Leu
225                 230                 235                 240

Asp Ile Ala Ala Phe Phe Pro Asn Tyr Asp Asn Arg Arg Tyr Pro Ile
                245                 250                 255

Gln Pro Val Gly Gln Leu Thr Arg Glu Val Tyr Thr Asp Pro Leu Ile
            260                 265                 270

Asn Phe Asn Pro Gln Leu Gln Ser Val Ala Gln Leu Pro Thr Phe Asn
        275                 280                 285

Val Met Glu Ser Ser Ala Ile Arg Asn Pro His Leu Phe Asp Ile Leu
    290                 295                 300

Asn Asn Leu Thr Ile Phe Thr Asp Trp Phe Ser Val Gly Arg Asn Phe
305                 310                 315                 320

Tyr Trp Gly Gly His Arg Val Ile Ser Ser Leu Ile Gly Gly Gly Asn
                325                 330                 335

Ile Thr Ser Pro Ile Tyr Gly Arg Glu Ala Asn Gln Glu Pro Pro Arg
            340                 345                 350

Ser Phe Thr Phe Asn Gly Pro Val Phe Arg Thr Leu Ser Asn Pro Thr
        355                 360                 365

Leu Arg Leu Leu Gln Gln Pro Trp Pro Ala Pro Pro Phe Asn Leu Arg
    370                 375                 380

Gly Val Glu Gly Val Glu Phe Ser Thr Pro Thr Asn Ser Phe Thr Tyr
385                 390                 395                 400

Arg Gly Arg Gly Thr Val Asp Ser Leu Thr Glu Leu Pro Pro Glu Asp
                405                 410                 415

Asn Ser Val Pro Pro Arg Glu Gly Tyr Ser His Arg Leu Cys His Ala
            420                 425                 430

Thr Phe Val Gln Arg Ser Gly Thr Pro Phe Leu Thr Thr Gly Val Val
        435                 440                 445

Phe Ser Trp Thr His Arg Ser Ala Thr Leu Thr Asn Thr Ile Asp Pro
    450                 455                 460

Glu Arg Ile Asn Gln Ile Pro Leu Val Lys Gly Phe Arg Val Trp Gly
465                 470                 475                 480

Gly Thr Ser Val Ile Thr Gly Pro Gly Phe Thr Gly Gly Asp Ile Leu
                485                 490                 495

Arg Arg Asn Thr Phe Gly Asp Phe Val Ser Leu Gln Val Asn Ile Asn
            500                 505                 510

Ser Pro Ile Thr Gln Arg Tyr Arg Leu Arg Phe Arg Tyr Ala Ser Ser
        515                 520                 525

Arg Asp Ala Arg Val Ile Val Leu Thr Gly Ala Ala Ser Thr Gly Val
    530                 535                 540

Gly Gly Gln Val Ser Val Asn Met Pro Leu Gln Lys Thr Met Glu Ile
545                 550                 555                 560

Gly Glu Asn Leu Thr Ser Arg Thr Phe Arg Tyr Thr Asp Phe Ser Asn
                565                 570                 575

Pro Phe Ser Phe Arg Ala Asn Pro Asp Ile Ile Gly Ile Ser Glu Gln
            580                 585                 590

Pro Leu Phe Gly Ala Gly Ser Ile Ser Ser Gly Glu Leu Tyr Ile Asp

```
        595                 600                 605

Lys Ile Glu Ile Ile Leu Ala Asp Ala Thr Phe Glu Ala Glu Ser Asp
    610                 615                 620

Leu Glu Arg Ala Gln Lys Ala Val Asn Ala Leu Phe Thr Ser Ser Asn
625                 630                 635                 640

Gln Ile Gly Leu Lys Thr Asp Val Thr Asp Tyr His Ile Asp Gln Val
                645                 650                 655

Ser Asn Leu Val Asp Cys Leu Ser Asp Glu Phe Cys Leu Asp Glu Lys
            660                 665                 670

Arg Glu Leu Ser Glu Lys Val Lys His Ala Lys Arg Leu Ser Asp Glu
        675                 680                 685

Arg Asn Leu Leu Gln Asp Pro Asn Phe Arg Gly Ile Asn Arg Gln Pro
    690                 695                 700

Asp Arg Gly Trp Arg Gly Ser Thr Asp Ile Thr Ile Gln Gly Gly Asp
705                 710                 715                 720

Asp Val Phe Lys Glu Asn Tyr Val Thr Leu Pro Gly Thr Val Asp Glu
                725                 730                 735

Cys Tyr Pro Thr Tyr Leu Tyr Gln Lys Ile Asp Glu Ser Lys Leu Lys
            740                 745                 750

Ala Tyr Thr Arg Tyr Glu Leu Arg Gly Tyr Ile Glu Asp Ser Gln Asp
        755                 760                 765

Leu Glu Ile Tyr Leu Ile Arg Tyr Asn Ala Lys His Glu Ile Val Asn
    770                 775                 780

Val Pro Gly Thr Gly Ser Leu Trp Pro Leu Ser Ala Gln Ser Pro Ile
785                 790                 795                 800

Gly Lys Cys Gly Glu Pro Asn Arg Cys Ala Pro His Leu Glu Trp Asn
                805                 810                 815

Pro Asp Leu Asp Cys Ser Cys Arg Asp Gly Glu Lys Cys Ala His His
            820                 825                 830

Ser His His Phe Thr Leu Asp Ile Asp Val Gly Cys Thr Asp Leu Asn
        835                 840                 845

Glu Asp Leu Gly Val Trp Val Ile Phe Lys Ile Lys Thr Gln Asp Gly
    850                 855                 860

His Ala Arg Leu Gly Asn Leu Glu Phe Leu Glu Glu Lys Pro Leu Leu
865                 870                 875                 880

Gly Glu Ala Leu Ala Arg Val Lys Arg Ala Glu Lys Lys Trp Arg Asp
                885                 890                 895

Lys Arg Glu Lys Leu Gln Leu Glu Thr Asn Ile Val Tyr Lys Glu Ala
            900                 905                 910

Lys Glu Ser Val Asp Ala Leu Phe Val Asn Ser Gln Tyr Asp Arg Leu
        915                 920                 925

Gln Val Asp Thr Asn Ile Ala Met Ile His Ala Ala Asp Lys Arg Val
    930                 935                 940

His Arg Ile Arg Glu Ala Tyr Leu Pro Glu Leu Ser Val Ile Pro Gly
945                 950                 955                 960

Val Asn Ala Ala Ile Phe Glu Glu Leu Glu Gly Arg Ile Phe Thr Ala
                965                 970                 975

Tyr Ser Leu Tyr Asp Ala Arg Asn Val Ile Lys Asn Gly Asp Phe Asn
            980                 985                 990

Asn Gly Leu Leu Cys Trp Asn Val Lys Gly His Val Asp Val Glu Glu
        995                 1000                1005

Gln Asn Asn His Arg Ser Val Leu Val Ile Pro Glu Trp Glu Ala Glu
    1010                1015                1020
```

-continued

```
Val Ser Gln Glu Val Arg Val Cys Pro Gly Arg Gly Tyr Ile Leu Arg
1025                1030                1035                1040

Val Thr Ala Tyr Lys Glu Gly Tyr Gly Glu Gly Cys Val Thr Ile His
                1045                1050                1055

Glu Ile Glu Asp Asn Thr Asp Glu Leu Lys Phe Ser Asn Cys Val Glu
            1060                1065                1070

Glu Glu Val Tyr Pro Asn Asn Thr Val Thr Cys Asn Asn Tyr Thr Gly
        1075                1080                1085

Thr Gln Glu Glu Tyr Glu Gly Thr Tyr Thr Ser Arg Asn Gln Gly Tyr
    1090                1095                1100

Asp Glu Ala Tyr Gly Asn Asn Pro Ser Val Pro Ala Asp Tyr Ala Ser
1105                1110                1115                1120

Val Tyr Glu Glu Lys Ser Tyr Thr Asp Gly Arg Arg Glu Asn Pro Cys
                1125                1130                1135

Glu Ser Asn Arg Gly Tyr Gly Asp Tyr Thr Pro Leu Pro Ala Gly Tyr
            1140                1145                1150

Val Thr Lys Asp Leu Glu Tyr Phe Pro Glu Thr Asp Lys Val Trp Ile
        1155                1160                1165

Glu Ile Gly Glu Thr Glu Gly Thr Phe Ile Val Asp Ser Val Glu Leu
    1170                1175                1180

Leu Leu Met Glu Glu
1185
```

(2) INFORMATION FOR SEQ ID NO:9:

(i) SEQUENCE CHARACTERISTICS:
(A) LENGTH: 3567 base pairs
(B) TYPE: nucleic acid
(C) STRANDEDNESS: single
(D) TOPOLOGY: linear (ix) FEATURE:
(A) NAME/KEY: CDS
(B) LOCATION: 1..3567

(xi) SEQUENCE DESCRIPTION: SEQ ID NO:9:

```
ATG GAG GAA AAT AAT CAA AAT CAA TGC ATA CCT TAC AAT TGT TTA AGT       48
Met Glu Glu Asn Asn Gln Asn Gln Cys Ile Pro Tyr Asn Cys Leu Ser
  1               5                  10                  15

AAT CCT GAA GAA GTA CTT TTG GAT GGA GAA CGG ATA TCA ACT GGT AAT       96
Asn Pro Glu Glu Val Leu Leu Asp Gly Glu Arg Ile Ser Thr Gly Asn
             20                  25                  30

TCA TCA ATT GAT ATT TCT CTG TCA CTT GTT CAG TTT CTG GTA TCT AAC      144
Ser Ser Ile Asp Ile Ser Leu Ser Leu Val Gln Phe Leu Val Ser Asn
         35                  40                  45

TTT GTA CCA GGG GGA GGA TTT TTA GTT GGA TTA ATA GAT TTT GTA TGG      192
Phe Val Pro Gly Gly Gly Phe Leu Val Gly Leu Ile Asp Phe Val Trp
     50                  55                  60

GGA ATA GTT GGC CCT TCT CAA TGG GAT GCA TTT CTA GTA CAA ATT GAA      240
Gly Ile Val Gly Pro Ser Gln Trp Asp Ala Phe Leu Val Gln Ile Glu
 65                  70                  75                  80

CAA TTA ATT AAT GAA AGA ATA GCT GAA TTT GCT AGG AAT GCT GCT ATT      288
Gln Leu Ile Asn Glu Arg Ile Ala Glu Phe Ala Arg Asn Ala Ala Ile
                 85                  90                  95

GCT AAT TTA GAA GGA TTA GGA AAC AAT TTC AAT ATA TAT GTG GAA GCA      336
Ala Asn Leu Glu Gly Leu Gly Asn Asn Phe Asn Ile Tyr Val Glu Ala
            100                 105                 110

TTT AAA GAA TGG GAA GTA GAT CCT AAT AAT CCT GGA ACC AGG ACC AGA      384
Phe Lys Glu Trp Glu Val Asp Pro Asn Asn Pro Gly Thr Arg Thr Arg
        115                 120                 125
```

-continued

GTA ATT GAT CGC TTT CGT ATA CTT GAT GGG CTA CTT GAA AGG GAC ATT 432
Val Ile Asp Arg Phe Arg Ile Leu Asp Gly Leu Leu Glu Arg Asp Ile
130 135 140

CCT TCG TTT CGA ATT TCT GGA TTT GAA GTA CCC CTT TTA TCC GTT TAT 480
Pro Ser Phe Arg Ile Ser Gly Phe Glu Val Pro Leu Leu Ser Val Tyr
145 150 155 160

GCT CAA GCG GCC AAT CTG CAT CTA GCT ATA TTA AGA GAT TCT GTA ATT 528
Ala Gln Ala Ala Asn Leu His Leu Ala Ile Leu Arg Asp Ser Val Ile
165 170 175

TTT GGA GAA AGA TGG GGA TTG ACA ACG ATA AAT GTC AAT GAA AAC TAT 576
Phe Gly Glu Arg Trp Gly Leu Thr Thr Ile Asn Val Asn Glu Asn Tyr
180 185 190

AAT AGA CTA ATT AGG CAT ATT GAT GAA TAT GCT GAT CAC TGT GCA AAT 624
Asn Arg Leu Ile Arg His Ile Asp Glu Tyr Ala Asp His Cys Ala Asn
195 200 205

ACG TAT AAT CGG GGA TTA AAT AAT TTA CCG AAA TCT ACG TAT CAA GAT 672
Thr Tyr Asn Arg Gly Leu Asn Asn Leu Pro Lys Ser Thr Tyr Gln Asp
210 215 220

TGG ATA ACA TAT AAT CGA TTA CGG AGA GAC TTA ACA TTG ACT GTA TTA 720
Trp Ile Thr Tyr Asn Arg Leu Arg Arg Asp Leu Thr Leu Thr Val Leu
225 230 235 240

GAT ATC GCC GCT TTC TTT CCA AAC TAT GAC AAT AGG AGA TAT CCA ATT 768
Asp Ile Ala Ala Phe Phe Pro Asn Tyr Asp Asn Arg Arg Tyr Pro Ile
245 250 255

CAG CCA GTT GGT CAA CTA ACA AGG GAA GTT TAT ACG GAC CCA TTA ATT 816
Gln Pro Val Gly Gln Leu Thr Arg Glu Val Tyr Thr Asp Pro Leu Ile
260 265 270

AAT TTT AAT CCA CAG TTA CAG TCT GTA GCT CAA TTA CCT ACT TTT AAC 864
Asn Phe Asn Pro Gln Leu Gln Ser Val Ala Gln Leu Pro Thr Phe Asn
275 280 285

GTT ATG GAG AGC AGC GCA ATT AGA AAT CCT CAT TTA TTT GAT ATA TTG 912
Val Met Glu Ser Ser Ala Ile Arg Asn Pro His Leu Phe Asp Ile Leu
290 295 300

AAT AAT CTT ACA ATC TTT ACG GAT TGG TTT AGT GTT GGA CGC AAT TTT 960
Asn Asn Leu Thr Ile Phe Thr Asp Trp Phe Ser Val Gly Arg Asn Phe
305 310 315 320

TAT TGG GGA GGA CAT CGA GTA ATA TCT AGC CTT ATA GGA GGT GGT AAC 1008
Tyr Trp Gly Gly His Arg Val Ile Ser Ser Leu Ile Gly Gly Gly Asn
325 330 335

ATA ACA TCT CCT ATA TAT GGA AGA GAG GCG AAC CAG GAG CCT CCA AGA 1056
Ile Thr Ser Pro Ile Tyr Gly Arg Glu Ala Asn Gln Glu Pro Pro Arg
340 345 350

TCC TTT ACT TTT AAT GGA CCG GTA TTT AGG ACT TTA TCA AAT CCT ACT 1104
Ser Phe Thr Phe Asn Gly Pro Val Phe Arg Thr Leu Ser Asn Pro Thr
355 360 365

TTA CGA TTA TTA CAG CAA CCT TGG CCA GCG CCA CCA TTT AAT TTA CGT 1152
Leu Arg Leu Leu Gln Gln Pro Trp Pro Ala Pro Pro Phe Asn Leu Arg
370 375 380

GGT GTT GAA GGA GTA GAA TTT TCT ACA CCT ACA AAT AGC TTT ACG TAT 1200
Gly Val Glu Gly Val Glu Phe Ser Thr Pro Thr Asn Ser Phe Thr Tyr
385 390 395 400

CGA GGA AGA GGT ACG GTT GAT TCT TTA ACT GAA TTA CCG CCT GAG GAT 1248
Arg Gly Arg Gly Thr Val Asp Ser Leu Thr Glu Leu Pro Pro Glu Asp
405 410 415

AAT AGT GTG CCA CCT CGC GAA GGA TAT AGT CAT CGT TTA TGT CAT GCA 1296
Asn Ser Val Pro Pro Arg Glu Gly Tyr Ser His Arg Leu Cys His Ala
420 425 430

ACT TTT GTT CAA AGA TCT GGA ACA CCT TTT TTA ACA ACT GGT GTA GTA 1344
Thr Phe Val Gln Arg Ser Gly Thr Pro Phe Leu Thr Thr Gly Val Val
435 440 445

-continued

```
TTT TCT TGG ACG CAT CGT AGT GCA ACT CTT ACA AAT ACA ATT GAT CCA     1392
Phe Ser Trp Thr His Arg Ser Ala Thr Leu Thr Asn Thr Ile Asp Pro
    450                 455                 460

GAG AGA ATT AAT CAA ATA CCT TTA GTG AAA GGA TTT AGA GTT TGG GGG     1440
Glu Arg Ile Asn Gln Ile Pro Leu Val Lys Gly Phe Arg Val Trp Gly
465                 470                 475                 480

GGC ACC TCT GTC ATT ACA GGA CCA GGA TTT ACA GGA GGG GAT ATC CTT     1488
Gly Thr Ser Val Ile Thr Gly Pro Gly Phe Thr Gly Gly Asp Ile Leu
                485                 490                 495

CGA AGA AAT ACC TTT GGT GAT TTT GTA TCT CTA CAA GTC AAT ATT AAT     1536
Arg Arg Asn Thr Phe Gly Asp Phe Val Ser Leu Gln Val Asn Ile Asn
            500                 505                 510

TCA CCA ATT ACC CAA AGA TAC CGT TTA AGA TTT CGT TAC GCT TCC AGT     1584
Ser Pro Ile Thr Gln Arg Tyr Arg Leu Arg Phe Arg Tyr Ala Ser Ser
        515                 520                 525

AGG GAT GCA CGA GTT ATA GTA TTA ACA GGA GCG GCA TCC ACA GGA GTG     1632
Arg Asp Ala Arg Val Ile Val Leu Thr Gly Ala Ala Ser Thr Gly Val
    530                 535                 540

GGA GGC CAA GTT AGT GTA AAT ATG CCT CTT CAG AAA ACT ATG GAA ATA     1680
Gly Gly Gln Val Ser Val Asn Met Pro Leu Gln Lys Thr Met Glu Ile
545                 550                 555                 560

GGG GAG AAC TTA ACA TCT AGA ACA TTT AGA TAT ACC GAT TTT AGT AAT     1728
Gly Glu Asn Leu Thr Ser Arg Thr Phe Arg Tyr Thr Asp Phe Ser Asn
                565                 570                 575

CCT TTT TCA TTT AGA GCT AAT CCA GAT ATA ATT GGG ATA AGT GAA CAA     1776
Pro Phe Ser Phe Arg Ala Asn Pro Asp Ile Ile Gly Ile Ser Glu Gln
            580                 585                 590

CCT CTA TTT GGT GCA GGT TCT ATT AGT AGC GGT GAA CTT TAT ATA GAT     1824
Pro Leu Phe Gly Ala Gly Ser Ile Ser Ser Gly Glu Leu Tyr Ile Asp
        595                 600                 605

AAA ATT GAA ATT ATT CTA GCA GAT GCA ACA TTT GAA GCA GAA TCT GAT     1872
Lys Ile Glu Ile Ile Leu Ala Asp Ala Thr Phe Glu Ala Glu Ser Asp
    610                 615                 620

TTA GAA AGA GCA CAA AAG GCG GTG AAT GCC CTG TTT ACT TCT TCC AAT     1920
Leu Glu Arg Ala Gln Lys Ala Val Asn Ala Leu Phe Thr Ser Ser Asn
625                 630                 635                 640

CAA ATC GGG TTA AAA ACC GAT GTG ACG GAT TAT CAT ATT GAT CAA GTA     1968
Gln Ile Gly Leu Lys Thr Asp Val Thr Asp Tyr His Ile Asp Gln Val
                645                 650                 655

TCC AAT TTA GTG GAT TGT TTA TCA GAT GAA TTT TGT CTG GAT GAA AAG     2016
Ser Asn Leu Val Asp Cys Leu Ser Asp Glu Phe Cys Leu Asp Glu Lys
            660                 665                 670

CGA GAA TTG TCC GAG AAA GTC AAA CAT GCG AAG CGA CTC AGT GAT GAG     2064
Arg Glu Leu Ser Glu Lys Val Lys His Ala Lys Arg Leu Ser Asp Glu
        675                 680                 685

CGG AAT TTA CTT CAA GAT CCA AAC TTC AGA GGG ATC AAT AGA CAA CCA     2112
Arg Asn Leu Leu Gln Asp Pro Asn Phe Arg Gly Ile Asn Arg Gln Pro
    690                 695                 700

GAC CGT GGC TGG AGA GGA AGT ACA GAT ATT ACC ATC CAA GGA GGA GAT     2160
Asp Arg Gly Trp Arg Gly Ser Thr Asp Ile Thr Ile Gln Gly Gly Asp
705                 710                 715                 720

GAC GTA TTC AAA GAG AAT TAC GTC ACA CTA CCG GGT ACC GTT GAT GAG     2208
Asp Val Phe Lys Glu Asn Tyr Val Thr Leu Pro Gly Thr Val Asp Glu
                725                 730                 735

TGC TAT CCA ACG TAT TTA TAT CAG AAA ATA GAT GAG TCG AAA TTA AAA     2256
Cys Tyr Pro Thr Tyr Leu Tyr Gln Lys Ile Asp Glu Ser Lys Leu Lys
            740                 745                 750

GCT TAT ACC CGT TAT GAA TTA AGA GGG TAT ATC GAA GAT AGT CAA GAC     2304
Ala Tyr Thr Arg Tyr Glu Leu Arg Gly Tyr Ile Glu Asp Ser Gln Asp
        755                 760                 765
```

-continued

```
TTA GAA ATC TAT TTG ATC CGT TAC AAT GCA AAA CAC GAA ATA GTA AAT     2352
Leu Glu Ile Tyr Leu Ile Arg Tyr Asn Ala Lys His Glu Ile Val Asn
    770                 775                 780

GTG CCA GGC ACG GGT TCC TTA TGG CCG CTT TCA GCC CAA AGT CCA ATC     2400
Val Pro Gly Thr Gly Ser Leu Trp Pro Leu Ser Ala Gln Ser Pro Ile
785                 790                 795                 800

GGA AAG TGT GGA GAA CCG AAT CGA TGC GCG CCA CAC CTT GAA TGG AAT     2448
Gly Lys Cys Gly Glu Pro Asn Arg Cys Ala Pro His Leu Glu Trp Asn
                805                 810                 815

CCT GAT CTA GAT TGT TCC TGC AGA GAC GGG GAA AAA TGT GCA CAT CAT     2496
Pro Asp Leu Asp Cys Ser Cys Arg Asp Gly Glu Lys Cys Ala His His
            820                 825                 830

TCC CAT CAT TTC ACC TTG GAT ATT GAT GTT GGA TGT ACA GAC TTA AAT     2544
Ser His His Phe Thr Leu Asp Ile Asp Val Gly Cys Thr Asp Leu Asn
        835                 840                 845

GAG GAC TTA GGT GTA TGG GTG ATA TTC AAG ATT AAG ACG CAA GAT GGC     2592
Glu Asp Leu Gly Val Trp Val Ile Phe Lys Ile Lys Thr Gln Asp Gly
    850                 855                 860

CAT GCA AGA CTA GGG AAT CTA GAG TTT CTC GAA GAG AAA CCA TTA TTA     2640
His Ala Arg Leu Gly Asn Leu Glu Phe Leu Glu Glu Lys Pro Leu Leu
865                 870                 875                 880

GGG GAA GCA CTA GCT CGT GTG AAA AGA GCG GAG AAG AAG TGG AGA GAC     2688
Gly Glu Ala Leu Ala Arg Val Lys Arg Ala Glu Lys Lys Trp Arg Asp
                885                 890                 895

AAA CGA GAG AAA CTG CAG TTG GAA ACA AAT ATT GTT TAT AAA GAG GCA     2736
Lys Arg Glu Lys Leu Gln Leu Glu Thr Asn Ile Val Tyr Lys Glu Ala
            900                 905                 910

AAA GAA TCT GTA GAT GCT TTA TTT GTA AAC TCT CAA TAT GAT AGA TTA     2784
Lys Glu Ser Val Asp Ala Leu Phe Val Asn Ser Gln Tyr Asp Arg Leu
        915                 920                 925

CAA GTG GAT ACG AAC ATC GCA ATG ATT CAT GCG GCA GAT AAA CGC GTT     2832
Gln Val Asp Thr Asn Ile Ala Met Ile His Ala Ala Asp Lys Arg Val
    930                 935                 940

CAT AGA ATC CGG GAA GCG TAT CTG CCA GAG TTG TCT GTG ATT CCA GGT     2880
His Arg Ile Arg Glu Ala Tyr Leu Pro Glu Leu Ser Val Ile Pro Gly
945                 950                 955                 960

GTC AAT GCG GCC ATT TTC GAA GAA TTA GAG GGA CGT ATT TTT ACA GCG     2928
Val Asn Ala Ala Ile Phe Glu Glu Leu Glu Gly Arg Ile Phe Thr Ala
                965                 970                 975

TAT TCC TTA TAT GAT GCG AGA AAT GTC ATT AAA AAT GGC GAT TTC AAT     2976
Tyr Ser Leu Tyr Asp Ala Arg Asn Val Ile Lys Asn Gly Asp Phe Asn
            980                 985                 990

AAT GGC TTA TTA TGC TGG AAC GTG AAA GGT CAT GTA GAT GTA GAA GAG     3024
Asn Gly Leu Leu Cys Trp Asn Val Lys Gly His Val Asp Val Glu Glu
        995                 1000                1005

CAA AAC AAC CAC CGT TCG GTC CTT GTT ATC CCA GAA TGG GAG GCA GAA     3072
Gln Asn Asn His Arg Ser Val Leu Val Ile Pro Glu Trp Glu Ala Glu
    1010                1015                1020

GTG TCA CAA GAG GTT CGT GTC TGT CCA GGT CGT GGC TAT ATC CTT CGT     3120
Val Ser Gln Glu Val Arg Val Cys Pro Gly Arg Gly Tyr Ile Leu Arg
1025                1030                1035                1040

GTC ACA GCA TAT AAA GAG GGA TAT GGA GAG GGC TGC GTA ACG ATC CAT     3168
Val Thr Ala Tyr Lys Glu Gly Tyr Gly Glu Gly Cys Val Thr Ile His
                1045                1050                1055

GAG ATC GAA GAC AAT ACA GAC GAA CTG AAA TTC AGC AAC TGT GTA GAA     3216
Glu Ile Glu Asp Asn Thr Asp Glu Leu Lys Phe Ser Asn Cys Val Glu
            1060                1065                1070

GAG GAA GTA TAT CCA AAC AAC ACA GTA ACG TGT AAT AAT TAT ACT GGG     3264
Glu Glu Val Tyr Pro Asn Asn Thr Val Thr Cys Asn Asn Tyr Thr Gly
        1075                1080                1085
```

```
ACT CAA GAA GAA TAT GAG GGT ACG TAC ACT TCT CGT AAT CAA GGA TAT     3312
Thr Gln Glu Glu Tyr Glu Gly Thr Tyr Thr Ser Arg Asn Gln Gly Tyr
    1090                1095                1100

GAC GAA GCC TAT GGT AAT AAC CCT TCC GTA CCA GCT GAT TAC GCT TCA     3360
Asp Glu Ala Tyr Gly Asn Asn Pro Ser Val Pro Ala Asp Tyr Ala Ser
1105                1110                1115                1120

GTC TAT GAA GAA AAA TCG TAT ACA GAT GGA CGA AGA GAG AAT CCT TGT     3408
Val Tyr Glu Glu Lys Ser Tyr Thr Asp Gly Arg Arg Glu Asn Pro Cys
                1125                1130                1135

GAA TCT AAC AGA GGC TAT GGG GAT TAC ACA CCA CTA CCG GCT GGT TAT     3456
Glu Ser Asn Arg Gly Tyr Gly Asp Tyr Thr Pro Leu Pro Ala Gly Tyr
            1140                1145                1150

GTA ACA AAG GAT TTA GAG TAC TTC CCA GAG ACC GAT AAG GTA TGG ATT     3504
Val Thr Lys Asp Leu Glu Tyr Phe Pro Glu Thr Asp Lys Val Trp Ile
        1155                1160                1165

GAG ATC GGA GAA ACA GAA GGA ACA TTC ATC GTG GAT AGC GTG GAA TTA     3552
Glu Ile Gly Glu Thr Glu Gly Thr Phe Ile Val Asp Ser Val Glu Leu
    1170                1175                1180

CTC CTT ATG GAG GAA                                                 3567
Leu Leu Met Glu Glu
1185
```

(2) INFORMATION FOR SEQ ID NO:10:

(i) SEQUENCE CHARACTERISTICS:
(A) LENGTH: 1189 amino acids
(B) TYPE: amino acid
(D) TOPOLOGY: linear (ii) MOLECULE TYPE: protein (xi) SEQUENCE DESCRIPTION: SEQ ID NO:10:

```
Met Glu Glu Asn Asn Gln Asn Gln Cys Ile Pro Tyr Asn Cys Leu Ser
  1               5                  10                  15

Asn Pro Glu Glu Val Leu Leu Asp Gly Glu Arg Ile Ser Thr Gly Asn
            20                  25                  30

Ser Ser Ile Asp Ile Ser Leu Ser Leu Val Gln Phe Leu Val Ser Asn
        35                  40                  45

Phe Val Pro Gly Gly Gly Phe Leu Val Gly Leu Ile Asp Phe Val Trp
    50                  55                  60

Gly Ile Val Gly Pro Ser Gln Trp Asp Ala Phe Leu Val Gln Ile Glu
 65                  70                  75                  80

Gln Leu Ile Asn Glu Arg Ile Ala Glu Phe Ala Arg Asn Ala Ala Ile
                85                  90                  95

Ala Asn Leu Glu Gly Leu Gly Asn Asn Phe Asn Ile Tyr Val Glu Ala
            100                 105                 110

Phe Lys Glu Trp Glu Val Asp Pro Asn Asn Pro Gly Thr Arg Thr Arg
        115                 120                 125

Val Ile Asp Arg Phe Arg Ile Leu Asp Gly Leu Leu Glu Arg Asp Ile
    130                 135                 140

Pro Ser Phe Arg Ile Ser Gly Phe Glu Val Pro Leu Leu Ser Val Tyr
145                 150                 155                 160

Ala Gln Ala Ala Asn Leu His Leu Ala Ile Leu Arg Asp Ser Val Ile
                165                 170                 175

Phe Gly Glu Arg Trp Gly Leu Thr Thr Ile Asn Val Asn Glu Asn Tyr
            180                 185                 190

Asn Arg Leu Ile Arg His Ile Asp Glu Tyr Ala Asp His Cys Ala Asn
        195                 200                 205

Thr Tyr Asn Arg Gly Leu Asn Asn Leu Pro Lys Ser Thr Tyr Gln Asp
```

```
    210                 215                 220

Trp Ile Thr Tyr Asn Arg Leu Arg Arg Asp Leu Thr Leu Thr Val Leu
225                 230                 235                 240

Asp Ile Ala Ala Phe Phe Pro Asn Tyr Asp Asn Arg Arg Tyr Pro Ile
                245                 250                 255

Gln Pro Val Gly Gln Leu Thr Arg Glu Val Tyr Thr Asp Pro Leu Ile
            260                 265                 270

Asn Phe Asn Pro Gln Leu Gln Ser Val Ala Gln Leu Pro Thr Phe Asn
        275                 280                 285

Val Met Glu Ser Ser Ala Ile Arg Asn Pro His Leu Phe Asp Ile Leu
    290                 295                 300

Asn Asn Leu Thr Ile Phe Thr Asp Trp Phe Ser Val Gly Arg Asn Phe
305                 310                 315                 320

Tyr Trp Gly Gly His Arg Val Ile Ser Ser Leu Ile Gly Gly Gly Asn
                325                 330                 335

Ile Thr Ser Pro Ile Tyr Gly Arg Glu Ala Asn Gln Glu Pro Pro Arg
            340                 345                 350

Ser Phe Thr Phe Asn Gly Pro Val Phe Arg Thr Leu Ser Asn Pro Thr
        355                 360                 365

Leu Arg Leu Leu Gln Gln Pro Trp Pro Ala Pro Pro Phe Asn Leu Arg
    370                 375                 380

Gly Val Glu Gly Val Glu Phe Ser Thr Pro Thr Asn Ser Phe Thr Tyr
385                 390                 395                 400

Arg Gly Arg Gly Thr Val Asp Ser Leu Thr Glu Leu Pro Pro Glu Asp
                405                 410                 415

Asn Ser Val Pro Pro Arg Glu Gly Tyr Ser His Arg Leu Cys His Ala
            420                 425                 430

Thr Phe Val Gln Arg Ser Gly Thr Pro Phe Leu Thr Thr Gly Val Val
        435                 440                 445

Phe Ser Trp Thr His Arg Ser Ala Thr Leu Thr Asn Thr Ile Asp Pro
    450                 455                 460

Glu Arg Ile Asn Gln Ile Pro Leu Val Lys Gly Phe Arg Val Trp Gly
465                 470                 475                 480

Gly Thr Ser Val Ile Thr Gly Pro Gly Phe Thr Gly Gly Asp Ile Leu
                485                 490                 495

Arg Arg Asn Thr Phe Gly Asp Phe Val Ser Leu Gln Val Asn Ile Asn
            500                 505                 510

Ser Pro Ile Thr Gln Arg Tyr Arg Leu Arg Phe Arg Tyr Ala Ser Ser
        515                 520                 525

Arg Asp Ala Arg Val Ile Val Leu Thr Gly Ala Ala Ser Thr Gly Val
    530                 535                 540

Gly Gly Gln Val Ser Val Asn Met Pro Leu Gln Lys Thr Met Glu Ile
545                 550                 555                 560

Gly Glu Asn Leu Thr Ser Arg Thr Phe Arg Tyr Thr Asp Phe Ser Asn
                565                 570                 575

Pro Phe Ser Phe Arg Ala Asn Pro Asp Ile Ile Gly Ile Ser Glu Gln
            580                 585                 590

Pro Leu Phe Gly Ala Gly Ser Ile Ser Ser Gly Glu Leu Tyr Ile Asp
        595                 600                 605

Lys Ile Glu Ile Ile Leu Ala Asp Ala Thr Phe Glu Ala Glu Ser Asp
    610                 615                 620

Leu Glu Arg Ala Gln Lys Ala Val Asn Ala Leu Phe Thr Ser Ser Asn
625                 630                 635                 640
```

-continued

Gln Ile Gly Leu Lys Thr Asp Val Thr Asp Tyr His Ile Asp Gln Val
645 650 655

Ser Asn Leu Val Asp Cys Leu Ser Asp Glu Phe Cys Leu Asp Glu Lys
660 665 670

Arg Glu Leu Ser Glu Lys Val Lys His Ala Lys Arg Leu Ser Asp Glu
675 680 685

Arg Asn Leu Leu Gln Asp Pro Asn Phe Arg Gly Ile Asn Arg Gln Pro
690 695 700

Asp Arg Gly Trp Arg Gly Ser Thr Asp Ile Thr Ile Gln Gly Gly Asp
705 710 715 720

Asp Val Phe Lys Glu Asn Tyr Val Thr Leu Pro Gly Thr Val Asp Glu
725 730 735

Cys Tyr Pro Thr Tyr Leu Tyr Gln Lys Ile Asp Glu Ser Lys Leu Lys
740 745 750

Ala Tyr Thr Arg Tyr Glu Leu Arg Gly Tyr Ile Glu Asp Ser Gln Asp
755 760 765

Leu Glu Ile Tyr Leu Ile Arg Tyr Asn Ala Lys His Glu Ile Val Asn
770 775 780

Val Pro Gly Thr Gly Ser Leu Trp Pro Leu Ser Ala Gln Ser Pro Ile
785 790 795 800

Gly Lys Cys Gly Glu Pro Asn Arg Cys Ala Pro His Leu Glu Trp Asn
805 810 815

Pro Asp Leu Asp Cys Ser Cys Arg Asp Gly Glu Lys Cys Ala His His
820 825 830

Ser His His Phe Thr Leu Asp Ile Asp Val Gly Cys Thr Asp Leu Asn
835 840 845

Glu Asp Leu Gly Val Trp Val Ile Phe Lys Ile Lys Thr Gln Asp Gly
850 855 860

His Ala Arg Leu Gly Asn Leu Glu Phe Leu Glu Glu Lys Pro Leu Leu
865 870 875 880

Gly Glu Ala Leu Ala Arg Val Lys Arg Ala Glu Lys Lys Trp Arg Asp
885 890 895

Lys Arg Glu Lys Leu Gln Leu Glu Thr Asn Ile Val Tyr Lys Glu Ala
900 905 910

Lys Glu Ser Val Asp Ala Leu Phe Val Asn Ser Gln Tyr Asp Arg Leu
915 920 925

Gln Val Asp Thr Asn Ile Ala Met Ile His Ala Ala Asp Lys Arg Val
930 935 940

His Arg Ile Arg Glu Ala Tyr Leu Pro Glu Leu Ser Val Ile Pro Gly
945 950 955 960

Val Asn Ala Ala Ile Phe Glu Glu Leu Glu Gly Arg Ile Phe Thr Ala
965 970 975

Tyr Ser Leu Tyr Asp Ala Arg Asn Val Ile Lys Asn Gly Asp Phe Asn
980 985 990

Asn Gly Leu Leu Cys Trp Asn Val Lys Gly His Val Asp Val Glu Glu
995 1000 1005

Gln Asn Asn His Arg Ser Val Leu Val Ile Pro Glu Trp Glu Ala Glu
1010 1015 1020

Val Ser Gln Glu Val Arg Val Cys Pro Gly Arg Gly Tyr Ile Leu Arg
1025 1030 1035 1040

Val Thr Ala Tyr Lys Glu Gly Tyr Gly Glu Gly Cys Val Thr Ile His
1045 1050 1055

Glu Ile Glu Asp Asn Thr Asp Glu Leu Lys Phe Ser Asn Cys Val Glu
1060 1065 1070

```
Glu Glu Val Tyr Pro Asn Asn Thr Val Thr Cys Asn Asn Tyr Thr Gly
        1075                1080                1085

Thr Gln Glu Glu Tyr Glu Gly Thr Tyr Thr Ser Arg Asn Gln Gly Tyr
    1090                1095                1100

Asp Glu Ala Tyr Gly Asn Asn Pro Ser Val Pro Ala Asp Tyr Ala Ser
1105                1110                1115                1120

Val Tyr Glu Glu Lys Ser Tyr Thr Asp Gly Arg Arg Glu Asn Pro Cys
                1125                1130                1135

Glu Ser Asn Arg Gly Tyr Gly Asp Tyr Thr Pro Leu Pro Ala Gly Tyr
            1140                1145                1150

Val Thr Lys Asp Leu Glu Tyr Phe Pro Glu Thr Asp Lys Val Trp Ile
        1155                1160                1165

Glu Ile Gly Glu Thr Glu Gly Thr Phe Ile Val Asp Ser Val Glu Leu
    1170                1175                1180

Leu Leu Met Glu Glu
1185
```

(2) INFORMATION FOR SEQ ID NO:11:

(i) SEQUENCE CHARACTERISTICS:
(A) LENGTH: 3567 base pairs
(B) TYPE: nucleic acid
(C) STRANDEDNESS: single
(D) TOPOLOGY: linear (ix) FEATURE:
(A) NAME/KEY: CDS
(B) LOCATION: 1..3567

(xi) SEQUENCE DESCRIPTION: SEQ ID NO:11:

```
ATG GAG GAA AAT AAT CAA AAT CAA TGC ATA CCT TAC AAT TGT TTA AGT       48
Met Glu Glu Asn Asn Gln Asn Gln Cys Ile Pro Tyr Asn Cys Leu Ser
  1               5                  10                  15

AAT CCT GAA GAA GTA CTT TTG GAT GGA GAA CGG ATA TCA ACT GGT AAT       96
Asn Pro Glu Glu Val Leu Leu Asp Gly Glu Arg Ile Ser Thr Gly Asn
             20                  25                  30

TCA TCA ATT GAT ATT TCT CTG TCA CTT GTT CAG TTT CTG GTA TCT AAC      144
Ser Ser Ile Asp Ile Ser Leu Ser Leu Val Gln Phe Leu Val Ser Asn
         35                  40                  45

TTT GTA CCA GGG GGA GGA TTT TTA GTT GGA TTA ATA GAT TTT GTA TGG      192
Phe Val Pro Gly Gly Gly Phe Leu Val Gly Leu Ile Asp Phe Val Trp
     50                  55                  60

GGA ATA GTT GGC CCT TCT CAA TGG GAT GCA TTT CTA GTA CAA ATT GAA      240
Gly Ile Val Gly Pro Ser Gln Trp Asp Ala Phe Leu Val Gln Ile Glu
 65                  70                  75                  80

CAA TTA ATT AAT GAA AGA ATA GCT GAA TTT GCT AGG AAT GCT GCT ATT      288
Gln Leu Ile Asn Glu Arg Ile Ala Glu Phe Ala Arg Asn Ala Ala Ile
                 85                  90                  95

GCT AAT TTA GAA GGA TTA GGA AAC AAT TTC AAT ATA TAT GTG GAA GCA      336
Ala Asn Leu Glu Gly Leu Gly Asn Asn Phe Asn Ile Tyr Val Glu Ala
            100                 105                 110

TTT AAA GAA TGG GAA GAA GAT CCC CAT AAT CCA GCA ACC AGG ACC AGA      384
Phe Lys Glu Trp Glu Glu Asp Pro His Asn Pro Ala Thr Arg Thr Arg
        115                 120                 125

GTA ATT GAT CGC TTT CGT ATA CTT GAT GGG CTA CTT GAA AGG GAC ATT      432
Val Ile Asp Arg Phe Arg Ile Leu Asp Gly Leu Leu Glu Arg Asp Ile
    130                 135                 140

CCT TCG TTT CGA ATT TCT GGA TTT GAA GTA CCC CTT TTA TCC GTT TAT      480
Pro Ser Phe Arg Ile Ser Gly Phe Glu Val Pro Leu Leu Ser Val Tyr
145                 150                 155                 160
```

-continued

```
GCT CAA GCG GCC AAT CTG CAT CTA GCT ATA TTA AGA GAT TCT GTA ATT      528
Ala Gln Ala Ala Asn Leu His Leu Ala Ile Leu Arg Asp Ser Val Ile
                165                 170                 175

TTT GGA GAA AGA TGG GGA TTG ACA ACG ATA AAT GTC AAT GAA AAC TAT      576
Phe Gly Glu Arg Trp Gly Leu Thr Thr Ile Asn Val Asn Glu Asn Tyr
            180                 185                 190

AAT AGA CTA ATT AGG CAT ATT GAT GAA TAT GCT GAT CAC TGT GCA AAT      624
Asn Arg Leu Ile Arg His Ile Asp Glu Tyr Ala Asp His Cys Ala Asn
        195                 200                 205

ACG TAT AAT CGG GGA TTA AAT AAT TTA CCG AAA TCT ACG TAT CAA GAT      672
Thr Tyr Asn Arg Gly Leu Asn Asn Leu Pro Lys Ser Thr Tyr Gln Asp
    210                 215                 220

TGG ATA ACA TAT AAT CGA TTA CGG AGA GAC TTA ACA TTG ACT GTA TTA      720
Trp Ile Thr Tyr Asn Arg Leu Arg Arg Asp Leu Thr Leu Thr Val Leu
225                 230                 235                 240

GAT ATC GCC GCT TTC TTT CCA AAC TAT GAC AAT AGG AGA TAT CCA ATT      768
Asp Ile Ala Ala Phe Phe Pro Asn Tyr Asp Asn Arg Arg Tyr Pro Ile
                245                 250                 255

CAG CCA GTT GGT CAA CTA ACA AGG GAA GTT TAT ACG GAC CCA TTA ATT      816
Gln Pro Val Gly Gln Leu Thr Arg Glu Val Tyr Thr Asp Pro Leu Ile
            260                 265                 270

AAT TTT AAT CCA CAG TTA CAG TCT GTA GCT CAA TTA CCT ACT TTT AAC      864
Asn Phe Asn Pro Gln Leu Gln Ser Val Ala Gln Leu Pro Thr Phe Asn
        275                 280                 285

GTT ATG GAG AGC AGC GCA ATT AGA AAT CCT CAT TTA TTT GAT ATA TTG      912
Val Met Glu Ser Ser Ala Ile Arg Asn Pro His Leu Phe Asp Ile Leu
    290                 295                 300

AAT AAT CTT ACA ATC TTT ACG GAT TGG TTT AGT GTT GGA CGC AAT TTT      960
Asn Asn Leu Thr Ile Phe Thr Asp Trp Phe Ser Val Gly Arg Asn Phe
305                 310                 315                 320

TAT TGG GGA GGA CAT CGA GTA ATA TCT AGC CTT ATA GGA GGT GGT AAC     1008
Tyr Trp Gly Gly His Arg Val Ile Ser Ser Leu Ile Gly Gly Gly Asn
                325                 330                 335

ATA ACA TCT CCT ATA TAT GGA AGA GAG GCG AAC CAG GAG CCT CCA AGA     1056
Ile Thr Ser Pro Ile Tyr Gly Arg Glu Ala Asn Gln Glu Pro Pro Arg
            340                 345                 350

TCC TTT ACT TTT AAT GGA CCG GTA TTT AGG ACT TTA TCA AAT CCT ACT     1104
Ser Phe Thr Phe Asn Gly Pro Val Phe Arg Thr Leu Ser Asn Pro Thr
        355                 360                 365

TTA CGA TTA TTA CAG CAA CCT TGG CCA GCG CCA CCA TTT AAT TTA CGT     1152
Leu Arg Leu Leu Gln Gln Pro Trp Pro Ala Pro Pro Phe Asn Leu Arg
    370                 375                 380

GGT GTT GAA GGA GTA GAA TTT TCT ACA CCT ACA AAT AGC TTT ACG TAT     1200
Gly Val Glu Gly Val Glu Phe Ser Thr Pro Thr Asn Ser Phe Thr Tyr
385                 390                 395                 400

CGA GGA AGA GGT ACG GTT GAT TCT TTA ACT GAA TTA CCG CCT GAG GAT     1248
Arg Gly Arg Gly Thr Val Asp Ser Leu Thr Glu Leu Pro Pro Glu Asp
                405                 410                 415

AAT AGT GTG CCA CCT CGC GAA GGA TAT AGT CAT CGT TTA TGT CAT GCA     1296
Asn Ser Val Pro Pro Arg Glu Gly Tyr Ser His Arg Leu Cys His Ala
            420                 425                 430

ACT TTT GTT CAA AGA TCT GGA ACA CCT TTT TTA ACA ACT GGT GTA GTA     1344
Thr Phe Val Gln Arg Ser Gly Thr Pro Phe Leu Thr Thr Gly Val Val
        435                 440                 445

TTT TCT TGG ACG CAT CGT AGT GCA ACT CTT ACA AAT ACA ATT GAT CCA     1392
Phe Ser Trp Thr His Arg Ser Ala Thr Leu Thr Asn Thr Ile Asp Pro
    450                 455                 460

GAG AGA ATT AAT CAA ATA CCT TTA GTG AAA GGA TTT AGA GTT TGG GGG     1440
Glu Arg Ile Asn Gln Ile Pro Leu Val Lys Gly Phe Arg Val Trp Gly
465                 470                 475                 480
```

-continued

```
GGC ACC TCT GTC ATT ACA GGA CCA GGA TTT ACA GGA GGG GAT ATC CTT     1488
Gly Thr Ser Val Ile Thr Gly Pro Gly Phe Thr Gly Gly Asp Ile Leu
                485                 490                 495

CGA AGA AAT ACC TTT GGT GAT TTT GTA TCT CTA CAA GTC AAT ATT AAT     1536
Arg Arg Asn Thr Phe Gly Asp Phe Val Ser Leu Gln Val Asn Ile Asn
            500                 505                 510

TCA CCA ATT ACC CAA AGA TAC CGT TTA AGA TTT CGT TAC GCT TCC AGT     1584
Ser Pro Ile Thr Gln Arg Tyr Arg Leu Arg Phe Arg Tyr Ala Ser Ser
        515                 520                 525

AGG GAT GCA CGA GTT ATA GTA TTA ACA GGA GCG GCA TCC ACA GGA GTG     1632
Arg Asp Ala Arg Val Ile Val Leu Thr Gly Ala Ala Ser Thr Gly Val
    530                 535                 540

GGA GGC CAA GTT AGT GTA AAT ATG CCT CTT CAG AAA ACT ATG GAA ATA     1680
Gly Gly Gln Val Ser Val Asn Met Pro Leu Gln Lys Thr Met Glu Ile
545                 550                 555                 560

GGG GAG AAC TTA ACA TCT AGA ACA TTT AGA TAT ACC GAT TTT AGT AAT     1728
Gly Glu Asn Leu Thr Ser Arg Thr Phe Arg Tyr Thr Asp Phe Ser Asn
                565                 570                 575

CCT TTT TCA TTT AGA GCT AAT CCA GAT ATA ATT GGG ATA AGT GAA CAA     1776
Pro Phe Ser Phe Arg Ala Asn Pro Asp Ile Ile Gly Ile Ser Glu Gln
            580                 585                 590

CCT CTA TTT GGT GCA GGT TCT ATT AGT AGC GGT GAA CTT TAT ATA GAT     1824
Pro Leu Phe Gly Ala Gly Ser Ile Ser Ser Gly Glu Leu Tyr Ile Asp
        595                 600                 605

AAA ATT GAA ATT ATT CTA GCA GAT GCA ACA TTT GAA GCA GAA TCT GAT     1872
Lys Ile Glu Ile Ile Leu Ala Asp Ala Thr Phe Glu Ala Glu Ser Asp
    610                 615                 620

TTA GAA AGA GCA CAA AAG GCG GTG AAT GCC CTG TTT ACT TCT TCC AAT     1920
Leu Glu Arg Ala Gln Lys Ala Val Asn Ala Leu Phe Thr Ser Ser Asn
625                 630                 635                 640

CAA ATC GGG TTA AAA ACC GAT GTG ACG GAT TAT CAT ATT GAT CAA GTA     1968
Gln Ile Gly Leu Lys Thr Asp Val Thr Asp Tyr His Ile Asp Gln Val
                645                 650                 655

TCC AAT TTA GTG GAT TGT TTA TCA GAT GAA TTT TGT CTG GAT GAA AAG     2016
Ser Asn Leu Val Asp Cys Leu Ser Asp Glu Phe Cys Leu Asp Glu Lys
            660                 665                 670

CGA GAA TTG TCC GAG AAA GTC AAA CAT GCG AAG CGA CTC AGT GAT GAG     2064
Arg Glu Leu Ser Glu Lys Val Lys His Ala Lys Arg Leu Ser Asp Glu
        675                 680                 685

CGG AAT TTA CTT CAA GAT CCA AAC TTC AGA GGG ATC AAT AGA CAA CCA     2112
Arg Asn Leu Leu Gln Asp Pro Asn Phe Arg Gly Ile Asn Arg Gln Pro
    690                 695                 700

GAC CGT GGC TGG AGA GGA AGT ACA GAT ATT ACC ATC CAA GGA GGA GAT     2160
Asp Arg Gly Trp Arg Gly Ser Thr Asp Ile Thr Ile Gln Gly Gly Asp
705                 710                 715                 720

GAC GTA TTC AAA GAG AAT TAC GTC ACA CTA CCG GGT ACC GTT GAT GAG     2208
Asp Val Phe Lys Glu Asn Tyr Val Thr Leu Pro Gly Thr Val Asp Glu
                725                 730                 735

TGC TAT CCA ACG TAT TTA TAT CAG AAA ATA GAT GAG TCG AAA TTA AAA     2256
Cys Tyr Pro Thr Tyr Leu Tyr Gln Lys Ile Asp Glu Ser Lys Leu Lys
            740                 745                 750

GCT TAT ACC CGT TAT GAA TTA AGA GGG TAT ATC GAA GAT AGT CAA GAC     2304
Ala Tyr Thr Arg Tyr Glu Leu Arg Gly Tyr Ile Glu Asp Ser Gln Asp
        755                 760                 765

TTA GAA ATC TAT TTG ATC CGT TAC AAT GCA AAA CAC GAA ATA GTA AAT     2352
Leu Glu Ile Tyr Leu Ile Arg Tyr Asn Ala Lys His Glu Ile Val Asn
    770                 775                 780

GTG CCA GGC ACG GGT TCC TTA TGG CCG CTT TCA GCC CAA AGT CCA ATC     2400
Val Pro Gly Thr Gly Ser Leu Trp Pro Leu Ser Ala Gln Ser Pro Ile
785                 790                 795                 800
```

-continued

```
GGA AAG TGT GGA GAA CCG AAT CGA TGC GCG CCA CAC CTT GAA TGG AAT     2448
Gly Lys Cys Gly Glu Pro Asn Arg Cys Ala Pro His Leu Glu Trp Asn
                805                 810                 815

CCT GAT CTA GAT TGT TCC TGC AGA GAC GGG GAA AAA TGT GCA CAT CAT     2496
Pro Asp Leu Asp Cys Ser Cys Arg Asp Gly Glu Lys Cys Ala His His
            820                 825                 830

TCC CAT CAT TTC ACC TTG GAT ATT GAT GTT GGA TGT ACA GAC TTA AAT     2544
Ser His His Phe Thr Leu Asp Ile Asp Val Gly Cys Thr Asp Leu Asn
        835                 840                 845

GAG GAC TTA GGT GTA TGG GTG ATA TTC AAG ATT AAG ACG CAA GAT GGC     2592
Glu Asp Leu Gly Val Trp Val Ile Phe Lys Ile Lys Thr Gln Asp Gly
    850                 855                 860

CAT GCA AGA CTA GGG AAT CTA GAG TTT CTC GAA GAG AAA CCA TTA TTA     2640
His Ala Arg Leu Gly Asn Leu Glu Phe Leu Glu Glu Lys Pro Leu Leu
865                 870                 875                 880

GGG GAA GCA CTA GCT CGT GTG AAA AGA GCG GAG AAG AAG TGG AGA GAC     2688
Gly Glu Ala Leu Ala Arg Val Lys Arg Ala Glu Lys Lys Trp Arg Asp
                885                 890                 895

AAA CGA GAG AAA CTG CAG TTG GAA ACA AAT ATT GTT TAT AAA GAG GCA     2736
Lys Arg Glu Lys Leu Gln Leu Glu Thr Asn Ile Val Tyr Lys Glu Ala
            900                 905                 910

AAA GAA TCT GTA GAT GCT TTA TTT GTA AAC TCT CAA TAT GAT AGA TTA     2784
Lys Glu Ser Val Asp Ala Leu Phe Val Asn Ser Gln Tyr Asp Arg Leu
        915                 920                 925

CAA GTG GAT ACG AAC ATC GCA ATG ATT CAT GCG GCA GAT AAA CGC GTT     2832
Gln Val Asp Thr Asn Ile Ala Met Ile His Ala Ala Asp Lys Arg Val
    930                 935                 940

CAT AGA ATC CGG GAA GCG TAT CTG CCA GAG TTG TCT GTG ATT CCA GGT     2880
His Arg Ile Arg Glu Ala Tyr Leu Pro Glu Leu Ser Val Ile Pro Gly
945                 950                 955                 960

GTC AAT GCG GCC ATT TTC GAA GAA TTA GAG GGA CGT ATT TTT ACA GCG     2928
Val Asn Ala Ala Ile Phe Glu Glu Leu Glu Gly Arg Ile Phe Thr Ala
                965                 970                 975

TAT TCC TTA TAT GAT GCG AGA AAT GTC ATT AAA AAT GGC GAT TTC AAT     2976
Tyr Ser Leu Tyr Asp Ala Arg Asn Val Ile Lys Asn Gly Asp Phe Asn
            980                 985                 990

AAT GGC TTA TTA TGC TGG AAC GTG AAA GGT CAT GTA GAT GTA GAA GAG     3024
Asn Gly Leu Leu Cys Trp Asn Val Lys Gly His Val Asp Val Glu Glu
        995                 1000                1005

CAA AAC AAC CAC CGT TCG GTC CTT GTT ATC CCA GAA TGG GAG GCA GAA     3072
Gln Asn Asn His Arg Ser Val Leu Val Ile Pro Glu Trp Glu Ala Glu
    1010                1015                1020

GTG TCA CAA GAG GTT CGT GTC TGT CCA GGT CGT GGC TAT ATC CTT CGT     3120
Val Ser Gln Glu Val Arg Val Cys Pro Gly Arg Gly Tyr Ile Leu Arg
1025                1030                1035                1040

GTC ACA GCA TAT AAA GAG GGA TAT GGA GAG GGC TGC GTA ACG ATC CAT     3168
Val Thr Ala Tyr Lys Glu Gly Tyr Gly Glu Gly Cys Val Thr Ile His
                1045                1050                1055

GAG ATC GAA GAC AAT ACA GAC GAA CTG AAA TTC AGC AAC TGT GTA GAA     3216
Glu Ile Glu Asp Asn Thr Asp Glu Leu Lys Phe Ser Asn Cys Val Glu
            1060                1065                1070

GAG GAA GTA TAT CCA AAC AAC ACA GTA ACG TGT AAT AAT TAT ACT GGG     3264
Glu Glu Val Tyr Pro Asn Asn Thr Val Thr Cys Asn Asn Tyr Thr Gly
        1075                1080                1085

ACT CAA GAA GAA TAT GAG GGT ACG TAC ACT TCT CGT AAT CAA GGA TAT     3312
Thr Gln Glu Glu Tyr Glu Gly Thr Tyr Thr Ser Arg Asn Gln Gly Tyr
    1090                1095                1100

GAC GAA GCC TAT GGT AAT AAC CCT TCC GTA CCA GCT GAT TAC GCT TCA     3360
Asp Glu Ala Tyr Gly Asn Asn Pro Ser Val Pro Ala Asp Tyr Ala Ser
1105                1110                1115                1120
```

-continued

```
GTC TAT GAA GAA AAA TCG TAT ACA GAT GGA CGA AGA GAG AAT CCT TGT      3408
Val Tyr Glu Glu Lys Ser Tyr Thr Asp Gly Arg Arg Glu Asn Pro Cys
                1125                1130                1135

GAA TCT AAC AGA GGC TAT GGG GAT TAC ACA CCA CTA CCG GCT GGT TAT      3456
Glu Ser Asn Arg Gly Tyr Gly Asp Tyr Thr Pro Leu Pro Ala Gly Tyr
            1140                1145                1150

GTA ACA AAG GAT TTA GAG TAC TTC CCA GAG ACC GAT AAG GTA TGG ATT      3504
Val Thr Lys Asp Leu Glu Tyr Phe Pro Glu Thr Asp Lys Val Trp Ile
        1155                1160                1165

GAG ATC GGA GAA ACA GAA GGA ACA TTC ATC GTG GAT AGC GTG GAA TTA      3552
Glu Ile Gly Glu Thr Glu Gly Thr Phe Ile Val Asp Ser Val Glu Leu
    1170                1175                1180

CTC CTT ATG GAG GAA                                                  3567
Leu Leu Met Glu Glu
1185
```

(2) INFORMATION FOR SEQ ID NO:12:

(i) SEQUENCE CHARACTERISTICS:
(A) LENGTH: 1189 amino acids
(B) TYPE: amino acid
(D) TOPOLOGY: linear (ii) MOLECULE TYPE: protein (xi) SEQUENCE DESCRIPTION: SEQ ID NO:12:

```
Met Glu Glu Asn Asn Gln Asn Gln Cys Ile Pro Tyr Asn Cys Leu Ser
  1               5                  10                  15

Asn Pro Glu Glu Val Leu Leu Asp Gly Glu Arg Ile Ser Thr Gly Asn
             20                  25                  30

Ser Ser Ile Asp Ile Ser Leu Ser Leu Val Gln Phe Leu Val Ser Asn
         35                  40                  45

Phe Val Pro Gly Gly Gly Phe Leu Val Gly Leu Ile Asp Phe Val Trp
     50                  55                  60

Gly Ile Val Gly Pro Ser Gln Trp Asp Ala Phe Leu Val Gln Ile Glu
 65                  70                  75                  80

Gln Leu Ile Asn Glu Arg Ile Ala Glu Phe Ala Arg Asn Ala Ala Ile
                 85                  90                  95

Ala Asn Leu Glu Gly Leu Gly Asn Asn Phe Asn Ile Tyr Val Glu Ala
            100                 105                 110

Phe Lys Glu Trp Glu Glu Asp Pro His Asn Pro Ala Thr Arg Thr Arg
        115                 120                 125

Val Ile Asp Arg Phe Arg Ile Leu Asp Gly Leu Leu Glu Arg Asp Ile
    130                 135                 140

Pro Ser Phe Arg Ile Ser Gly Phe Glu Val Pro Leu Leu Ser Val Tyr
145                 150                 155                 160

Ala Gln Ala Ala Asn Leu His Leu Ala Ile Leu Arg Asp Ser Val Ile
                165                 170                 175

Phe Gly Glu Arg Trp Gly Leu Thr Thr Ile Asn Val Asn Glu Asn Tyr
            180                 185                 190

Asn Arg Leu Ile Arg His Ile Asp Glu Tyr Ala Asp His Cys Ala Asn
        195                 200                 205

Thr Tyr Asn Arg Gly Leu Asn Asn Leu Pro Lys Ser Thr Tyr Gln Asp
    210                 215                 220

Trp Ile Thr Tyr Asn Arg Leu Arg Arg Asp Leu Thr Leu Thr Val Leu
225                 230                 235                 240

Asp Ile Ala Ala Phe Phe Pro Asn Tyr Asp Asn Arg Arg Tyr Pro Ile
                245                 250                 255
```

-continued

```
Gln Pro Val Gly Gln Leu Thr Arg Glu Val Tyr Thr Asp Pro Leu Ile
            260                 265                 270

Asn Phe Asn Pro Gln Leu Gln Ser Val Ala Gln Leu Pro Thr Phe Asn
        275                 280                 285

Val Met Glu Ser Ser Ala Ile Arg Asn Pro His Leu Phe Asp Ile Leu
    290                 295                 300

Asn Asn Leu Thr Ile Phe Thr Asp Trp Phe Ser Val Gly Arg Asn Phe
305                 310                 315                 320

Tyr Trp Gly Gly His Arg Val Ile Ser Ser Leu Ile Gly Gly Gly Asn
                325                 330                 335

Ile Thr Ser Pro Ile Tyr Gly Arg Glu Ala Asn Gln Glu Pro Pro Arg
            340                 345                 350

Ser Phe Thr Phe Asn Gly Pro Val Phe Arg Thr Leu Ser Asn Pro Thr
        355                 360                 365

Leu Arg Leu Leu Gln Gln Pro Trp Pro Ala Pro Pro Phe Asn Leu Arg
    370                 375                 380

Gly Val Glu Gly Val Glu Phe Ser Thr Pro Thr Asn Ser Phe Thr Tyr
385                 390                 395                 400

Arg Gly Arg Gly Thr Val Asp Ser Leu Thr Glu Leu Pro Pro Glu Asp
                405                 410                 415

Asn Ser Val Pro Pro Arg Glu Gly Tyr Ser His Arg Leu Cys His Ala
            420                 425                 430

Thr Phe Val Gln Arg Ser Gly Thr Pro Phe Leu Thr Thr Gly Val Val
        435                 440                 445

Phe Ser Trp Thr His Arg Ser Ala Thr Leu Thr Asn Thr Ile Asp Pro
    450                 455                 460

Glu Arg Ile Asn Gln Ile Pro Leu Val Lys Gly Phe Arg Val Trp Gly
465                 470                 475                 480

Gly Thr Ser Val Ile Thr Gly Pro Gly Phe Thr Gly Gly Asp Ile Leu
                485                 490                 495

Arg Arg Asn Thr Phe Gly Asp Phe Val Ser Leu Gln Val Asn Ile Asn
            500                 505                 510

Ser Pro Ile Thr Gln Arg Tyr Arg Leu Arg Phe Arg Tyr Ala Ser Ser
        515                 520                 525

Arg Asp Ala Arg Val Ile Val Leu Thr Gly Ala Ala Ser Thr Gly Val
    530                 535                 540

Gly Gly Gln Val Ser Val Asn Met Pro Leu Gln Lys Thr Met Glu Ile
545                 550                 555                 560

Gly Glu Asn Leu Thr Ser Arg Thr Phe Arg Tyr Thr Asp Phe Ser Asn
                565                 570                 575

Pro Phe Ser Phe Arg Ala Asn Pro Asp Ile Ile Gly Ile Ser Glu Gln
            580                 585                 590

Pro Leu Phe Gly Ala Gly Ser Ile Ser Ser Gly Glu Leu Tyr Ile Asp
        595                 600                 605

Lys Ile Glu Ile Ile Leu Ala Asp Ala Thr Phe Glu Ala Glu Ser Asp
    610                 615                 620

Leu Glu Arg Ala Gln Lys Ala Val Asn Ala Leu Phe Thr Ser Ser Asn
625                 630                 635                 640

Gln Ile Gly Leu Lys Thr Asp Val Thr Asp Tyr His Ile Asp Gln Val
                645                 650                 655

Ser Asn Leu Val Asp Cys Leu Ser Asp Glu Phe Cys Leu Asp Glu Lys
            660                 665                 670

Arg Glu Leu Ser Glu Lys Val Lys His Ala Lys Arg Leu Ser Asp Glu
        675                 680                 685
```

-continued

```
Arg Asn Leu Leu Gln Asp Pro Asn Phe Arg Gly Ile Asn Arg Gln Pro
    690                 695                 700

Asp Arg Gly Trp Arg Gly Ser Thr Asp Ile Thr Ile Gln Gly Gly Asp
705                 710                 715                 720

Asp Val Phe Lys Glu Asn Tyr Val Thr Leu Pro Gly Thr Val Asp Glu
                725                 730                 735

Cys Tyr Pro Thr Tyr Leu Tyr Gln Lys Ile Asp Glu Ser Lys Leu Lys
            740                 745                 750

Ala Tyr Thr Arg Tyr Glu Leu Arg Gly Tyr Ile Glu Asp Ser Gln Asp
        755                 760                 765

Leu Glu Ile Tyr Leu Ile Arg Tyr Asn Ala Lys His Glu Ile Val Asn
    770                 775                 780

Val Pro Gly Thr Gly Ser Leu Trp Pro Leu Ser Ala Gln Ser Pro Ile
785                 790                 795                 800

Gly Lys Cys Gly Glu Pro Asn Arg Cys Ala Pro His Leu Glu Trp Asn
                805                 810                 815

Pro Asp Leu Asp Cys Ser Cys Arg Asp Gly Glu Lys Cys Ala His His
            820                 825                 830

Ser His His Phe Thr Leu Asp Ile Asp Val Gly Cys Thr Asp Leu Asn
        835                 840                 845

Glu Asp Leu Gly Val Trp Val Ile Phe Lys Ile Lys Thr Gln Asp Gly
    850                 855                 860

His Ala Arg Leu Gly Asn Leu Glu Phe Leu Glu Glu Lys Pro Leu Leu
865                 870                 875                 880

Gly Glu Ala Leu Ala Arg Val Lys Arg Ala Glu Lys Lys Trp Arg Asp
                885                 890                 895

Lys Arg Glu Lys Leu Gln Leu Glu Thr Asn Ile Val Tyr Lys Glu Ala
            900                 905                 910

Lys Glu Ser Val Asp Ala Leu Phe Val Asn Ser Gln Tyr Asp Arg Leu
        915                 920                 925

Gln Val Asp Thr Asn Ile Ala Met Ile His Ala Ala Asp Lys Arg Val
    930                 935                 940

His Arg Ile Arg Glu Ala Tyr Leu Pro Glu Leu Ser Val Ile Pro Gly
945                 950                 955                 960

Val Asn Ala Ala Ile Phe Glu Glu Leu Glu Gly Arg Ile Phe Thr Ala
                965                 970                 975

Tyr Ser Leu Tyr Asp Ala Arg Asn Val Ile Lys Asn Gly Asp Phe Asn
            980                 985                 990

Asn Gly Leu Leu Cys Trp Asn Val Lys Gly His Val Asp Val Glu Glu
        995                 1000                1005

Gln Asn Asn His Arg Ser Val Leu Val Ile Pro Glu Trp Glu Ala Glu
    1010                1015                1020

Val Ser Gln Glu Val Arg Val Cys Pro Gly Arg Gly Tyr Ile Leu Arg
1025                1030                1035                1040

Val Thr Ala Tyr Lys Glu Gly Tyr Gly Glu Gly Cys Val Thr Ile His
                1045                1050                1055

Glu Ile Glu Asp Asn Thr Asp Glu Leu Lys Phe Ser Asn Cys Val Glu
            1060                1065                1070

Glu Glu Val Tyr Pro Asn Asn Thr Val Thr Cys Asn Asn Tyr Thr Gly
        1075                1080                1085

Thr Gln Glu Glu Tyr Glu Gly Thr Tyr Thr Ser Arg Asn Gln Gly Tyr
    1090                1095                1100

Asp Glu Ala Tyr Gly Asn Asn Pro Ser Val Pro Ala Asp Tyr Ala Ser
```

```
1105                1110                1115                1120

Val Tyr Glu Glu Lys Ser Tyr Thr Asp Gly Arg Arg Glu Asn Pro Cys
                1125                1130                1135

Glu Ser Asn Arg Gly Tyr Gly Asp Tyr Thr Pro Leu Pro Ala Gly Tyr
            1140                1145                1150

Val Thr Lys Asp Leu Glu Tyr Phe Pro Glu Thr Asp Lys Val Trp Ile
        1155                1160                1165

Glu Ile Gly Glu Thr Glu Gly Thr Phe Ile Val Asp Ser Val Glu Leu
    1170                1175                1180

Leu Leu Met Glu Glu
1185
```

(2) INFORMATION FOR SEQ ID NO:13:

(i) SEQUENCE CHARACTERISTICS:
(A) LENGTH: 49 base pairs
(B) TYPE: nucleic acid
(C) STRANDEDNESS: single
(D) TOPOLOGY: linear (xi) SEQUENCE DESCRIPTION: SEQ ID NO:13:

GCATTTAAAG AATGGGAAGA AGATAATAAT CCAGCAACCA GGACCAGAG 49

(2) INFORMATION FOR SEQ ID NO:14:

(i) SEQUENCE CHARACTERISTICS:
(A) LENGTH: 55 base pairs
(B) TYPE: nucleic acid
(C) STRANDEDNESS: single
(D) TOPOLOGY: linear (xi) SEQUENCE DESCRIPTION: SEQ ID NO:14:

GCATTTAAAG AATGGGAAGA AGATCCTAAT GCAAATCCAG CAACCAGGAC CAGAG 55

(2) INFORMATION FOR SEQ ID NO:15:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:15:

CCCGATCGGC CGCATGC 17

(2) INFORMATION FOR SEQ ID NO:16:

(i) SEQUENCE CHARACTERISTICS:
(A) LENGTH: 51 base pairs
(B) TYPE: nucleic acid
(C) STRANDEDNESS: single
(D) TOPOLOGY: linear (xi) SEQUENCE DESCRIPTION: SEQ ID NO:16:

GCATTTAAAG AATGGGAAGG GATCCTAGGA ATCCAGCAAC CAGGACCAGA G 51

(2) INFORMATION FOR SEQ ID NO:17:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:17:

-continued

GAGCTCTTGT TAAAAAAGGT GTTCCAGATC 30

(2) INFORMATION FOR SEQ ID NO:18:

(i) SEQUENCE CHARACTERISTICS:
(A) LENGTH: 62 base pairs
(B) TYPE: nucleic acid
(C) STRANDEDNESS: single
(D) TOPOLOGY: linear (ix) FEATURE:
(A) NAME/KEY: modified_base
(B) LOCATION: 19..39
(D) OTHER INFORMATION: /note= "N = G, A, T or C"

(xi) SEQUENCE DESCRIPTION: SEQ ID NO:18:

GCATTTAAAG AATGGGAANN NNNNNNNNNN NNNNNNNNNA CCAGGACCAG AGTAATTGAT 60

CG 62

(2) INFORMATION FOR SEQ ID NO:19:

(i) SEQUENCE CHARACTERISTICS:
(A) LENGTH: 55 base pairs
(B) TYPE: nucleic acid
(C) STRANDEDNESS: single
(D) TOPOLOGY: linear (xi) SEQUENCE DESCRIPTION: SEQ ID NO:19:

GGGCTACTTG AAAGGGACAT TCCTTCGTTT GCAATTTCTG GATTTGAAGT ACCCC 55

(2) INFORMATION FOR SEQ ID NO:20:

(i) SEQUENCE CHARACTERISTICS:
(A) LENGTH: 39 base pairs
(B) TYPE: nucleic acid
(C) STRANDEDNESS: single
(D) TOPOLOGY: linear (xi) SEQUENCE DESCRIPTION: SEQ ID NO:20:

CCAAGAAAAT ACTAGAGCTC TTGTTAAAAA AGGTGTTCC 39

(2) INFORMATION FOR SEQ ID NO:21:

(i) SEQUENCE CHARACTERISTICS:
(A) LENGTH: 50 base pairs
(B) TYPE: nucleic acid
(C) STRANDEDNESS: single
(D) TOPOLOGY: linear (xi) SEQUENCE DESCRIPTION: SEQ ID NO:21:

GAGATTCTGT AATTTTTGGA GAAGCATGGG GGTTGACAAC GATAAATGTC 50

(2) INFORMATION FOR SEQ ID NO:22:

(i) SEQUENCE CHARACTERISTICS:
(A) LENGTH: 63 base pairs
(B) TYPE: nucleic acid
(C) STRANDEDNESS: single
(D) TOPOLOGY: linear (xi) SEQUENCE DESCRIPTION: SEQ ID NO:22:

GCATTTAAAG AATGGGAAGA AGATCCTAAT AATCCAGCAA CCAGGACCAG AGTAATTGAT 60

CGC 63

(2) INFORMATION FOR SEQ ID NO:23:

(i) SEQUENCE CHARACTERISTICS:

-continued (A) LENGTH: 7 amino acids
(B) TYPE: amino acid
(C) STRANDEDNESS: single
(D) TOPOLOGY: linear (xi) SEQUENCE DESCRIPTION: SEQ ID NO:23:

Glu Asp Pro Asn Asn Pro Ala
1 5

(2) INFORMATION FOR SEQ ID NO:24:

(i) SEQUENCE CHARACTERISTICS:
(A) LENGTH: 51 base pairs
(B) TYPE: nucleic acid
(C) STRANDEDNESS: single
(D) TOPOLOGY: linear (xi) SEQUENCE DESCRIPTION: SEQ ID NO:24:

GCATTTAAAG AATGGGAAGG GATCCTAGGA ATCCAGCAAC CAGGACCAGA G 51

(2) INFORMATION FOR SEQ ID NO:25:

(i) SEQUENCE CHARACTERISTICS:
(A) LENGTH: 63 base pairs
(B) TYPE: nucleic acid
(C) STRANDEDNESS: single
(D) TOPOLOGY: linear (xi) SEQUENCE DESCRIPTION: SEQ ID NO:25:

GCATTTAAAG AATGGGAAGA TGATCCTCAT AATCCCACAA CCAGGACCAG AGTAATTGAT 60

CGC 63

(2) INFORMATION FOR SEQ ID NO:26:

(i) SEQUENCE CHARACTERISTICS:
(A) LENGTH: 7 amino acids
(B) TYPE: amino acid
(C) STRANDEDNESS: single
(D) TOPOLOGY: linear (xi) SEQUENCE DESCRIPTION: SEQ ID NO:26:

Asp Asp Pro His Asn Pro Thr
1 5

(2) INFORMATION FOR SEQ ID NO:27:

(i) SEQUENCE CHARACTERISTICS:
(A) LENGTH: 7 amino acids
(B) TYPE: amino acid
(C) STRANDEDNESS: single
(D) TOPOLOGY: linear (xi) SEQUENCE DESCRIPTION: SEQ ID NO:27:

Val Asp Pro Asn Asn Pro Gly
1 5

(2) INFORMATION FOR SEQ ID NO:28:

(i) SEQUENCE CHARACTERISTICS:
(A) LENGTH: 50 amino acids
(B) TYPE: amino acid
(C) STRANDEDNESS: single
(D) TOPOLOGY: linear (xi) SEQUENCE DESCRIPTION: SEQ ID NO:28:

Thr Asn Pro Ala Leu Arg Glu Glu Met Arg Ile Gln Phe Asn Asp Met
1 5 10 15

-continued

Asn Ser Ala Leu Thr Thr Ala Ile Pro Leu Leu Ala Val Gln Asn Tyr
20 25 30

Gln Val Pro Leu Leu Ser Val Tyr Val Gln Ala Ala Asn Leu His Leu
35 40 45

Ser Val
50

(2) INFORMATION FOR SEQ ID NO:29:

(i) SEQUENCE CHARACTERISTICS:
(A) LENGTH: 50 amino acids
(B) TYPE: amino acid
(C) STRANDEDNESS: single
(D) TOPOLOGY: linear (xi) SEQUENCE DESCRIPTION: SEQ ID NO:29:

Thr Asn Pro Ala Leu Thr Glu Glu Met Arg Ile Gln Phe Asn Asp Met
1 5 10 15

Asn Ser Ala Leu Thr Thr Ala Ile Pro Leu Phe Thr Val Gln Asn Tyr
20 25 30

Gln Val Pro Leu Leu Ser Val Tyr Val Gln Ala Ala Asn Leu His Leu
35 40 45

Ser Val
50

(2) INFORMATION FOR SEQ ID NO:30:

(i) SEQUENCE CHARACTERISTICS:
(A) LENGTH: 50 amino acids
(B) TYPE: amino acid
(C) STRANDEDNESS: single
(D) TOPOLOGY: linear (xi) SEQUENCE DESCRIPTION: SEQ ID NO:30:

Thr Asn Pro Ala Leu Arg Glu Glu Met Arg Ile Gln Phe Asn Asp Met
1 5 10 15

Asn Ser Ala Leu Thr Thr Ala Ile Pro Leu Phe Ala Val Gln Asn Tyr
20 25 30

Gln Val Pro Leu Leu Ser Val Tyr Val Gln Ala Ala Asn Leu His Leu
35 40 45

Ser Val
50

(2) INFORMATION FOR SEQ ID NO:31:

(i) SEQUENCE CHARACTERISTICS:
(A) LENGTH: 50 amino acids
(B) TYPE: amino acid
(C) STRANDEDNESS: single
(D) TOPOLOGY: linear (xi) SEQUENCE DESCRIPTION: SEQ ID NO:31:

Thr Asn Pro Ala Leu Arg Glu Glu Met Arg Ile Gln Phe Asn Asp Met
1 5 10 15

Asn Ser Ala Leu Thr Thr Ala Ile Pro Leu Phe Thr Val Gln Asn Tyr
20 25 30

Gln Val Pro Leu Leu Ser Val Tyr Val Gln Ala Val Asn Leu His Leu
35 40 45

Ser Val
50

(2) INFORMATION FOR SEQ ID NO:32:

(i) SEQUENCE CHARACTERISTICS:
(A) LENGTH: 50 amino acids
(B) TYPE: amino acid
(C) STRANDEDNESS: single
(D) TOPOLOGY: linear (xi) SEQUENCE DESCRIPTION: SEQ ID NO:32:

```
Thr Asn Pro Ala Leu Arg Glu Glu Met Arg Ile Gln Phe Asn Asp Met
1               5                   10                  15

Asn Ser Ala Leu Thr Thr Ala Ile Pro Leu Phe Ala Val Gln Asn Tyr
            20                  25                  30

Gln Val Pro Leu Leu Ser Val Tyr Val Gln Ala Ala Asn Leu His Leu
        35                  40                  45

Ser Val
    50
```

(2) INFORMATION FOR SEQ ID NO:33:

(i) SEQUENCE CHARACTERISTICS:
(A) LENGTH: 50 amino acids
(B) TYPE: amino acid
(C) STRANDEDNESS: single
(D) TOPOLOGY: linear (xi) SEQUENCE DESCRIPTION: SEQ ID NO:33:

```
Asn Asn Ala Gln Leu Arg Glu Asp Val Arg Ile Arg Phe Ala Asn Thr
1               5                   10                  15

Asp Asp Ala Leu Ile Thr Ala Ile Asn Asn Phe Thr Leu Thr Ser Phe
            20                  25                  30

Glu Ile Pro Leu Leu Ser Val Tyr Val Gln Ala Ala Asn Leu His Leu
        35                  40                  45

Ser Leu
    50
```

(2) INFORMATION FOR SEQ ID NO:34:

(i) SEQUENCE CHARACTERISTICS:
(A) LENGTH: 50 amino acids
(B) TYPE: amino acid
(C) STRANDEDNESS: single
(D) TOPOLOGY: linear (xi) SEQUENCE DESCRIPTION: SEQ ID NO:34:

```
Asn Asn Ala Gln Leu Arg Glu Asp Val Arg Ile Arg Phe Ala Asn Thr
1               5                   10                  15

Asp Asp Ala Leu Ile Thr Ala Ile Asn Asn Phe Thr Leu Thr Ser Phe
            20                  25                  30

Glu Ile Pro Leu Leu Ser Val Tyr Val Gln Ala Ala Asn Leu His Leu
        35                  40                  45

Ser Leu
    50
```

(2) INFORMATION FOR SEQ ID NO:35:

(i) SEQUENCE CHARACTERISTICS:
(A) LENGTH: 50 amino acids
(B) TYPE: amino acid
(C) STRANDEDNESS: single
(D) TOPOLOGY: linear (xi) SEQUENCE DESCRIPTION: SEQ ID NO:35:

```
Asn Asn Pro Ala Ser Gln Glu Arg Val Arg Thr Arg Phe Arg Leu Thr
1               5                   10                  15
```

-continued

```
Asp Asp Ala Ile Val Thr Gly Leu Pro Thr Leu Ala Ile Arg Asn Leu
            20                  25                  30

Glu Val Val Asn Leu Ser Val Tyr Thr Gln Ala Ala Asn Leu His Leu
        35                  40                  45

Ser Leu
    50
```

(2) INFORMATION FOR SEQ ID NO:36:

(i) SEQUENCE CHARACTERISTICS:
(A) LENGTH: 50 amino acids
(B) TYPE: amino acid
(C) STRANDEDNESS: single
(D) TOPOLOGY: linear (xi) SEQUENCE DESCRIPTION: SEQ ID NO:36:

```
Asn Asn Pro Glu Thr Arg Thr Arg Val Ile Asp Arg Phe Arg Ile Leu
1               5                   10                  15

Asp Gly Leu Leu Glu Arg Asp Ile Pro Ser Phe Arg Ile Ser Gly Phe
            20                  25                  30

Glu Val Pro Leu Leu Ser Val Tyr Ala Gln Ala Ala Asn Leu His Leu
        35                  40                  45

Ala Ile
    50
```

(2) INFORMATION FOR SEQ ID NO:37:

(i) SEQUENCE CHARACTERISTICS:
(A) LENGTH: 50 amino acids
(B) TYPE: amino acid
(C) STRANDEDNESS: single
(D) TOPOLOGY: linear (xi) SEQUENCE DESCRIPTION: SEQ ID NO:37:

```
Asp Asn Pro Val Thr Arg Thr Arg Val Val Asp Arg Phe Arg Ile Leu
1               5                   10                  15

Asp Gly Leu Leu Glu Arg Asp Ile Pro Ser Phe Arg Ile Ala Gly Phe
            20                  25                  30

Glu Val Pro Leu Leu Ser Val Tyr Ala Gln Ala Ala Asn Leu His Leu
        35                  40                  45

Ala Ile
    50
```

(2) INFORMATION FOR SEQ ID NO:38:

(i) SEQUENCE CHARACTERISTICS:
(A) LENGTH: 50 amino acids
(B) TYPE: amino acid
(C) STRANDEDNESS: single
(D) TOPOLOGY: linear (xi) SEQUENCE DESCRIPTION: SEQ ID NO:38:

```
Thr Asn Pro Ala Leu Lys Glu Glu Met Arg Thr Gln Phe Asn Asp Met
1               5                   10                  15

Asn Ser Ile Leu Val Thr Ala Ile Pro Leu Phe Ser Val Gln Asn Tyr
            20                  25                  30

Gln Val Pro Phe Leu Ser Val Tyr Val Gln Ala Ala Asn Leu His Leu
        35                  40                  45

Ser Val
    50
```

(2) INFORMATION FOR SEQ ID NO:39:

(i) SEQUENCE CHARACTERISTICS:
(A) LENGTH: 50 amino acids
(B) TYPE: amino acid
(C) STRANDEDNESS: single
(D) TOPOLOGY: linear (xi) SEQUENCE DESCRIPTION: SEQ ID NO:39:

```
Thr Asn Pro Ala Leu Arg Glu Glu Met Arg Ile Gln Phe Asn Asp Met
1               5                   10                  15

Asn Ser Ala Leu Thr Thr Ala Ile Pro Leu Phe Ser Val Gln Gly Tyr
            20                  25                  30

Glu Ile Pro Leu Leu Ser Val Tyr Val Gln Ala Ala Asn Leu His Leu
        35                  40                  45

Ser Val
    50
```

(2) INFORMATION FOR SEQ ID NO:40:

(i) SEQUENCE CHARACTERISTICS:
(A) LENGTH: 50 amino acids
(B) TYPE: amino acid
(C) STRANDEDNESS: single
(D) TOPOLOGY: linear (xi) SEQUENCE DESCRIPTION: SEQ ID NO:40:

```
Thr Asn Pro Ala Leu Arg Glu Glu Met Arg Ile Gln Phe Asn Asp Met
1               5                   10                  15

Asn Ser Ala Leu Ile Thr Ala Ile Pro Leu Phe Arg Val Gln Asn Tyr
            20                  25                  30

Glu Val Ala Leu Leu Ser Val Tyr Val Gln Ala Ala Asn Leu His Leu
        35                  40                  45

Ser Ile
    50
```

(2) INFORMATION FOR SEQ ID NO:41:

(i) SEQUENCE CHARACTERISTICS:
(A) LENGTH: 50 amino acids
(B) TYPE: amino acid
(C) STRANDEDNESS: single
(D) TOPOLOGY: linear (xi) SEQUENCE DESCRIPTION: SEQ ID NO:41:

```
Ser Asn Pro Ala Leu Arg Glu Glu Met Arg Thr Gln Phe Asn Val Met
1               5                   10                  15

Asn Ser Ala Leu Ile Ala Ala Ile Pro Leu Leu Arg Val Arg Asn Tyr
            20                  25                  30

Glu Val Ala Leu Leu Ser Val Tyr Val Gln Ala Ala Asn Leu His Leu
        35                  40                  45

Ser Val
    50
```

(2) INFORMATION FOR SEQ ID NO:42:

(i) SEQUENCE CHARACTERISTICS:
(A) LENGTH: 50 amino acids
(B) TYPE: amino acid
(C) STRANDEDNESS: single
(D) TOPOLOGY: linear (xi) SEQUENCE DESCRIPTION: SEQ ID NO:42:

```
Asn Asn Glu Ala Leu Gln Gln Asp Val Arg Asn Arg Phe Ser Asn Thr
```

```
1               5                   10                  15

Asp Asn Ala Leu Ile Thr Ala Ile Pro Ile Leu Arg Glu Gln Gly Phe
            20                  25                  30

Glu Ile Pro Leu Leu Ser Val Tyr Val Gln Ala Ala Asn Leu His Leu
        35                  40                  45

Ser Leu
    50
```

(2) INFORMATION FOR SEQ ID NO:43:

(i) SEQUENCE CHARACTERISTICS:
(A) LENGTH: 50 amino acids
(B) TYPE: amino acid
(C) STRANDEDNESS: single
(D) TOPOLOGY: linear (xi) SEQUENCE DESCRIPTION: SEQ ID NO:43:

```
Asn Asn Glu Ser Leu Gln Gln Asp Val Arg Asn Arg Phe Ser Asn Thr
1               5                   10                  15

Asp Asn Ala Leu Ile Thr Ala Ile Pro Ile Leu Arg Glu Gln Gly Phe
            20                  25                  30

Glu Ile Pro Leu Leu Thr Val Tyr Val Gln Ala Ala Asn Leu His Leu
        35                  40                  45

Ser Leu
    50
```

(2) INFORMATION FOR SEQ ID NO:44:

(i) SEQUENCE CHARACTERISTICS:
(A) LENGTH: 50 amino acids
(B) TYPE: amino acid
(C) STRANDEDNESS: single
(D) TOPOLOGY: linear (xi) SEQUENCE DESCRIPTION: SEQ ID NO:44:

```
Asp Asn Glu Ala Ala Lys Ser Arg Val Ile Asp Arg Phe Arg Ile Leu
1               5                   10                  15

Asp Gly Leu Ile Glu Ala Asn Ile Pro Ser Phe Arg Ile Ile Gly Phe
            20                  25                  30

Glu Val Pro Leu Leu Ser Val Tyr Val Gln Ala Ala Asn Leu His Leu
        35                  40                  45

Ala Leu
    50
```

(2) INFORMATION FOR SEQ ID NO:45:

(i) SEQUENCE CHARACTERISTICS:
(A) LENGTH: 50 amino acids
(B) TYPE: amino acid
(C) STRANDEDNESS: single
(D) TOPOLOGY: linear (xi) SEQUENCE DESCRIPTION: SEQ ID NO:45:

```
Asp Asn Thr Ala Ala Arg Ser Arg Val Thr Glu Arg Phe Arg Ile Ile
1               5                   10                  15

Asp Ala Gln Ile Glu Ala Asn Ile Pro Ser Phe Arg Ile Pro Gly Phe
            20                  25                  30

Glu Val Pro Leu Leu Ser Val Tyr Ala Gln Ala Ala Asn Leu His Leu
        35                  40                  45

Ala Leu
    50
```

(2) INFORMATION FOR SEQ ID NO:46:

(i) SEQUENCE CHARACTERISTICS:
(A) LENGTH: 50 amino acids
(B) TYPE: amino acid
(C) STRANDEDNESS: single
(D) TOPOLOGY: linear (xi) SEQUENCE DESCRIPTION: SEQ ID NO:46:

```
Asp Asp Ala Arg Thr Arg Ser Val Leu Tyr Thr Gln Tyr Ile Ala Leu
1               5                   10                  15

Glu Leu Asp Phe Leu Asn Ala Met Pro Leu Phe Ala Ile Arg Asn Gln
            20                  25                  30

Glu Val Pro Leu Leu Met Val Tyr Ala Gln Ala Ala Asn Leu His Leu
        35                  40                  45

Leu Leu
    50
```

(2) INFORMATION FOR SEQ ID NO:47:

(i) SEQUENCE CHARACTERISTICS:
(A) LENGTH: 50 amino acids
(B) TYPE: amino acid
(C) STRANDEDNESS: single
(D) TOPOLOGY: linear (xi) SEQUENCE DESCRIPTION: SEQ ID NO:47:

```
Asn Asp Ala Arg Ser Arg Ser Ile Ile Leu Glu Arg Tyr Val Ala Leu
1               5                   10                  15

Glu Leu Asp Ile Thr Thr Ala Ile Pro Leu Phe Arg Ile Arg Asn Glu
            20                  25                  30

Glu Val Pro Leu Leu Met Val Tyr Ala Gln Ala Ala Asn Leu His Leu
        35                  40                  45

Leu Leu
    50
```

(2) INFORMATION FOR SEQ ID NO:48:

(i) SEQUENCE CHARACTERISTICS:
(A) LENGTH: 50 amino acids
(B) TYPE: amino acid
(C) STRANDEDNESS: single
(D) TOPOLOGY: linear (xi) SEQUENCE DESCRIPTION: SEQ ID NO:48:

```
Asn Asp Ala Arg Ser Arg Ser Ile Ile Leu Glu Arg Tyr Val Ala Leu
1               5                   10                  15

Glu Leu Asp Ile Thr Thr Ala Ile Pro Leu Phe Arg Ile Arg Asn Glu
            20                  25                  30

Glu Val Pro Leu Leu Met Val Tyr Ala Gln Ala Ala Asn Leu His Leu
        35                  40                  45

Leu Leu
    50
```

(2) INFORMATION FOR SEQ ID NO:49:

(i) SEQUENCE CHARACTERISTICS:
(A) LENGTH: 50 amino acids
(B) TYPE: amino acid
(C) STRANDEDNESS: single
(D) TOPOLOGY: linear (xi) SEQUENCE DESCRIPTION: SEQ ID NO:49:

```
Asn Asp Ala Arg Ser Arg Ser Ile Ile Arg Glu Arg Tyr Ile Ala Leu
1               5                   10                  15

Glu Leu Asp Ile Thr Thr Ala Ile Pro Leu Phe Ser Ile Arg Asn Glu
            20                  25                  30

Glu Val Pro Leu Leu Met Val Tyr Ala Gln Ala Ala Asn Leu His Leu
        35                  40                  45

Leu Leu
    50
```

(2) INFORMATION FOR SEQ ID NO:50:

(i) SEQUENCE CHARACTERISTICS:
(A) LENGTH: 50 amino acids
(B) TYPE: amino acid
(C) STRANDEDNESS: single
(D) TOPOLOGY: linear (xi) SEQUENCE DESCRIPTION: SEQ ID NO:50:

```
Asn Asn Thr Arg Ala Arg Ser Val Val Lys Ser Gln Tyr Ile Ala Leu
1               5                   10                  15

Glu Leu Met Phe Val Gln Lys Leu Pro Ser Phe Ala Val Ser Gly Glu
            20                  25                  30

Glu Val Pro Leu Leu Pro Ile Tyr Ala Gln Ala Ala Asn Leu His Leu
        35                  40                  45

Leu Leu
    50
```

(2) INFORMATION FOR SEQ ID NO:51:

(i) SEQUENCE CHARACTERISTICS:
(A) LENGTH: 50 amino acids
(B) TYPE: amino acid
(C) STRANDEDNESS: single
(D) TOPOLOGY: linear (xi) SEQUENCE DESCRIPTION: SEQ ID NO:51:

```
Asn Asn Thr Arg Ala Arg Ser Val Val Lys Asn Gln Tyr Ile Ala Leu
1               5                   10                  15

Glu Leu Met Phe Val Gln Lys Leu Pro Ser Phe Ala Val Ser Gly Glu
            20                  25                  30

Glu Val Pro Leu Leu Pro Ile Tyr Ala Gln Ala Ala Asn Leu His Leu
        35                  40                  45

Leu Leu
    50
```

(2) INFORMATION FOR SEQ ID NO:52:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO:52:

```
GGATCCCTCG AGCTGCAGGA GC                                           22
```

(2) INFORMATION FOR SEQ ID NO:53:

(i) SEQUENCE CHARACTERISTICS:
(A) LENGTH: 55 base pairs
(B) TYPE: nucleic acid
(C) STRANDEDNESS: single
(D) TOPOLOGY: linear -continued (ix) FEATURE:
(A) NAME/KEY: modified_base
(B) LOCATION: 31..33
(D) OTHER INFORMATION: /note= "N = C, A, T or G"

(xi) SEQUENCE DESCRIPTION: SEQ ID NO:53:

GGGCTACTTG AAAGGGACAT TCCTTCGTTT NNNATTTCTG GATTTGAAGT ACCCC 55

(2) INFORMATION FOR SEQ ID NO:54:

(i) SEQUENCE CHARACTERISTICS:
(A) LENGTH: 63 base pairs
(B) TYPE: nucleic acid
(C) STRANDEDNESS: single
(D) TOPOLOGY: linear (xi) SEQUENCE DESCRIPTION: SEQ ID NO:54:

GCATTTAAAG AATGGGAAGT AGATCCTAAT AATCCTGGAA CCAGGACCAG AGTAATTGAT 60

CGC 63

(2) INFORMATION FOR SEQ ID NO:55:

(i) SEQUENCE CHARACTERISTICS:
(A) LENGTH: 7 amino acids
(B) TYPE: amino acid
(C) STRANDEDNESS:
(D) TOPOLOGY: linear (xi) SEQUENCE DESCRIPTION: SEQ ID NO:55:

Val Asp Pro Asn Asn Pro Gly
1 5

(2) INFORMATION FOR SEQ ID NO:56:

(i) SEQUENCE CHARACTERISTICS:
(A) LENGTH: 63 base pairs
(B) TYPE: nucleic acid
(C) STRANDEDNESS: single
(D) TOPOLOGY: linear (xi) SEQUENCE DESCRIPTION: SEQ ID NO:56:

GCATTTAAAG AATGGGAAGA AGATCCCCAT AATCCAGCAA CCAGGACCAG AGTAATTGAT 60

CGC 63

(2) INFORMATION FOR SEQ ID NO:57:

(i) SEQUENCE CHARACTERISTICS:
(A) LENGTH: 7 amino acids
(B) TYPE: amino acid
(C) STRANDEDNESS:
(D) TOPOLOGY: linear (xi) SEQUENCE DESCRIPTION: SEQ ID NO:57:

Glu Asp Pro His Asn Pro Ala
1 5

(2) INFORMATION FOR SEQ ID NO:58:

(i) SEQUENCE CHARACTERISTICS:
(A) LENGTH: 3567 base pairs
(B) TYPE: nucleic acid
(C) STRANDEDNESS: single
(D) TOPOLOGY: linear (ix) FEATURE:
(A) NAME/KEY: CDS
(B) LOCATION: 1..3567

-continued (xi) SEQUENCE DESCRIPTION: SEQ ID NO:58:

ATG GAG GAA AAT AAT CAA AAT CAA TGC ATA CCT TAC AAT TGT TTA AGT 48
Met Glu Glu Asn Asn Gln Asn Gln Cys Ile Pro Tyr Asn Cys Leu Ser
1 5 10 15

AAT CCT GAA GAA GTA CTT TTG GAT GGA GAA CGG ATA TCA ACT GGT AAT 96
Asn Pro Glu Glu Val Leu Leu Asp Gly Glu Arg Ile Ser Thr Gly Asn
20 25 30

TCA TCA ATT GAT ATT TCT CTG TCA CTT GTT CAG TTT CTG GTA TCT AAC 144
Ser Ser Ile Asp Ile Ser Leu Ser Leu Val Gln Phe Leu Val Ser Asn
35 40 45

TTT GTA CCA GGG GGA GGA TTT TTA GTT GGA TTA ATA GAT TTT GTA TGG 192
Phe Val Pro Gly Gly Gly Phe Leu Val Gly Leu Ile Asp Phe Val Trp
50 55 60

GGA ATA GTT GGC CCT TCT CAA TGG GAT GCA TTT CTA GTA CAA ATT GAA 240
Gly Ile Val Gly Pro Ser Gln Trp Asp Ala Phe Leu Val Gln Ile Glu
65 70 75 80

CAA TTA ATT AAT GAA AGA ATA GCT GAA TTT GCT AGG AAT GCT GCT ATT 288
Gln Leu Ile Asn Glu Arg Ile Ala Glu Phe Ala Arg Asn Ala Ala Ile
85 90 95

GCT AAT TTA GAA GGA TTA GGA AAC AAT TTC AAT ATA TAT GTG GAA GCA 336
Ala Asn Leu Glu Gly Leu Gly Asn Asn Phe Asn Ile Tyr Val Glu Ala
100 105 110

TTT AAA GAA TGG GAA GAA GAT CCT AAT AAT CCA GCA ACC AGG ACC AGA 384
Phe Lys Glu Trp Glu Glu Asp Pro Asn Asn Pro Ala Thr Arg Thr Arg
115 120 125

GTA ATT GAT CGC TTT CGT ATA CTT GAT GGG CTA CTT GAA AGG GAC ATT 432
Val Ile Asp Arg Phe Arg Ile Leu Asp Gly Leu Leu Glu Arg Asp Ile
130 135 140

CCT TCG TTT GCA ATT TCT GGA TTT GAA GTA CCC CTT TTA TCC GTT TAT 480
Pro Ser Phe Ala Ile Ser Gly Phe Glu Val Pro Leu Leu Ser Val Tyr
145 150 155 160

GCT CAA GCG GCC AAT CTG CAT CTA GCT ATA TTA AGA GAT TCT GTA ATT 528
Ala Gln Ala Ala Asn Leu His Leu Ala Ile Leu Arg Asp Ser Val Ile
165 170 175

TTT GGA GAA AGA TGG GGA TTG ACA ACG ATA AAT GTC AAT GAA AAC TAT 576
Phe Gly Glu Arg Trp Gly Leu Thr Thr Ile Asn Val Asn Glu Asn Tyr
180 185 190

AAT AGA CTA ATT AGG CAT ATT GAT GAA TAT GCT GAT CAC TGT GCA AAT 624
Asn Arg Leu Ile Arg His Ile Asp Glu Tyr Ala Asp His Cys Ala Asn
195 200 205

ACG TAT AAT CGG GGA TTA AAT AAT TTA CCG GCT AGC ACG TAT CAA GAT 672
Thr Tyr Asn Arg Gly Leu Asn Asn Leu Pro Ala Ser Thr Tyr Gln Asp
210 215 220

TGG ATA ACA TAT AAT CGA TTA CGG AGA GAC TTA ACA TTG ACT GTA TTA 720
Trp Ile Thr Tyr Asn Arg Leu Arg Arg Asp Leu Thr Leu Thr Val Leu
225 230 235 240

GAT ATC GCC GCT TTC TTT CCA AAC TAT GAC AAT AGG AGA TAT CCA ATT 768
Asp Ile Ala Ala Phe Phe Pro Asn Tyr Asp Asn Arg Arg Tyr Pro Ile
245 250 255

CAG CCA GTT GGT CAA CTA ACA AGG GAA GTT TAT ACG GAC CCA TTA ATT 816
Gln Pro Val Gly Gln Leu Thr Arg Glu Val Tyr Thr Asp Pro Leu Ile
260 265 270

AAT TTT AAT CCA CAG TTA CAG TCT GTA GCT CAA TTA CCT ACT TTT AAC 864
Asn Phe Asn Pro Gln Leu Gln Ser Val Ala Gln Leu Pro Thr Phe Asn
275 280 285

GTT ATG GAG AGC AGC GCA ATT AGA AAT CCT CAT TTA TTT GAT ATA TTG 912
Val Met Glu Ser Ser Ala Ile Arg Asn Pro His Leu Phe Asp Ile Leu
290 295 300

AAT AAT CTT ACA ATC TTT ACG GAT TGG TTT AGT GTT GGA CGC AAT TTT 960
Asn Asn Leu Thr Ile Phe Thr Asp Trp Phe Ser Val Gly Arg Asn Phe

-continued

```
305                 310                 315                 320

TAT TGG GGA GGA CAT CGA GTA ATA TCT AGC CTT ATA GGA GGT GGT AAC     1008
Tyr Trp Gly Gly His Arg Val Ile Ser Ser Leu Ile Gly Gly Gly Asn
                325                 330                 335

ATA ACA TCT CCT ATA TAT GGA AGA GAG GCG AAC CAG GAG CCT CCA AGA     1056
Ile Thr Ser Pro Ile Tyr Gly Arg Glu Ala Asn Gln Glu Pro Pro Arg
            340                 345                 350

TCC TTT ACT TTT AAT GGA CCG GTA TTT AGG ACT TTA TCA AAT CCT ACT     1104
Ser Phe Thr Phe Asn Gly Pro Val Phe Arg Thr Leu Ser Asn Pro Thr
        355                 360                 365

TTA CGA TTA TTA CAG CAA CCT TGG CCA GCG CCA CCA TTT AAT TTA CGT     1152
Leu Arg Leu Leu Gln Gln Pro Trp Pro Ala Pro Pro Phe Asn Leu Arg
    370                 375                 380

GGT GTT GAA GGA GTA GAA TTT TCT ACA CCT ACA AAT AGC TTT ACG TAT     1200
Gly Val Glu Gly Val Glu Phe Ser Thr Pro Thr Asn Ser Phe Thr Tyr
385                 390                 395                 400

CGA GGA AGA GGT ACG GTT GAT TCT TTA ACT GAA TTA CCG CCT GAG GAT     1248
Arg Gly Arg Gly Thr Val Asp Ser Leu Thr Glu Leu Pro Pro Glu Asp
                405                 410                 415

AAT AGT GTG CCA CCT CGC GAA GGA TAT AGT CAT CGT TTA TGT CAT GCA     1296
Asn Ser Val Pro Pro Arg Glu Gly Tyr Ser His Arg Leu Cys His Ala
            420                 425                 430

ACT TTT GTT CAA AGA TCT GGA ACA CCT TTT TTA ACA ACT GGT GTA GTA     1344
Thr Phe Val Gln Arg Ser Gly Thr Pro Phe Leu Thr Thr Gly Val Val
        435                 440                 445

TTT TCT TGG ACG CAT CGT AGT GCA ACT CTT ACA AAT ACA ATT GAT CCA     1392
Phe Ser Trp Thr His Arg Ser Ala Thr Leu Thr Asn Thr Ile Asp Pro
    450                 455                 460

GAG AGA ATT AAT CAA ATA CCT TTA GTG AAA GGA TTT AGA GTT TGG GGG     1440
Glu Arg Ile Asn Gln Ile Pro Leu Val Lys Gly Phe Arg Val Trp Gly
465                 470                 475                 480

GGC ACC TCT GTC ATT ACA GGA CCA GGA TTT ACA GGA GGG GAT ATC CTT     1488
Gly Thr Ser Val Ile Thr Gly Pro Gly Phe Thr Gly Gly Asp Ile Leu
                485                 490                 495

CGA AGA AAT ACC TTT GGT GAT TTT GTA TCT CTA CAA GTC AAT ATT AAT     1536
Arg Arg Asn Thr Phe Gly Asp Phe Val Ser Leu Gln Val Asn Ile Asn
            500                 505                 510

TCA CCA ATT ACC CAA AGA TAC CGT TTA AGA TTT CGT TAC GCT TCC AGT     1584
Ser Pro Ile Thr Gln Arg Tyr Arg Leu Arg Phe Arg Tyr Ala Ser Ser
        515                 520                 525

AGG GAT GCA CGA GTT ATA GTA TTA ACA GGA GCG GCA TCC ACA GGA GTG     1632
Arg Asp Ala Arg Val Ile Val Leu Thr Gly Ala Ala Ser Thr Gly Val
    530                 535                 540

GGA GGC CAA GTT AGT GTA AAT ATG CCT CTT CAG AAA ACT ATG GAA ATA     1680
Gly Gly Gln Val Ser Val Asn Met Pro Leu Gln Lys Thr Met Glu Ile
545                 550                 555                 560

GGG GAG AAC TTA ACA TCT AGA ACA TTT AGA TAT ACC GAT TTT AGT AAT     1728
Gly Glu Asn Leu Thr Ser Arg Thr Phe Arg Tyr Thr Asp Phe Ser Asn
                565                 570                 575

CCT TTT TCA TTT AGA GCT AAT CCA GAT ATA ATT GGG ATA AGT GAA CAA     1776
Pro Phe Ser Phe Arg Ala Asn Pro Asp Ile Ile Gly Ile Ser Glu Gln
            580                 585                 590

CCT CTA TTT GGT GCA GGT TCT ATT AGT AGC GGT GAA CTT TAT ATA GAT     1824
Pro Leu Phe Gly Ala Gly Ser Ile Ser Ser Gly Glu Leu Tyr Ile Asp
        595                 600                 605

AAA ATT GAA ATT ATT CTA GCA GAT GCA ACA TTT GAA GCA GAA TCT GAT     1872
Lys Ile Glu Ile Ile Leu Ala Asp Ala Thr Phe Glu Ala Glu Ser Asp
    610                 615                 620

TTA GAA AGA GCA CAA AAG GCG GTG AAT GCC CTG TTT ACT TCT TCC AAT     1920
Leu Glu Arg Ala Gln Lys Ala Val Asn Ala Leu Phe Thr Ser Ser Asn
```

```
625                 630                 635                 640

CAA ATC GGG TTA AAA ACC GAT GTG ACG GAT TAT CAT ATT GAT CAA GTA     1968
Gln Ile Gly Leu Lys Thr Asp Val Thr Asp Tyr His Ile Asp Gln Val
                645                 650                 655

TCC AAT TTA GTG GAT TGT TTA TCA GAT GAA TTT TGT CTG GAT GAA AAG     2016
Ser Asn Leu Val Asp Cys Leu Ser Asp Glu Phe Cys Leu Asp Glu Lys
            660                 665                 670

CGA GAA TTG TCC GAG AAA GTC AAA CAT GCG AAG CGA CTC AGT GAT GAG     2064
Arg Glu Leu Ser Glu Lys Val Lys His Ala Lys Arg Leu Ser Asp Glu
        675                 680                 685

CGG AAT TTA CTT CAA GAT CCA AAC TTC AGA GGG ATC AAT AGA CAA CCA     2112
Arg Asn Leu Leu Gln Asp Pro Asn Phe Arg Gly Ile Asn Arg Gln Pro
    690                 695                 700

GAC CGT GGC TGG AGA GGA AGT ACA GAT ATT ACC ATC CAA GGA GGA GAT     2160
Asp Arg Gly Trp Arg Gly Ser Thr Asp Ile Thr Ile Gln Gly Gly Asp
705                 710                 715                 720

GAC GTA TTC AAA GAG AAT TAC GTC ACA CTA CCG GGT ACC GTT GAT GAG     2208
Asp Val Phe Lys Glu Asn Tyr Val Thr Leu Pro Gly Thr Val Asp Glu
                725                 730                 735

TGC TAT CCA ACG TAT TTA TAT CAG AAA ATA GAT GAG TCG AAA TTA AAA     2256
Cys Tyr Pro Thr Tyr Leu Tyr Gln Lys Ile Asp Glu Ser Lys Leu Lys
            740                 745                 750

GCT TAT ACC CGT TAT GAA TTA AGA GGG TAT ATC GAA GAT AGT CAA GAC     2304
Ala Tyr Thr Arg Tyr Glu Leu Arg Gly Tyr Ile Glu Asp Ser Gln Asp
        755                 760                 765

TTA GAA ATC TAT TTG ATC CGT TAC AAT GCA AAA CAC GAA ATA GTA AAT     2352
Leu Glu Ile Tyr Leu Ile Arg Tyr Asn Ala Lys His Glu Ile Val Asn
    770                 775                 780

GTG CCA GGC ACG GGT TCC TTA TGG CCG CTT TCA GCC CAA AGT CCA ATC     2400
Val Pro Gly Thr Gly Ser Leu Trp Pro Leu Ser Ala Gln Ser Pro Ile
785                 790                 795                 800

GGA AAG TGT GGA GAA CCG AAT CGA TGC GCG CCA CAC CTT GAA TGG AAT     2448
Gly Lys Cys Gly Glu Pro Asn Arg Cys Ala Pro His Leu Glu Trp Asn
                805                 810                 815

CCT GAT CTA GAT TGT TCC TGC AGA GAC GGG GAA AAA TGT GCA CAT CAT     2496
Pro Asp Leu Asp Cys Ser Cys Arg Asp Gly Glu Lys Cys Ala His His
            820                 825                 830

TCC CAT CAT TTC ACC TTG GAT ATT GAT GTT GGA TGT ACA GAC TTA AAT     2544
Ser His His Phe Thr Leu Asp Ile Asp Val Gly Cys Thr Asp Leu Asn
        835                 840                 845

GAG GAC TTA GGT GTA TGG GTG ATA TTC AAG ATT AAG ACG CAA GAT GGC     2592
Glu Asp Leu Gly Val Trp Val Ile Phe Lys Ile Lys Thr Gln Asp Gly
    850                 855                 860

CAT GCA AGA CTA GGG AAT CTA GAG TTT CTC GAA GAG AAA CCA TTA TTA     2640
His Ala Arg Leu Gly Asn Leu Glu Phe Leu Glu Glu Lys Pro Leu Leu
865                 870                 875                 880

GGG GAA GCA CTA GCT CGT GTG AAA AGA GCG GAG AAG AAG TGG AGA GAC     2688
Gly Glu Ala Leu Ala Arg Val Lys Arg Ala Glu Lys Lys Trp Arg Asp
                885                 890                 895

AAA CGA GAG AAA CTG CAG TTG GAA ACA AAT ATT GTT TAT AAA GAG GCA     2736
Lys Arg Glu Lys Leu Gln Leu Glu Thr Asn Ile Val Tyr Lys Glu Ala
            900                 905                 910

AAA GAA TCT GTA GAT GCT TTA TTT GTA AAC TCT CAA TAT GAT AGA TTA     2784
Lys Glu Ser Val Asp Ala Leu Phe Val Asn Ser Gln Tyr Asp Arg Leu
        915                 920                 925

CAA GTG GAT ACG AAC ATC GCA ATG ATT CAT GCG GCA GAT AAA CGC GTT     2832
Gln Val Asp Thr Asn Ile Ala Met Ile His Ala Ala Asp Lys Arg Val
    930                 935                 940

CAT AGA ATC CGG GAA GCG TAT CTG CCA GAG TTG TCT GTG ATT CCA GGT     2880
His Arg Ile Arg Glu Ala Tyr Leu Pro Glu Leu Ser Val Ile Pro Gly
```

-continued

```
945                 950                 955                 960

GTC AAT GCG GCC ATT TTC GAA GAA TTA GAG GGA CGT ATT TTT ACA GCG      2928
Val Asn Ala Ala Ile Phe Glu Glu Leu Glu Gly Arg Ile Phe Thr Ala
                965                 970                 975

TAT TCC TTA TAT GAT GCG AGA AAT GTC ATT AAA AAT GGC GAT TTC AAT      2976
Tyr Ser Leu Tyr Asp Ala Arg Asn Val Ile Lys Asn Gly Asp Phe Asn
            980                 985                 990

AAT GGC TTA TTA TGC TGG AAC GTG AAA GGT CAT GTA GAT GTA GAA GAG      3024
Asn Gly Leu Leu Cys Trp Asn Val Lys Gly His Val Asp Val Glu Glu
        995                 1000                1005

CAA AAC AAC CAC CGT TCG GTC CTT GTT ATC CCA GAA TGG GAG GCA GAA      3072
Gln Asn Asn His Arg Ser Val Leu Val Ile Pro Glu Trp Glu Ala Glu
    1010                1015                1020

GTG TCA CAA GAG GTT CGT GTC TGT CCA GGT CGT GGC TAT ATC CTT CGT      3120
Val Ser Gln Glu Val Arg Val Cys Pro Gly Arg Gly Tyr Ile Leu Arg
1025                1030                1035                1040

GTC ACA GCA TAT AAA GAG GGA TAT GGA GAG GGC TGC GTA ACG ATC CAT      3168
Val Thr Ala Tyr Lys Glu Gly Tyr Gly Glu Gly Cys Val Thr Ile His
                1045                1050                1055

GAG ATC GAA GAC AAT ACA GAC GAA CTG AAA TTC AGC AAC TGT GTA GAA      3216
Glu Ile Glu Asp Asn Thr Asp Glu Leu Lys Phe Ser Asn Cys Val Glu
            1060                1065                1070

GAG GAA GTA TAT CCA AAC AAC ACA GTA ACG TGT AAT AAT TAT ACT GGG      3264
Glu Glu Val Tyr Pro Asn Asn Thr Val Thr Cys Asn Asn Tyr Thr Gly
        1075                1080                1085

ACT CAA GAA GAA TAT GAG GGT ACG TAC ACT TCT CGT AAT CAA GGA TAT      3312
Thr Gln Glu Glu Tyr Glu Gly Thr Tyr Thr Ser Arg Asn Gln Gly Tyr
    1090                1095                1100

GAC GAA GCC TAT GGT AAT AAC CCT TCC GTA CCA GCT GAT TAC GCT TCA      3360
Asp Glu Ala Tyr Gly Asn Asn Pro Ser Val Pro Ala Asp Tyr Ala Ser
1105                1110                1115                1120

GTC TAT GAA GAA AAA TCG TAT ACA GAT GGA CGA AGA GAG AAT CCT TGT      3408
Val Tyr Glu Glu Lys Ser Tyr Thr Asp Gly Arg Arg Glu Asn Pro Cys
                1125                1130                1135

GAA TCT AAC AGA GGC TAT GGG GAT TAC ACA CCA CTA CCG GCT GGT TAT      3456
Glu Ser Asn Arg Gly Tyr Gly Asp Tyr Thr Pro Leu Pro Ala Gly Tyr
            1140                1145                1150

GTA ACA AAG GAT TTA GAG TAC TTC CCA GAG ACC GAT AAG GTA TGG ATT      3504
Val Thr Lys Asp Leu Glu Tyr Phe Pro Glu Thr Asp Lys Val Trp Ile
        1155                1160                1165

GAG ATC GGA GAA ACA GAA GGA ACA TTC ATC GTG GAT AGC GTG GAA TTA      3552
Glu Ile Gly Glu Thr Glu Gly Thr Phe Ile Val Asp Ser Val Glu Leu
    1170                1175                1180

CTC CTT ATG GAG GAA                                                  3567
Leu Leu Met Glu Glu
1185
```

(2) INFORMATION FOR SEQ ID NO:59:

(i) SEQUENCE CHARACTERISTICS:
(A) LENGTH: 1189 amino acids
(B) TYPE: amino acid
(D) TOPOLOGY: linear (ii) MOLECULE TYPE: protein (xi) SEQUENCE DESCRIPTION: SEQ ID NO:59:

```
Met Glu Glu Asn Asn Gln Asn Gln Cys Ile Pro Tyr Asn Cys Leu Ser
  1               5                  10                  15

Asn Pro Glu Glu Val Leu Leu Asp Gly Glu Arg Ile Ser Thr Gly Asn
             20                  25                  30
```

```
Ser Ser Ile Asp Ile Ser Leu Ser Leu Val Gln Phe Leu Val Ser Asn
        35                  40                  45

Phe Val Pro Gly Gly Gly Phe Leu Val Gly Leu Ile Asp Phe Val Trp
    50                  55                  60

Gly Ile Val Gly Pro Ser Gln Trp Asp Ala Phe Leu Val Gln Ile Glu
65                  70                  75                  80

Gln Leu Ile Asn Glu Arg Ile Ala Glu Phe Ala Arg Asn Ala Ala Ile
                85                  90                  95

Ala Asn Leu Glu Gly Leu Gly Asn Asn Phe Asn Ile Tyr Val Glu Ala
            100                 105                 110

Phe Lys Glu Trp Glu Glu Asp Pro Asn Asn Pro Ala Thr Arg Thr Arg
        115                 120                 125

Val Ile Asp Arg Phe Arg Ile Leu Asp Gly Leu Leu Glu Arg Asp Ile
    130                 135                 140

Pro Ser Phe Ala Ile Ser Gly Phe Glu Val Pro Leu Leu Ser Val Tyr
145                 150                 155                 160

Ala Gln Ala Ala Asn Leu His Leu Ala Ile Leu Arg Asp Ser Val Ile
                165                 170                 175

Phe Gly Glu Arg Trp Gly Leu Thr Thr Ile Asn Val Asn Glu Asn Tyr
            180                 185                 190

Asn Arg Leu Ile Arg His Ile Asp Glu Tyr Ala Asp His Cys Ala Asn
        195                 200                 205

Thr Tyr Asn Arg Gly Leu Asn Asn Leu Pro Ala Ser Thr Tyr Gln Asp
    210                 215                 220

Trp Ile Thr Tyr Asn Arg Leu Arg Arg Asp Leu Thr Leu Thr Val Leu
225                 230                 235                 240

Asp Ile Ala Ala Phe Phe Pro Asn Tyr Asp Asn Arg Arg Tyr Pro Ile
                245                 250                 255

Gln Pro Val Gly Gln Leu Thr Arg Glu Val Tyr Thr Asp Pro Leu Ile
            260                 265                 270

Asn Phe Asn Pro Gln Leu Gln Ser Val Ala Gln Leu Pro Thr Phe Asn
        275                 280                 285

Val Met Glu Ser Ser Ala Ile Arg Asn Pro His Leu Phe Asp Ile Leu
    290                 295                 300

Asn Asn Leu Thr Ile Phe Thr Asp Trp Phe Ser Val Gly Arg Asn Phe
305                 310                 315                 320

Tyr Trp Gly Gly His Arg Val Ile Ser Ser Leu Ile Gly Gly Gly Asn
                325                 330                 335

Ile Thr Ser Pro Ile Tyr Gly Arg Glu Ala Asn Gln Glu Pro Pro Arg
            340                 345                 350

Ser Phe Thr Phe Asn Gly Pro Val Phe Arg Thr Leu Ser Asn Pro Thr
        355                 360                 365

Leu Arg Leu Leu Gln Gln Pro Trp Pro Ala Pro Pro Phe Asn Leu Arg
    370                 375                 380

Gly Val Glu Gly Val Glu Phe Ser Thr Pro Thr Asn Ser Phe Thr Tyr
385                 390                 395                 400

Arg Gly Arg Gly Thr Val Asp Ser Leu Thr Glu Leu Pro Pro Glu Asp
                405                 410                 415

Asn Ser Val Pro Pro Arg Glu Gly Tyr Ser His Arg Leu Cys His Ala
            420                 425                 430

Thr Phe Val Gln Arg Ser Gly Thr Pro Phe Leu Thr Thr Gly Val Val
        435                 440                 445

Phe Ser Trp Thr His Arg Ser Ala Thr Leu Thr Asn Thr Ile Asp Pro
    450                 455                 460
```

-continued

```
Glu Arg Ile Asn Gln Ile Pro Leu Val Lys Gly Phe Arg Val Trp Gly
465                 470                 475                 480

Gly Thr Ser Val Ile Thr Gly Pro Gly Phe Thr Gly Gly Asp Ile Leu
                485                 490                 495

Arg Arg Asn Thr Phe Gly Asp Phe Val Ser Leu Gln Val Asn Ile Asn
            500                 505                 510

Ser Pro Ile Thr Gln Arg Tyr Arg Leu Arg Phe Arg Tyr Ala Ser Ser
        515                 520                 525

Arg Asp Ala Arg Val Ile Val Leu Thr Gly Ala Ala Ser Thr Gly Val
    530                 535                 540

Gly Gly Gln Val Ser Val Asn Met Pro Leu Gln Lys Thr Met Glu Ile
545                 550                 555                 560

Gly Glu Asn Leu Thr Ser Arg Thr Phe Arg Tyr Thr Asp Phe Ser Asn
                565                 570                 575

Pro Phe Ser Phe Arg Ala Asn Pro Asp Ile Ile Gly Ile Ser Glu Gln
            580                 585                 590

Pro Leu Phe Gly Ala Gly Ser Ile Ser Ser Gly Glu Leu Tyr Ile Asp
        595                 600                 605

Lys Ile Glu Ile Ile Leu Ala Asp Ala Thr Phe Glu Ala Glu Ser Asp
    610                 615                 620

Leu Glu Arg Ala Gln Lys Ala Val Asn Ala Leu Phe Thr Ser Ser Asn
625                 630                 635                 640

Gln Ile Gly Leu Lys Thr Asp Val Thr Asp Tyr His Ile Asp Gln Val
                645                 650                 655

Ser Asn Leu Val Asp Cys Leu Ser Asp Glu Phe Cys Leu Asp Glu Lys
            660                 665                 670

Arg Glu Leu Ser Glu Lys Val Lys His Ala Lys Arg Leu Ser Asp Glu
        675                 680                 685

Arg Asn Leu Leu Gln Asp Pro Asn Phe Arg Gly Ile Asn Arg Gln Pro
    690                 695                 700

Asp Arg Gly Trp Arg Gly Ser Thr Asp Ile Thr Ile Gln Gly Gly Asp
705                 710                 715                 720

Asp Val Phe Lys Glu Asn Tyr Val Thr Leu Pro Gly Thr Val Asp Glu
                725                 730                 735

Cys Tyr Pro Thr Tyr Leu Tyr Gln Lys Ile Asp Glu Ser Lys Leu Lys
            740                 745                 750

Ala Tyr Thr Arg Tyr Glu Leu Arg Gly Tyr Ile Glu Asp Ser Gln Asp
        755                 760                 765

Leu Glu Ile Tyr Leu Ile Arg Tyr Asn Ala Lys His Glu Ile Val Asn
    770                 775                 780

Val Pro Gly Thr Gly Ser Leu Trp Pro Leu Ser Ala Gln Ser Pro Ile
785                 790                 795                 800

Gly Lys Cys Gly Glu Pro Asn Arg Cys Ala Pro His Leu Glu Trp Asn
                805                 810                 815

Pro Asp Leu Asp Cys Ser Cys Arg Asp Gly Glu Lys Cys Ala His His
            820                 825                 830

Ser His His Phe Thr Leu Asp Ile Asp Val Gly Cys Thr Asp Leu Asn
        835                 840                 845

Glu Asp Leu Gly Val Trp Val Ile Phe Lys Ile Lys Thr Gln Asp Gly
    850                 855                 860

His Ala Arg Leu Gly Asn Leu Glu Phe Leu Glu Glu Lys Pro Leu Leu
865                 870                 875                 880

Gly Glu Ala Leu Ala Arg Val Lys Arg Ala Glu Lys Lys Trp Arg Asp
```

```
            885                 890                 895

Lys Arg Glu Lys Leu Gln Leu Glu Thr Asn Ile Val Tyr Lys Glu Ala
            900                 905                 910

Lys Glu Ser Val Asp Ala Leu Phe Val Asn Ser Gln Tyr Asp Arg Leu
        915                 920                 925

Gln Val Asp Thr Asn Ile Ala Met Ile His Ala Ala Asp Lys Arg Val
    930                 935                 940

His Arg Ile Arg Glu Ala Tyr Leu Pro Glu Leu Ser Val Ile Pro Gly
945                 950                 955                 960

Val Asn Ala Ala Ile Phe Glu Glu Leu Glu Gly Arg Ile Phe Thr Ala
            965                 970                 975

Tyr Ser Leu Tyr Asp Ala Arg Asn Val Ile Lys Asn Gly Asp Phe Asn
            980                 985                 990

Asn Gly Leu Leu Cys Trp Asn Val Lys Gly His Val Asp Val Glu Glu
        995                 1000                1005

Gln Asn Asn His Arg Ser Val Leu Val Ile Pro Glu Trp Glu Ala Glu
    1010                1015                1020

Val Ser Gln Glu Val Arg Val Cys Pro Gly Arg Gly Tyr Ile Leu Arg
1025                1030                1035                1040

Val Thr Ala Tyr Lys Glu Gly Tyr Gly Glu Gly Cys Val Thr Ile His
            1045                1050                1055

Glu Ile Glu Asp Asn Thr Asp Glu Leu Lys Phe Ser Asn Cys Val Glu
            1060                1065                1070

Glu Glu Val Tyr Pro Asn Asn Thr Val Thr Cys Asn Asn Tyr Thr Gly
        1075                1080                1085

Thr Gln Glu Glu Tyr Glu Gly Thr Tyr Thr Ser Arg Asn Gln Gly Tyr
    1090                1095                1100

Asp Glu Ala Tyr Gly Asn Asn Pro Ser Val Pro Ala Asp Tyr Ala Ser
1105                1110                1115                1120

Val Tyr Glu Glu Lys Ser Tyr Thr Asp Gly Arg Arg Glu Asn Pro Cys
            1125                1130                1135

Glu Ser Asn Arg Gly Tyr Gly Asp Tyr Thr Pro Leu Pro Ala Gly Tyr
            1140                1145                1150

Val Thr Lys Asp Leu Glu Tyr Phe Pro Glu Thr Asp Lys Val Trp Ile
        1155                1160                1165

Glu Ile Gly Glu Thr Glu Gly Thr Phe Ile Val Asp Ser Val Glu Leu
    1170                1175                1180

Leu Leu Met Glu Glu
1185
```

(2) INFORMATION FOR SEQ ID NO:60:

(i) SEQUENCE CHARACTERISTICS:
(A) LENGTH: 3567 base pairs
(B) TYPE: nucleic acid
(C) STRANDEDNESS: single
(D) TOPOLOGY: linear (ix) FEATURE:
(A) NAME/KEY: CDS
(B) LOCATION: 1..3567

(xi) SEQUENCE DESCRIPTION: SEQ ID NO:60:

```
ATG GAG GAA AAT AAT CAA AAT CAA TGC ATA CCT TAC AAT TGT TTA AGT       48
Met Glu Glu Asn Asn Gln Asn Gln Cys Ile Pro Tyr Asn Cys Leu Ser
  1               5                  10                  15

AAT CCT GAA GAA GTA CTT TTG GAT GGA GAA CGG ATA TCA ACT GGT AAT       96
Asn Pro Glu Glu Val Leu Leu Asp Gly Glu Arg Ile Ser Thr Gly Asn
```

-continued

```
            20                  25                  30

TCA TCA ATT GAT ATT TCT CTG TCA CTT GTT CAG TTT CTG GTA TCT AAC       144
Ser Ser Ile Asp Ile Ser Leu Ser Leu Val Gln Phe Leu Val Ser Asn
        35                  40                  45

TTT GTA CCA GGG GGA GGA TTT TTA GTT GGA TTA ATA GAT TTT GTA TGG       192
Phe Val Pro Gly Gly Gly Phe Leu Val Gly Leu Ile Asp Phe Val Trp
    50                  55                  60

GGA ATA GTT GGC CCT TCT CAA TGG GAT GCA TTT CTA GTA CAA ATT GAA       240
Gly Ile Val Gly Pro Ser Gln Trp Asp Ala Phe Leu Val Gln Ile Glu
65                  70                  75                  80

CAA TTA ATT AAT GAA AGA ATA GCT GAA TTT GCT AGG AAT GCT GCT ATT       288
Gln Leu Ile Asn Glu Arg Ile Ala Glu Phe Ala Arg Asn Ala Ala Ile
                85                  90                  95

GCT AAT TTA GAA GGA TTA GGA AAC AAT TTC AAT ATA TAT GTG GAA GCA       336
Ala Asn Leu Glu Gly Leu Gly Asn Asn Phe Asn Ile Tyr Val Glu Ala
            100                 105                 110

TTT AAA GAA TGG GAA GAA GAT CCT AAT AAT CCA GCA ACC AGG ACC AGA       384
Phe Lys Glu Trp Glu Glu Asp Pro Asn Asn Pro Ala Thr Arg Thr Arg
        115                 120                 125

GTA ATT GAT CGC TTT CGT ATA CTT GAT GGG CTA CTT GAA AGG GAC ATT       432
Val Ile Asp Arg Phe Arg Ile Leu Asp Gly Leu Leu Glu Arg Asp Ile
    130                 135                 140

CCT TCG TTT GAC ATT TCT GGA TTT GAA GTA CCC CTT TTA TCC GTT TAT       480
Pro Ser Phe Asp Ile Ser Gly Phe Glu Val Pro Leu Leu Ser Val Tyr
145                 150                 155                 160

GCT CAA GCG GCC AAT CTG CAT CTA GCT ATA TTA AGA GAT TCT GTA ATT       528
Ala Gln Ala Ala Asn Leu His Leu Ala Ile Leu Arg Asp Ser Val Ile
                165                 170                 175

TTT GGA GAA AGA TGG GGA TTG ACA ACG ATA AAT GTC AAT GAA AAC TAT       576
Phe Gly Glu Arg Trp Gly Leu Thr Thr Ile Asn Val Asn Glu Asn Tyr
            180                 185                 190

AAT AGA CTA ATT AGG CAT ATT GAT GAA TAT GCT GAT CAC TGT GCA AAT       624
Asn Arg Leu Ile Arg His Ile Asp Glu Tyr Ala Asp His Cys Ala Asn
        195                 200                 205

ACG TAT AAT CGG GGA TTA AAT AAT TTA CCG GCT AGC ACG TAT CAA GAT       672
Thr Tyr Asn Arg Gly Leu Asn Asn Leu Pro Ala Ser Thr Tyr Gln Asp
    210                 215                 220

TGG ATA ACA TAT AAT CGA TTA CGG AGA GAC TTA ACA TTG ACT GTA TTA       720
Trp Ile Thr Tyr Asn Arg Leu Arg Arg Asp Leu Thr Leu Thr Val Leu
225                 230                 235                 240

GAT ATC GCC GCT TTC TTT CCA AAC TAT GAC AAT AGG AGA TAT CCA ATT       768
Asp Ile Ala Ala Phe Phe Pro Asn Tyr Asp Asn Arg Arg Tyr Pro Ile
                245                 250                 255

CAG CCA GTT GGT CAA CTA ACA AGG GAA GTT TAT ACG GAC CCA TTA ATT       816
Gln Pro Val Gly Gln Leu Thr Arg Glu Val Tyr Thr Asp Pro Leu Ile
            260                 265                 270

AAT TTT AAT CCA CAG TTA CAG TCT GTA GCT CAA TTA CCT ACT TTT AAC       864
Asn Phe Asn Pro Gln Leu Gln Ser Val Ala Gln Leu Pro Thr Phe Asn
        275                 280                 285

GTT ATG GAG AGC AGC GCA ATT AGA AAT CCT CAT TTA TTT GAT ATA TTG       912
Val Met Glu Ser Ser Ala Ile Arg Asn Pro His Leu Phe Asp Ile Leu
    290                 295                 300

AAT AAT CTT ACA ATC TTT ACG GAT TGG TTT AGT GTT GGA CGC AAT TTT       960
Asn Asn Leu Thr Ile Phe Thr Asp Trp Phe Ser Val Gly Arg Asn Phe
305                 310                 315                 320

TAT TGG GGA GGA CAT CGA GTA ATA TCT AGC CTT ATA GGA GGT GGT AAC      1008
Tyr Trp Gly Gly His Arg Val Ile Ser Ser Leu Ile Gly Gly Gly Asn
                325                 330                 335

ATA ACA TCT CCT ATA TAT GGA AGA GAG GCG AAC CAG GAG CCT CCA AGA      1056
Ile Thr Ser Pro Ile Tyr Gly Arg Glu Ala Asn Gln Glu Pro Pro Arg
```

-continued 340 345 350

TCC TTT ACT TTT AAT GGA CCG GTA TTT AGG ACT TTA TCA AAT CCT ACT 1104
Ser Phe Thr Phe Asn Gly Pro Val Phe Arg Thr Leu Ser Asn Pro Thr
355 360 365

TTA CGA TTA TTA CAG CAA CCT TGG CCA GCG CCA CCA TTT AAT TTA CGT 1152
Leu Arg Leu Leu Gln Gln Pro Trp Pro Ala Pro Pro Phe Asn Leu Arg
370 375 380

GGT GTT GAA GGA GTA GAA TTT TCT ACA CCT ACA AAT AGC TTT ACG TAT 1200
Gly Val Glu Gly Val Glu Phe Ser Thr Pro Thr Asn Ser Phe Thr Tyr
385 390 395 400

CGA GGA AGA GGT ACG GTT GAT TCT TTA ACT GAA TTA CCG CCT GAG GAT 1248
Arg Gly Arg Gly Thr Val Asp Ser Leu Thr Glu Leu Pro Pro Glu Asp
405 410 415

AAT AGT GTG CCA CCT CGC GAA GGA TAT AGT CAT CGT TTA TGT CAT GCA 1296
Asn Ser Val Pro Pro Arg Glu Gly Tyr Ser His Arg Leu Cys His Ala
420 425 430

ACT TTT GTT CAA AGA TCT GGA ACA CCT TTT TTA ACA ACT GGT GTA GTA 1344
Thr Phe Val Gln Arg Ser Gly Thr Pro Phe Leu Thr Thr Gly Val Val
435 440 445

TTT TCT TGG ACG CAT CGT AGT GCA ACT CTT ACA AAT ACA ATT GAT CCA 1392
Phe Ser Trp Thr His Arg Ser Ala Thr Leu Thr Asn Thr Ile Asp Pro
450 455 460

GAG AGA ATT AAT CAA ATA CCT TTA GTG AAA GGA TTT AGA GTT TGG GGG 1440
Glu Arg Ile Asn Gln Ile Pro Leu Val Lys Gly Phe Arg Val Trp Gly
465 470 475 480

GGC ACC TCT GTC ATT ACA GGA CCA GGA TTT ACA GGA GGG GAT ATC CTT 1488
Gly Thr Ser Val Ile Thr Gly Pro Gly Phe Thr Gly Gly Asp Ile Leu
485 490 495

CGA AGA AAT ACC TTT GGT GAT TTT GTA TCT CTA CAA GTC AAT ATT AAT 1536
Arg Arg Asn Thr Phe Gly Asp Phe Val Ser Leu Gln Val Asn Ile Asn
500 505 510

TCA CCA ATT ACC CAA AGA TAC CGT TTA AGA TTT CGT TAC GCT TCC AGT 1584
Ser Pro Ile Thr Gln Arg Tyr Arg Leu Arg Phe Arg Tyr Ala Ser Ser
515 520 525

AGG GAT GCA CGA GTT ATA GTA TTA ACA GGA GCG GCA TCC ACA GGA GTG 1632
Arg Asp Ala Arg Val Ile Val Leu Thr Gly Ala Ala Ser Thr Gly Val
530 535 540

GGA GGC CAA GTT AGT GTA AAT ATG CCT CTT CAG AAA ACT ATG GAA ATA 1680
Gly Gly Gln Val Ser Val Asn Met Pro Leu Gln Lys Thr Met Glu Ile
545 550 555 560

GGG GAG AAC TTA ACA TCT AGA ACA TTT AGA TAT ACC GAT TTT AGT AAT 1728
Gly Glu Asn Leu Thr Ser Arg Thr Phe Arg Tyr Thr Asp Phe Ser Asn
565 570 575

CCT TTT TCA TTT AGA GCT AAT CCA GAT ATA ATT GGG ATA AGT GAA CAA 1776
Pro Phe Ser Phe Arg Ala Asn Pro Asp Ile Ile Gly Ile Ser Glu Gln
580 585 590

CCT CTA TTT GGT GCA GGT TCT ATT AGT AGC GGT GAA CTT TAT ATA GAT 1824
Pro Leu Phe Gly Ala Gly Ser Ile Ser Ser Gly Glu Leu Tyr Ile Asp
595 600 605

AAA ATT GAA ATT ATT CTA GCA GAT GCA ACA TTT GAA GCA GAA TCT GAT 1872
Lys Ile Glu Ile Ile Leu Ala Asp Ala Thr Phe Glu Ala Glu Ser Asp
610 615 620

TTA GAA AGA GCA CAA AAG GCG GTG AAT GCC CTG TTT ACT TCT TCC AAT 1920
Leu Glu Arg Ala Gln Lys Ala Val Asn Ala Leu Phe Thr Ser Ser Asn
625 630 635 640

CAA ATC GGG TTA AAA ACC GAT GTG ACG GAT TAT CAT ATT GAT CAA GTA 1968
Gln Ile Gly Leu Lys Thr Asp Val Thr Asp Tyr His Ile Asp Gln Val
645 650 655

TCC AAT TTA GTG GAT TGT TTA TCA GAT GAA TTT TGT CTG GAT GAA AAG 2016
Ser Asn Leu Val Asp Cys Leu Ser Asp Glu Phe Cys Leu Asp Glu Lys

-continued

```
            660                 665                 670

CGA GAA TTG TCC GAG AAA GTC AAA CAT GCG AAG CGA CTC AGT GAT GAG      2064
Arg Glu Leu Ser Glu Lys Val Lys His Ala Lys Arg Leu Ser Asp Glu
        675                 680                 685

CGG AAT TTA CTT CAA GAT CCA AAC TTC AGA GGG ATC AAT AGA CAA CCA      2112
Arg Asn Leu Leu Gln Asp Pro Asn Phe Arg Gly Ile Asn Arg Gln Pro
    690                 695                 700

GAC CGT GGC TGG AGA GGA AGT ACA GAT ATT ACC ATC CAA GGA GGA GAT      2160
Asp Arg Gly Trp Arg Gly Ser Thr Asp Ile Thr Ile Gln Gly Gly Asp
705                 710                 715                 720

GAC GTA TTC AAA GAG AAT TAC GTC ACA CTA CCG GGT ACC GTT GAT GAG      2208
Asp Val Phe Lys Glu Asn Tyr Val Thr Leu Pro Gly Thr Val Asp Glu
                725                 730                 735

TGC TAT CCA ACG TAT TTA TAT CAG AAA ATA GAT GAG TCG AAA TTA AAA      2256
Cys Tyr Pro Thr Tyr Leu Tyr Gln Lys Ile Asp Glu Ser Lys Leu Lys
            740                 745                 750

GCT TAT ACC CGT TAT GAA TTA AGA GGG TAT ATC GAA GAT AGT CAA GAC      2304
Ala Tyr Thr Arg Tyr Glu Leu Arg Gly Tyr Ile Glu Asp Ser Gln Asp
        755                 760                 765

TTA GAA ATC TAT TTG ATC CGT TAC AAT GCA AAA CAC GAA ATA GTA AAT      2352
Leu Glu Ile Tyr Leu Ile Arg Tyr Asn Ala Lys His Glu Ile Val Asn
    770                 775                 780

GTG CCA GGC ACG GGT TCC TTA TGG CCG CTT TCA GCC CAA AGT CCA ATC      2400
Val Pro Gly Thr Gly Ser Leu Trp Pro Leu Ser Ala Gln Ser Pro Ile
785                 790                 795                 800

GGA AAG TGT GGA GAA CCG AAT CGA TGC GCG CCA CAC CTT GAA TGG AAT      2448
Gly Lys Cys Gly Glu Pro Asn Arg Cys Ala Pro His Leu Glu Trp Asn
                805                 810                 815

CCT GAT CTA GAT TGT TCC TGC AGA GAC GGG GAA AAA TGT GCA CAT CAT      2496
Pro Asp Leu Asp Cys Ser Cys Arg Asp Gly Glu Lys Cys Ala His His
            820                 825                 830

TCC CAT CAT TTC ACC TTG GAT ATT GAT GTT GGA TGT ACA GAC TTA AAT      2544
Ser His His Phe Thr Leu Asp Ile Asp Val Gly Cys Thr Asp Leu Asn
        835                 840                 845

GAG GAC TTA GGT GTA TGG GTG ATA TTC AAG ATT AAG ACG CAA GAT GGC      2592
Glu Asp Leu Gly Val Trp Val Ile Phe Lys Ile Lys Thr Gln Asp Gly
    850                 855                 860

CAT GCA AGA CTA GGG AAT CTA GAG TTT CTC GAA GAG AAA CCA TTA TTA      2640
His Ala Arg Leu Gly Asn Leu Glu Phe Leu Glu Glu Lys Pro Leu Leu
865                 870                 875                 880

GGG GAA GCA CTA GCT CGT GTG AAA AGA GCG GAG AAG AAG TGG AGA GAC      2688
Gly Glu Ala Leu Ala Arg Val Lys Arg Ala Glu Lys Lys Trp Arg Asp
                885                 890                 895

AAA CGA GAG AAA CTG CAG TTG GAA ACA AAT ATT GTT TAT AAA GAG GCA      2736
Lys Arg Glu Lys Leu Gln Leu Glu Thr Asn Ile Val Tyr Lys Glu Ala
            900                 905                 910

AAA GAA TCT GTA GAT GCT TTA TTT GTA AAC TCT CAA TAT GAT AGA TTA      2784
Lys Glu Ser Val Asp Ala Leu Phe Val Asn Ser Gln Tyr Asp Arg Leu
        915                 920                 925

CAA GTG GAT ACG AAC ATC GCA ATG ATT CAT GCG GCA GAT AAA CGC GTT      2832
Gln Val Asp Thr Asn Ile Ala Met Ile His Ala Ala Asp Lys Arg Val
    930                 935                 940

CAT AGA ATC CGG GAA GCG TAT CTG CCA GAG TTG TCT GTG ATT CCA GGT      2880
His Arg Ile Arg Glu Ala Tyr Leu Pro Glu Leu Ser Val Ile Pro Gly
945                 950                 955                 960

GTC AAT GCG GCC ATT TTC GAA GAA TTA GAG GGA CGT ATT TTT ACA GCG      2928
Val Asn Ala Ala Ile Phe Glu Glu Leu Glu Gly Arg Ile Phe Thr Ala
                965                 970                 975

TAT TCC TTA TAT GAT GCG AGA AAT GTC ATT AAA AAT GGC GAT TTC AAT      2976
Tyr Ser Leu Tyr Asp Ala Arg Asn Val Ile Lys Asn Gly Asp Phe Asn
```

-continued

```
        980                 985                 990

AAT GGC TTA TTA TGC TGG AAC GTG AAA GGT CAT GTA GAT GTA GAA GAG      3024
Asn Gly Leu Leu Cys Trp Asn Val Lys Gly His Val Asp Val Glu Glu
        995                1000                1005

CAA AAC AAC CAC CGT TCG GTC CTT GTT ATC CCA GAA TGG GAG GCA GAA      3072
Gln Asn Asn His Arg Ser Val Leu Val Ile Pro Glu Trp Glu Ala Glu
    1010                1015                1020

GTG TCA CAA GAG GTT CGT GTC TGT CCA GGT CGT GGC TAT ATC CTT CGT      3120
Val Ser Gln Glu Val Arg Val Cys Pro Gly Arg Gly Tyr Ile Leu Arg
1025                1030                1035                1040

GTC ACA GCA TAT AAA GAG GGA TAT GGA GAG GGC TGC GTA ACG ATC CAT      3168
Val Thr Ala Tyr Lys Glu Gly Tyr Gly Glu Gly Cys Val Thr Ile His
                1045                1050                1055

GAG ATC GAA GAC AAT ACA GAC GAA CTG AAA TTC AGC AAC TGT GTA GAA      3216
Glu Ile Glu Asp Asn Thr Asp Glu Leu Lys Phe Ser Asn Cys Val Glu
            1060                1065                1070

GAG GAA GTA TAT CCA AAC AAC ACA GTA ACG TGT AAT AAT TAT ACT GGG      3264
Glu Glu Val Tyr Pro Asn Asn Thr Val Thr Cys Asn Asn Tyr Thr Gly
        1075                1080                1085

ACT CAA GAA GAA TAT GAG GGT ACG TAC ACT TCT CGT AAT CAA GGA TAT      3312
Thr Gln Glu Glu Tyr Glu Gly Thr Tyr Thr Ser Arg Asn Gln Gly Tyr
    1090                1095                1100

GAC GAA GCC TAT GGT AAT AAC CCT TCC GTA CCA GCT GAT TAC GCT TCA      3360
Asp Glu Ala Tyr Gly Asn Asn Pro Ser Val Pro Ala Asp Tyr Ala Ser
1105                1110                1115                1120

GTC TAT GAA GAA AAA TCG TAT ACA GAT GGA CGA AGA GAG AAT CCT TGT      3408
Val Tyr Glu Glu Lys Ser Tyr Thr Asp Gly Arg Arg Glu Asn Pro Cys
                1125                1130                1135

GAA TCT AAC AGA GGC TAT GGG GAT TAC ACA CCA CTA CCG GCT GGT TAT      3456
Glu Ser Asn Arg Gly Tyr Gly Asp Tyr Thr Pro Leu Pro Ala Gly Tyr
            1140                1145                1150

GTA ACA AAG GAT TTA GAG TAC TTC CCA GAG ACC GAT AAG GTA TGG ATT      3504
Val Thr Lys Asp Leu Glu Tyr Phe Pro Glu Thr Asp Lys Val Trp Ile
        1155                1160                1165

GAG ATC GGA GAA ACA GAA GGA ACA TTC ATC GTG GAT AGC GTG GAA TTA      3552
Glu Ile Gly Glu Thr Glu Gly Thr Phe Ile Val Asp Ser Val Glu Leu
    1170                1175                1180

CTC CTT ATG GAG GAA                                                  3567
Leu Leu Met Glu Glu
1185
```

(2) INFORMATION FOR SEQ ID NO:61:

(i) SEQUENCE CHARACTERISTICS:
(A) LENGTH: 1189 amino acids
(B) TYPE: amino acid
(D) TOPOLOGY: linear (ii) MOLECULE TYPE: protein (xi) SEQUENCE DESCRIPTION: SEQ ID NO:61:

```
Met Glu Glu Asn Asn Gln Asn Gln Cys Ile Pro Tyr Asn Cys Leu Ser
  1               5                  10                  15

Asn Pro Glu Glu Val Leu Leu Asp Gly Glu Arg Ile Ser Thr Gly Asn
            20                  25                  30

Ser Ser Ile Asp Ile Ser Leu Ser Leu Val Gln Phe Leu Val Ser Asn
        35                  40                  45

Phe Val Pro Gly Gly Gly Phe Leu Val Gly Leu Ile Asp Phe Val Trp
    50                  55                  60

Gly Ile Val Gly Pro Ser Gln Trp Asp Ala Phe Leu Val Gln Ile Glu
 65                  70                  75                  80
```

Gln Leu Ile Asn Glu Arg Ile Ala Glu Phe Ala Arg Asn Ala Ala Ile
85 90 95

Ala Asn Leu Glu Gly Leu Gly Asn Asn Phe Asn Ile Tyr Val Glu Ala
100 105 110

Phe Lys Glu Trp Glu Glu Asp Pro Asn Asn Pro Ala Thr Arg Thr Arg
115 120 125

Val Ile Asp Arg Phe Arg Ile Leu Asp Gly Leu Leu Glu Arg Asp Ile
130 135 140

Pro Ser Phe Asp Ile Ser Gly Phe Glu Val Pro Leu Leu Ser Val Tyr
145 150 155 160

Ala Gln Ala Ala Asn Leu His Leu Ala Ile Leu Arg Asp Ser Val Ile
165 170 175

Phe Gly Glu Arg Trp Gly Leu Thr Thr Ile Asn Val Asn Glu Asn Tyr
180 185 190

Asn Arg Leu Ile Arg His Ile Asp Glu Tyr Ala Asp His Cys Ala Asn
195 200 205

Thr Tyr Asn Arg Gly Leu Asn Asn Leu Pro Ala Ser Thr Tyr Gln Asp
210 215 220

Trp Ile Thr Tyr Asn Arg Leu Arg Arg Asp Leu Thr Leu Thr Val Leu
225 230 235 240

Asp Ile Ala Ala Phe Phe Pro Asn Tyr Asp Asn Arg Arg Tyr Pro Ile
245 250 255

Gln Pro Val Gly Gln Leu Thr Arg Glu Val Tyr Thr Asp Pro Leu Ile
260 265 270

Asn Phe Asn Pro Gln Leu Gln Ser Val Ala Gln Leu Pro Thr Phe Asn
275 280 285

Val Met Glu Ser Ser Ala Ile Arg Asn Pro His Leu Phe Asp Ile Leu
290 295 300

Asn Asn Leu Thr Ile Phe Thr Asp Trp Phe Ser Val Gly Arg Asn Phe
305 310 315 320

Tyr Trp Gly Gly His Arg Val Ile Ser Ser Leu Ile Gly Gly Gly Asn
325 330 335

Ile Thr Ser Pro Ile Tyr Gly Arg Glu Ala Asn Gln Glu Pro Pro Arg
340 345 350

Ser Phe Thr Phe Asn Gly Pro Val Phe Arg Thr Leu Ser Asn Pro Thr
355 360 365

Leu Arg Leu Leu Gln Gln Pro Trp Pro Ala Pro Pro Phe Asn Leu Arg
370 375 380

Gly Val Glu Gly Val Glu Phe Ser Thr Pro Thr Asn Ser Phe Thr Tyr
385 390 395 400

Arg Gly Arg Gly Thr Val Asp Ser Leu Thr Glu Leu Pro Pro Glu Asp
405 410 415

Asn Ser Val Pro Pro Arg Glu Gly Tyr Ser His Arg Leu Cys His Ala
420 425 430

Thr Phe Val Gln Arg Ser Gly Thr Pro Phe Leu Thr Thr Gly Val Val
435 440 445

Phe Ser Trp Thr His Arg Ser Ala Thr Leu Thr Asn Thr Ile Asp Pro
450 455 460

Glu Arg Ile Asn Gln Ile Pro Leu Val Lys Gly Phe Arg Val Trp Gly
465 470 475 480

Gly Thr Ser Val Ile Thr Gly Pro Gly Phe Thr Gly Gly Asp Ile Leu
485 490 495

Arg Arg Asn Thr Phe Gly Asp Phe Val Ser Leu Gln Val Asn Ile Asn

```
            500                 505                 510

Ser Pro Ile Thr Gln Arg Tyr Arg Leu Arg Phe Arg Tyr Ala Ser Ser
        515                 520                 525

Arg Asp Ala Arg Val Ile Val Leu Thr Gly Ala Ala Ser Thr Gly Val
    530                 535                 540

Gly Gly Gln Val Ser Val Asn Met Pro Leu Gln Lys Thr Met Glu Ile
545                 550                 555                 560

Gly Glu Asn Leu Thr Ser Arg Thr Phe Arg Tyr Thr Asp Phe Ser Asn
                565                 570                 575

Pro Phe Ser Phe Arg Ala Asn Pro Asp Ile Ile Gly Ile Ser Glu Gln
            580                 585                 590

Pro Leu Phe Gly Ala Gly Ser Ile Ser Ser Gly Glu Leu Tyr Ile Asp
        595                 600                 605

Lys Ile Glu Ile Ile Leu Ala Asp Ala Thr Phe Glu Ala Glu Ser Asp
    610                 615                 620

Leu Glu Arg Ala Gln Lys Ala Val Asn Ala Leu Phe Thr Ser Ser Asn
625                 630                 635                 640

Gln Ile Gly Leu Lys Thr Asp Val Thr Asp Tyr His Ile Asp Gln Val
                645                 650                 655

Ser Asn Leu Val Asp Cys Leu Ser Asp Glu Phe Cys Leu Asp Glu Lys
            660                 665                 670

Arg Glu Leu Ser Glu Lys Val Lys His Ala Lys Arg Leu Ser Asp Glu
        675                 680                 685

Arg Asn Leu Leu Gln Asp Pro Asn Phe Arg Gly Ile Asn Arg Gln Pro
    690                 695                 700

Asp Arg Gly Trp Arg Gly Ser Thr Asp Ile Thr Ile Gln Gly Gly Asp
705                 710                 715                 720

Asp Val Phe Lys Glu Asn Tyr Val Thr Leu Pro Gly Thr Val Asp Glu
                725                 730                 735

Cys Tyr Pro Thr Tyr Leu Tyr Gln Lys Ile Asp Glu Ser Lys Leu Lys
            740                 745                 750

Ala Tyr Thr Arg Tyr Glu Leu Arg Gly Tyr Ile Glu Asp Ser Gln Asp
        755                 760                 765

Leu Glu Ile Tyr Leu Ile Arg Tyr Asn Ala Lys His Glu Ile Val Asn
    770                 775                 780

Val Pro Gly Thr Gly Ser Leu Trp Pro Leu Ser Ala Gln Ser Pro Ile
785                 790                 795                 800

Gly Lys Cys Gly Glu Pro Asn Arg Cys Ala Pro His Leu Glu Trp Asn
                805                 810                 815

Pro Asp Leu Asp Cys Ser Cys Arg Asp Gly Glu Lys Cys Ala His His
            820                 825                 830

Ser His His Phe Thr Leu Asp Ile Asp Val Gly Cys Thr Asp Leu Asn
        835                 840                 845

Glu Asp Leu Gly Val Trp Val Ile Phe Lys Ile Lys Thr Gln Asp Gly
    850                 855                 860

His Ala Arg Leu Gly Asn Leu Glu Phe Leu Glu Glu Lys Pro Leu Leu
865                 870                 875                 880

Gly Glu Ala Leu Ala Arg Val Lys Arg Ala Glu Lys Lys Trp Arg Asp
                885                 890                 895

Lys Arg Glu Lys Leu Gln Leu Glu Thr Asn Ile Val Tyr Lys Glu Ala
            900                 905                 910

Lys Glu Ser Val Asp Ala Leu Phe Val Asn Ser Gln Tyr Asp Arg Leu
        915                 920                 925
```

```
Gln Val Asp Thr Asn Ile Ala Met Ile His Ala Ala Asp Lys Arg Val
    930                 935                 940

His Arg Ile Arg Glu Ala Tyr Leu Pro Glu Leu Ser Val Ile Pro Gly
945                 950                 955                 960

Val Asn Ala Ala Ile Phe Glu Glu Leu Glu Gly Arg Ile Phe Thr Ala
                965                 970                 975

Tyr Ser Leu Tyr Asp Ala Arg Asn Val Ile Lys Asn Gly Asp Phe Asn
            980                 985                 990

Asn Gly Leu Leu Cys Trp Asn Val Lys Gly His Val Asp Val Glu Glu
        995                 1000                1005

Gln Asn Asn His Arg Ser Val Leu Val Ile Pro Glu Trp Glu Ala Glu
    1010                1015                1020

Val Ser Gln Glu Val Arg Val Cys Pro Gly Arg Gly Tyr Ile Leu Arg
1025                1030                1035                1040

Val Thr Ala Tyr Lys Glu Gly Tyr Gly Glu Gly Cys Val Thr Ile His
                1045                1050                1055

Glu Ile Glu Asp Asn Thr Asp Glu Leu Lys Phe Ser Asn Cys Val Glu
            1060                1065                1070

Glu Glu Val Tyr Pro Asn Asn Thr Val Thr Cys Asn Asn Tyr Thr Gly
        1075                1080                1085

Thr Gln Glu Glu Tyr Glu Gly Thr Tyr Thr Ser Arg Asn Gln Gly Tyr
    1090                1095                1100

Asp Glu Ala Tyr Gly Asn Asn Pro Ser Val Pro Ala Asp Tyr Ala Ser
1105                1110                1115                1120

Val Tyr Glu Glu Lys Ser Tyr Thr Asp Gly Arg Arg Glu Asn Pro Cys
                1125                1130                1135

Glu Ser Asn Arg Gly Tyr Gly Asp Tyr Thr Pro Leu Pro Ala Gly Tyr
            1140                1145                1150

Val Thr Lys Asp Leu Glu Tyr Phe Pro Glu Thr Asp Lys Val Trp Ile
        1155                1160                1165

Glu Ile Gly Glu Thr Glu Gly Thr Phe Ile Val Asp Ser Val Glu Leu
    1170                1175                1180

Leu Leu Met Glu Glu
1185
```

(2) INFORMATION FOR SEQ ID NO:62:

(i) SEQUENCE CHARACTERISTICS:
(A) LENGTH: 47 base pairs
(B) TYPE: nucleic acid
(C) STRANDEDNESS: single
(D) TOPOLOGY: linear (xi) SEQUENCE DESCRIPTION: SEQ ID NO:62:

```
CGGGGATTAA ATAATTTACC GGCTAGCACG TATCAAGATT GGATAAC                  47
```

(2) INFORMATION FOR SEQ ID NO:63:

(i) SEQUENCE CHARACTERISTICS:
(A) LENGTH: 45 base pairs
(B) TYPE: nucleic acid
(C) STRANDEDNESS: single
(D) TOPOLOGY: linear (xi) SEQUENCE DESCRIPTION: SEQ ID NO:63:

```
CGGGGATTAA ATAATTTACC GAAAAACGTA TCAAGATTGG ATAAC                    45
```

(2) INFORMATION FOR SEQ ID NO:64:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO:64:

GGATAGCACT CATCAAAGGT ACC 23

(2) INFORMATION FOR SEQ ID NO:65:

(i) SEQUENCE CHARACTERISTICS:
(A) LENGTH: 45 base pairs
(B) TYPE: nucleic acid
(C) STRANDEDNESS: single
(D) TOPOLOGY: linear (xi) SEQUENCE DESCRIPTION: SEQ ID NO:65:

CGGGGATTAA ATAATACCGA AAAGCACGTA TCAAGATTGG ATAAC 45

(2) INFORMATION FOR SEQ ID NO:66:

(i) SEQUENCE CHARACTERISTICS:
(A) LENGTH: 45 base pairs
(B) TYPE: nucleic acid
(C) STRANDEDNESS: single
(D) TOPOLOGY: linear (xi) SEQUENCE DESCRIPTION: SEQ ID NO:66:

CGGGGATTAA ATAATTTAAA AAAGCACGTA TCAAGATTGG ATAAC 45

(2) INFORMATION FOR SEQ ID NO:67:

(i) SEQUENCE CHARACTERISTICS:
(A) LENGTH: 45 base pairs
(B) TYPE: nucleic acid
(C) STRANDEDNESS: single
(D) TOPOLOGY: linear (xi) SEQUENCE DESCRIPTION: SEQ ID NO:67:

CGGGGATTAA ATAATTTACC GAAGCACGTA TCAAGATTGG ATAAC 45

(2) INFORMATION FOR SEQ ID NO:68:

(i) SEQUENCE CHARACTERISTICS:
(A) LENGTH: 51 base pairs
(B) TYPE: nucleic acid
(C) STRANDEDNESS: single
(D) TOPOLOGY: linear (xi) SEQUENCE DESCRIPTION: SEQ ID NO:68:

GGATTAAATA ATTTACCGAA AAGCATATCA AGATTGGATA ACATATAATC G 51

(2) INFORMATION FOR SEQ ID NO:69:

(i) SEQUENCE CHARACTERISTICS:
(A) LENGTH: 51 base pairs
(B) TYPE: nucleic acid
(C) STRANDEDNESS: single
(D) TOPOLOGY: linear (xi) SEQUENCE DESCRIPTION: SEQ ID NO:69:

GGATTAAATA ATTTACCGAA AAGCACGACA AGATTGGATA ACATATAATC G 51

(2) INFORMATION FOR SEQ ID NO:70:

(i) SEQUENCE CHARACTERISTICS:
(A) LENGTH: 50 base pairs (B) TYPE: nucleic acid
(C) STRANDEDNESS: single
(D) TOPOLOGY: linear (xi) SEQUENCE DESCRIPTION: SEQ ID NO:70:

GATTCTGTAA TTTTTAGAAA GATGGGGATT GACAACGATA AATGTCAATG 50

(2) INFORMATION FOR SEQ ID NO:71:

(i) SEQUENCE CHARACTERISTICS:
(A) LENGTH: 50 base pairs
(B) TYPE: nucleic acid
(C) STRANDEDNESS: single
(D) TOPOLOGY: linear (xi) SEQUENCE DESCRIPTION: SEQ ID NO:71:

GATTCTGTAA TTTTTGGAAA GATGGGGATT GACAACGATA AATGTCAATG 50

(2) INFORMATION FOR SEQ ID NO:72:

(i) SEQUENCE CHARACTERISTICS:
(A) LENGTH: 50 base pairs
(B) TYPE: nucleic acid
(C) STRANDEDNESS: single
(D) TOPOLOGY: linear (xi) SEQUENCE DESCRIPTION: SEQ ID NO:72:

GATTCTGTAA TTTTTGGAGA AATGGGGATT GACAACGATA AATGTCAATG 50

(2) INFORMATION FOR SEQ ID NO:73:

(i) SEQUENCE CHARACTERISTICS:
(A) LENGTH: 52 base pairs
(B) TYPE: nucleic acid
(C) STRANDEDNESS: single
(D) TOPOLOGY: linear (xi) SEQUENCE DESCRIPTION: SEQ ID NO:73:

TCTGTAATTT TTGGAGAAAG AAGGATTGAC AACGATAAAT GTCAATGAAA AC 52

(2) INFORMATION FOR SEQ ID NO:74:

(i) SEQUENCE CHARACTERISTICS:
(A) LENGTH: 49 base pairs
(B) TYPE: nucleic acid
(C) STRANDEDNESS: single
(D) TOPOLOGY: linear (xi) SEQUENCE DESCRIPTION: SEQ ID NO:74:

GTAATTTTTG GAGAAAGATG GATTGACAAC GATAAATGTC AATGAAAAC 49

(2) INFORMATION FOR SEQ ID NO:75:

(i) SEQUENCE CHARACTERISTICS:
(A) LENGTH: 49 base pairs
(B) TYPE: nucleic acid
(C) STRANDEDNESS: single
(D) TOPOLOGY: linear (xi) SEQUENCE DESCRIPTION: SEQ ID NO:75:

GTAATTTTTG GAGAAAGATG GGGAAACAAC GATAAATGTC AATGAAAAC 49

(2) INFORMATION FOR SEQ ID NO:76:

(i) SEQUENCE CHARACTERISTICS:
(A) LENGTH: 49 base pairs
(B) TYPE: nucleic acid
(C) STRANDEDNESS: single -continued (D) TOPOLOGY: linear (xi) SEQUENCE DESCRIPTION: SEQ ID NO:76:

```
GTAATTTTTG GAGAAAGATG GGGATTGAAC GATAAATGTC AATGAAAAC          49
```

TRANSGENIC PLANTS EXPRESSING LEPIDOPTERAN-ACTIVE δ-ENDOTOXINS

The present invention is a continuation-in-part of U.S. patent application Ser. No. 08/757,536, filed Nov. 27, 1996, the entire contents of which is specifically incorporated herein by reference.

1.0 BACKGROUND OF THE INVENTION

1.1 Field of the Invention

The present invention relates generally to the fields of insect control. Certain embodiments concern methods and compositions comprising nucleic acid segments which encode *Bacillus thuringiensis*-derived δ-endotoxins. Disclosed are methods of altering Cry1 crystal proteins by mutagenesis of the loop regions between the α-helices of the protein's domain 1 or of the loop region between α-helix 7 of domain 1 and β-strand 1 of domain 2 to give rise to modified Cry1 proteins (Cry1*) which have improved activity against Lepidopteran insects. Various methods for making and using these recombinantly-engineered proteins and nucleic acid segments, including development of transgenic plant cells and recombinant host cells are also disclosed.

1.2 Description of the Related Art

The most widely used microbial pesticides are derived from the bacterium *Bacillus thuringiensis. B. thuringiensis* is a Gram-positive bacterium that produces crystal proteins which are specifically toxic to certain orders and species of insects. Many different strains of *B. thuringiensis* have been shown to produce insecticidal crystal proteins. Compositions including *B. thuringiensis* strains which produce insecticidal proteins have been commercially-available and used as enviromnentally-acceptable insecticides because they are quite toxic to the specific target insect, but are harmless to plants and other non-targeted organisms.

δ-endotoxins are used to control a wide range of leaf-eating caterpillars and beetles, as well as mosquitoes. *B. thuringiensis* produces a proteinaceous parasporal body or crystal which is toxic upon ingestion by a susceptible insect host. For example, *B. thuringiensis* subsp. *kurstaki* HD-1 produces a crystal inclusion comprising δ-endotoxins which are toxic to the larvae of a number of insects in the order Lepidoptera (Schnepf and Whiteley, 1981).

1.2.1 δ-Endotoxins

δ-endotoxins are a large collection of insecticidal proteins produced by *B. thuringiensis*. Over the past decade research on the structure and function of *B. thuringiensis* toxins has covered all of the major toxin categories, and while these toxins differ in specific structure and function, general similarities in the structure and function are assumed. Based on the accumulated knowledge of *B. thuringiensis* toxins, a generalized mode of action for *B. thuringiensis* toxins has been created and includes: ingestion by the insect, solubilization in the insect midgut (a combination stomach and small intestine), resistance to digestive enzymes sometimes with partial digestion actually "activating" the toxin, binding to the midgut cells, formation of a pore in the insect cells and the disruption of cellular homeostasis (English and Slatin, 1992).

1.2.2 Genes Encoding Crystal Proteins

Many of the δ-endotoxins are related to various degrees by similarities in their amino acid sequences. Historically, the proteins and the genes which encode them were classified based largely upon their spectrum of insecticidal activity. The review by Höfte and Whiteley (1989) discusses the genes and proteins that were identified in *B. thuringiensis* prior to 1990, and sets forth the nomenclature and classification scheme which has traditionally been applied to *B. thuringiensis* genes and proteins. cryI genes encode lepidopteran-toxic CryI proteins. cryII genes encode CryII proteins that are toxic to both lepidopterans and dipterans. cryIII genes encode coleopteran-toxic CryIII proteins, while cryIV genes encode dipteran-toxic CryIV proteins.

Based on the degree of sequence similarity, the proteins were further classified into subfamilies; more highly related proteins within each family were assigned divisional letters such as CryIA, CryIB, CryIC, etc. Even more closely related proteins within each division were given names such as CryIC1, CryIC2, etc.

Recently a new nomenclature has been proposed which systematically classifies the Cry proteins based upon amino acid sequence homology rather than upon insect target specificities. This classification scheme is summarized in Table 1.

TABLE 1

REVISED *B. THURINGIENSIS* δ-ENDOTOXIN NOMENCLATURE[A]

| New | Old | GenBank Accession # |
|---|---|---|
| Cry1Aa | CryIA(a) | M11250 |
| Cry1Ab | CryIA(b) | M13898 |
| Cry1Ac | CryIA(c) | M11068 |
| Cry1Ad | CryIA(d) | M73250 |
| Cry1Ae | CryIA(e) | M65252 |
| Cry1Ba | CryIB | X06711 |
| Cry1Bb | ET5 | L32020 |
| Cry1Bc | PEG5 | Z46442 |
| Cry1Bd | CryE1 | U70726 |
| Cry1Ca | CryIC | X07518 |
| Cry1Cb | CryIC(b) | M97880 |
| Cry1Da | CryID | X54160 |
| Cry1Db | PrtB | Z22511 |
| Cry1Ea | CryIE | X53985 |
| Cry1Eb | CryIE(b) | M73253 |
| Cry1Fa | CryIF | M63897 |
| Cry1Fb | PrtD | Z22512 |
| Cry1Ga | PrtA | Z22510 |
| Cry1Gb | CryH2 | U70725 |
| Cry1Ha | PrtC | Z22513 |
| Cry1Hb | | U35780 |
| Cry1Ia | CryV | X62821 |
| Cry1Ib | CryV | U07642 |
| Cry1Ja | ET4 | L32019 |
| Cry1Jb | ET1 | U31527 |
| Cry1K | | U28801 |
| Cry2Aa | CryIIA | M31738 |
| Cry2Ab | CryIIB | M23724 |
| Cry2Ac | CryIIC | X57252 |
| Cry3A | CryIIIA | M22472 |
| Cry3Ba | CryIIIB | X17123 |
| Cry3Bb | CryIIIB2 | M89794 |
| Cry3C | CryIIID | X59797 |
| Cry4A | CryIVA | Y00423 |
| Cry4B | CryIVB | X07423 |
| Cry5Aa | CryVA(a) | L07025 |
| Cry5Ab | CryVA(b) | L07026 |
| Cry5B | | U19725 |
| Cry6A | CryVIA | L07022 |
| Cry6B | CryVIB | L07024 |
| Cry7Aa | CryIIIC | M64478 |
| Cry7Ab | CryIIICb | U04367 |
| Cry8A | CryIIIE | U04364 |
| Cry8B | CryIIIG | U04365 |
| Cry8C | CryIIIF | U04366 |
| Cry9A | CryIG | X58120 |
| Cry9B | CryIX | X75019 |
| Cry9C | CryIH | Z37527 |
| Cry10A | CryIVC | M12662 |

TABLE 1-continued

REVISED *B. THURINGIENSIS* δ-ENDOTOXIN NOMENCLATURE[A]

| New | Old | GenBank Accession # |
|---|---|---|
| Cry11A | CryIVD | M31737 |
| Cry11B | Jeg80 | X86902 |
| Cry12A | CryVB | L07027 |
| Cry13A | CryVC | L07023 |
| Cry14A | CryVD | U13955 |
| Cry15A | 34kDa | M76442 |
| Cry16A | cbm71 | X94146 |
| Cry17A | cbm71 | X99478 |
| Cry18A | CryBP1 | X99049 |
| Cry19A | Jeg65 | Y08920 |
| Cyt1Aa | CytA | X03182 |
| Cyt1Ab | CytM | X98793 |
| Cyt1B | | U37196 |
| Cyt2A | CytB | Z14147 |
| Cyt2B | CytB | U52043 |

[a]Adapted from: http://epunix.biols.susx.ac.uk/Home/Neil_Crickmore/Bt/index.html 1.2.3 Crystal Proteins Find Utility as Bioinsecticides The utility of bacterial crystal proteins as insecticides was extended when the first isolation of a coleopteran-toxic *B. thuringiensis* strain was reported (Krieg et al., 1983; 1984). This strain (described in U.S. Pat. No. 4,766,203, specifically incorporated herein by reference), designated *B. thuringiensis* var. *tenebrionis*, is reported to be toxic to larvae of the coleopteran insects *Agelastica alni* (blue alder leaf beetle) and *Leptinotarsa decemlineata* (Colorado potato beetle).

U.S. Pat. No. 5,024,837 also describes hybrid *B. thuringiensis* var. *kurstaki* strains which showed activity against lepidopteran insects. U.S. Pat. No. 4,797,279 (corresponding to EP 0221024) discloses a hybrid *B. thuringiensis* containing a plasmid from *B. thuringiensis* var. *kurstaki* encoding a lepidopteran-toxic crystal protein-encoding gene and a plasmid from *B. thuringiensis tenebrionis* encoding a coleopteran-toxic crystal protein-encoding gene. The hybrid *B. thuringiensis* strain produces crystal proteins characteristic of those made by both *B. thuringiensis kurstaki* and *B. thuringiensis tenebrionis*. U.S. Pat. No. 4,910,016 (corresponding to EP 0303379) discloses a *B. thuringiensis* isolate identified as *B. thuringiensis* MT 104 which has insecticidal activity against coleopterans and lepidopterans.

1.2.4 Cry1 Endotoxins

The characterization of the lepidopteran-toxic *B. thuringiensis* Cry1Aa crystal protein, and the cloning, DNA sequencing, and expression of the gene which encodes it have been described (Schnepf and Whitely, 1981; Schnepf et al., 1985). In related publications, U.S. Pat. No. 4,448,885 and U.S. Pat. No. 4,467,036 (specifically incorporated herein by reference), the expression of the native *B. thuringiensis* Cry1Aa crystal protein in *E. coli* is disclosed.

Several cry1C genes have been described in the prior art. A cry1C gene truncated at the 3' end was isolated from *B. thuringiensis* subsp. *aizawai* 7.29 by Sanchis et al. (1988). The truncated protein exhibited toxicity towards Spodoptera species. The sequence of the truncated cry1C gene and its encoded protein was disclosed in PCT WO 88/09812 and in Sanchis et al., (1989). The sequence of a cry1C gene isolated from *B. thuringiensis* subsp. *entomocidus* 60.5 was described by Honee et al., (1988). This gene is recognized as the holotype cry1C gene by Höfte and Whiteley (1989). The sequence of a cry1C gene is also described in U.S. Pat. No. 5,126,133.

The cry1C gene from *B. thuringiensis* subsp. *aizawai* EG6346, contained on plasmids pEG315 and pEG916 described herein, encodes a Cry1C protein identical to that described in the aforementioned U.S. Pat. No. 5,126,133. The Cry1C protein described by Sanchis et al., (1989) and in PCT WO 88/09812 differs from the EG6346 Cry1C protein at several positions that can be described as substitutions within the EG6346 Cry1C protein: Cry1C N366I, W376C, P377Q, A378R, P379H, P380H, V386G, R775A.

Significantly, the amino acid positions 376–380 correspond to amino acid residues predicted to lie within the loop region between β strand 6 and β strand 7 of Cry1C, using the nomenclature adopted by Li et al. (1991) for identifying structures within Cry3A. Bioassay comparisons between the Cry1C protein of strain EG6346 and the Cry1C protein of strain *aizawai* 7.29 revealed no significant differences in insecticidal activity towards *S. exigua, T ni*, or *P. xylostella*. These results suggested that the two Cry1C proteins exhibited the same insecticidal specificity in spite of their different amino acid sequences within the predicted loop region between β strand 6 and β strand 7.

Smith and Ellar (1994) reported the cloning of a cry1C gene from *B. thuringiensis* strain HD229 and demonstrated that amino acid substitutions within the putative loop region between β strand 6 and β strand 7 ("loop β 6–7") altered the insecticidal specificity of Cry1C towards *Spodoptera frugiperda* and *Aedes aegypti* but did not improve the toxicity of Cry1C towards either insect pest. These results appeared to conflict with the aforementioned bioassay comparison between the EG6346 Cry1C protein and the *aizawai* 7.29 Cry1C protein showing no effect of amino acid substitutions within loop β 6–7 of Cry1C on insecticidal specificity. Accordingly, the cry1C gene from strain *aizawai* 7.29 was re-sequenced where variant codons for the active toxin region were reported by Sanchis et al., (1989) and in PCT WO 88/09812. The results of that sequence analysis revealed no differences in the amino acid sequences of the active toxins of Cry1C from strain EG6346 and of Cry1C from strain *aizawai* 7.29. Thus, the prior art on the Cry1C protein of strain *aizawai* 7.29, in light of the aforementioned bioassay comparisons with the Cry1C protein of strain EG6346, incorrectly taught that multiple amino acid substitutions within loop β 6–7 of Cry1C had no effect on insecticidal specificity. Recently, Smith et al., (1996) also reported unspecified sequencing errors in the *aizawai* 7.29 cry1C gene.

1.2.5 Molecular Genetic Techniques Facilitate Protein Engineering

The revolution in molecular genetics over the past decade has facilitated a logical and orderly approach to engineering proteins with improved properties. Site specific and random mutagenesis methods, the advent of polymerase chain reaction (PCR™) methodologies, and related advances in the field have permitted an extensive collection of tools for changing both amino acid sequence, and underlying genetic sequences for a variety of proteins of commercial, medical, and agricultural interest.

Following the rapid increase in the number and types of crystal proteins which have been identified in the past decade, researchers began to theorize about using such techniques to improve the insecticidal activity of various crystal proteins. In theory, improvements to δ-endotoxins should be possible using the methods available to protein engineers working in the art, and it was logical to assume that it would be possible to isolate improved variants of the wild-type crystal proteins isolated to date. By strengthening one or more of the aforementioned steps in the mode of action of the toxin, improved molecules should provide enhanced activity, and therefore, represent a breakthrough in the field. If specific amino acid residues on the protein are identified to be responsible for a specific step in the mode of action, then these residues can be targeted for mutagenesis to improve performance.

1.2.6 Structural Analyses of Crystal Proteins

The combination of structural analyses of *B. thuringiensis* toxins followed by an investigation of the function of such structures, motifs, and the like has taught that specific regions of crystal protein endotoxins are, in a general way, responsible for particular functions.

For example, the structure of Cry3A (Li et al., 1991) and Cry1Aa (Grochulski et al., 1995) illustrated that the Cry1 and Cry3 δ-endotoxins have three distinct domains. Each of these domains has, to some degree, been experimentally determined to assist in a particular function. Domain 1, for example, from Cry3B2 and Cry1Ac has been found to be responsible for ion channel activity, the initial step in formation of a pore (Walters et al., 1993, Von Tersch et al., 1994). Domains 2 and 3 have been found to be responsible for receptor binding and insecticidal specificity (Aronson et al., 1995; Caramori et al., 1991; Chen et al. 1993; de Maagd et al., 1996; Ge et al., 1991; Lee et al., 1992; Lee et al., 1995; Lu et al., 1994; Smedley and Ellar, 1996; Smith and Ellar, 1994; Rajamohan et al., 1995; Rajamohan et al., 1996; Wu and Dean, 1996). Regions in domain 3 can also impact the ion channel activity of some toxins (Chen et al., 1993, Wolfersberger et al., 1996).

1.3 Deficiencies in the Prior Art

Unfortunately, while many laboratories have attempted to make mutated crystal proteins, few have succeeded in making mutated crystal proteins with improved lepidopteran toxicity. In almost all of the examples of genetically-engineered *B. thuringiensis* toxins in the literature, the biological activity of the mutated crystal protein is no better than that of the wild-type protein, and in many cases, the activity is decreased or destroyed altogether (Almond and Dean, 1993; Aronson et al., 1995; Chen et al., 1993, Chen et al., 1995; Ge et al., 1991; Kwak et al., 1995; Lu et al., 1994; Rajamohan et al., 1995; Rajamohan et al., 1996; Smedley and Ellar, 1996; Smith and Ellar, 1994; Wolfersberger et al., 1996; Wu and Aronson, 1992). For a crystal protein having approximately 650 amino acids in the sequence of its active toxin, and the possibility of 20 different amino acids at each of these sites, the likelihood of arbitrarily creating a successful new structure is remote, even if a general function to a stretch of 250–300 amino acids can be assigned. Indeed, the above prior art with respect to crystal protein gene mutagenesis has been concerned primarily with studying the structure and function of the crystal proteins, using mutagenesis to perturb some step in the mode of action, rather than with engineering improved toxins.

Several examples, however, do exist in the prior art where improvements to biological activity were achieved by preparing a recombinant crystal protein. Angsuthanasamnbat et al. (1993) demonstrated that a stretch of amino acids in the dipteran-toxic Cry4B delta-endotoxin is proteolytically sensitive and, by repairing this site, the dipteran toxicity of this protein was increased three-fold. In contrast, the elimination of a trypsin cleavage site on the lepidopteran-toxic Cry9C protein was reported to have no effect on insecticidal activity (Lambert et al., 1996). In another example, Wu and Dean (1996) demonstrated that specific changes to amino acids at residues 481–486 (domain 2) in the coleopteran-toxic Cry3A protein increased the biological activity of this protein by 2.4-fold against one target insect, presumably by altering toxin binding. Finally, chimeric Cry1 proteins containing exchanges of domain 2 or domain 3 sequences and exhibiting improved toxicity have been reported, but there is no evidence that toxicity has been improved for more than one lepidopteran insect pest or that insecticidal activity towards other lepidopteran pests has been retained (Caramori et al., 1991; Ge et al., 1991, de Maagd et al., 1996). Based on the prior art, exchanges involving domain 2 or domain 3 would be expected to change insecticidal specificity.

The prior art also provides examples of Cry1A mutants containing mutations encoding amino acid substitutions within the predicted a helices of domain 1 (Wu and Aronson, 1992; Aronson et al., 1995, Chen et al., 1995). None of these mutations resulted in improved insecticidal activity and many resulted in a reduction in activity, particularly those encoding substitutions within the predicted helix 5 (Wu and Aronson, 1992). Extensive mutagenesis of loop regions within domain 2 have been shown to alter the insecticidal specificity of Cry1C but to not improve its toxicity towards any one insect pest (Smith and Ellar, 1994). Similarly, extensive mutagenesis of loop regions in domain 2 and of β-strand structures in domain 3 of the Cry1A proteins have failed to produce Cry1A mutants with improved toxicity (Aronson et al., 1995; Chen et al., 1993; Kwak et al., 1995; Smedley and Ellar, 1996; Rajamohan et al., 1995; Rajamohan et al., 1996). These results demonstrate the difficulty in engineering improved insecticidal proteins and illustrate that successful engineering of *B. thuringiensis* toxins does not follow simple and predictable rules.

Collectively, the limited successes in the art to develop synthetic toxins with improved insecticidal activity have stifled progress in this area and confounded the search for improved endotoxins or crystal proteins. Rather than following simple and predictable rules, the successful engineering of an improved crystal protein may involve different strategies, depending on the crystal protein being improved and the insect pests being targeted. Thus, the process is highly empirical.

Accordingly, traditional recombinant DNA technology is clearly not routine experimentation for providing improved insecticidal crystal proteins. What are lacking in the prior art are rational methods for producing genetically-engineered *B. thuringiensis* Cry1 crystal proteins that have improved insecticidal activity and, in particular, improved toxicity towards a wide range of lepidopteran insect pests.

2.0 SUMMARY OF THE INVENTION

The present invention seeks to overcome these and other drawbacks inherent in the prior art by providing genetically-engineered modified *B. thuringiensis* Cry1 δ-endotoxin genes, and in particular, cry1C genes, that encode modified crystal proteins having improved insecticidal activity against lepidopterans. Disclosed are novel methods for constructing synthetic Cry1 proteins, synthetically-modified nucleic acid sequences encoding such proteins, and compositions arising therefrom. Also provided are synthetic cry1* expression constructs and various methods of using the improved genes and vectors. In a preferred embodiment, the invention discloses and claims Cry1C* proteins and cry1C* genes which encode the modified proteins.

An isolated nucleic acid segment that encodes a polypeptide having insecticidal activity against Lepidopterans is one aspect of the invention. Such a nucleic acid segment is isolatable from *Bacillus thuringiensis* NRRL B-21590, NRRL B-21591, NRRL B-21592, NRRL B-21638, NRRL B-21639, NRRL B-21640, NRRL B-21609, or NRRL B-21610, and preferably encodes a polypeptide comprising the amino acid sequence of SEQ ID NO:2, SEQ ID NO:4, SEQ ID NO:6, SEQ ID NO:8 SEQ ID NO:10, SEQ ID NO:12, SEQ ID NO:59 or SEQ ID NO:61. Exemplary nucleic acid segments specifically hybridizes to, or comprise the nucleic acid sequence of SEQ ID NO: 1, SEQ ID NO:3, SEQ ID NO:5, SEQ ID NO:7, SEQ ID NO:9, SEQ ID NO:11, SEQ ID NO:58, or SEQ ID NO:60 or a complement thereof.

In certain embodiments, such a nucleic acid segment may be operably linked to a promoter that expresses the nucleic acid segment in a host cell. In those instances, the nucleic acid segment is typically comprised within a recombinant vector such as a plasmid, cosmid, phage, phagemid, viral, baculovirus, bacterial artificial chromosome, or yeast artificial chromsome. As such, the nucleic acid segment may be used in a recombinant expression method to prepare a recombinant polypeptide, to prepare an insect resistant transgenic plant, or to express the nucleic acid segment in a host cell.

A further aspect of the invention is a host cell which comprises one or more of the nucleic acid segment disclosed herein which encode a modified Cry1* protein. Preferred host cells include bacterial cells, such as *E. coli B. thuringiensis, B. subtilis, B. megaterium*, or Pseudomonas spp. cells, with *B. thuringiensis* NRRL B-21590, NRRL B-21591, NRRL B-21592, NRRL B-21638, NRRL B-21639, NRRL B-21640, NRRL B-21609, and NRRL B-21610 cells being highly preferred. Another preferred host cell is an eukaryotic cell such as a fungal, animal, or plant cell, with plant cells such as grain, tree, vegetable, fruit, berry, nut, grass, cactus, succulent, and ornamental plant cells being highly preferred. Transgenic plant cells such as corn, rice, tobacco, potato, tomato, flax, canola, sunflower, cotton, wheat, oat, barley, and rye cells are particularly preferred.

Host cells which produce one or more of the polypeptide having insecticidal activity against Lepidopterans, host cells which are useful in preparation of recombinant toxin polypeptides, and host cells used in the preparation of a transgenic plant or in generation of pluripotent plant cells represent important aspects of the invention. Such host cells may find particular use in the preparation of an insecticidal polypeptide formulation, such as a polypeptide that comprises the amino acid sequence of SEQ ID NO:2, SEQ ID NO:4, SEQ ID NO:6, SEQ ID NO:8, SEQ ID NO:10, SEQ ID NO:12, SEQ ID NO:59, or SEQ ID NO:61, and which is insecticidally active against Lepidopterans.

A polypeptide composition such as those described herein are particularly desirable for use in killing an insect cell, and in the preparation of an insecticidal formulation, such as a plant protective spray formulation. The polypeptide composition may be prepared by culturing a *B. thuringiensis* NRRL B-21590, NRRL B-21591, NRRL B-21592, NRRL B-21638, NRRL B-21639, NRRL B-21640, NRRL B-21609, or NRRL B-21610 cell under conditions effective to produce a *B. thuringiensis* crystal protein; and obtaining the *B. thuringiensis* crystal protein from the cell.

The polypeptide may be used in a method of killing an insect cell. This method generally involves providing to an insect cell an insecticidally-effective amount of the polypeptide composition. Typically, the insect cell is comprised within an insect, and the insect is killed by ingesting the composition directly, or alternatively by ingesting a plant coated with the composition, or ingesting a transgenic plant which expresses the polypeptide composition.

Another important embodiment of the invention is a purified antibody that specifically binds to a polypeptide having the amino acid sequence of SEQ ID NO:2, SEQ ID NO:4, SEQ ID NO:6, SEQ ID NO:8, SEQ ID NO:10, SEQ ID NO:12, SEQ ID NO:59, or SEQ ID NO:61. Such antibody compositions may be operatively attached to a detectable label, or comprised within an immunodetection kit. Such antibodies find particular use in methods for detecting an insecticidal polypeptide in a biological sample. The method generally involves contacting a biological sample suspected of containing such a polypeptide with an antibody under conditions effective to allow the formation of immunecomplexes, and detecting the immunecomplexes so formed.

A transgenic plant having incorporated into its genome a transgene that encodes a polypeptide comprising the amino sequence of SEQ ID NO:2, SEQ ID NO:4, SEQ ID NO:6, SEQ ID NO:8, SEQ ID NO:10, SEQ ID NO:12, SEQ ID NO:59, or SEQ ID NO:61 also represents an important embodiment of the present invention. Such a transgenic plant preferably comprises the nucleic acid sequence of SEQ ID NO:1, SEQ ID NO:3, SEQ ID NO:5, SEQ ID NO:7, SEQ ID NO:9, SEQ ID NO:11, SEQ ID NO:58, or SEQ ID NO:60. Progeny and seed from such a plant and its progeny are also important aspects of the invention.

A method of selecting a Cry1 polypeptide having increased insecticidal activity against a Lepidopteran insect comprising mutagenizing a population of polynucleotides to prepare a population of polypeptides encoded by said polynucleotides and testing said population of polypeptides and identifying a polypeptide having one or more modified amino acids in a loop region of domain 1 or in a loop region between domain 1 and domain 2, wherein said polypeptide has increased insecticidal activity against said insects.

Another important embodiment of the invention is a method of generating a Cry1 polypeptide having increased insecticidal activity against a Lepidopteran insect. Such a method generally involves identifying in such a polypeptide a loop region between adjacent α-helices of domain 1 or between an α-helix of domain 1 and a β strand of domain 2, then mutagenizing the polypeptide in at least one or more amino acids of one or more of the identified loop regions; and, finally, testing the mutagenized polypeptide to identify a polypeptide having increased insecticidal activity against a Lepidopteran pest.

A method of mutagenizing a Cry1 polypeptide to increase the insecticidal activity of the polypeptide against a Lepidopteran insect is also provided by the invention. This method comprises predicting in such a polypeptide a contiguous amino acid sequence encoding a loop region between adjacent α-helices of domain 1 or between an α-helix of domain 1 and a β strand of domain 2; mutagenizing one or more of these amino acid residues to produce a population of polypeptides having one or more altered loop regions; testing the population of polypeptides for insecticidal activity against Lepidopterans; and identifying a polypeptide in the population which has increased insecticidal activity against a Lepidopteran insect.

In such methods, the modified amino acid sequence preferably comprises a loop region between α helices 1 and 2a, α helices 2b and 3, α helices 3 and 4, α helices 4 and 5, α helices 5 and 6, or α helices 6 and 7 of domain 1, or between α helix 7 of domain 1 and β strand 1 of domain 2. Preferably, the loop region between α helices 1 and 2a comprises an amino acid sequence of from about amino acid 41 to about amino acid 47 of a Cry1 protein. Likewise, the loop region between α helices 2b and 3 comprises an amino acid sequence of from about amino acid 83 to about amino acid 89 of a Cry1 protein, and the loop region between α helices 3 and 4 comprises an amino acid sequence of from about amino acid 118 to about amino acid 124 of a Cry1 protein. The loop region between α helices 4 and 5 preferably comprises an amino acid sequence of from about amino acid 148 to about amino acid 156 of a Cry1 protein, while the loop region between α helices 5 and 6 comprises an amino acid sequence of from about amino acid 176 to about amino acid 85 of a Cry1 protein. The loop loop region between α helices 6 and 7 preferably comprises an amino acid sequence of from about amino acid 217 to about amino acid 222 of a Cry1 protein, while the loop region between α helix 7 of domain 1 and β strand 1 of domain 2 preferably comprises an amino acid sequence of from about amino acid 249 to about amino acid 259 of a Cry1 protein.

Exemplary Cry1 proteins include Cry1A, Cry1B, Cry1C, Cry1D, Cry1E, Cry1F, Cry1G, Cry1H, Cry1I, Cry1J, and Cry1K crystal proteins, with Cry1Aa, Cry1Ab, Cry1Ac, Cry1Ad, Cry1Ae, Cry1Ba, Cry1Bb, Cry1Bc, Cry1Ca, Cry1Cb, Cry1Da, Cry1Db, Cry1Ea, Cry1Eb, Cry1Fa, Cry1Fb, Cry1Hb, Cry1Ia, Cry1Ib, Cry1Ja, and Cry1Jb crystal proteins being highly preferred.

These loop region mutations may include changing any one or more amino acids to any other amino acid, so long as the resulting protein has increased Lepidopteran insecticidal activity. The inventors have shown that exemplary substitutions such as changing one or more arginine residues to any other amino acid results in polypeptides having increased insecticidal activity. Particularly preferred substitutions of arginine residues include those substituted by alanine, leucine, methionine, glycine or aspartic acid. Likewise, the inventors have shown that substitution of lysine residues by any other amino acid, such as an alanine residue, also results in insecticidally-activetoxins. Indeed any such modification is contemplated by the inventors to be useful, so long as the substitution, addition, deletion, or modification of one or more of the amino acid residues in the preferred loop region results in a polypeptide which has improved insecticidal activity when compared to an unmodified Cry1 polypeptide. The inventors contemplate that combinatorial mutants as described herein will find particular use in the generation of a polypeptide having one or more mutations in multiple loop regions, or alternatively, in the generation of a polypeptide having multiple mutations with a single loop region. Such combinatorial mutants, as the inventors have shown herein often result in mutagenized polypeptides which have significantly improved insecticidal activity over the wild-type unmodified sequence.

Of course, one of skill in the art will realize that these amino acid modifications need not be made in the polypeptides themselves (although chemical synthesis of such polypeptides is well-known to those of skill in the art), but may also be made via mutagenesis of a nucleic acid segment which encodes such a polypeptide. Means for such DNA mutagenesis are described herein in detail, and exemplary polypeptides constructed using such methods are described in detail in the Examples which follow herein.

2.1 Mutagenized Cry1 Genes and Polypeptides

Accordingly, the present invention provides mutagenized Cry1C protein genes and methods of making and using such genes. As used herein the term "mutagenized Cry1C protein gene(s)" means one or more genes that have been mutagenized or altered to contain one or more nucleotide sequences which are not present in the wild type sequences, and which encode mutant Cry1C crystal proteins (Cry1C*) showing improved insecticidal activity. Preferably the novel sequences comprise nucleic acid sequences in which at least one, and preferably, more than one, and most preferably, a significant number, of wild-type Cry1C nucleotides have been replaced with one or more nucleotides, or where one or more nucleotides have been added to or deleted from the native nucleotide sequence for the purpose of altering, adding, or deleting the corresponding amino acids encoded by the nucleic acid sequence so mutagenized. The desired result, therefore, is alteration of the amino acid sequence of the encoded crystal protein to provide toxins having improved or altered activity and/or specificity compared to that of the unmodified crystal protein. Modified cry1C gene sequences have been termed cry1C* by the inventors, while modified Cry1C crystal proteins encoded therein are termed Cry1C* proteins.

Contrary to the teachings of the prior art which have focused attention on the α-helices of crystal proteins as sites for genetic engineering to improve toxin activity, the present invention differs markedly by providing methods for creating modified loop regions between adjacent α-helices within one or more of the protein's domains. In a particular illustrative embodiment, the inventors have shown remarkable success in generating toxins with improved insecticidal activity using these methods. In particular, the inventors have identified unique loop regions within domain 1 of a Cry1 crystal protein which have been targeted for specific and random mutagenesis.

In a preferred embodiment, the inventors have identified the predicted loop regions between α-helices 1 and 2a; α-helices 2b and 3; α-helices 3 and 4; α-helices 4 and 5; α-helices 5 and 6, α-helices 6 and 7; and between α-helix 7 and β-strand 1 in Cry1 crystal proteins. Using Cry1C as an exemplary model, the inventors have generated amino acid substitutions within or adjacent to these predicted loop regions to produce synthetically-modified Cry1C* toxins which demonstrated improved insecticidal activity. In mutating specific residues within these loop regions, the inventors were able to produce synthetic crystal proteins which retained or possessed enhanced insecticidal activity against certain lepidopteran pests, including the beet armyworm, *S. exigua*.

Claimed is an isolated *B. thuringiensis* crystal protein that has one or more modified amino acid sequences in one or more loop regions of domain 1, or between α helix 7 of domain 1 and β strand 1 of domain 2. These synthetically-modified crystal proteins have insecticidal activity against Lepidopteran insects. The modified amino acid sequences may occur in one or more of the following loop regions: between α helices 1 and 2a, α helices 2b and 3, α helices 3 and 4, α helices 4 and 5, α helices 5 and 6, α helices 6 and 7 of domain 1, or between the α helix 7 of domain 1 and β strand 1 of domain 2.

In an illustrative embodiment, the invention encompasses modifications which may be made in or immediately adjacent to the loop region between α helices 1 and 2a of a Cry1C protein. This loop region extends from about amino acid 42 to about amino acid 46, with adjacent amino acids extending from about amino acid 39 to about amino acid 41 and from about amino acid 47 to about amino acid 49.

The invention also encompasses modifications which may be made in or immediately adjacent to the loop region between α helices 2b and 3 of a Cry1C protein. This loop region extends from about amino acid 84 to about amino acid 88, with adjacent amino acids extending from about amino acid 81 to about amino acid 83, and from about amino acid 89 to about amino acid 91.

The invention also encompasses modifications which may be made in or immediately adj acent to the loop region between α helices 3 and 4 of a Cry1C protein. This loop region extends from about amino acid 119 to about amino acid 123, with the adjacent amino acids extending from about amino acid 116 to about amino acid 118, and from about amino acid 124 to about amino acid 126.

Likewise, the invention also encompasses modifications which may be made in or immediately adjacent to the loop region between α helices 4 and 5 of a Cry1C protein. This loop region extends from about amino acid 149 to about amino acid 155, with the adjacent amino acids extending from about amino acid 146 to about amino acid 148, and from about amino acid 156 to about amino acid 158.

The invention further encompasses modifications which may be made in or immediately adjacent to the loop region between α helices 5 and 6 of a Cry1C protein. This loop region extends from about amino acid 177 to about amino acid 184, with the adjacent amino acids extending from about amino acid 174 to about amino acid 176, and from about amino acid 185 to about amino acid 187.

Another aspect of the invention encompasses modifications in the amino acid sequence which may be made in or immediately adjacent to the loop region between α helices 6 and 7 of a Cry1C protein. This loop region extends from about amino acid 218 to about amino acid 221, with the adjacent amino acids extending from about amino acid 215 to about amino acid 217, and from about amino acid 222 to about amino acid 224.

In a similar fashion, the invention also encompasses modifications in the amino acid sequence which may be made in or immediately adjacent to the loop region between α helix 7 of domain 1 and β strand 1 of domain 2 of a Cry1C protein. This loop region extends from about amino acid 250 to about amino acid 259, with the adjacent amino acids extending from about amino acid 247 to about amino acid 249, and from about amino acid 260 to about amino acid 262.

In addition to modifications of Cry1C peptides, those having benefit of the present teaching are now also able to make mutations in the loop regions of proteins which are related to Cry1C structurally. In fact, the inventors contemplate that any crystal protein or peptide having helices which are linked together by loop regions may be altered using the methods disclosed herein to produce crystal proteins having altered loop regions For example, the inventors contemplate that the particular Cry1 crystal proteins in which such modifications may be made include the Cry1A, Cry1B, Cry1C, Cry1D, Cry1E, Cry1F, Cry1G, Cry1H, Cry1I, Cry1J, and Cry1K crystal proteins which are known in the art, as well as other crystal proteins not yet described or characterized which may be classified as a Cry1 crystal protein based upon amino acid similarity to the known Cry1 proteins. Preferred Cry1 proteins presently described which are contemplated by the inventors to be modified by the methods disclosed herein for the purpose of producing crystal proteins with altered activity or specificity include, but are not limited to Cry1Aa, Cry1Ab, Cry1Ac, Cry1Ad, Cry1Ae, Cry1Ba, Cry1Bb, Cry1Bc, Cry1Ca, Cry1Cb, Cry1Da, Cry1Db, Cry1Ea, Cry1Eb, Cry1Fa, Cry1Fb, Cry1Hb, Cry1Ia, Cry1Ib, Cry1Ja, and Cry1Jb crystal proteins, with Cry1Ca crystal proteins being particularly preferred.

Modifications which may be made to these loop regions which are contemplated by the inventors to be most preferred in producing crystal proteins with improved insecticidal activity include, but are not limited to, substitution of one or more amino acids by one or more amino acids not normally found at the particular site of substitution in the wild-type protein. In particular, substitutions of one or more arginine residues by an alanine, leucine, methionine, glycine, or aspartic acid residues have been shown to be particularly useful in the production of such enhanced proteins. Likewise, the inventors have demonstrated that substitutions of one or more lysine residues contained within or immediately adjacent to the loop regions with an alanine residue produce mutant proteins which have desirable insecticidal properties not found in the parent, or wild-type protein. Particularly preferred arginine residues in the Cry1C protein include Arg86, Arg148, Arg180, Arg252, and Arg253, while a particularly preferred lysine residue in Cry1C is Lys219.

Mutant proteins which have been developed by the inventors demonstrating the efficiency and efficacy of this mutagenesis strategy include the Cry1C-R148L, Cry1C-R148M, Cry1C-R148D, Cry1C-R148A, Cry1C-R148G, and Cry1C-R180A strains described in detail herein.

Disclosed and claimed herein is a method for preparing a modified crystal protein which generally involves the steps of identifying a crystal protein having one or more loop regions between adjacent α-helices, introducing one or more mutations into at least one of those loop regions, or alternatively, into the amino acid residues immediately flanking the loop regions, and then obtaining the modified crystal protein so produced. The modified crystal proteins obtained by such a method are also important aspects of this invention.

According to the invention, base substitutions may be made in the cry1C nucleotide sequence in order to change particular amino acids within or near the predicted loop regions of Cry1C between the α-helices of domain 1. The resulting Cry1C* proteins may then be assayed for bioinsecticide activity using the techniques disclosed herein to identifying proteins having improved toxin activity.

As an illustrative embodiment, changes in three such amino acids within the loop region between α-helices 3 and 4 of domain 1 produced modified crystal proteins with enhanced insecticidal activity (Cry1C.499, Cry1C.563, Cry1C.579).

As a second illustrative embodiment, an alanine substitution for an arginine residue within or adjacent to the loop region between α-helices 4 and 5 produced a modified crystal protein with enhanced insecticidal activity (Cry1C-R148A). Although this substitution removes a potential trypsin-cleavage site within domain 1, trypsin digestion of this modified crystal protein revealed no difference in proteolytic stability from the native Cry1C protein.

As a third illustrative embodiment, an alanine substitution for an arginine residue within or adjacent to the loop region between α-helices 5 and 6, the R180A substitution in Cry1C (Cry1C-R180A) also removes a potential trypsin cleavage site in domain 1, yet this substitution has no effect on insecticidal activity. Thus, the steps in the Cry1C protein mode-of-action impacted by these amino acid substitutions have not been determined nor is it obvious what substitutions need to be made to improve insecticidal activity.

Because the structures for Cry3A and Cry1Aa show a remarkable conservation of protein tertiary structure (Grochulski et al., 1995), and because many crystal proteins show significant amino acid sequence identity to the Cry1C amino acid sequence within domain 1, including proteins of the Cry1, Cry2, Cry3, Cry4, Cry5, Cry7, Cry8, Cry9, Cry10, Cry11, Cry12, Cry13, Cry14, and Cry16 classes (Table 1), now in light of the inventors' surprising discovery, for the first time, those of skill in the art having benefit of the teachings disclosed herein will be able to broadly apply the methods of the invention to modifying a host of crystal proteins with improved activity or altered specificity. Such methods will not only be limited to the crystal proteins disclosed in Table 1, but may also been applied to any other related crystal protein, including those yet to be identified, which comprise one or more loop regions between one or more pairs of adjacent α-ahelices.

In particular, such methods may be now applied to preparation of modified crystal proteins having one or more alterations in the loop regions of domain 1. The inventors further contemplate that similar loop regions may be identified in other domains of crystal proteins which may be similarly modified through site-specific or random mutagenesis to generate toxins having improved activity, or alternatively, altered insect specificity. In certain applications, the creation of altered toxins having increased activity against one or more insects is desired. Alternatively, it may be desirable to utilize the methods described herein for creating and identifying altered crystal proteins which are active against a wider spectrum of susceptible insects. The inventors further contemplate that the creation of chimeric crystal proteins comprising one or more loop regions as described herein may be desirable for preparing "super" toxins which have the combined advantages of increased insecticidal activity and concomitant broad specificity.

In light of the present disclosure, the mutagenesis of codons encoding amino acids within or adjacent to the loop regions between the α-helices of domain 1 of these proteins may also result in the generation of a host of related insecticidal proteins having improved activity. As an illustrative example, alignment of Cry1 amino acid sequences spanning the loop region between α-helices 4 and 5 reveals that several Cry1 proteins contain an arginine residue at the position homologous to R148 of Cry1C. Since the Cry1C R148A mutant exhibits improved toxicity towards a number of lepidopteran pests, it is contemplated by the inventors that similar substitutions in these other Cry1 proteins will also yield improved insecticidal proteins. While exemplary mutations have been described for three of the loop regions which resulted in crystal proteins having improved toxicity, the inventors contemplate that mutations may also be made in other loop regions or other portions of the active toxin which will give rise to functional bioinsecticidal crystal proteins. All such mutations are considered to fall within the scope of this disclosure.

In one illustrative embodiment, mutagenized cry1C* genes are obtained which encode Cry1C* variants that are generally based upon the wild-type Cry1C sequence, but that have one or more changes incorporated into or adjacent to the loop regions in domain1. A particular example is a mutated cry1C-R148A gene (SEQ ID NO:1) that encodes a Cry1C* with an amino acid sequence of SEQ ID NO:2 in which Arginine at position 148 has been replaced by Alanine.

In a second illustrative embodiment, mutagenized cry1C* genes will encode Cry1C* variants that are generally based upon the wild-type Cry1C sequence, but that have certain changes. A particular example is a mutated cry1C-R180A gene (SEQ ID NO:5) that encodes a Cry1C* with an amino acid sequence of SEQ ID NO:6 in which Arginine at position 180 has been replaced by Alanine.

In a third illustrative embodiment, mutagenized cry1C* genes will encode Cry1C* variants that are generally based upon the wild-type Cry1C sequence, but that have certain changes. A particular example is a mutated cry1C.563 gene (SEQ ID NO:7) that encodes a Cry1C with an amino acid sequence of SEQ ID NO:8 in which mutations in nucleic acid residues 354, 361, 369, and 370, resulted in point mutations A to T, A to C, A to C, and G to A, respectively. These mutations modified the amino acid sequence at positions 118 (Glu to Asp), 121 (Asn to His), and 124 (Ala to Thr). Using the nomenclature convention described above, such a mutation could also properly be described as a Cry1C-E118D-N121H-A124T mutant.

In a fourth illustrative embodiment, mutagenized cry1C* genes will encode Cry1C* variants that are generally based upon the wild-type Cry1C sequence, but that have certain changes. A particular example is a mutated cry1C.579 gene (SEQ ID NO:9) that encodes a Cry1C* with an amino acid sequence of SEQ ID NO:10 in which mutations in nucleic acid residues 353, 369, and 371, resulted in point mutations A to T, A to T, and C to G, respectively. These mutations modified the amino acid sequence at positions 118 (Glu to Val) and 124 (Ala to Gly). Using the nomenclature convention described above, such a mutation could also properly be described as a Cry1C-E118V-A124G mutant.

In a fifth illustrative embodiment, mutagenized cry1C* genes will encode Cry1C* variants that are generally based upon the wild-type Cry1C sequence, but that have certain changes. A particular example is a mutated cry1C.499 gene (SEQ ID NO:11) that encodes a Cry1C* with an amino acid sequence of SEQ ID NO:12 in which mutations in nucleic acid residues 360 and 361 resulted in point mutations T to C and A to C, respectively. These mutations modified the amino acid sequence at position 121 (Asn to His). Using the nomenclature convention described above, such a mutation could also properly be described as a Cry1C-N121H mutant.

In a sixth illustrative embodiment, mutagenized cry1C* genes will encode Cry1C* variants that are generally based upon the wild-type Cry1C sequence, but that have certain changes. A particular example is a mutated cry1C-R148D gene (SEQ ID NO:3) that encodes a Cry1C* with an amino acid sequence of SEQ ID NO:4 in which Arg at position 148 has been replaced by Asp.

The mutated genes of the present invention are also definable by genes in which at least one or more of the codon positions contained within or adjacent to one or more loop regions between 2 or more α-helices contain one or more substituted codons. That is, they contain one or more codons that are not present in the wild-type gene at the particular site(s) of mutagenesis and that encode one or more amino acid substitutions.

In other embodiments, the mutated genes will have at least about 10%, about 15%, about 20%, about 25%, about 30%, about 35%, about 40%, about 45%, or even about 50% or more of the codon positions within a loop region between 2 α-helices substituted by one or more codons not present in the wild-type gene sequence at the particular site of mutagenesis and/or amino acid substitution. Mutated cry1C* genes wherein at least about 50%, 60%, 70%, 80%, 90% or above of the codon positions contained within a loop region between 2 α-helices have been altered are also contemplated to be useful in the practice of the present invention.

Also contemplated to fall within the scope of the invention are combinatorial mutants which contain two or more modified loop regions, or alternatively, contain two or more mutations within a single loop region, or alternatively, two or more modified loop regions with each domain containing two or more modifications. cry1C* genes wherein modifications have been made in a combination of two or more helices, e.g., α-helices 1 and 2a, α-helices 2b and 3, α-helices 3 and 4, α-helices 4 and 5, α-helices 5 and 6, α-helices 6 and 7, and/or modifications between α-helix 7 and β-strand 1, are also important aspects of the present invention.

As an illustrative example, a mutated crystal protein that the inventors designate Cry1C-R148A.563. contains an arginine to alanine substitution at position 148, as well as incorporate the mutations present in Cry1C.563. Such a mutated crystal protein would, therefore, have modified both the α 3/4 loop region and the α 4/5 loop region. For sake of clarity, an "α 3/4 loop region" is intended to mean the loop region between the 3rd and 4th α helices, while an "α 4/5 loop region" is intended to mean the loop region between the 4th and 5th α helices, etc. Other helices and their corresponding loop regions have been similarly identified throughout this specification. FIG. 1 illustrates graphically the placement of loop regions between helices for Cry1C.

Preferred mutated cry1C genes of the invention are those genes that contain certain key changes. Examples are genes that comprise amino acid substitutions from Arg to Ala or Asp (particularly at amino acid residues 86, 148, 180, 252, and 253); or Lys to Ala or Asp (particularly at amino acid residue 219).

Genes mutated in the manner of the invention may also be operatively linked to other protein-encoding nucleic acid sequences. This will generally result in the production of a fusion protein following expression of such a nucleic acid construct. Both N-terminal and C-terminal fusion proteins are contemplated.

Virtually any protein- or peptide-encoding DNA sequence, or combinations thereof, may be fused to a mutated cry1C* sequence in order to encode a fusion protein. This includes DNA sequences that encode targeting peptides, proteins for recombinant expression, proteins to which one or more targeting peptides is attached, protein subunits, domains from one or more crystal proteins, and the like.

In one aspect, the invention discloses and claims host cells comprising one or more of the modified crystal proteins disclosed herein, and in particular, cells of the novel *B. thuringiensis* strains EG12111, EG 12121, EG11811, EG11815, EG11740, EG11746, EG11822, EG11831, EG11832, and EG11747 which comprise recombinant DNA segments encoding synthetically-modified Cry1C* crystal proteins which demonstrates improved insecticidal activity against members of the Order Lepidoptera.

Likewise, the invention also discloses and claims cell cultures of *B. thuringiensis* EG12111, EG12121, EG11811, EG11815, EG11740, EG11746, EG11822, EG11831, EG11832, and EG11747. Such cell cultures may be biologically-pure cultures consisting of a single strain, or alternatively may be cell co-cultures consisting of one or more strains. Such cell cultures may be cultivated under conditions in which one or more additional *B. thuringiensis* or other bacterial strains are simultaneously co-cultured with one or more of the disclosed cultures, or alternatively, one or more of the cell cultures of the present invention may be combined with one or more additional *B. thuringiensis* or other bacterial strains following the independent culture of each. Such procedures may be useful when suspensions of cells containing two or more different crystal proteins are desired.

The subject cultures have been deposited under conditions that assure that access to the cultures will be available during the pendency of this patent application to one determined by the Commissioner of Patents and Trademarks to be entitled thereto under 37 C.F.R. §1.14 and 35 U.S.C. §122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the finishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

Cultures of the strains listed in Table 2 were deposited in the permanent collection of the Agricultural Research Service Culture Collection, Northern Regional Research Laboratory (NRRL) under the terms of the Budapest Treaty:

TABLE 2

STRAINS DEPOSITED UNDER THE TERMS OF THE BUDAPEST TREATY

| Strain | Protein/Plasmid | Accession Number | Deposit Date |
|---|---|---|---|
| *B. thuringiensis* EG11740 | Cry1C.563 | NRRL B-21590 | Jun. 25, 1996 |
| *B. thuringiensis* EG11746 | Cry1C.579 | NRRL B-21591 | Jun. 25, 1996 |
| *B. thuringiensis* EG11811 | Cry1C-R148A | NRRL B-21592 | Jun. 25, 1996 |
| *B. thuringiensis* EG11747 | Cry1C.499 | NRRL B-21609 | Aug. 2, 1996 |
| *B. thuringiensis* EG11815 | Cry1C-R180A | NRRL B-21610 | Aug. 2, 1996 |
| *B. thuringiensis* EG11822 | Cry1C-R148A | NRRL B-21638 | Oct. 28, 1996 |
| *B. thuringiensis* EG11831 | Cry1C-R148A | NRRL B-21639 | Oct. 28, 1996 |
| *B. thuringiensis* EG11832 | Cry1C-R148D | NRRL B-21640 | Oct. 28, 1996 |
| *B. thuringiensis* EG12111 | Cry1C-R148A-K219A | NRRL B-XXXXX | Nov. XX, 1997 |
| *B. thuringiensis* EG12121 | Cry1C-R148D-K219A | NRRL B-XXXXX | Nov. XX, 1997 |
| *E. coli* EG1597 | pEG597 | NRRL B-18630 | Mar. 27, 1990 |
| *E. coli* EG7529 | pEG853 | NRRL B-18631 | Mar. 27, 1990 |
| *E. coli* EG7534 | pEG854 | NRRL B-18632 | Mar. 27, 1990 |

2.2 Methods for Producing Cry1C* Protein Compositions

The modified Cry1 * crystal proteins of the present invention are preparable by a process which generally involves the steps of: (a) identifying a Cry1 crystal protein having one or more loop regions between two adjacent α helices or between an α helix and a β strand; (b) introducing one or more mutations into at least one of these loop regions; and (c) obtaining the modified Cry1* crystal protein so produced. As described above, these loop regions occur between α helices 1 and 2, α helices 2 and 3, α helices 3 and 4, α helices 4 and 5, α helices 5 and 6, and α helices 6 and 7 of domain 1 of the crystal protein, and between α helix 7 of domain 1 and the β strand 1 of domain 2.

Preferred crystal proteins which are preparable by this claimed process include the crystal proteins which have the amino acid sequence of SEQ ID NO:2, SEQ ID NO:4, SEQ ID NO:6, SEQ ID NO:8, SEQ ID NO:10, SEQ ID NO:12, SEQ ID NO:59, or SEQ ID NO:61, and most preferably, the crystal proteins which are encoded by the nucleic acid sequence of SEQ ID NO:1, SEQ ID NO:3, SEQ ID NO:5, SEQ ID NO:7, SEQ ID NO:9, SEQ ID NO:11, SEQ ID NO:58, or SEQ ID NO:60, or a nucleic acid sequence which hybridizes to the nucleic acid sequence of SEQ ID NO:1, SEQ ID NO:3, SEQ ID NO:5, SEQ ID NO:7, SEQ ID NO:9, SEQ ID NO:11, SEQ ID NO:58, or SEQ ID NO:60 under conditions of moderate to high stringency.

A second method for preparing a modified Cry1* crystal protein is a further embodiment of the invention. This method generally involves identifying a Cry1 crystal protein having one or more loop regions, introducing one or more mutations into one or more of the loop regions, and obtaining the resulting modified crystal protein. Preferred Cry1* crystal proteins preparable by either of these methods include the Cry1A*, Cry1B*, Cry1C*, Cry1D*, Cry1E*, Cry1F*, Cry1G*, Cry1H*, Cry1I*, Cry1J*, and Cry1K* crystal proteins, and more preferably, the Cry1Aa*, Cry1Ab*, Cry1Ac*, Cry1Ad*, Cry1Ae*, Cry1Ba*, Cry1Bb*, Cry1Bc*, Cry1Ca*, Cry1Cb*, Cry1Da*, Cry1Db*, Cry1Ea*, Cry1Eb*, Cry1Fa*, Cry1Fb*, Cry1Hb*, Cry1Ia*, Cry1Ib*, Cry1Ja*, and Cry1Jb* crystal proteins. Highly preferred proteins include Cry1Ca* crystal proteins, such as those comprising the amino acid sequence of SEQ ID NO:2, SEQ ID NO:4, SEQ ID NO:6, SEQ ID NO:8, SEQ ID NO:10, SEQ ID NO:12, SEQ ID NO:59, or SEQ ID NO:61, and those encoded by a nucleic acid sequence having the sequence of SEQ ID NO:1, SEQ ID NO:3, SEQ ID NO:5, SEQ ID NO:7, SEQ ID NO:9, SEQ ID NO:11, SEQ ID NO:58, or SEQ ID NO:60, or a nucleic acid sequence which hybridizes to the nucleic acid sequence of SEQ ID NO:1, SEQ ID NO:3, SEQ ID NO:5, SEQ ID NO:7, SEQ ID NO:9, SEQ ID NO:11, SEQ ID NO:58, or SEQ ID NO:60 under conditions of moderate stringency.

Amino acid, peptide and protein sequences within the scope of the present invention include, and are not limited to the sequences set forth in SEQ ID NO:2, SEQ ID NO:4, SEQ ID NO:6, SEQ ID NO:8, SEQ ID NO:10, SEQ ID NO:12, SEQ ID NO:59, and SEQ ID NO:61, and alterations in the amino acid sequences including alterations, deletions, mutations, and homologs. Compositions which comprise from about 0.5% to about 99% by weight of the crystal protein, or more preferably from about 5% to about 75%, or from about 25% to about 50% by weight of the crystal protein are provided herein. Such compositions may readily be prepared using techniques of protein production and purification well-known to those of skill, and the methods disclosed herein. Such a process for preparing a Cry1C* crystal protein generally involves the steps of culturing a host cell which expresses the Cry1C* protein (such as a *Bacillus thuringiensis* NRRL B-21590, NRRL B-21591, NRRL B-21638, NRRL B-21639, NRRL, B-21640, NRRL, B-21609, NRRL, B-21610, or NRRL B-21592 cell) under conditions effective to produce the crystal protein, and then obtaining the crystal protein so produced. The protein may be present within intact cells, and as such, no subsequent protein isolation or purification steps may be required. Alternatively, the cells may be broken, sonicated, lysed, disrupted, or plasmolyzed to free the crystal protein(s) from the remaining cell debris. In such cases, one may desire to isolate, concentrate, or further purify the resulting crystals containing the proteins prior to use, such as, for example, in the formulation of insecticidal compositions. The composition may ultimately be purified to consist almost entirely of the pure protein, or alternatively, be purified or isolated to a degree such that the composition comprises the crystal protein(s) in an amount of from between about 0.5% and about 99% by weight, or in an amount of from between about 5% and about 90% by weight, or in an amount of from between about 25% and about 75% by weight, etc.

2.3 Recombinant Vectors Expressing the Mutagenized Cry1 Genes

One important embodiment of the invention is a recombinant vector which comprises a nucleic acid segment encoding one or more *B. thuringiensis* crystal proteins having a modified amino acid sequence in one or more loop regions of domain 1, or between α helix 7 of domain 1 and β strand 1 of domain 2. Such a vector may be transferred to and replicated in a prokaryotic or eukaryotic host, with bacterial cells being particularly preferred as prokaryotic hosts, and plant cells being particularly preferred as eukaryotic hosts.

The amino acid sequence modifications may include one or more modified loop regions between α helices 1 and 2, α helices 2 and 3, α helices 3 and 4, α helices 4 and 5, α helices 5 and 6, or α helices 6 and 7 of domain 1, or between α helix 7 of domain 1 and β strand 1 of domain 2. Preferred recombinant vectors are those which contain one or more nucleic acid segments which encode modified Cry1A, Cry1B, Cry1C, Cry1D, Cry1E, Cry1F, Cry1G, Cry1H, Cry1I, Cry1J, or Cry1K crystal proteins. Particularly preferred recombinant vectors are those which contain one or more nucleic acid segments which encode modified Cry1Aa, Cry1Ab, Cry1Ac, Cry1Ad, Cry1Ae, Cry1Ba, Cry1Bb, Cry1Bc, Cry1Ca, Cry1Cb, Cry1Da, Cry1Db, Cry1Ea, Cry1Eb, Cry1Fa, Cry1Fb, Cry1Hb, Cry1Ia, Cry1Ib, Cry1Ja, or Cry1Jb crystal proteins, with modified Cry1Ca crystal proteins being particularly preferred.

In preferred embodiments, the recombinant vector comprises a nucleic acid segment encoding the amino acid sequence of SEQ ID NO:2, SEQ ID NO:4, SEQ ID NO:6, SEQ ID NO:8, SEQ ID NO:10, SEQ ID NO:12, SEQ ID NO:59, or SEQ ID NO:61. Highly preferred nucleic acid segments are those which have the sequence of SEQ ID NO:1, SEQ ID NO:3, SEQ ID NO:5, SEQ ID NO:7, SEQ ID NO:9, SEQ ID NO:11, SEQ ID NO:58, or SEQ ID NO:60.

Another important embodiment of the invention is a transformed host cell which expresses one or more of these recombinant vectors. The host cell may be either prokaryotic or eukaryotic, and particularly preferred host cells are those which express the nucleic acid segment(s) comprising the recombinant vector which encode one or more *B. thuring-*

*iensis* crystal protein comprising modified amino acid sequences in one or more loop regions of domain 1, or between α helix 7 of domain 1 and β strand 1 of domain 2. Bacterial cells are particularly preferred as prokaryotic hosts, and plant cells are particularly preferred as eukaryotic hosts.

In an important embodiment, the invention discloses and claims a host cell wherein the modified amino acid sequences comprise one or more loop regions between α helices 1 and 2, α helices 2 and 3, α helices 3 and 4, α helices 4 and 5, α helices 5 and 6 or α helices 6 and 7 of domain 1, or between α helix 7 of domain 1 and β strand 1 of domain 2. A particularly preferred host cell is one that comprises the amino acid sequence of SEQ ID NO:2, SEQ ID NO:4, SEQ ID NO:6, SEQ ID NO:8, SEQ ID NO:10, SEQ ID NO:12, SEQ ID NO:59, or SEQ ID NO:61, and more preferably, one that comprises the nucleic acid sequence of SEQ ID NO:1, SEQ ID NO:3, SEQ ID NO:5, SEQ ID NO:7, SEQ ID NO:9, SEQ ID NO:11, SEQ ID NO:58, or SEQ ID NO:60.

Bacterial host cells transformed with a nucleic acid segment encoding a modified Cry1C crystal protein according to the present invention are disclosed and claimed herein, and in particular, a *Bacillus thuringiensis* cell having the NRRL accession NRRL B-21590, NRRL B-21591, NRRL B-21592, NRRL B-21638, NRRL B-21639, NRRL B21640, NRRL B-21609, or NRRL B-21610.

In another embodiment, the invention encompasses a method of using a nucleic acid segment of the present invention that encodes a cry1C* gene. The method generally comprises the steps of: (a) preparing a recombinant vector in which the cry1C* gene is positioned under the control of a promoter; (b) introducing the recombinant vector into a host cell; (c) culturing the host cell under conditions effective to allow expression of the Cry1C* crystal protein encoded by said cry1C* gene; and (d) obtaining the expressed Cry1C* crystal protein or peptide.

A wide variety of ways are available for introducing a *B. thuringiensis* gene expressing a toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger RNA, particularly by using an active promoter, as well as by employing sequences, which enhance the stability of the messenger RNA. The transcriptional and translational termination region will involve stop codon(s), a terminator region, and optionally, a polyadenylation signal. A hydrophobic "leader" sequence may be employed at the amino terminus of the translated polypeptide sequence in order to promote secretion of the protein across the inner membrane.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, more preferably at least about 1000 bp, and usually not more than about 2000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lost the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the λL and λR promoters, the tac promoter, the naturally-occurring promoters associated with the δ-endotoxin gene, where functional in the host. See for example, U.S. Pat. No. 4,332,898; U.S. Pat. No. 4,342,832; and U.S. Pat. No. 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pR01614, and the like. See for example, Olson et al. (1982); Bagdasarian et al. (1981), Baum et al., 1990, and U.S. Pat. No. 4,356,270; 4,362,817; 4,371,625, and 5,441,884, each incorporated specifically herein by reference.

The *B. thuringiensis* gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity. If desired, unwanted or ancillary DNA sequences may be selectively removed from the recombinant bacterium by employing site-specific recombination systems, such as those described in U.S. Pat. No. 5,441,884 (specifically incorporated herein by reference).

2.4 Synthetic Cry1C* DNA Segments

A *B. thuringiensis* cry1* gene encoding a crystal protein having insecticidal activity against Lepidopteran insects comprising a modified amino acid sequence in one or more loop regions of domain 1 or in a loop region between domain 1 and domain 2 represents an important aspect of the invention. Preferably, the cry1* gene encodes an amino acid sequence in which one or more loop regions have been modified for the purpose of altering the insecticidal activity of the crystal protein. As described above, such loop domains include those between α helices 1 and 2, α helices 2 and 3, α helices 3 and 4, α helices 4 and 5, α helices 5 and 6, or α helices 6 and 7 of domain 1, or between α helix 7 of domain 1 and β strand 1 of domain 2 (FIG. 1). Preferred cry1* genes of the invention include cry1A*, cry1B*, cry1C*, cry1D*, cry1E*, cry1F*, cry1G*, cry1H*, cry1I*, cry1J*, and cry1K* genes, with cry1Aa*, cry1Ab*, cry1Ac*, cry1Ad*, cry1Ae*, cry1Ba*) cry1Bb*, cry1Bc*, cry1Ca*, cry1Cb*, cry1Da*, cry1Db*, crylEa*, cry1Eb*, cry1Fa*, cry1Fb*, cry1Hb*, cry1Ia*, cry1Ib*, cry1Ja*, and cry1Jb* genes being highly preferred.

In accordance with the present invention, nucleic acid sequences include and are not limited to DNA, including and not limited to cDNA and genomic DNA, genes; RNA, including and not limited to mRNA and tRNA; antisense sequences, nucleosides, and suitable nucleic acid sequences such as those set forth in SEQ ID NO:1, SEQ ID NO:3, SEQ ID NO:5, SEQ ID NO:7, SEQ ID NO:9, SEQ ID NO:11, SEQ ID NO:58, and SEQ ID NO:60 and alterations in the nucleic acid sequences including alterations, deletions, mutations, and homologs capable of expressing the *B. thuringiensis* modified toxins of the present invention.

In an illustrative embodiment, the inventors used the methods described herein to produce modified cry1Ca* genes which had improved insecticidal activity against lepidopterans. In these illustrative examples, loop regions were modified by changing one or more arginine residues to alanine or aspartic acid residues, such as mutations at arginine residues Arg148 and Arg180.

As such the present invention also concerns DNA segments, that are free from total genomic DNA and that encode the novel synthetically-modified crystal proteins disclosed herein. DNA segments encoding these peptide species may prove to encode proteins, polypeptides, subunits, fuinctional domains, and the like of crystal protein-related or other non-related gene products. In addition these DNA segments may be synthesized entirely in vitro using methods that are well-known to those of skill in the art.

As used herein, the term "DNA segment" refers to a DNA molecule that has been isolated free of total genomic DNA of a particular species. Therefore, a DNA segment encoding a crystal protein or peptide refers to a DNA segment that contains crystal protein coding sequences yet is isolated away from, or purified free from, total genomic DNA of the species from which the DNA segment is obtained, which in the instant case is the genome of the Gram-positive bacterial genus, Bacillus, and in particular, the species of Bacillus known as *B. thuringiensis*. Included within the term "DNA segment", are DNA segments and smaller fragments of such segments, and also recombinant vectors, including, for example, plasmids, cosmids, phagemids, phage, viruses, and the like.

Similarly, a DNA segment comprising an isolated or purified crystal protein-encoding gene refers to a DNA segment which may include in addition to peptide encoding sequences, certain other elements such as, regulatory sequences, isolated substantially away from other naturally occurring genes or protein-encoding sequences. In this respect, the term "gene" is used for simplicity to refer to a functional protein-, polypeptide- or peptide-encoding unit. As will be understood by those in the art, this functional term includes both genomic sequences, operon sequences and smaller engineered gene segments that express, or may be adapted to express, proteins, polypeptides or peptides.

"Isolated substantially away from other coding sequences" means that the gene of interest, in this case, a gene encoding a bacterial crystal protein, forms the significant part of the coding region of the DNA segment, and that the DNA segment does not contain large portions of naturally-occurring coding DNA, such as large chromosomal fragments or other functional genes or operon coding regions. Of course, this refers to the DNA segment as originally isolated, and does not exclude genes, recombinant genes, synthetic linkers, or coding regions later added to the segment by the hand of man.

Particularly preferred DNA sequences are those encoding Cry1C-R148A, Cry1CR148D, Cry1C-R180A, Cry1C.499, Cry1C.563 or Cry1C.579 crystal proteins, and in particular cry1C* genes such as cry1C-R148A, cry1C-R148D, cry1C-R180A, cry1C.499, cry1C.563 and cry1C.579 nucleic acid sequences. In particular embodiments, the invention concerns isolated DNA segments and recombinant vectors incorporating DNA sequences that encode a Cry peptide species that includes within its amino acid sequence an amino acid sequence essentially as set forth in SEQ ID NO:2, SEQ ID NO:4, SEQ ID NO:6, SEQ ID NO:8, SEQ ID NO:10, SEQ ID NO:12, SEQ ID NO:59, or SEQ ID NO:61.

The term "a sequence essentially as set forth in SEQ ID NO:2, SEQ ID NO:4, SEQ ID NO:6, SEQ ID NO:8, SEQ ID NO:10, SEQ ID NO:12, SEQ ID NO:59, or SEQ ID NO:61" means that the sequence substantially corresponds to a portion of the sequence of SEQ ID NO:2, SEQ ID NO:4, SEQ ID NO:6, SEQ ID NO:8, SEQ ID NO:10, SEQ ID NO:12, SEQ ID NO:59, or SEQ ID NO:61, and has relatively few amino acids that are not identical to, or a biologically functional equivalent of, the amino acids of any of these sequences. The term "biologically functional equivalent" is well understood in the art and is further defined in detail herein (e.g., see Illustrative Embodiments). Accordingly, sequences that have between about 70% and about 80%, or more preferably between about 81% and about 90%, or even more preferably between about 91% and about 99% amino acid sequence identity or functional equivalence to the amino acids of SEQ ID NO:2, SEQ ID NO:4, SEQ ID NO:6, SEQ ID NO:8, SEQ ID NO:10, SEQ ID NO:12, SEQ ID NO:59, or SEQ ID NO:61will be sequences that are "essentially as set forth in SEQ ID NO:2, SEQ ID NO:4, SEQ ID NO:6 SEQ ID NO:8, SEQ ID NO:10, SEQ ID NO:12, SEQ ID NO:59, or SEQ ID NO:61."

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, ie., introns, which are known to occur within genes.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared that include a short contiguous stretch encoding the peptide sequence disclosed in SEQ ID NO:2, SEQ ID NO:4, SEQ ID NO:6, SEQ ID NO:8, SEQ ID NO:10, SEQ ID NO:12, SEQ ID NO:59, or SEQ ID NO:61, or that are identical to or complementary to DNA sequences which encode the peptide disclosed in SEQ ID NO:2, SEQ ID NO:4, SEQ ID NO:6, SEQ ID NO:8, SEQ ID NO:10, SEQ ID NO:12, SEQ ID NO:59, or SEQ ID NO:61, and particularly the DNA segments disclosed in SEQ ID NO:1, SEQ ID NO:3, SEQ ID NO:5, SEQ ID NO:7, SEQ ID NO:9, SEQ ID NO:11, SEQ ID NO:58, and SEQ ID NO:60. For example, DNA sequences such as about 14 nucleotides, and that are up to about 10,000, about 5,000, about 3,000, about 2,000, about 1,000, about 500, about 200, about 100, about 50, and about 14 base pairs in length (including all intermediate lengths) are also contemplated to be useful.

It will be readily understood that "intermediate lengths", in these contexts, means any length between the quoted ranges, such as 14, 15, 16, 17, 18, 19, 20, etc.; 21, 22, 23, etc.; 30, 31, 32, etc.; 50, 51, 52, 53, etc.; 100, 101, 102, 103, etc.; 150, 151, 152, 153, etc.; including all integers through the 200–500; 500–1,000; 1,000–2,000; 2,000–3,000; 3,000–5,000; and up to and including sequences of about 10,000 nucleotides and the like.

It will also be understood that this invention is not limited to the particular nucleic acid sequences which encode peptides of the present invention, or which encode the amino acid sequence of SEQ ID NO:2, SEQ ID NO:4, SEQ ID NO:6, SEQ ID NO:8, SEQ ID NO:10, SEQ ID NO:12, SEQ ID NO:59, or SEQ ID NO:61, including the DNA sequences which are particularly disclosed in SEQ ID NO:1, SEQ ID NO:3, SEQ ID NO:5, SEQ ID NO:7, SEQ ID NO:9, SEQ ID NO:11, SEQ ID NO:58, or SEQ ID NO:60. Recombinant vectors and isolated DNA segments may therefore variously include the peptide-coding regions themselves, coding regions bearing selected alterations or modifications in the basic coding region, or they may encode larger polypeptides that nevertheless include these peptide-coding regions or may encode biologically functional equivalent proteins or peptides that have variant amino acids sequences.

The DNA segments of the present invention encompass biologically-functional, equivalent peptides. Such sequences may arise as a consequence of codon redundancy and functional equivalency that are known to occur naturally within nucleic acid sequences and the proteins thus encoded. Alternatively, functionally-equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine activity at the molecular level.

If desired, one may also prepare fusion proteins and peptides, e.g., where the peptide-coding regions are aligned within the same expression unit with other proteins or peptides having desired functions, such as for purification or immunodetection purposes (e.g., proteins that may be purified by affinity chromatography and enzyme label coding regions, respectively).

Recombinant vectors form further aspects of the present invention. Particularly useful vectors are contemplated to be those vectors in which the coding portion of the DNA segment, whether encoding a full-length protein or smaller peptide, is positioned under the control of a promoter. The promoter may be in the form of the promoter that is naturally associated with a gene encoding peptides of the present invention, as may be obtained by isolating the 5' non-coding sequences located upstream of the coding segment or exon, for example, using recombinant cloning and/or PCR™ technology, in connection with the compositions disclosed herein.

2.5 Recombinant Vectors and Protein Expression

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DNA segment encoding a crystal protein or peptide in its natural environment. Such promoters may include promoters normally associated with other genes, and/or promoters isolated from any bacterial, viral, eukaryotic, or plant cell. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the Pichia expression vector system (Pharmacia LKB Biotechnology).

In connection with expression embodiments to prepare recombinant proteins and peptides, it is contemplated that longer DNA segments will most often be used, with DNA segments encoding the entire peptide sequence being most preferred. However, it will be appreciated that the use of shorter DNA segments to direct the expression of crystal peptides or epitopic core regions, such as may be used to generate anti-crystal protein antibodies, also falls within the scope of the invention. DNA segments that encode peptide antigens from about 8 to about 50 amino acids in length, or more preferably, from about 8 to about 30 amino acids in length, or even more preferably, from about 8 to about 20 amino acids in length are contemplated to be particularly useful. Such peptide epitopes may be amino acid sequences which comprise contiguous amino acid sequence from SEQ ID NO:2, SEQ ID NO:4, SEQ ID NO:6, SEQ ID NO:8, SEQ ID NO:10, SEQ ID NO:12, SEQ ID NO:59, or SEQ ID NO:61.

2.6 Methods for Preparing Mutagenized Cry1* Gene Segments

The present invention encompasses both site-specific mutagenesis methods and random mutagenesis of a nucleic acid segment encoding one of the crystal proteins described herein. In particular, methods are disclosed for the random mutagenesis of nucleic acid segments encoding the amino acid sequences identified as being in, or immediately adjacent to, a loop region of domain 1 of the crystal protein, or between the last α helix of domain one and the first β strand of domain 2. The mutagenesis of this nucleic acid segment results in one or more modifications to one or more loop regions of the encoded crystal protein. Using the assay methods described herein, one may then identify mutants arising from this procedure which have improved insecticidal properties or altered specificity, either intraorder or interorder.

In a preferred embodiment, the randomly-mutagenized contiguous nucleic acid segment encodes an amino acid sequence in a loop region of domain 1 or a modified amino acid sequence in a loop region between domain 1 and domain 2 of a *B. thuringiensis* crystal protein having insecticidal activity against Lepidopteran insects. Preferably, the modified amino acid sequence comprises a loop region between α helices 1 and 2, α helices 2 and 3, α helices 3 and 4, α helices 4 and 5, α helices 5 and 6, or α helices 6 and 7 of domain 1, or between α helix 7 of domain 1 and β strand 1 of domain 2. Preferred crystal proteins include Cry1A, Cry1B, Cry1C, Cry1D, Cry1E, Cry1F, Cry1G, Cry1H, Cry1I, Cry1J, and Cry1K crystal protein, with Cry1Aa, Cry1Ab, Cry1Ac, Cry1Ad, Cry1Ae, Cry1Ba, Cry1Bb, Cry1Bc, Cry1Ca, Cry1Cb, Cry1Da, Cry1Db, Cry1Ea, Cry1Eb, Cry1Fa, Cry1Fb, Cry1Hb, Cry1Ia, Cry1Ib, Cry1Ja, and Cry1Jb crystal proteins being particularly preferred.

In an illustrative embodiment, a nucleic acid segment (SEQ ID NO:7).encoding a Cry1Ca crystal protein was mutagenized in a region corresponding to about amino acid residue 118 to about amino acid residue 124 of the Cry1Ca protein (SEQ ID NO:8). The modified Cry1Ca* resulting from the mutagenesis was termed, Cry1C.563.

In a second illustrative embodiment, a nucleic acid segment (SEQ ID NO:9).encoding a Cry1Ca crystal protein was mutagenized in a region corresponding to about amino acid residue 118 to about amino acid residue 124 of the Cry1Ca protein (SEQ ID NO:10). The modified Cry1Ca* resulting from the mutagenesis was termed, Cry1C.579.

In a third illustrative embodiment, a nucleic acid segment (SEQ ID NO:11).encoding a Cry1Ca crystal protein was mutagenized in a region corresponding to about amino acid residue 118 to about amino acid residue 124 of the Cry1Ca protein (SEQ ID N0:12). The modified Cry1Ca* resulting from the mutagenesis was termed, Cry1C.499.

The means for mutagenizing a DNA segment encoding a crystal protein having one or more loop regions in its amino acid sequence are well-known to those of skill in the art. Modifications to such loop regions may be made by random, or site-specific mutagenesis procedures. The loop region may be modified by altering its structure through the addition or deletion of one or more nucleotides from the sequence which encodes the corresponding unmodified loop region.

Mutagenesis may be performed in accordance with any of the techniques known in the art such as and not limited to synthesizing an oligonucleotide having one or more mutations within the sequence of a particular crystal protein. A "suitable host" is any host which will express Cry, such as and not limited to *Bacillus thuringiensis* and *Escherichia coli*. Screening for insecticidal activity, in the case of Cry1C includes and is not limited to lepidopteran-toxic activity which may be screened for by techniques known in the art.

In particular, site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as *E. coli* cells, and clones are selected which include recombinant vectors bearing the mutated sequence arrangement. A genetic selection scheme was devised by Kunkel et al. (1987) to enrich for clones incorporating the mutagenic oligonucleotide. Alternatively, the use of PCR™ with commercially available thermostable enzymes such as Taq polymerase may be used to incorporate a mutagenic oligonucleotide primer into an amplified DNA fragment that can then be cloned into an appropriate cloning or expression vector. The PCR™-mediated mutagenesis procedures of Tomic et al. (1990) and Upender et al. (1995) provide two examples of such protocols. A PCR™ employing a thermostable ligase in addition to a thermostable polymerase may also be used to incorporate a phosphorylated mutagenic oligonucleotide into an amplified DNA fragment that may then be cloned into an appropriate cloning or expression vector. The mutagenesis procedure described by Michael (1994) provides an example of one such protocol.

In a preferred embodiment of the invention, oligonucleotide-directed mutagenesis may be used to insert or delete amino acid residues within a loop region. For instance, this mutagenic oligonucleotide could be used to delete a proline residue (P120) within loop α 3–4 of the Cry1C protein from EG6346 or *aizawai* strain 7.29:

5'-GCATTTAAAGAATGGGAAGAAGATAATAATCC AGCAACCAGGACCAGAG-3' (SEQ ID NO:13)

Likewise, this mutagenic oligonucleotide may be used to add an alanine residue between amino acid residues N121 and N122 within loop α 3–4 of the Cry1C protein from EG6346 or *aizawai* strain 7.29:

5'-GCATTTAAAGAATGGGAAGAAGATCCTAAT GCAAATCCAGCAACCAGGACCAGAG-3' (SEQ ID NO:14)

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

A number of template dependent processes are available to amplify the target sequences of interest present in a sample. One of the best known amplification methods is the polymerase chain reaction (PCR™) which is described in detail in U. S. Pat. Nos. 4,683,195, 4,683,202 and 4,800,159, each of which is incorporated herein by reference in its entirety. Briefly, in PCR™,two primer sequences are prepared which are complementary to regions on opposite complementary strands of the target sequence. An excess of deoxynucleoside triphosphates are added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction products and the process is repeated. Preferably a reverse transcriptase PCR™ amplification procedure may be performed in order to quantify the amount of mRNA amplified. Polymerase chain reaction methodologies are well known in the art.

Another method for amplification is the ligase chain reaction (referred to as LCR), disclosed in Eur. Pat. Appl. Publ. No. 320,308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750, incorporated herein by reference in its entirety, describes an alternative method of amplification similar to LCR for binding probe pairs to a target sequence.

Qbeta Replicase, described in PCT Intl. Pat. Appl. Publ. No. PCT/US87/00880, incorporated herein by reference in its entirety, may also be used as still another amplification method in the present invention. In this method, a replicative sequence of RNA which has a region complementary to that of a target is added to a sample in the presence of an RNA polymerase. The polymerase will copy the replicative sequence which can then be detected.

An isothermal amplification method, in which restriction endonucleases and ligases are used to achieve the amplification of target molecules that contain nucleotide 5'-[α-thio] triphosphates in one strand of a restriction site (Walker et al., 1992, incorporated herein by reference in its entirety), may also be useful in the amplification of nucleic acids in the present invention.

Strand Displacement Amplification (SDA) is another method of carrying out isothermal amplification of nucleic acids which involves multiple rounds of strand displacement and synthesis, i.e. nick translation. A similar method, called Repair Chain Reaction (RCR) is another method of amplification which may be useful in the present invention and is involves annealing several probes throughout a region targeted for amplification, followed by a repair reaction in which only two of the four bases are present. The other two bases can be added as biotinylated derivatives for easy detection. A similar approach is used in SDA.

Sequences can also be detected using a cyclic probe reaction (CPR). In CPR, a probe having a 3' and 5' sequences of non-Cry1C specific DNA and middle sequence of Cry1C protein specific RNA is hybridized to DNA which is present in a sample. Upon hybridization, the reaction is treated with RNaseH, and the products of the probe identified as distinctive products generating a signal which are released after digestion. The original template is annealed to another cycling probe and the reaction is repeated. Thus, CPR involves amplifying a signal generated by hybridization of a probe to a cry1C specific expressed nucleic acid.

Still other amplification methods described in Great Britain Pat. Appl. No. 2 202 328, and in PCT Intl. Pat. Appl. Publ. No. PCT/US89/01025, each of which is incorporated herein by reference in its entirety, may be used in accordance with the present invention. In the former application, "modified" primers are used in a PCR like, template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS) (Kwoh et al., 1989; PCT Intl. Pat. Appl. Publ. No. WO 88/10315, incorporated herein by reference in its entirety), including nucleic acid sequence based amplification (NASBA) and 3SR. In NASBA, the nucleic acids can be prepared for amplification by standard phenol/chloroform extraction, heat denaturation of a sample, treatment with lysis buffer and minispin columns for isolation of DNA and RNA or guanidinium chloride extraction of RNA. These amplification techniques involve annealing a primer which has crystal protein-specific sequences. Following polymerization, DNA/RNA hybrids are digested with RNase H while double stranded DNA molecules are heat denatured again. In either case the single stranded DNA is made fully double stranded by addition of second crystal protein-specific primer, followed by polymerization. The double stranded DNA molecules are then multiply transcribed by a polymerase such as T7 or SP6. In an isothermal cyclic reaction, the RNAs are reverse transcribed into double stranded DNA, and transcribed once against with a polymerase such as T7 or SP6. The resulting products, whether truncated or complete, indicate crystal protein-specific sequences.

Eur. Pat. Appl. Publ. No. 329,822, incorporated herein by reference in its entirety, disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from resulting DNA:RNA duplex by the action of ribonuclease H (RNase H, an RNase specific for RNA in a duplex with either DNA or RNA). The resultant ssDNA is a second template for a second primer, which also includes the sequences of an RNA polymerase promoter (exemplified by T7 RNA polymerase) 5' to its homology to its template. This primer is then extended by DNA polymerase (exemplified by the large "Klenow" fragment of *E. coli* DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

PCT Intl. Pat. Appl. Publ. No. WO 89/06700, incorporated herein by reference in its entirety, disclose a nucleic acid sequence amplification scheme based on the hybridization of a promoter/primer sequence to a target single-stranded DNA ("ssDNA") followed by transcription of many RNA copies of the sequence. This scheme is not cyclic; i.e. new templates are not produced from the resultant RNA transcripts. Other amplification methods include "RACE" (Frohman, 1990), and "one-sided PCR" (Ohara, 1989) which are well-known to those of skill in the art.

Methods based on ligation of two (or more) oligonucleotides in the presence of nucleic acid having the sequence of the resulting "di-oligonucleotide", thereby amplifying the di-oligonucleotide (Wu and Dean, 1996, incorporated herein by reference in its entirety), may also be used in the amplification of DNA sequences of the present invention.

2.7 Phage-Resistant Variant

To prepare phage resistant variants of the *B. thuringiensis* mutants, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is plated in the center of the plate and allowed to dry. Resistant cultures showed no lysis in the area where the phage lysate has been placed after incubation at 30° C. for 24 hours.

2.8 Transgenic Hosts/Transformed Cells Comprising Cry1C* DNA Segments

The invention also discloses and claims host cells, both native, and genetically engineered, which express the novel cry1C* genes to produce Cry1C* polypeptides. Preferred examples of bacterial host cells include *Bacillus thuringiensis* NRRL B-21590, NRRL B-21591, NRRL B-21592, NRRL B-21638, NRRL B-21639, NRRL B-21640, NRRL B-21609. and NRRL B-21610.

Methods of using such cells to produce Cry1C* crystal proteins are also disclosed. Such methods generally involve culturing the host cell (such as *Bacillus thuringiensis* NRRL B-21590, NRRL B-21591, NRRL B-21592, NRRL B-21638, NRRL B-21639, NRRL B-21640, NRRL B-21609. or NRRL B-21610) under conditions effective to produce a Cry1C* crystal protein, and obtaining the Cry1C* crystal protein from said cell.

In yet another aspect, the present invention provides methods for producing a transgenic plant which expresses a nucleic acid segment encoding the novel recombinant crystal proteins of the present invention. The process of producing transgenic plants is well-known in the art. In general, the method comprises transforming a suitable host cell with one or more DNA segments which contain one or more promoters operatively linked to a coding region that encodes one or more of the novel *B. thuringiensis* Cry1C-R148A, Cry1C-R148G, Cry1C-R148M, Cry1C-R148L, Cry1C-R180A, Cry1C-R148D, Cry1C.499, Cry1C563 and Cry1C.579 crystal proteins. Such a coding region is generally operatively linked to a transcription-terminating region, whereby the promoter is capable of driving the transcription of the coding region in the cell, and hence providing the cell the ability to produce the recombinant protein in vivo. Alternatively, in instances where it is desirable to control, regulate, or decrease the amount of a particular recombinant crystal protein expressed in a particular transgenic cell, the invention also provides for the expression of crystal protein antisense mRNA. The use of antisense mRNA as a means of controlling or decreasing the amount of a given protein of interest in a cell is well-known in the art.

Another aspect of the invention comprises a transgenic plant which express a gene or gene segment encoding one or more of the novel polypeptide compositions disclosed herein. As used herein, the term "transgenic plant" is intended to refer to a plant that has incorporated DNA sequences, including but not limited to genes which are perhaps not normally present, DNA sequences not normally transcribed into RNA or translated into a protein ("expressed"), or any other genes or DNA sequences which one desires to introduce into the non-transformed plant, such as genes which may normally be present in the non-transformed plant but which one desires to either genetically engineer or to have altered expression.

It is contemplated that in some instances the genome of a transgenic plant of the present invention will have been augmented through the stable introduction of one or more Cry1C-R148A-, Cry1C-R148D-, Cry1C-R148G, Cry1C-R148M, Cry1C-R148L, Cry1C-R180A- Cry1C.499-, Cry1C.563-, or Cry1C.579-encoding transgenes, either native, synthetically modified, or mutated. In some instances, more than one transgene will be incorporated into the genome of the transformed host plant cell. Such is the case when more than one crystal protein-encoding DNA segment is incorporated into the genome of such a plant. In certain situations, it may be desirable to have one, two, three, four, or even more *B. thuringiensis* crystal proteins (either native or recombinantly-engineered) incorporated and stably expressed in the transformed transgenic plant.

A preferred gene which may be introduced includes, for example, a crystal protein-encoding a DNA sequence from bacterial origin, and particularly one or more of those described herein which are obtained from Bacillus spp. Highly preferred nucleic acid sequences are those obtained from *B. thuringiensis*, or any of those sequences which have been genetically engineered to decrease or increase the insecticidal activity of the crystal protein in such a transformed host cell.

Means for transforming a plant cell and the preparation of a transgenic cell line are well-known in the art, and are discussed herein. Vectors, plasmids, cosmids, YACs (yeast artificial chromosomes) and DNA segments for use in transforming such cells will, of course, generally comprise either the operons, genes, or gene-derived sequences of the present invention, either native, or synthetically-derived, and particularly those encoding the disclosed crystal proteins. These DNA constructs can further include structures such as promoters, enhancers, polylinkers, or even gene sequences which have positively- or negatively-regulating activity upon the particular genes of interest as desired. The DNA segment or gene may encode either a native or modified crystal protein, which will be expressed in the resultant recombinant cells, and/or which will impart an improved phenotype to the regenerated plant.

Such transgenic plants may be desirable for increasing the insecticidal resistance of a monocotyledonous or dicotyledonous plant, by incorporating into such a plant, a transgenic DNA segment encoding a Cry1C-R148A, Cry1C-R148D, Cry1C-R148G, Cry1C-R148L, Cry1C-R148M, Cry1C-R180A, Cry1C.499, Cry1C.563, and/or Cry1C.579 crystal protein which is toxic to lepidopteran insects. Particularly preferred plants include grains such as corn, wheat, barley, maize, and oats; legumes such as soybeans; cotton; turf and pasture grasses; ornamental plants; shrubs; trees; vegetables, berries, fruits, and other commercially-important crops including garden and houseplants.

In a related aspect, the present invention also encompasses a seed produced by the transformed plant, a progeny from such seed, and a seed produced by the progeny of the original transgenic plant, produced in accordance with the above process. Such progeny and seeds will have one or more crystal protein transgene(s) stably incorporated into its genome, and such progeny plants will inherit the traits afforded by the introduction of a stable transgene in Mendelian fashion. All such transgenic plants having incorporated into their genome transgenic DNA segments encoding one or more Cry1C-R148A, Cry1C-R148D, Cry1C-R148G, Cry1C-R148M, Cry1C-R148L, Cry1C-R180A, Cry1C.499, Cry1C.563 or Cry1C.579 crystal proteins or polypeptides are aspects of this invention. Particularly preferred transgenes for the practice of the invention include nucleic acid segments comprising one or more cry1C-R148A, cry1C-R148D, cry1CR148G, cry1C-R148M, cry1C-R148L, cry1C-R180A, cry1C.499, cry1C563 or cry1C.579 gene(s).

2.9 Crystal Protein Compositions as Insecticides and Methods of Use

The inventors contemplate that the crystal protein compositions disclosed herein will find particular utility as insecticides for topical and/or systemic application to field crops, grasses, fruits and vegetables, and ornamental plants.

Disclosed and claimed is a composition comprising an insecticidally-effective amount of a Cry1C* crystal protein composition. The composition preferably comprises the amino acid sequence of SEQ ID NO:2, SEQ ID NO:4, SEQ ID NO:6, SEQ ID NO:8, SEQ ID NO:10, SEQ ID NO:12, SEQ ID NO:59, or SEQ ID NO:61 or biologically-functional equivalents thereof. The insecticide composition may also comprise a Cry1C* crystal protein that is encoded by a nucleic acid sequence having the sequence of SEQ ID NO:1, SEQ ID NO:3, SEQ ID NO:5, SEQ ID NO:7, SEQ ID NO:9, SEQ ID NO:11, SEQ ID NO:58, or SEQ ID NO:60, or, alternatively, a nucleic acid sequence which hybridizes to the nucleic acid sequence of SEQ ID NO:1, SEQ ID NO:3, SEQ ID NO:5, SEQ ID NO:7, SEQ ID NO:9, SEQ ID NO:11, SEQ ID NO:58, or SEQ ID NO:60 under conditions of moderate stringency.

The insecticide comprises a *Bacillus thuringiensis* NRRL B-21590, NRRL B21591, NRRL B-21592, NRRL B-21638, NRRL B-21639, NRRL B-21640, NRRL B-21609, or NRRL B-21610 cell, or a culture of these cells, or a mixture of one or more *B. thuringiensis* cells which express one or more of the novel crystal proteins of the invention. In certain aspects it may be desirable to prepare compositions which contain a plurality of crystal proteins, either native or modified, for treatment of one or more types of susceptible insects.

The inventors contemplate that any formulation methods known to those of skill in the art may be employed using the proteins disclosed herein to prepare such bioinsecticide compositions. It may be desirable to formulate whole cell preparations, cell extracts, cell suspensions, cell homogenates, cell lysates, cell supernatants, cell filtrates, or cell pellets of a cell culture (preferably a bacterial cell culture such as a *Bacillus thuringiensis* NRRL B-21590, NRRL B-21591, NRRL B-21592, NRRL B-21638, NRRL B-21639, NRRL B-21640, NRRL B-21609, or NRRL B-21610 culture) that expresses one or more cry1C* DNA segments to produce the encoded Cry1C* protein(s) or peptide(s). The methods for preparing such formulations are known to those of skill in the art, and may include, e.g., desiccation, lyophilization, homogenization, extraction, filtration, centrifugation, sedimentation, or concentration of one or more cultures of bacterial cells, such as Bacillus NRRL B-21590, NRRL B-21591, NRRL B-21592, NRRL B-21638, NRRL B-21639, NRRL B-21640, NRRL B-21609, or NRRL B-21610 cells, which express the Cry1C* peptide(s) of interest.

In one preferred embodiment, the bioinsecticide composition comprises an oil flowable suspension comprising lysed or unlysed bacterial cells, spores, or crystals which contain one or more of the novel crystal proteins disclosed herein. Preferably the cells are *B. thuringiensis* cells, however, any such bacterial host cell expressing the novel nucleic acid segments disclosed herein and producing a crystal protein is contemplated to be useful, such as Bacillus spp., including *B. megaterium, B. subtilis; B. cereus*, Escherichia spp., including *E. coli*, and/or Pseudomonas spp., including *P. cepacia, P. aeruginosa*, and *P. fluorescens*. Alternatively, the oil flowable suspension may consist of a combination of one or more of the following compositions: lysed or unlysed bacterial cells, spores, crystals, and/or purified crystal proteins.

In a second preferred embodiment, the bioinsecticide composition comprises a water dispersible granule or powder. This granule or powder may comprise lysed or unlysed bacterial cells, spores, or crystals which contain one or more of the novel crystal proteins disclosed herein. Preferred sources for these compositions include bacterial cells such as *B. thuringiensis* cells, however, bacteria of the genera Bacillus, Escherichia, and Pseudomonas which have been transformed with a DNA segment disclosed herein and expressing the crystal protein are also contemplated to be useful. Alternatively, the granule or powder may consist of a combination of one or more of the following compositions: lysed or unlysed bacterial cells, spores, crystals, and/or purified crystal proteins.

In a third important embodiment, the bioinsecticide composition comprises a wettable powder, spray, emulsion, colloid, aqueous or organic solution, dust, pellet, or collodial concentrate. Such a composition may contain either unlysed or lysed bacterial cells, spores, crystals, or cell extracts as described above, which contain one or more of the novel crystal proteins disclosed herein. Preferred bacterial cells are *B. thuringiensis* cells, however, bacteria such as *B. megaterium, B. subtilis, B. cereus, E. coli*, or Pseudomonas spp. cells transformed with a DNA segment disclosed herein and expressing the crystal protein are also contemplated to be usefuil. Such dry forms of the insecticidal compositions may be formulated to dissolve immediately upon wetting, or alternatively, dissolve in a controlled-release, sustained-release, or other time-dependent manner. Alternatively, such a composition may consist of a combination of one or more of the following compositions: lysed or unlysed bacterial cells, spores, crystals, and/or purified crystal proteins.

In a fourth important embodiment, the bioinsecticide composition comprises an aqueous solution or suspension or cell culture of lysed or unlysed bacterial cells, spores, crystals, or a mixture of lysed or unlysed bacterial cells, spores, and/or crystals, such as those described above which contain one or more of the novel crystal proteins disclosed herein. Such aqueous solutions or suspensions may be provided as a concentrated stock solution which is diluted prior to application, or alternatively, as a diluted solution ready-to-apply.

For these methods involving application of bacterial cells, the cellular host containing the Crystal protein gene(s) may be grown in any convenient nutrient medium, where the DNA construct provides a selective advantage, providing for a selective medium so that substantially all or all of the cells retain the *B. thuringiensis* gene. These cells may then be harvested in accordance with conventional ways. Alternatively, the cells can be treated prior to harvesting.

When the insecticidal compositions comprise *B. thuringiensis* cells, spores, and/or crystals containing the modified crystal protein(s) of interest, such compositions may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, suspensions, emulsifiable concentrates, or the like. The ingredients may include rheological agents, surfactants, emulsifiers, dispersants, or polymers.

Alternatively, the novel Cry1C-derived mutated crystal proteins may be prepared by native or recombinant bacterial expression systems in vitro and isolated for subsequent field application. Such protein may be either in crude cell lysates, suspensions, colloids, etc., or alternatively may be purified, refined, buffered, and/or further processed, before formulating in an active biocidal formulation. Likewise, under certain circumstances, it may be desirable to isolate crystals and/or spores from bacterial cultures expressing the crystal protein and apply solutions, suspensions, or collodial preparations of such crystals and/or spores as the active bioinsecticidal composition.

Another important aspect of the invention is a method of controlling lepidopteran insects which are susceptible to the novel compositions disclosed herein. Such a method generally comprises contacting the insect or insect population, colony, etc., with an insecticidally-effective amount of a Cry1C* crystal protein composition. The method may utilize Cry1C* crystal proteins such as those disclosed in SEQ ID NO:2, SEQ ID NO:4, SEQ ID NO:6, SEQ ID NO:8, SEQ ID NO:10, SEQ ID NO:12, SEQ ID NO:59, or SEQ ID NO:61, or biologically functional equivalents thereof. Alternatively, the method may utilize one or more Cry1C* crystal proteins which are encoded by the nucleic acid sequences of SEQ ID NO:1, SEQ ID NO:3, SEQ ID NO:5, SEQ ID NO:7, SEQ ID NO:9, SEQ ID NO:11, SEQ ID NO:58, or SEQ ID NO:60, or by one or more nucleic acid sequences which hybridize to the sequences of SEQ ID NO:1, SEQ ID NO:3, SEQ ID NO:5, SEQ ID NO:7, SEQ ID NO:9, SEQ ID NO:11, SEQ ID NO:58, or SEQ ID NO:60, under conditions of moderate, or higher, stringency. The methods for identifying sequences which hybridize to those disclosed under conditions of moderate or higher stringency are well-known to those of skill in the art, and are discussed herein.

Regardless of the method of application, the amount of the active component(s) are applied at an insecticidally-effective amount, which will vary depending on such factors as, for example, the specific lepidopteran insects to be controlled, the specific plant or crop to be treated, the environmental conditions, and the method, rate, and quantity of application of the insecticidally-active composition.

The insecticide compositions described may be made by formulating either the bacterial cell, crystal and/or spore suspension, or isolated protein component with the desired agriculturally-acceptable carrier. The compositions may be formulated prior to administration in an appropriate means such as lyophilized, freeze-dried, dessicated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, e.g., inert components, dispersants, surfactants, tackifiers, binders, etc. that are ordinarily used in insecticide formulation technology; these are well known to those skilled in insecticide formulation. The formulations may be mixed with one or more solid or liquid adjuvants and prepared by various means, e.g., by homogeneously mixing, blending and/or grinding the insecticidal composition with suitable adjuvants using conventional formulation techniques.

The insecticidal compositions of this invention are applied to the environment of the target lepidopteran insect, typically onto the foliage of the plant or crop to be protected, by conventional methods, preferably by spraying. The strength and duration of insecticidal application will be set with regard to conditions specific to the particular pest(s), crop(s) to be treated and particular environmental conditions. The proportional ratio of active ingredient to carrier will naturally depend on the chemical nature, solubility, and stability of the insecticidal composition, as well as the particular formulation contemplated.

Other application techniques, e.g., dusting, sprinkling, soaking, soil injection, seed coating, seedling coating, spraying, aerating, misting, atomizing, and the like, are also feasible and may be required under certain circumstances such as e.g., insects that cause root or stalk infestation, or for application to delicate vegetation or ornamental plants. These application procedures are also well-known to those of skill in the art.

The insecticidal composition of the invention may be employed in the method of the invention singly or in combination with other compounds, including and not limited to other pesticides. The method of the invention may also be used in conjunction with other treatments such as surfactants, detergents, polymers or time-release formulations. The insecticidal compositions of the present invention may be formulated for either systemic or topical use.

The concentration of insecticidal composition which is used for environmental, systemic, or foliar application will vary widely depending upon the nature of the particular formulation, means of application, environmental conditions, and degree of biocidal activity. Typically, the bioinsecticidal composition will be present in the applied formulation at a concentration of at least about 1% by weight and may be up to and including about 99% by weight. Dry formulations of the compositions may be from about 1% to about 99% or more by weight of the composition, while liquid formulations may generally comprise from about 1% to about 99% or more of the active ingredient by weight. Formulations which comprise intact bacterial cells will generally contain from about $10^4$ to about $10^{12}$ cells/mg.

The insecticidal formulation may be administered to a particular plant or target area in one or more applications as needed, with a typical field application rate per hectare ranging on the order of from about 1 g to about 1 kg, 2 kg, 5, kg, or more of active ingredient.

2.10 Biological Functional Equivalents

Modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. In particular embodiments of the invention, mutated crystal proteins are contemplated to be useful for increasing the insecticidal activity of the protein, and consequently increasing the insecticidal activity and/or expression of the recombinant transgene in a plant cell. The amino acid changes may be achieved by changing the codons of the DNA sequence, according to the codons given in Table 3.

TABLE 3

| Amino Acid | | | Codons | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |
| Isoleucine | Ile | I | AUA | AUC | AUU | |
| Lysine | Lys | K | AAA | AAG | | |

TABLE 3-continued

| Amino Acid | | | Codons | | | | | |
|---|---|---|---|---|---|---|---|---|
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

3.0 BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. Schematic diagram of the Cry1C crystal protein from *B. thuringiensis*. α helices are depicted by the rectangles and are labeled according to the convention adopted by Li et al., (1991). Adopting the convention of Li et al, the present inventors have designated helix two as comprising two portions helix 2a and helix 2b.

Figure 2:
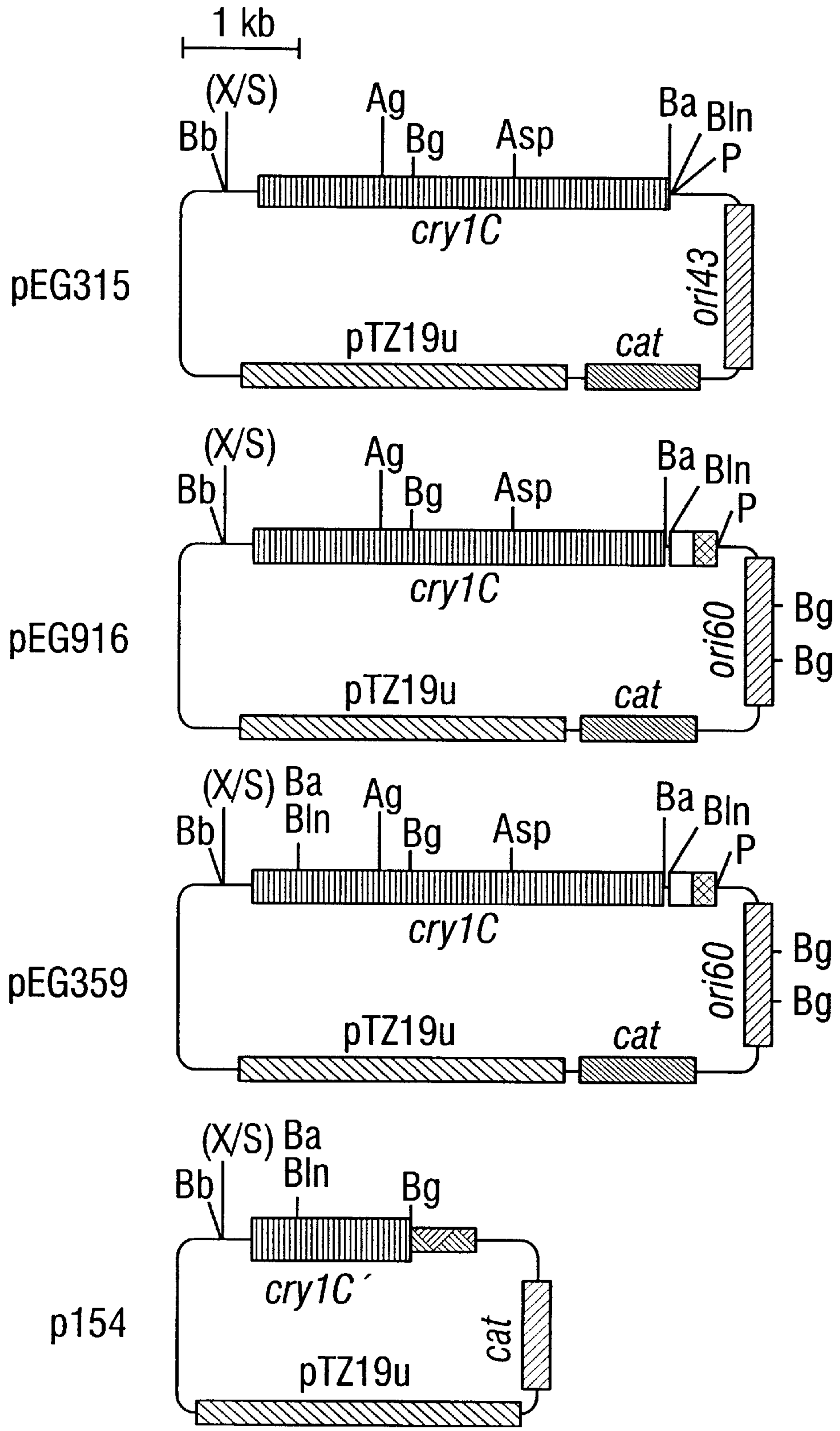

FIG. 2. Shown are the structural maps of pEG315, pEG916, pEG359, and p154. Boxed arrows and segments indicate genes or functional DNA elements. Designations: pTZ19u=*E. coli* phagemid vector pTZ19u, cat=chloramphenicol (Cml) acetyltransferase gene, ori43 and ori60=*B. thuringiensis* plasmid replication origins, cry1C =cry1C insecticidal crystal protein gene. Restriction site abbreviations: Ag=AgeI, Asp=Asp718, Ba=BamHI, Bb=BbuI, Bg=BglII, Bln=BlnI, P=PstI, S=SalI, X=XhoI. The 1 kb scale refers to only the cry1C gene segment. pEG315 gave rise to pEG 1635 and pEG1636, which contain the Arg148Ala and Arg180Ala mutations, respectively. pEG916 gave rise to pEG370, pEG373, and pEG374, which contain the cry1C.563, cry1C.579, and cry1C.499 mutations, respectively. These mutants are described in detail in Section 5.

Figure 3:
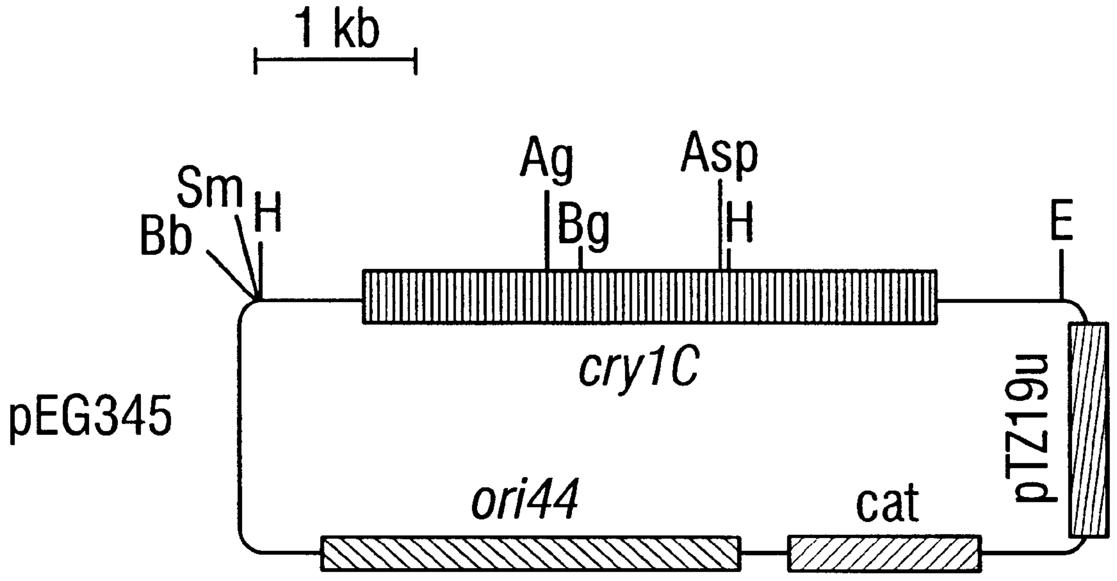

FIG. 3. Shown is the structural map of pEG345. Boxed arrows and segments indicate genes or functional DNA elements. Designations: pTZ19u=*E. coli* phagemid vector pTZ19u, cat=Cml acetyltransferase gene, ori44=*B. thuringiensis* plasmid replication origin, cry1C=cry1C insecticidal crystal protein gene. Restriction site abbreviations: Ag=AgeI, Asp=Asp718, Bb=BbuI, Bg=BglII, E=EcoRI, H=HindIII, Sm=SmaI. The 1 kb scale refers to only the cry1C gene segment.

FIG. 4. Depicted is a flow chart indicating the mutations contained within the cry1C gene encoded by pEG359 and the mutations contained within the cry1C.563, cry1C.579, and cry1C.499 genes generated by random mutagenesis.

Figure 5:
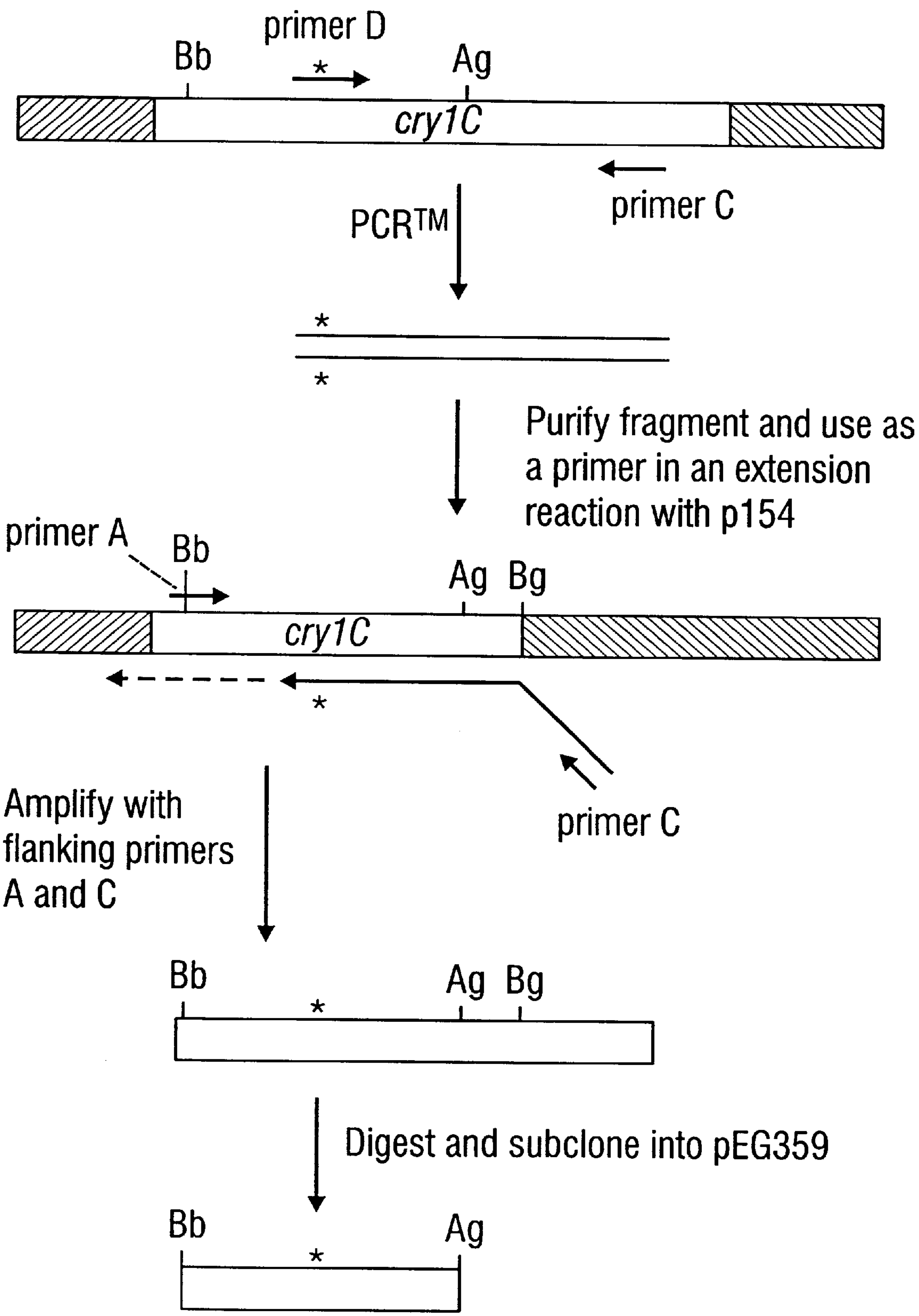

FIG. 5. Shown is the PCR™-mediated mutagenesis procedure used to generate the mutant cry1C.499, cry1C.563, and cry1C.579 genes in strains EG11747, EG11740, and EG11746, respectively. The asterisk denotes mutations incorporated into the cry1C gene sequence. Restriction sites abbreviations: Ag=AgeI, Bb=BbuI, and Bg=BglII.

FIG. 6. Shown is the alignment of a loop region of 24 related Cry1 proteins.

Figure 7A:
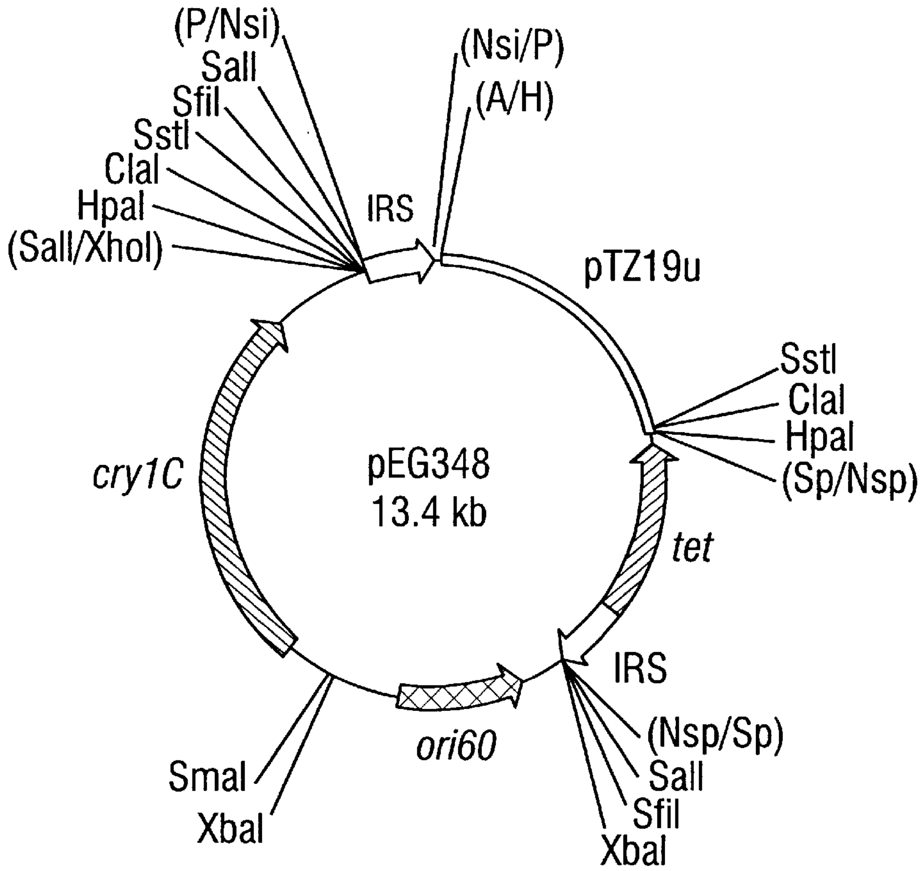
Figure 7B:
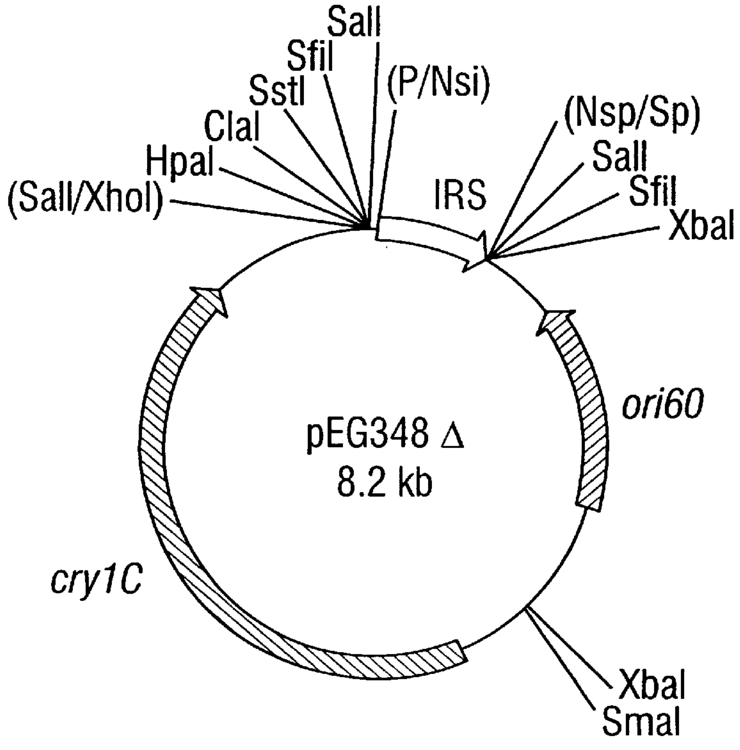

FIG. 7. Structural maps of the cry1C-encoding plasmids pEG348 and pEG348A. Boxed arrows and segments indicate genes or functional DNA elements. Designations: pTZ19u=*E. coli* phagemid vector pTZ19u, tet=tetracycline resistance gene, ori60 *B. thuringiensis* plasmid replication origin, cry1C=cry1C insecticidal crystal protein gene, IRS=DNA fragment containing the internal resolution site region of transposon Tn5401. Restriction site abbreviations: A=Asp718, H=HindIII, Nsi=NsiI, Nsp=NspI, P=PstI, Sp=SphI.

Figure 8A:
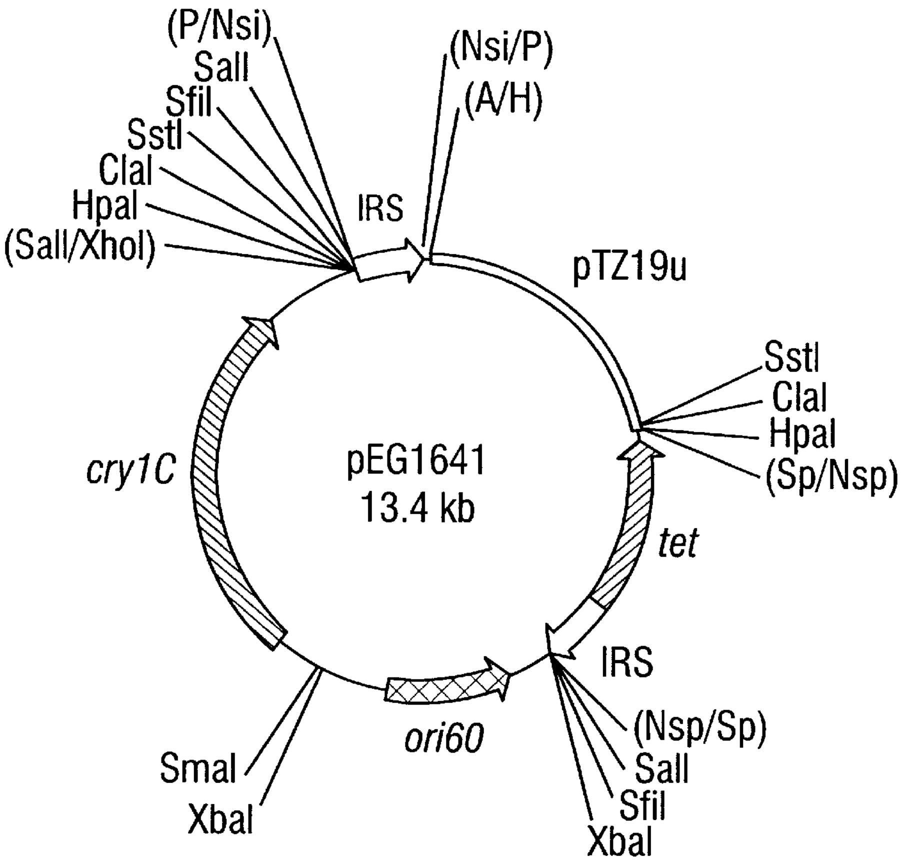
Figure 8B:
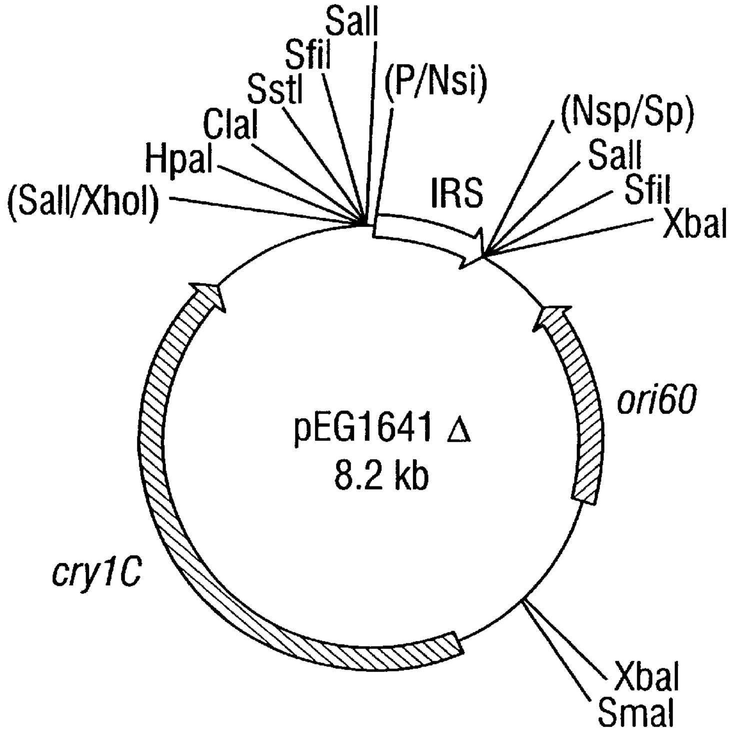

FIG. 8. Structural maps of the cry1C-encoding plasmids pEG1641 and pEG1641A. Boxed arrows and segments indicate genes or functional DNA elements. Designations: pTZ19u=*E. coli* phagemid vector pTZ19u, tet=tetracycline resistance gene, ori60=*B. thuringiensis* plasmid replication origin, cry1C=cry1C insecticidal crystal protein gene, IRS=DNA fragment containing the internal resolution site region of transposon Tn5401. Restriction site abbreviations: A=Asp718, H=HindIII, Nsi=NsiI, Nsp=NspI, P=PstI, Sp=SphI.

Figure 9:
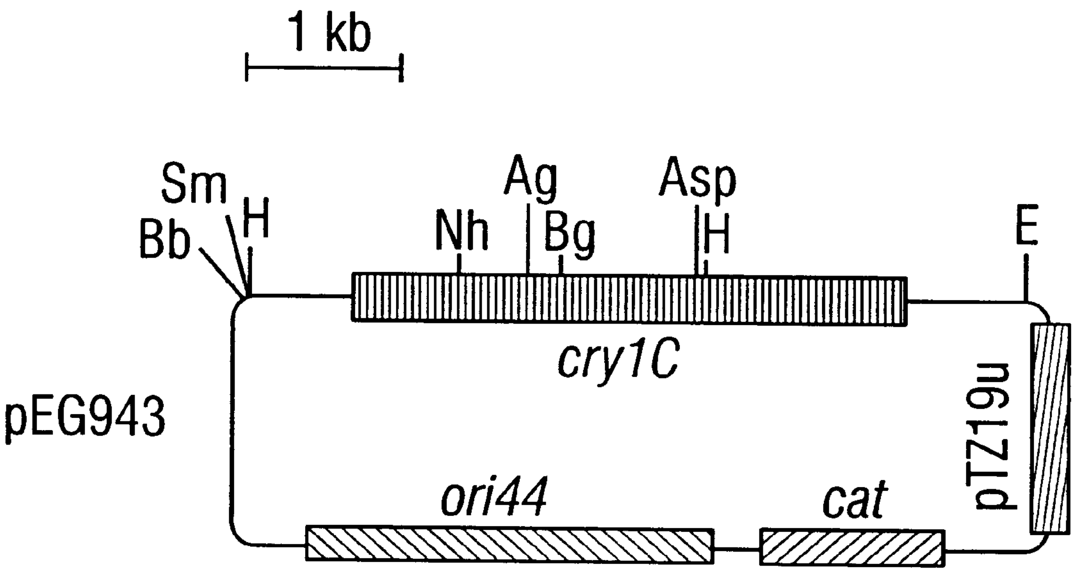

FIG. 9. Shown is the structural map of pEG943. Boxed arrows and segments indicate genes or functional DNA elements. Designations: pTZ19u=*E. coli* phagemid vector pTZ19u, cat Cml acetyltransferase gene, ori44=*B. thuringiensis* plasmid replication origin, cry1C=cry1C insecticidal crystal protein gene. Restriction site abbreviations: Ag=AgeI, Asp=Asp718, Bb=BbuI, Bg=BglII, E=EcoRI, H=HindIII, Nh=NheI, Sm=Smal. The 1 kb scale refers to only the cry1C gene segment.

Figure 10:
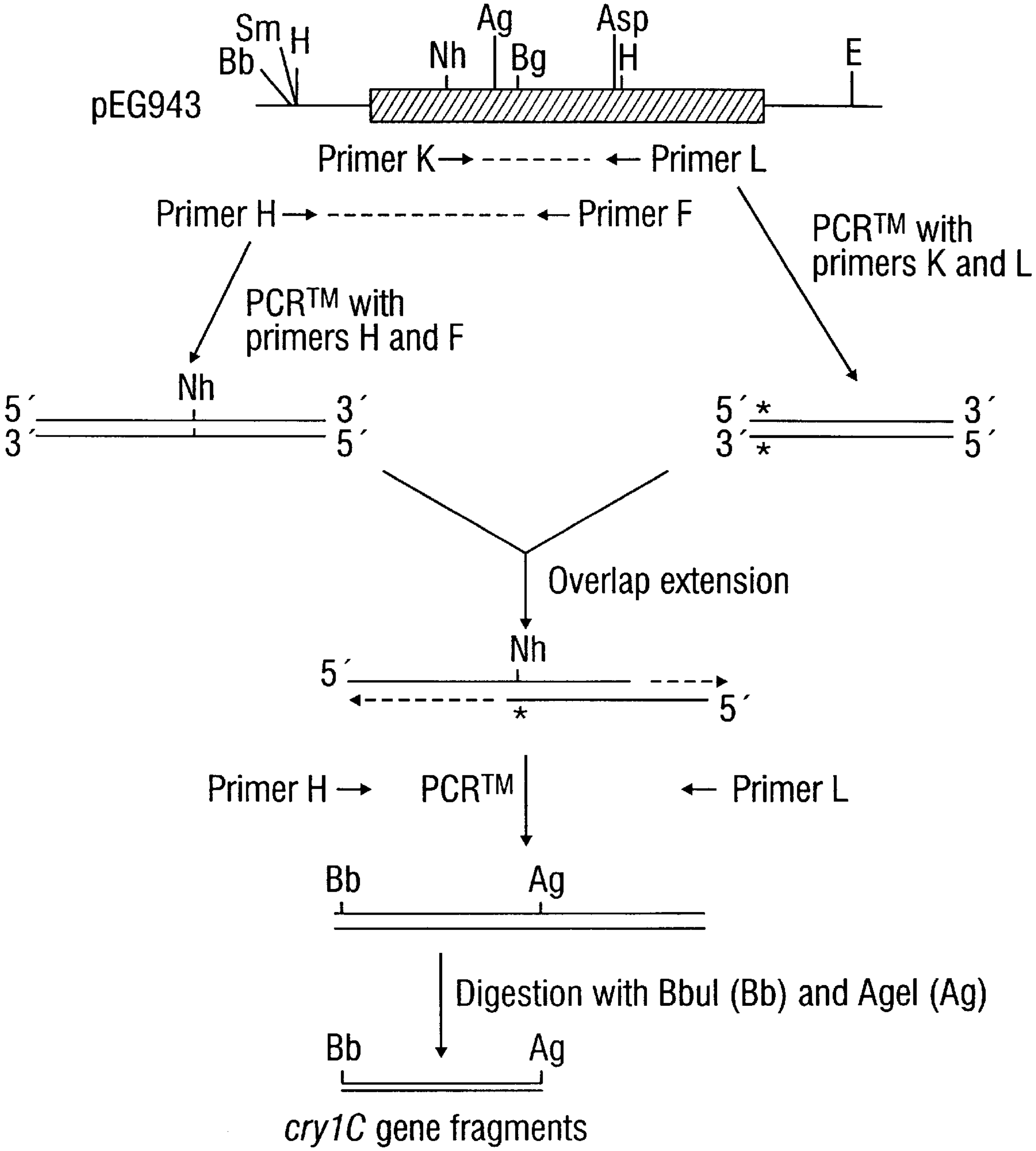

FIG. 10. Shown is the overlap extension PCR™ procedure used to generate Cry1C-R148D combinatorial mutants with amino acid substitutions in loop α 6–7. The asterisk denotes mutations incorporated into the cry1C gene sequence. The PCR™ with the flanking prirmers H and L yielded a sub-population of fragments encoding mutations in loop α 6–7 and lacking the NheI site derived from the pEG943 template. Restriction site abbreviations: Ag=AgeI, Asp=Asp718, Bb=BbuI, Bg=BglII, E=EcoRI, H=HindIII, Nh=NheI, Sm=SmaI.

Figure 11:
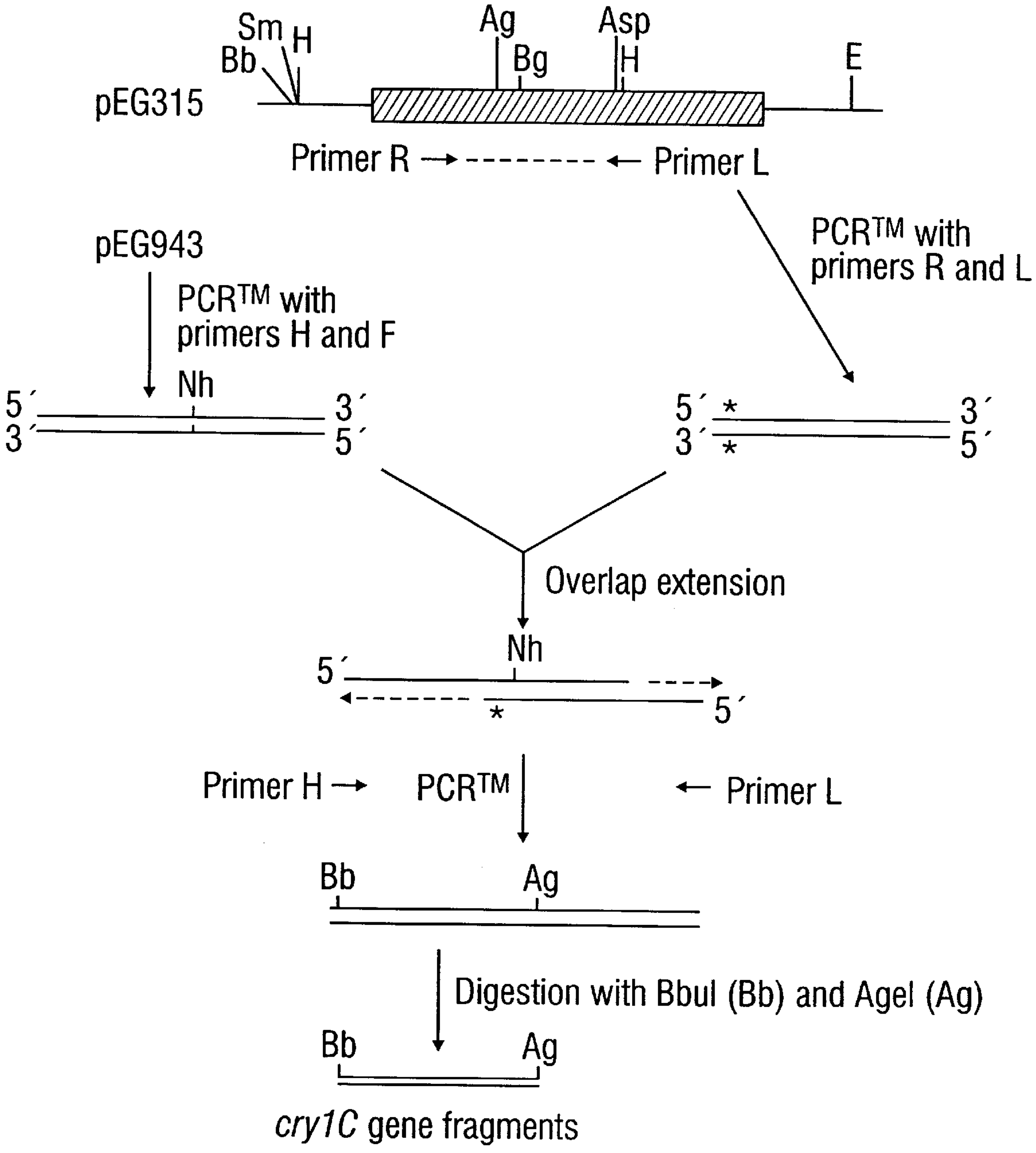

FIG. 11. Shown is the overlap extension PCR™ procedure used to generate Cry1C-R148D combinatorial mutants with amino acid substitutions in loop α 5–6. The asterisk denotes mutations incorporated into the cry1C gene sequence. The PCR™ with the flanking primers H and L yielded a sub-population of fragments encoding mutations in loop α 5–6 and lacking the NheI site derived from the pEG943 template. Restriction site abbreviations: Ag=AgeI, Asp=Asp718, Bb=BbuI, Bg=BglII, E=EcoRI, H=HindIII, Nh=NheI, Sm=SmaI.

4.0 DESCRIPTION OF ILLUSTRATIVE EMBODIMENTS

4.1 Some Advantages of the Invention

Mutagenesis experiments with cry1 genes have failed to identify mutant crystal proteins with improved broad-spectrum insecticidal activity, that is, with improved toxicity towards a range of insect pest species. Since agricultural crops are typically threatened by more than one insect pest species at any given time, desirable mutant crystal proteins are preferably those that exhibit improvements in toxicity towards multiple insect pest species. Previous failures to identify such mutants may be attributed to the choice of sites targeted for mutagenesis. Sites within domain 2 and domain 3 have been the principal targets of previous Cry1 mutagenesis efforts, primarily because these domains are believed to be important for receptor binding and in determining insecticidal specificity (Aronson et al., 1995; Chen et al. 1993; de Maagd et al., 1996; Lee et al., 1992; Lee et al., 1995; Lu et al., 1994; Smedley and Ellar, 1996; Smith and Ellar, 1994; Rajamohan et al., 1995; Rajamohan et al., 1996).

In contrast, the present inventors reasoned that the toxicity of Cry1 proteins, and specifically the toxicity of the Cry1C protein, may be improved against a broader array of lepidopteran pests by targeting regions involved in ion channel function rather than regions of the molecule directly involved in receptor interactions, namely domains 2 and 3. Accordingly, the inventors opted to target regions within domain 1 of Cry1C for mutagenesis in the hopes of isolating Cry1C mutants with improved broad spectrum toxicity. Indeed, in the present invention, Cry1C mutants are described that show improved toxicity towards several lepidopteran pests, including *Spodoptera exigua, Spodoptera frugiperda, Trichoplusia ni*, and *Heliothis virescens*, while maintaining excellent activity against *Plutella xylostella.*

At least one, and probably more than one, α helix of domain 1 is involved in the formation of ion channels and pores within the insect midgut epithelium (Gazit and Shai, 1993; Gazit and Shai, 1995). Rather than target for mutagenesis the sequences encoding the α helices of domain 1 as others have (Wu and Aronson, 1992; Aronson et al., 1995; Chen et al., 1995), the present inventors opted to target exclusively sequences encoding amino acid residues adjacent to or lying within the predicted loop regions of Cry1C that separate these x helices. Amino acid residues within these loop regions or amino acid residues capping the end of an α helix and lying adjacent to these loop regions may affect the spatial relationships among these α helices. Consequently, the substitution of these amino acid residues may result in subtle changes in tertiary structure, or even quaternary structure, that positively impact the function of the ion channel. Amino acid residues in the loop regions of domain 1 are exposed to the solvent and thus are available for various molecular interactions. Altering these amino acids could result in greater stability of the protein by eliminating or occluding protease-sensitive sites. Amino acid substitutions that change the surface charge of domain 1 could alter ion channel efficiency or alter interactions with the brush border membrane or with other portions of the toxin molecule, allowing binding or insertion to be more effective.

In mutating specific residues within these loop regions, the inventors were able to produce synthetic crystal proteins which retained or even enhanced insecticidal activity against lepidopteran insects.

According to this invention, base substitutions are made in cry1C codons in order to change the particular codons with the loop regions of the polypeptides, and particularly, in those loop regions between α-helices. As an illustrative embodiment, changes in three such amino acids within the loop region between α-helices 3 and 4 of domain 1 produced modified crystal proteins with enhanced insecticidal activity.

The insecticidal activity of a crystal protein ultimately dictates the level of crystal protein required for effective insect control. The potency of an insecticidal protein should be maximized as much as possible in order to provide for its economic and efficient utilization in the field. The increased potency of an insecticidal protein in a bioinsecticide formulation would be expected to improve the field performance of the bioinsecticide product. Alternatively, increased potency of an insecticidal protein in a bioinsecticide formulation may promote use of reduced amounts of bioinsecticide per unit area of treated crop, thereby allowing for more cost-effective use of the bioinsecticide product. When expressed in planta, the production of crystal proteins with improved insecticidal activity can be expected to improve plant resistance to susceptible insect pests.

The most effective crystal protein against the beet armyworm, *Spodoptera exigua*, is the Cry1C protein, yet the toxicity of this toxin towards *S. exigua* is ~40-fold less than the toxicity of Cry1Ac towards the tobacco budworm, *Heliothis virescens*, and ~50-fold less than the toxicity of Cry1Ba towards the diamondback moth, *Plutella xylostella* (Lambert et al., 1996). Accordingly, there is a need to improve the toxicity of Cry1C towards *S. exigua* as well as towards other lepidopteran pests. Previously, site-directed mutagenesis was used to probe the flnction of two surface-exposed loop regions found in domain 2 of the Cry1C protein (Smith and Ellar, 1994). Although amino acid substitutions within domain 2 were found to affect insecticidal specificity, Cry1C mutants with improved insecticidal activity were not obtained.

In sharp contrast to the prior art which has focused on generating amino acid substitutions within the predicted α-helices of domain 1 in Cry1A, the novel mutagenesis strategies of the present invention focus on generating amino acid substitutions at positions near or within the predicted loop regions connecting the α-helices of domain 1. These loop regions are shown in the schematic of crystal protein domains shown in FIG. 1. In mutating specific residues within these loop regions, the inventors were able to produce synthetic crystal proteins which retained or possessed enhanced insecticidal activity against certain lepidopteran pests, including the beet armyworm, *S. exigua*.

According to this invention, base substitutions are made in cry1C codons in order to change the particular codons encoding amino acids within or near the predicted loop regions between the α-helices of domain 1. As an illustrative embodiment, changes in three such amino acids within the loop region between α-helices 3 and 4 of domain 1 produced modified crystal proteins with enhanced insecticidal activity (Cry1C.499, Cry1C.563, Cry1C.579). As a second illustrative embodiment, an alanine substitution for an arginine residue within or adjacent to the loop region between α-helices 4 and 5 produced a modified crystal protein with enhanced insecticidal activity (Cry1C-R148A). Although this substitution removes a potential trypsin-cleavage site within domain 1, trypsin digestion of this modified crystal protein revealed no difference in proteolytic stability from the native Cry1C protein. Furthermore, the R180A substitution in Cry1C (Cry1C-R180A) also removes a potential trypsin cleavage site in domain 1, yet this substitution has no effect on insecticidal activity. Thus, the steps in the Cry1C protein mode-of-action impacted by these amino acid substitutions have not been determined nor is it obvious what substitutions need to be made to improve insecticidal activity.

Many crystal proteins show significant amino acid sequence identity to the Cry1C amino acid sequence within domain 1, including proteins of the Cry1, Cry2, Cry3, Cry4, Cry5, Cry7, Cry8, Cry9, Cry10, Cry11, Cry12, Cry13, Cry14, and Cry16 classes defined by the new cry gene nomenclature (Table 1). Furthermore, the structures for CryIIIA (Cry3A) and CryIAa (Cry1Aa) show a remarkable conservation of protein tertiary structure (Grochulski et al., 1995). Thus, it is anticipated that the mutagenesis of codons encoding amino acids within or near the loop regions between the α-helices of domain 1 of these proteins may also result in the generation of improved insecticidal proteins. Indeed, an alignment of Cry1 amino acid sequences spanning the loop region between α-helices 4 and 5 reveals that several Cry1 proteins contain an arginine residue at the position homologous to R148 of Cry1C. Since the Cry1C R148A mutant exhibits improved toxicity towards a number of lepidopteran pests, the inventors contemplate that similar substitutions in these other Cry1 proteins will also yield improved insecticidal proteins.

4.2 Methods for Producing Cry1C* Proteins

The *B. thuringiensis* strains described herein may be cultured using standard known media and fermentation techniques. Upon completion of the fermentation cycle, the bacteria may be harvested by first separating the *B. thuringiensis* spores and crystals from the fermentation broth by means well known in the art. The recovered *B. thuringiensis* spores and crystals can be formulated into a wettable powder, a liquid concentrate, granules or other formulations by the addition of surfactants, dispersants, inert carriers and other components to facilitate handling and application for particular target pests. The formulation and application procedures are all well known in the art and are used with commercial strains of *B. thuringiensis* (HD-1) active against Lepidoptera, e.g., caterpillars.

4.3 Recombinant Host Cells for Expressing the Cry1C* Genes

The nucleotide sequences of the subject invention can be introduced into a wide variety of microbial hosts. Expression of the toxin gene results, directly or indirectly, in the intracellular production and maintenance of the pesticide. With suitable hosts, e.g., Pseudomonas, the microbes can be applied to the sites of lepidopteran insects where they will proliferate and be ingested by the insects. The result is a control of the unwanted insects. Alternatively, the microbe hosting the toxin gene can be treated under conditions that prolong the activity of the toxin produced in the cell. The treated cell then can be applied to the environment of target pest(s). The resulting product retains the toxicity of the *B. thuringiensis* toxin.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility or toxicity to a mammalian host. As hosts, of particular interest will be the prokaryotes and the lower eukaryotes, such as fingi. Illustrative prokaryotes, both Gram-negative and Gram-positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae, Actinomycetales, and Nitrobacteraceae. Among eukaryotes are fingi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the *B. thuringiensis* gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., Streptomyces sp., and the like. Specific organisms include *Pseudomonas aeruginosa, Pseudomonas fluorescens, Saccharomyces cerevisiae, Bacillus thuringiensis, Escherichia coli, Bacillus subtilis, Bacillus megaterium, Bacillus cereus, Streptomyces lividans* and the like.

Treatment of the microbial cell, e.g., a microbe containing the *B. thuringiensis* toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Lugol's iodine, Bouin's fixative, and Helly's fixatives, (see e.g., Humason, 1967); or a combination of physical (heat) and chemical agents. that preserve and prolong the activity of the toxin produced in the cell when the cell is administered to the host animal. Examples of physical means are short wavelength radiation such as γ-radiation and X-radiation, freezing, UV irradiation, lyophilization, and the like. The cells employed will usually be intact and be substantially in the proliferative form when treated, rather than in a spore form, although in some instances spores may be employed.

Where the *B. thuringiensis* toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene of expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Bacillus, Pseudomonas, Erwinia, Serratia, Klebsiella, Zanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; flingi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodobacter sphaeroides, Xanthomonas campestris, Rhizobium melioti, Alcaligenes eutrophus*, and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans.*

4.4 Definitions

As used herein, the designations "CryI" and "Cry1" are synonymous, as are the designations "CryIC" and "Cry1C." Likewise, the inventors have utilized the generic term Cry1C* to denote any and all Cry1C variants which comprise amino acid sequences modified in the loop region of domain 1. Similarly, cry1C* is meant to denote any and all nucleic acid segments and/or genes which encode such modified Cry1C* proteins. In similar regard, the inventors have used the terms Cry1* to denote any and all Cry1 variants which comprise amino acid sequences modified in the loop region of domain 1. Similarly, cry1* is meant to denote any and all nucleic acid segments and/or genes which encode such modified Cry1* proteins. A similar convention is used to described modified loop domain variants in any of the related crystal proteins and genes which encode them.

In accordance with the present invention, nucleic acid sequences include and are not limited to DNA (including and not limited to genomic or extragenomic DNA), genes, RNA (including and not limited to mRNA and tRNA), nucleosides, and suitable nucleic acid segments either obtained from native sources, chemically synthesized, modified, or otherwise prepared by the hand of man. The following words and phrases have the meanings set forth below.

Broad spectrum: refers to a wide range of insect species.

Broad spectrum insecticidal activity: toxicity towards a wide range of insect species.

Expression: The combination of intracellular processes, including transcription and translation undergone by a coding DNA molecule such as a structural gene to produce a polypeptide.

Insecticidal activity: toxicity towards insects.

Insecticidal specificity: the toxicity exhibited by a crystal protein towards multiple insect species.

Intraorder specificity: the toxicity of a particular crystal protein towards insect species within an Order of insects (e.g., Order Lepidoptera).

Interorder specificity: the toxicity of a particular crystal protein towards insect species of different Orders (e.g., Orders Lepidoptera and Diptera).

$LC_{50}$: the lethal concentration of crystal protein that causes 50% mortality of the insects treated.

$LC_{95}$: the lethal concentration of crystal protein that causes 95% mortality of the insects treated.

Promoter: A recognition site on a DNA sequence or group of DNA sequences that provide an expression control element for a structural gene and to which RNA polymerase specifically binds and initiates RNA synthesis (transcription) of that gene.

Regeneration: The process of growing a plant from a plant cell (e.g., plant protoplast or explant).

Structural gene: A gene that is expressed to produce a polypeptide.

Transformation: A process of introducing an exogenous DNA sequence (erg., a vector, a recombinant DNA molecule) into a cell or protoplast in which that exogenous DNA is incorporated into a chromosome or is capable of autonomous replication.

Transformed cell: A cell whose DNA has been altered by the introduction of an exogenous DNA molecule into that cell.

Transgenic cell: Any cell derived or regenerated from a transformed cell or derived from a transgenic cell. Exemplary transgenic cells include plant calli derived from a transformed plant cell and particular cells such as leaf, root, stem, e.g., somatic cells, or reproductive (gerrn) cells obtained from a transgenic plant.

Transgenic plant: A plant or progeny thereof derived from a transformed plant cell or protoplast, wherein the plant DNA contains an introduced exogenous DNA molecule not originally present in a native, non-transgenic plant of the same strain. The terms "transgenic plant" and "transformed plant" have sometimes been used in the art as synonymous terms to define a plant whose DNA contains an exogenous DNA molecule. However, it is thought more scientifically correct to refer to a regenerated plant or callus obtained from a transformed plant cell or protoplast as being a transgenic plant, and that usage will be followed herein.

Vector: A DNA molecule capable of replication in a host cell and/or to which another DNA segment can be operatively linked so as to bring about replication of the attached segment. Plasmids, phagemids, cosmids, phage, virus, YACs, and BACs are all exemplary vectors.

4.5 Probes and Primers

In another aspect, DNA sequence information provided by the invention allows for the preparation of relatively short DNA (or RNA) sequences having the ability to specifically hybridize to gene sequences of the selected polynucleotides disclosed herein. In these aspects, nucleic acid probes of an appropriate length are prepared based on a consideration of a selected crystal protein gene sequence, e.g., a sequence such as that shown in SEQ ID NO:1, SEQ ID NO:3, SEQ ID NO:5, SEQ ID NO:7, SEQ ID NO:9, SEQ ID NO:11, SEQ ID NO:58, or SEQ ID NO:60. The ability of such nucleic acid probes to specifically hybridize to a crystal protein-encoding gene sequence lends them particular utility in a variety of embodiments. Most importantly, the probes may be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined segment of a crystal protein gene from *B. thuringiensis* using PCR™ technology. Segments of related crystal protein genes from other species may also be amplified by PCR™ using such primers.

To provide certain of the advantages in accordance with the present invention, a preferred nucleic acid sequence employed for hybridization studies or assays includes sequences that are complementary to at least a 14 to 30 or so long nucleotide stretch of a crystal protein-encoding sequence, such as that shown in SEQ ID NO:1, SEQ ID NO:3, SEQ ID NO:5, SEQ ID NO:7, SEQ ID NO:9, SEQ ID NO:11, SEQ ID NO:58, or SEQ ID NO:60. A size of at least 14 nucleotides in length helps to ensure that the fragment will be of sufficient length to form a duplex molecule that is both stable and selective. Molecules having complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of 14 to 20 nucleotides, or even longer where desired. Such fragments may be readily prepared by, for example, directly synthesizing the fragment by chemical means, by application of nucleic acid reproduction technology, such as the PCR™ technology of U.S. Pat. Nos. 4,683,195, and 4,683,202, herein incorporated by reference, or by excising selected DNA fragments from recombinant plasmids containing appropriate inserts and suitable restriction sites.

A particularly preferred oligonucleotide is the 63-mer identified in SEQ ID NO:18. The oligonucleotide is particularly preferred for preparation of mutagenized nucleic acid sequences to produce toxins with improved properties. Mutagenic oligonucleotides may be prepared with known or random substitutions, by methods well-known to those of skill in the art. Such oligonucleotides may be provided by commercial firms that perform custom syntheses.

Accordingly, a nucleotide sequence of the invention can be used for its ability to selectively form duplex molecules with complementary stretches of the gene. Depending on the application envisioned, one will desire to employ varying conditions of hybridization to achieve varying degree of selectivity of the probe toward the target sequence. For applications requiring a high degree of selectivity, one will typically desire to employ relatively stringent conditions to form the hybrids, for example, one will select relatively low salt and/or high temperature conditions, such as provided by about 0.02M to about 0.15M NaCl at temperatures of about 50° C. to about 70° C. These conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate a crystal protein-coding sequences for related species, functional equivalents, or the like, less stringent hybridization conditions will typically be needed in order to allow formation of the heteroduplex. In these circumstances, one may desire to employ conditions such as about 0.15M to about 0.9M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

4.6 Expression Vectors

The present invention contemplates an expression vector comprising a polynucleotide of the present invention. Thus, in one embodiment an expression vector is an isolated and purified DNA molecule comprising a promoter operatively linked to an coding region that encodes a polypeptide of the present invention, which coding region is operatively linked to a transcription-terminating region, whereby the promoter drives the transcription of the coding region.

As used herein, the term "operatively linked" means that a promoter is connected to an coding region in such a way that the transcription of that coding region is controlled and regulated by that promoter. Means for operatively linking a promoter to a coding region are well known in the art.

IIn a preferred embodiment, the recombinant expression of DNAs encoding the crystal proteins of the present invention is preferable in a Bacillus host cell. Preferred host cells include *B. thuringiensis, B. megaterium, B. cereus, B. subtilis*, and related *bacilli*, with *B. thuringiensis* host cells being highly preferred. Promoters that function in bacteria are well-known in the art. An exemplary and preferred promoter for the Bacillus crystal proteins include any of the known crystal protein gene promoters, including native crystal protein encoding gene promoters. Alternatively, mutagenized or recombinant crystal protein-encoding gene promoters may be engineered by the hand of man and used to promote expression of the novel gene segments disclosed herein.

In an alternate embodiment, the recombinant expression of DNAs encoding the crystal proteins of the present invention is performed using a transformed Gram-negative bacterium such as an *E. coli* or Pseudomonas spp. host cell. Promoters which function in high-level expression of target polypeptides in *E. coli* and other Gram-negative host cells are also well-known in the art.

Where an expression vector of the present invention is to be used to transform a plant, a promoter is selected that has the ability to drive expression in plants. Promoters that function in plants are also well known in the art. Useful in expressing the polypeptide in plants are promoters that are inducible, viral, synthetic, constitutive as described (Poszkowski et al., 1989; Odell et al., 1985), and temporally regulated, spatially regulated, and spatio-temporally regulated (Chau et al., 1989).

A promoter is also selected for its ability to direct the transformed plant cell's or transgenic plant's transcriptional activity to the coding region. Structural genes can be driven by a variety of promoters in plant tissues. Promoters can be near-constitutive, such as the CaMV 35S promoter, or tissue-specific or developmentally specific promoters affecting dicots or monocots.

Where the promoter is a near-constitutive promoter such as CaMV 35S, increases in polypeptide expression are found in a variety of transformed plant tissues (e.g., callus, leaf, seed and root). Alternatively, the effects of transformation can be directed to specific plant tissues by using plant integrating vectors containing a tissue-specific promoter.

An exemplary tissue-specific promoter is the lectin promoter, which is specific for seed tissue. The Lectin protein in soybean seeds is encoded by a single gene (Le1) that is only expressed during seed maturation and accounts for about 2 to about 5% of total seed mRNA. The lectin gene and seed-specific promoter have been fully characterized and used to direct seed specific expression in transgenic tobacco plants (Vodkin et al., 1983;

Lindstrom et al., 1990.)

An expression vector containing a coding region that encodes a polypeptide of interest is engineered to be under control of the lectin promoter and that vector is introduced into plants using, for example, a protoplast transformation method (Dhir et al., 1991). The expression of the polypeptide is directed specifically to the seeds of the transgenic plant.

A transgenic plant of the present invention produced from a plant cell transformed with a tissue specific promoter can be crossed with a second transgenic plant developed from a plant cell transformed with a different tissue specific promoter to produce a hybrid transgenic plant that shows the effects of transformation in more than one specific tissue.

Exemplary tissue-specific promoters are corn sucrose synthetase 1 (Yang et al., 1990), corn alcohol dehydrogenase 1 (Vogel et al., 1989), corn light harvesting complex (Simpson, 1986), corn heat shock protein (Odell et al., 1985), pea small subunit RuBP carboxylase (Poulsen et al., 1986; Cashmore et al., 1983), Ti plasmid mannopine synthase (Langridge et al., 1989), Ti plasmid nopaline synthase (Langridge et al., 1989), petunia chalcone isomerase (Van Tunen et al., 1988), bean glycine rich protein 1 (Keller et al., 1989), CaMV 35s transcript (Odell et al., 1985) and Potato patatin (Wenzler et al., 1989). Preferred promoters are the cauliflower mosaic virus (CaMV 35S) promoter and the S-E9 small subunit RuBP carboxylase promoter.

The choice of which expression vector and ultimately to which promoter a polypeptide coding region is operatively linked depends directly on the fimctional properties desired, e.g., the location and timing of protein expression, and the host cell to be transformed. These are well known limitations inherent in the art of constructing recombinant DNA molecules. However, a vector useful in practicing the present invention is capable of directing the expression of the polypeptide coding region to which it is operatively linked.

Typical vectors useful for expression of genes in higher plants are well known in the art and include vectors derived from the tumor-inducing (Ti) plasmid of *Agrobacterium tumefaciens* described (Rogers et al., 1987). However, several other plant integrating vector systems are known to function in plants including pCaMVCN transfer control vector described (Fromm et al., 1985). Plasmid pCaMVCN (available from Pharmacia, Piscataway, N.J.) includes the cauliflower mosaic virus CaMV 35S promoter.

In preferred embodiments, the vector used to express the polypeptide includes a selection marker that is effective in a plant cell, preferably a drug resistance selection marker. One preferred drug resistance marker is the gene whose expression results in kanamycin resistance; ie., the chimeric gene containing the nopaline synthase promoter, Tn5 neomycin phosphotransferase II (nptII) and nopaline synthase 3' non-translated region described (Rogers et al., 1988).

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

Means for preparing expression vectors are well known in the art. Expression (transformation vectors) used to transform plants and methods of making those vectors are described in U.S. Pat. Nos. 4,971,908, 4,940,835, 4,769,061 and 4,757,011, the disclosures of which are incorporated herein by reference. Those vectors can be modified to include a coding sequence in accordance with the present invention.

A variety of methods has been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

A coding region that encodes a polypeptide having the ability to confer insecticidal activity to a cell is preferably a Cry1C-R148A, Cry1C-R180A, Cry1C.563, Cry1C.579 or Cry1C.499 *B. thuringiensis* crystal protein-encoding gene. In preferred embodiments, such a polypeptide has the amino acid residue sequence of SEQ ID NO:2, SEQ ID NO:4, SEQ ID NO:6, SEQ ID NO:8, SEQ ID NO:10, or SEQ ID NO::12, respectively, or a functional equivalent of those sequences. In accordance with such embodiments, a coding region comprising the DNA sequence of SEQ ID NO:1, SEQ ID NO:3, SEQ ID NO:5, SEQ ID NO:7, SEQ ID NO:9, SEQ ID NO:11, SEQ ID NO:58, or SEQ ID NO:60 is also preferred.

4.7 DNA Segments as Hybridization Probes and Primers

In addition to their use in directing the expression of crystal proteins or peptides of the present invention, the nucleic acid sequences contemplated herein also have a variety of other uses. For example, they also have utility as probes or primers in nucleic acid hybridization embodiments. As such, it is contemplated that nucleic acid segments that comprise a sequence region that consists of at least a 14 nucleotide long contiguous sequence that has the same sequence as, or is complementary to, a 14 nucleotide long contiguous DNA segment of SEQ ID NO:1, SEQ ID NO:3, SEQ ID NO:5, SEQ ID NO:7, SEQ ID NO:9, SEQ ID NO:11, SEQ ID NO:58, or SEQ ID NO:60 will find particular utility. Longer contiguous identical or complementary sequences, e.g., those of about 20, 30, 40, 50, 100, 200, 500, 1000, 2000, 5000, 10000 etc. (including all intermediate lengths and up to and including full-length sequences will also be of use in certain embodiments.

The ability of such nucleic acid probes to specifically hybridize to crystal protein-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of 10–14, 15–20, 30, 50, or even of 100–200 nucleotides or so, identical or complementary to DNA sequences of SEQ ID NO:1, SEQ ID NO:3, SEQ ID NO:5, SEQ ID NO:7, SEQ ID NO:9, SEQ ID NO:11, SEQ ID NO:58, or SEQ ID NO:60 are particularly contemplated as hybridization probes for use in, e.g., Southern and Northern blotting. Smaller fragments will generally find use in hybridization embodiments, wherein the length of the contiguous complementary region may be varied, such as between about 10–14 and about 100 or 200 nucleotides, but larger contiguous complementarity stretches may be used, according to the length complementary sequences one wishes to detect.

The use of a hybridization probe of about 14 nucleotides in length allows the formation of a duplex molecule that is both stable and selective. Molecules having contiguous complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 contiguous nucleotides, or even longer where desired.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. Nos. 4,683,195 and 4,683,202 (each incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02M to about 0.15M NaCl at temperatures of about 50° C. to about 70° C. Such selective conditions tolerate little, if any, mismatch between the probe and the template or target strand, and would be particularly suitable for isolating crystal protein-encoding DNA segments. Detection of DNA segments via hybridization is well-known to those of skill in the art, and the teachings of U.S. Pat. Nos. 4,965,188 and 5,176,995 (each incorporated herein by reference) are exemplary of the methods of hybridization analyses. Teachings such as those found in the texts of Maloy et al, 1994; Segal 1976; Prokop, 1991; and Kuby, 1994, are particularly relevant.

Of course, for some applications, for example, where one desires to prepare mutants employing a mutant primer strand hybridized to an underlying template or where one seeks to isolate crystal protein-encoding sequences from related species, functional equivalents, or the like, less stringent hybridization conditions will typically be needed in order to allow formation of the heteroduplex. In these circumstances, one may desire to employ conditions such as about 0.15M to about 0.9M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, colorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

4.8 Characteristics of Cry1C* Proteins

The present invention provides novel polypeptides that define a whole or a portion of a *B. thuringiensis* Cry1C-R18OA, Cry1C-R148A, Cry!C-R148D, Cry1C-R148L, Cry1C-R148M, Cry1C-R148G, Cry1C.563, Cry1C.499, or Cry1C.579 crystal protein.

In a preferred embodiment, the invention discloses and claims a purified Cry1C-R148A protein. The Cry1C-R148A protein comprises an 1189-amino acid sequence, which is given in SEQ ID NO:2.

In a second embodiment, the invention discloses and claims a purified Cry1C-R148D protein. The Cry1C-R148D protein comprises an 1189-amino acid sequence, which is given in SEQ ID NO:4.

In a third embodiment, the invention discloses and claims a purified Cry1C-R180A protein. The Cry1C-R180A protein comprises an 1189-amino acid sequence, which is given in SEQ ID NO:6.

In a fourth embodiment, the invention discloses and claims a purified Cry1C.563 protein. The Cry1C.563 protein comprises an 1189-amino acid sequence, which is given in SEQ ID NO:8.

In a fifth embodiment, the invention discloses and claims a purified Cry1C.579 protein. The Cry1C.579 protein comprises an 1189-amino acid sequence, which is given in SEQ ID NO:10.

In a sixth embodiment, the invention discloses and claims a purified Cry1C.499 protein. The Cry1C.499 protein comprises an 1189-amino acid sequence, which is given in SEQ ID NO:12.

4.9 Nomenclature of Cry1* Proteins

The inventors have arbitrarily assigned the designations Cry1C-R148A, Cry1C-R148D, Cry1C-R148L, Cry1C-R148M, Cry1C-R148G, Cry1C-R180A, Cry1C.563, Cry1C.579 and Cry1C.499 to the novel proteins of the invention. Likewise, the arbitrary designations of cry1C-R148A, cry1C-R148D, cry1C-R148L, cry1C-R148M, cry1C-R148G, cry1C-R180A, cry1C.563, cry1C.579 and cry1C.499 have been assigned to the novel nucleic acid sequences which encode these polypeptides, respectively. While formal assignment of gene and protein designations based on the revised nomenclature of crystal protein endotoxins (Table 1) may be made by the committee on the nomenclature of *B. thuringiensis*, any re-designations of the compositions of the present invention are also contemplated to be fully within the scope of the present disclosure.

4.10 Transformed Host Cells and Transgenic Plants

A bacterium, a yeast cell, or a plant cell or a plant transformed with an expression vector of the present invention is also contemplated. A transgenic bacterium, yeast cell, plant cell or plant derived from such a transformed or transgenic cell is also contemplated. Means for transforming bacteria and yeast cells are well known in the art. Typically, means of transformation are similar to those well known means used to transform other bacteria or yeast such as *E. coli* or *Saccharomyces cerevisiae*.

Methods for DNA transformation of plant cells include Agrobacterium-mediated plant transformation, protoplast transformation, gene transfer into pollen, injection into reproductive organs, injection into immature embryos and particle bombardment. Each of these methods has distinct advantages and disadvantages. Thus, one particular method of introducing genes into a particular plant strain may not necessarily be the most effective for another plant strain, but it is well known which methods are useful for a particular plant strain.

There are many methods for introducing transforming DNA segments into cells, but not all are suitable for delivering DNA to plant cells. Suitable methods are believed to include virtually any method by which DNA can be introduced into a cell, such as by Agrobacterium infection, direct delivery of DNA such as, for example, by PEG-mediated transformation of protoplasts (Omirulleh et al., 1993), by desiccation/inhibition-mediated DNA uptake, by electroporation, by agitation with silicon carbide fibers, by acceleration of DNA coated particles, etc. In certain embodiments, acceleration methods are preferred and include, for example, microprojectile bombardment and the like.

Technology for introduction of DNA into cells is well-known to those of skill in the art. Four general methods for delivering a gene into cells have been described: (1) chemical methods (Graham and van der Eb, 1973; Zatloukal et al., 1992); (2) physical methods such as microinjection (Capecchi, 1980), electroporation (Wong and Neumann, 1982; Fromm et al., 1985) and the gene gun (Johnston and Tang, 1994; Fynan et al., 1993); (3) viral vectors (Clapp, 1993; Lu et al., 1993; Eglitis and Anderson, 1988a; 1988b); and (4) receptor-mediated mechanisms (Curiel et al., 1991; 1992; Wagner et al., 1992).

4.10.1 Electroporation

The application of brief, high-voltage electric pulses to a variety of animal and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of clones genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

The introduction of DNA by means of electroporation, is well-known to those of skill in the art. In this method, certain cell wall-degrading enzymes, such as pectin-degrading enzymes, are employed to render the target recipient cells more susceptible to transformation by electroporation than untreated cells. Alternatively, recipient cells are made more susceptible to transformation, by mechanical wounding. To effect transformation by electroporation one may employ either friable tissues such as a suspension culture of cells, or embryogenic callus, or alternatively, one may transform immature embryos or other organized tissues directly. One would partially degrade the cell walls of the chosen cells by exposing them to pectin-degrading enzymes (pectolyases) or mechanically wounding in a controlled manner. Such cells would then be recipient to DNA transfer by electroporation, which may be carried out at this stage, and transformed cells then identified by a suitable selection or screening protocol dependent on the nature of the newly incorporated DNA.

4.10.2 Microprojectile Bombardment

A further advantageous method for delivering transforming DNA segments to plant cells is microprojectile bombardment. In this method, particles may be coated with nucleic acids and delivered into cells by a propelling force. Exemplary particles include those comprised of tungsten, gold, platinum, and the like.

An advantage of microprojectile bombardment, in addition to it being an effective means of reproducibly stably transforming monocots, is that neither the isolation of protoplasts (Cristou et al., 1988) nor the susceptibility to Agrobacterium infection is required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with corn cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing damage inflicted on the recipient cells by projectiles that are too large.

For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from 1 to 10 and average 1 to 3.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust various of the bombardment parameters in small scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

4.10.3 Agrobacterium-Mediated Transfer

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example, the methods described (Fraley et al., 1985; Rogers et al., 1987). Further, the integration of the Ti-DNA is a relatively precise process resulting in few rearrangements. The region of DNA to be transferred is defined by the border sequences, and intervening DNA is usually inserted into the plant genome as described (Spielmann et al, 1986; Jorgensen et al., 1987).

Modern Agrobacterium transformation vectors are capable of replication in *E. coli* as well as Agrobacterium, allowing for convenient manipulations as described (Klee et al, 1985). Moreover, recent technological advances in vectors for Agrobacterium-mediated gene transfer have improved the arrangement of genes and restriction sites in the vectors to facilitate construction of vectors capable of expressing various polypeptide coding genes. The vectors described (Rogers et al, 1987), have convenient multi-linker regions flanked by a promoter and a polyadenylation site for direct expression of inserted polypeptide coding genes and are suitable for present purposes. In addition, Agrobacterium containing both armed and disarmed Ti genes can be used for the transformations. In those plant strains where Agrobacterium-mediated transformation is efficient, it is the method of choice because of the facile and defined nature of the gene transfer.

Agrobacterium-mediated transformation of leaf disks and other tissues such as cotyledons and hypocotyls appears to be limited to plants that Agrobacterium naturally infects. Agrobacterium-mediated transformation is most efficient in dicotyledonous plants. Few monocots appear to be natural hosts for Agrobacterium, although transgenic plants have been produced in asparagus using Agrobacterium vectors as described (Bytebier et al, 1987). Therefore, commercially important cereal grains such as rice, corn, and wheat must usually be transformed using alternative methods. However, as mentioned above, the transformation of asparagus using Agrobacterium can also be achieved (see, for example, Bytebier et al., 1987).

A transgenic plant formed using Agrobacterium transformation methods typically contains a single gene on one chromosome. Such transgenic plants can be referred to as being heterozygous for the added gene. However, inasmuch as use of the word "heterozygous" usually implies the presence of a complementary gene at the same locus of the second chromosome of a pair of chromosomes, and there is no such gene in a plant containing one added gene as here, it is believed that a more accurate name for such a plant is an independent segregant, because the added, exogenous gene segregates independently during mitosis and meiosis.

More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selling) an independent segregant transgenic plant that contains a single added gene, germinating some of the seed produced and analyzing the resulting plants produced for enhanced carboxylase activity relative to a control (native, non-transgenic) or an independent segregant transgenic plant.

It is to be understood that two different transgenic plants can also be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated.

Transformation of plant protoplasts can be achieved using methods based on calcium phosphate precipitation, polyethylene glycol treatment, electroporation, and combinations of these treatments (see, e.g., Potrykus et al, 1985; Lorz et al., 1985; Fromm et al., 1985; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts are described (Fujimura et al, 1985; Toriyama et al., 1986; Yamada et al, 1986; Abdullah et al., 1986).

To transform plant strains that cannot be successfully regenerated from protoplasts, other ways to introduce DNA into intact cells or tissues can be utilized. For example, regeneration of cereals from immature embryos or explants can be effected as described (Vasil, 1988). In addition, "particle gun" or high-velocity microprojectile technology can be utilized (Vasil, 1992).

Using that latter technology, DNA is carried through the cell wall and into the cytoplasm on the surface of small metal particles as described (Klein et al., 1987; Klein et al., 1988; McCabe et al., 1988). The metal particles penetrate through several layers of cells and thus allow the transformation of cells within tissue explants.

4.10.4 Gene Expression in Plants

The fact that plant codon usage more closely resembles that of humans and other higher organisms than unicellular organisms, such as bacteria, unmodified bacterial genes are often poorly expressed in transgenic plant cells. The apparent overall preference for GC content in codon position three has been described in detail by Murray et al. (1990). The 207 plant genes described in this work permitted the compilation of codon preferences for amino acids in plants. These authors describe the difference between codon usage in monocots and dicots, as well as differences between chloroplast encoded genes and those which are nuclear encoded. Utilizing the codon frequency tables provided, those of skill in the art can engineer such a bacterial sequence for expression in plants by modifying the DNA sequences to provide a codon bias for G or C in the third position. The reference provides an exhaustive list of tables to guide molecular geneticists in preparing synthetic gene sequences which encode the polypeptides of the invention, and which are expressed in transformed plant cells in a suitable fashion to permit synthesis of the polypeptide of interest in planta.

A similar work by Diehn et al. (1996) details the modification of prokaryotic-derived gene sequences necessary to permit expression in plants.

Iannacone et al. (1997) describe the transformation of egg plant with a genetically engineered *B. thuringiensis* gene encoding a cry3 class endotoxin. Utilizing sequences which avoid polyadenylation sequences, ATTA sequences, and splicing sites a synthetic gene was constructed which permitted expression of the encoded toxin in planta.

Expression of heterologous proteins in transgenic tobacco has been described by Rouwendal et al. (1997). Using a synthetic gene, the third position codon bias for C+G was created to permit expression of the jellyfish green fluorescent protein-encoding gene in planta.

Fütterer and Hohn (1996) describe the effects of mRNA sequence, leader sequences, polycistronic messages, and internal ribosome binding site motis, on expression in plants. Modification of such sequences by construction of synthetic genes permitted expression of viral mRNAs in transgenic plant cells.

Preparation of transgenic plants which express genes encoding non-native proteins (such as *B. thuringiensis* crystal proteins) is becoming a critical step in the formulation of plant varieties which express insect resistance genes. In recent years considerable research has yielded tools for the manipulation of endotoxin-encoding genes to permit expression of their encoded proteins in planta. Scientists have shown that maintaining a significant level of an mRNA species in a plant is often a critical factor. Unfortunately, the causes for low steady state levels of mRNA encoding foreign proteins are many. First, full-length RNA synthesis may not occur at a high frequency. This could, for example, be caused by the premature termination of RNA during transcription or due to unexpected mRNA processing during transcription. Second, fill-length RNA may be produced in the plant cell, but then processed (splicing, polyA addition) in the nucleus in a fashion that creates a nonfunctional mRNA. If the RNA is not properly synthesized, terminated and polyadenylated, it cannot move to the cytoplasm for translation. Similarly, in the cytoplasm, if mRNAs have reduced half lives (which are determined by their primary or secondary sequence) inisufficient protein product will be produced. In addition, there is an effect, whose magnitude is uncertain, of translational efficiency on mRNA half-life. In addition, every RNA molecule folds into a particular structure, or perhaps family of structures, which is determined by its sequence. The particular structure of any RNA might lead to greater or lesser stability in the cytoplasm. Structure per se is probably also a determinant of mRNA processing in the nucleus. Unfortunately, it is impossible to predict, and nearly impossible to determine, the structure of any RNA (except for tRNA) in vitro or in vivo. However, it is likely that dramatically changing the sequence of an RNA will have a large effect on its folded structure It is likely that structure per se or particular structural features also have a role in determining RNA stability.

To overcome these limitations in foreign gene expression, researchers have identified particular sequences and signals in RNAs that have the potential for having a specific effect on RNA stability. In certain embodiments of the invention, therefore, there is a desire to optimize expression of the disclosed nucleic acid segments in planta. One particular method of doing so, is by alteration of the bacterial gene to remove sequences or motifs which decrease expression in a transformed plant cell. The process of engineering a coding sequence for optimal expression in planta is often referred to as "plantizing" a DNA sequence.

Particularly problematic sequences are those which are A+T rich. Unfortunately, since *B. thuringiensis* has an A+T rich genome, native crystal protein gene sequences must often be modified for optimal expression in a plant. The sequence motif ATTTA (or AUUUA as it appears in RNA) has been implicated as a destabilizing sequence in mammalian cell mRNA (Shaw and Kamen, 1986). Many short lived mRNAs have A+T rich 3' untranslated regions, and these regions often have the ATTTA sequence, sometimes present in multiple copies or as multimers (e.g., ATTTATTTA . . . ). Shaw and Kamen showed that the transfer of the 3' end of an unstable mRNA to a stable RNA (globin or VA1) decreased the stable RNA's half life dramatically. They further showed that a pentamer of ATTTA had a profound destabilizing effect on a stable message, and that this signal could exert its effect whether it was located at the 3' end or within the coding sequence. However, the number of ATTTA sequences and/or the sequence context in which they occur also appear to be important in determining whether they function as destabilizing sequences. Shaw and Kamen showed that a trimer of ATTTA had much less effect than a pentamer on mRNA stability and a dimer or a monomer had no effect on stability (Shaw and Kamen, 1987). Note that multimers of ATTTA such as a pentamer automatically create an A+T rich region. This was shown to be a cytoplasmic effect, not nuclear. In other unstable mRNAs, the ATTTA sequence may be present in only a single copy, but it is often contained in an A+T rich region. From the animal cell data collected to date, it appears that ATTTA at least in some contexts is important in stability, but it is not yet possible to predict which occurrences of ATTTA are destabiling elements or whether any of these effects are likely to be seen in plants.

Some studies on mRNA degradation in animal cells also indicate that RNA degradation may begin in some cases with nucleolytic attack in A+T rich regions. It is not clear if these cleavages occur at ATTTA sequences. There are also examples of mRNAs that have differential stability depending on the cell type in which they are expressed or on the stage within the cell cycle at which they are expressed. For example, histone mRNAs are stable during DNA synthesis but unstable if DNA synthesis is disrupted. The 3' end of some histone mRNAs seems to be responsible for this effect (Pandey and Marzluff, 1987). It does not appear to be mediated by ATTTA, nor is it clear what controls the differential stability of this mRNA. Another example is the differential stability of IgG mRNA in B lymphocytes during B cell maturation (Genovese and Milcarek, 1988). A final example is the instability of a mutant β-thallesemic globin mRNA. In bone marrow cells, where this gene is normally expressed, the mutant mRNA is unstable, while the wild-type mRNA is stable. When the mutant gene is expressed in HeLa or L cells in vitro, the mutant mRNA shows no instability (Lim et al., 1992). These examples all provide evidence that mRNA stability can be mediated by cell type or cell cycle specific factors. Furthermore this type of instability is not yet associated with specific sequences. Given these uncertainties, it is not possible to predict which RNAs are likely to be unstable in a given cell. In addition, even the ATTTA motif may act differentially depending on the nature of the cell in which the RNA is present. Shaw and Kamen (1987) have reported that activation of protein kinase C can block degradation mediated by ATTTA.

The addition of a polyadenylate string to the 3' end is comnmon to most eukaryotic mRNAs, both plant and animal. The currently accepted view of polyA addition is that the nascent transcript extends beyond the mature 3' terminus. Contained within this transcript are signals for polyadenylation and proper 3' end formation. This processing at the 3' end involves cleavage of the mRNA and addition of polyA to the mature 3' end. By searching for consensus sequences near the polyA tract in both plant and animal mRNAs, it has been possible to identify consensus sequences that apparently are involved in polyA addition and 3' end cleavage. The same consensus sequences seem to be important to both of these processes. These signals are typically a variation on the sequence AATAAA. In animal cells, some variants of this sequence that are functional have been identified, in plant cells there seems to be an extended range of functional sequences (Wickens and Stephenson, 1984; Dean et al., 1986). Because all of these consensus sequences are variations on AATAAA, they all are A+T rich sequences. This sequence is typically found 15 to 20 bp before the polyA tract in a mature mRNA. Studies in animal cells indicate that this sequence is involved in both polyA addition and 3' maturation. Site directed mutations in this sequence can disrupt these functions (Conway and Wickens, 1988; Wickens et al., 1987). However, it has also been observed that sequences up to 50 to 100 bp 3' to the putative polyA signal are also required; i.e., a gene that has a normal AATAAA but has been replaced or disrupted downstream does not get properly polyadenylated (Gil and Proudfoot, 1984; Sadofsky and Alwine, 1984; McDevitt et al., 1984). That is, the polyA signal itself is not sufficient for complete and proper processing. It is not yet known what specific downstream sequences are required in addition to the polyA signal, or if there is a specific sequence that has this function. Therefore, sequence analysis can only identify potential polyA signals.

In naturally occurring mRNAs that are normally polyadenylated, it has been observed that disruption of this process, either by altering the polyA signal or other sequences in the mRNA, profound effects can be obtained in the level of functional mRNA. This has been observed in several naturally occurring mRNAs, with results that are gene-specific so far.

It has been shown that in natural mRNAs proper polyadenylation is important in mRNA accumulation, and that disruption of this process can effect mRNA levels significantly. However, insufficient knowledge exists to predict the effect of changes in a normal gene. In a heterologous gene, it is even harder to predict the consequences. However, it is possible that the putative sites identified are dysfunctional. That is, these sites may not act as proper polyA sites, but instead function as aberrant sites that give rise to unstable mRNAs.

In animal cell systems, AATAAA is by far the most common signal identified in mRNAs upstream of the polyA, but at least four variants have also been found (Wickens and Stephenson, 1984). In plants, not nearly so much analysis has been done, but it is clear that multiple sequences similar to AATAAA can be used. The plant sites in Table 4 called major or minor refer only to the study of Dean et al. (1986) which analyzed only three types of plant gene. The designation of polyadenylation sites as major or minor refers only to the frequency of their occurrence as functional sites in naturally occurring genes that have been analyzed. In the case of plants this is a very limited database. It is hard to predict with any certainty that a site designated major or minor is more or less likely to function partially or completely when found in a heterologous gene such as those encoding the crystal proteins of the present invention.

TABLE 4

POLYADENYLATION SITES IN PLANT GENES

| | | |
|---|---|---|
| PA | AATAAA | Major consensus site |
| P1A | AATAAT | Major plant site |
| P2A | AACCAA | Minor plant site |
| P3A | ATATAA | " |
| P4A | AATCAA | " |
| P5A | ATACTA | " |
| P6A | ATAAAA | " |
| P7A | ATGAAA | " |
| P8A | AAGCAT | " |
| P9A | ATTAAT | " |
| P10A | ATACAT | " |
| P11A | AAAATA | " |
| P12A | ATTAAA | Minor animal site |
| P13A | AATTAA | " |
| P14A | AATACA | " |
| P15A | CATAAA | " |

The present invention provides a method for preparing synthetic plant genes which genes express their protein product at levels significantly higher than the wild-type genes which were commonly employed in plant transformation heretofore. In another aspect, the present invention also provides novel synthetic plant genes which encode non-plant proteins.

As described above, the expression of native *B. thuringiensis* genes in plants is often problematic. The nature of the coding sequences of *B. thuringiensis* genes distinguishes them from plant genes as well as many other heterologous genes expressed in plants. In particular, *B. thuringiensis* genes are very rich (~62%) in adenine (A) and thymine (T) while plant genes and most other bacterial genes which have been expressed in plants are on the order of 45–55% A+T.

Due to the degeneracy of the genetic code and the limited number of codon choices for any amino acid, most of the "excess" A+T of the structural coding sequences of some Bacillus species are found in the third position of the codons. That is, genes of some Bacillus species have A or T as the third nucleotide in many codons. Thus A+T content in part can determine codon usage bias. In addition, it is clear that genes evolve for maximum function in the organism in which they evolve. This means that particular nucleotide sequences found in a gene from one organism, where they may play no role except to code for a particular stretch of amino acids, have the potential to be recognized as gene control elements in another organism (such as transcriptional promoters or terminators, polyA addition sites, intron splice sites, or specific mRNA degradation signals). It is perhaps surprising that such misread signals are not a more common feature of heterologous gene expression, but this can be explained in part by the relatively homogeneous A+T content (~50%) of many organisms. This A+T content plus the nature of the genetic code put clear constraints on the likelihood of occurrence of any particular oligonucleotide sequence. Thus, a gene from *E. coli* with a 50% A+T content is much less likely to contain any particular A+T rich segment than a gene from *B. thuringiensis.*

Typically, to obtain high-level expression of the S-endotoxin genes in plants, existing structural coding sequence ("structural gene") which codes for the S-endotoxin are modified by removal of ATTTA sequences and putative polyadenylation signals by site directed mutagenesis of the DNA comprising the structural gene. It is most preferred that substantially all the polyadenylation signals and ATTTA sequences are removed although enhanced expression levels are observed with only partial removal of either of the above identified sequences. Alternately if a synthetic gene is prepared which codes for the expression of the subject protein, codons are selected to avoid the ATTTA sequence and putative polyadenylation signals. For purposes of the present invention putative polyadenylation signals include, but are not necessarily limited to, AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA and CATAAA. In replacing the ATTTA sequences and polyadenylation signals, codons are preferably utilized which avoid the codons which are rarely found in plant genomes.

The selected DNA sequence is scanned to identify regions with greater than four consecutive adenine (A) or thymine (T) nucleotides. The A+T regions are scanned for potential plant polyadenylation signals. Although the absence of five or more consecutive A or T nucleotides eliminates most plant polyadenylation signals, if there are more than one of the minor polyadenylation signals identified within ten nucleotides of each other, then the nucleotide sequence of this region is preferably altered to remove these signals while maintaining the original encoded amino acid sequence.

The second step is to consider the about 15 to about 30 or so nucleotide residues surrounding the A+T rich region identified in step one. If the A+T content of the surrounding region is less than 80%, the region should be examined for polyadenylation signals. Alteration of the region based on polyadenylation signals is dependent upon (1) the number of polyadenylation signals present and (2) presence of a major plant polyadenylation signal.

The extended region is examined for the presence of plant polyadenylation signals. The polyadenylation signals are removed by site-directed mutagenesis of the DNA sequence. The extended region is also examined for multiple copies of the ATTTA sequence which are also removed by mutagenesis.

It is also preferred that regions comprising many consecutive A+T bases or G+C bases are disrupted since these regions are predicted to have a higher likelihood to form hairpin structure due to self-complementarity. Therefore, insertion of heterogeneous base pairs would reduce the likelihood of self-complementary secondary structure formation which are known to inhibit transcription and/or translation in some organisms. In most cases, the adverse effects may be minimized by using sequences which do not contain more than five consecutive A+T or G+C.

4.11 Methods for Producing Insect-Resistant Transgenic Plants

By transforming a suitable host cell, such as a plant cell, with a recombinant cry1C* gene-containing segment, the expression of the encoded crystal protein (i.e., a bacterial crystal protein or polypeptide having insecticidal activity against lepidopterans) can result in the formation of insect-resistant plants.

By way of example, one may utilize an expression vector containing a coding region for a *B. thuringiensis* crystal protein and an appropriate selectable marker to transform a suspension of embryonic plant cells, such as wheat or corn cells using a method such as particle bombardment (Maddock et al., 1991; Vasil et al, 1992) to deliver the DNA coated on microprojectiles into the recipient cells. Transgenic plants are then regenerated from transformed embryonic calli that express the insecticidal proteins.

The formation of transgenic plants may also be accomplished using other methods of cell transformation which are known in the art such as Agrobacterium-mediated DNA transfer (Fraley et al, 1983). Alternatively, DNA can be introduced into plants by direct DNA transfer into pollen (Zhou et al., 1983; Hess, 1987; Luo et al., 1988), by injection of the DNA into reproductive organs of a plant (Pena et al., 1987), or by direct injection of DNA into the cells of immature embryos followed by the rehydration of desiccated embryos (Neuhaus et al., 1987; Benbrook et al, 1986).

The regeneration, development, and cultivation of plants from single plant protoplast transformants or from various transformed explants is well known in the art (Weissbach and Weissbach, 1988). This regeneration and growth process typically includes the steps of selection of transformed cells, culturing those individualized cells through the usual stages of embryonic development through the rooted plantlet stage.

Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by Agrobacterium from leaf explants can be achieved by methods well known in the art such as described (Horsch et al., 1985). In this procedure, transformants are cultured in the presence of a selection agent and in a medium that induces the regeneration of shoots in the plant strain being transformed as described (Fraley et al., 1983).

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, as discussed before. Otherwise, pollen obtained from the regenerated plants is crossed to seed-grown plants of agronomically important, preferably inbred lines. Conversely, pollen from plants of those important lines is used to pollinate regenerated plants. A transgenic plant of the present invention containing a desired polypeptide is cultivated using methods well known to one skilled in the art.

A transgenic plant of this invention thus has an increased amount of a coding region (e.g., a cry1C* gene) that encodes the Cry1C* polypeptide of interest. A preferred transgenic plant is an independent segregant and can transmit that gene and its activity to its progeny. A more preferred transgenic plant is homozygous for that gene, and transmits that gene to all of its offspring on sexual mating. Seed from a transgenic plant may be grown in the field or greenhouse, and resulting sexually mature transgenic plants are self-pollinated to generate true breeding plants. The progeny from these plants become true breeding lines that are evaluated for, by way of example, increased insecticidal capacity against lepidopteran insects, preferably in the field, under a range of environmental conditions. The inventors contemplate that the present invention will find particular utility in the creation of transgenic plants of commercial interest including various turf grasses, wheat, corn, rice, barley, oats, a variety of ornamental plants and vegetables, as well as a number of nut- and fruit-bearing trees and plants.

4.12 Methods For Producing Cry1C* Proteins Having Multiple Mutations

Cry1C mutants containing substitutions in multiple loop regions may be constructed via a number of techniques. For instance, sequences of highly related genes can be readily shuffled using the PCR-based technique described by Stemmer (1994). Alternatively, if suitable restriction sites are available, the mutations of one cry1C gene may be combined with the mutations of a second cry1C gene by routine subcloning methodologies. If a suitable restriction site is not available, one may be generated by oligonucleotide directed mutagenesis using any number of procedures known to those skilled in the art. Alternatively, splice-overlap extension PCR (Horton et al., 1989) may be used to combine mutations in different loop regions of Cry1C. In this procedure, overlapping DNA fragments generated by the PCR and containing different mutations within their unique sequences may be annealed and used as a template for amplification using flanking primers to generate a hybrid gene sequence. Finally, cry1C mutants may be combined by simply using one cry1C mutant as a template for oligonucleotide-directed mutagenesis using any number of protocols such as those described herein.

4.13 Ribozymes

Ribozymes are enzymatic RNA molecules which cleave particular mRNA species. In certain embodiments, the inventors contemplate the selection and utilization of ribozymes capable of cleaving the RNA segments of the present invention, and their use to reduce activity of target mRNAs in particular cell types or tissues.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., 1992). Thus, the specificity of action of a ribozyme is greater than that of an antisense oligonucleotide binding the same RNA site.

The enzymatic nucleic acid molecule may be formed in a hammerhead, hairpin, a hepatitis δ virus, group I intron or RNaseP RNA (in association with an RNA guide sequence) or Neurospora VS RNA motif. Examples of hammerhead motifs are described by Rossi et al. (1992); examples of hairpin motifs are described by Hampel et al. (Eur. Pat. EP 0360257), Hampel and Tritz (1989), Hampel et al. (1990) and Cech et al. (U.S. Pat. No. 5,631,359; an example of the hepatitis δ virus motif is described by Perrotta and Been (1992); an example of the RNaseP motif is described by Guerrier-Takada et al. (1983); Neurospora VS RNA ribozyme motif is described by Collins (Saville and Collins, 1990; Saville and Collins, 1991; Collins and Olive, 1993); and an example of the Group I intron is described by Cech et al. (U.S. Pat. No. 4,987,071). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

The invention provides a method for producing a class of enzymatic cleaving agents which exhibit a high degree of specificity for the RNA of a desired target. The enzymatic nucleic acid molecule is preferably targeted to a highly conserved sequence region of a target mRNA such that specific treatment of a disease or condition can be provided with either one or several enzymatic nucleic acids. Such enzymatic nucleic acid molecules can be delivered exogenously to specific cells as required. Alternatively, the ribozymes can be expressed from DNA or RNA vectors that are delivered to specific cells.

Small enzymatic nucleic acid motifs (e.g., of the hammerhead or the hairpin structure) may be used for exogenous delivery. The simple structure of these molecules increases the ability of the enzymatic nucleic acid to invade targeted regions of the mRNA structure. Alternatively, catalytic RNA molecules can be expressed within cells from eukaryotic promoters (e.g., Scanlon etal, 1991; Kashani-Sabet et al., 1992; Dropulic et al., 1992; Weerasinghe etal., 1991; Ojwang et al., 1992; Chen et al., 1992; Sarver et al., 1990). Those skilled in the art realize that any ribozyme can be expressed in eukaryotic cells from the appropriate DNA vector. The activity of such ribozymes can be augmented by their release from the primary transcript by a second ribozyme (Draper et al., Int. Pat. Appl. Publ. No. WO 93/23569, and Sullivan et al., Int. Pat. Appl. Publ. No. WO 94/02595, both hereby incorporated in their totality by reference herein; Ohkawa et al., 1992; Taira et al., 1991; Ventura et al., 1993).

Ribozymes may be added directly, or can be complexed with cationic lipids, lipid complexes, packaged within liposomes, or otherwise delivered to target cells. The RNA or RNA complexes can be locally administered to relevant tissues ex vivo, or in vivo through injection, aerosol inhalation, infusion pump or stent, with or without their incorporation in biopolymers.

Ribozymes may be designed as described in Draper et al. (Int. Pat. Appl. Publ. No. WO 93/23569), or Sullivan et al., (Int. Pat. Appl. Publ. No. WO 94/02595) and synthesized to be tested in vitro and in vivo, as described. Such ribozymes can also be optimized for delivery. While specific examples are provided, those in the art will recognize that equivalent RNA targets in other species can be utilized when necessary.

Hammerhead or hairpin ribozymes may be individually analyzed by computer folding (Jaeger et al., 1989) to assess whether the ribozyme sequences fold into the appropriate secondary structure. Those ribozymes with unfavorable intramolecular interactions between the binding arms and the catalytic core are eliminated from consideration. Varying binding arm lengths can be chosen to optimize activity. Generally, at least 5 bases on each arm are able to bind to, or otherwise interact with, the target RNA.

Ribozymes of the hammerhead or hairpin motif may be designed to anneal to various sites in the MRNA message, and can be chemically synthesized. The method of synthesis used follows the procedure for normal RNA synthesis as described in Usman etal. (1987) and in Scaringe etal. (1990) and makes use of common nucleic acid protecting and coupling groups, such as dimethoxytrityl at the 5'-end, and phosphoramidites at the 3'-end. Average stepwise coupling yields are typically >98%. Hairpin ribozymes may be synthesized in two parts and annealed to reconstruct an active ribozyme (Chowrira and Burke, 1992). Ribozymes may be modified extensively to enhance stability by modification with nuclease resistant groups, for example, 2'-amino, 2'-C-allyl, 2'-flouro, 2'-o-methyl, 2'-H (for a review see Usman and Cedergren, 1992). Ribozymes may be purified by gel electrophoresis using general methods or by high pressure liquid chromatography and resuspended in water.

Ribozyme activity can be optimized by altering the length of the ribozyme binding arms, or chemically synthesizing ribozymes with modifications that prevent their degradation by serum ribonucleases (see e.g., Int. Pat. Appl. Publ. No. WO 92/07065; Perrault et al, 1990; Pieken et al., 1991; Usman and Cedergren, 1992; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Sullivan et al. (Int. Pat. Appl. Publ. No. WO 94/02595) describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan et al. (Int. Pat. Appl. Publ. No. WO 94/02595) and Draper et al. (Int. Pat. Appl. Publ. No. WO 93/23569) which have been incorporated by reference herein.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells (Elroy-Stein and Moss, 1990; Gao and Huang, 1993; Lieber et al., 1993; Zhou et al., 1990). Ribozymes expressed from such promoters can function in mammalian cells (e.g. Kashani-Saber et al., 1992; Ojwang et al., 1992; Chen et al., 1992; Yu et al., 1993; L'Huillier et al., 1992; Lisziewicz et al., 1993). Such transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, semliki forest virus, sindbis virus vectors).

Ribozymes of this invention may be used as diagnostic tools to examine genetic drift and mutations within cell lines or cell types. They can also be used to assess levels of the target RNA molecule. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in particular cells or cell types.

4.14 Isolating Homologous Gene and Gene Fragments

The genes and δ-endotoxins according to the subject invention include not only the full-length sequences disclosed herein but also fragments of these sequences, or fusion proteins, which retain the characteristic insecticidal activity of the sequences specifically exemplified herein.

It should be apparent to a person skill in this art that insecticidal δ-endotoxins can be identified and obtained through several means. The specific genes, or portions thereof, may be obtained from a culture depository, or constructed synthetically, for example, by use of a gene machine. Variations of these genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which code for active fragments may be obtained using a variety of other restriction enzymes. Proteases may be used to directly obtain active fragments of these δ-endotoxins.

Equivalent δ-endotoxins and/or genes encoding these equivalent δ-endotoxins can also be isolated from Bacillus strains and/or DNA libraries using the teachings provided herein. For example, antibodies to the δ-endotoxins disclosed and claimed herein can be used to identify and isolate other δ-endotoxins from a mixture of proteins. Specifically, antibodies may be raised to the portions of the δ-endotoxins which are most constant and most distinct from other *B. thuringiensis* δ-endotoxins. These antibodies can then be used to specifically identify equivalent δ-endotoxins with the characteristic insecticidal activity by immunoprecipitation, enzyme linked immunoassay (ELISA), or Western blotting.

A further method for identifying the δ-endotoxins and genes of the subject invention is through the use of oligonucleotide probes. These probes are nucleotide sequences having a detectable label. As is well known in the art, if the probe molecule and nucleic acid sample hybridize by forming a strong bond between the two molecules, it can be reasonably assumed that the probe and sample are essentially identical. The probe's detectable label provides a means for determining in a known manner whether hybridization has occurred. Such a probe analysis provides a rapid method for identifying formicidal δ-endotoxin genes of the subject invention.

The nucleotide segments which are used as probes according to the invention can be synthesized by use of DNA synthesizers using standard procedures. In the use of the nucleotide segments as probes, the particular probe is labeled with any suitable label known to those skilled in the art, including radioactive and non-radioactive labels. Typical radioactive labels include $^{32}P$, $^{125}I$, $^{35}S$, or the like. A probe labeled with a radioactive isotope can be constructed from a nucleotide sequence complementary to the DNA sample by a conventional nick translation reaction, using a DNase and DNA polymerase. The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting.

Non-radioactive labels include, for example, ligands such as biotin or thyroxine, as well as enzymes such as hydrolases or peroxidases, or the various chemiluminescers such as luciferin, or fluorescent compounds like fluorescein and its derivatives. The probe may also be labeled at both ends with different types of labels for ease of separation, as, for example, by using an isotopic label at the end mentioned above and a biotin label at the other end.

Duplex formation and stability depend on substantial complementarity between the two strands of a hybrid, and, as noted above, a certain degree of mismatch can be tolerated. Therefore, the probes of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, by methods currently known to an ordinarily skilled artisan, and perhaps by other methods which may become known in the future.

The potential variations in the probes listed is due, in part, to the redundancy of the genetic code. Because of the redundancy of the genetic code, i.e., more than one coding nucleotide triplet (codon) can be used for most of the amino acids used to make proteins. Therefore different nucleotide sequences can code for a particular amino acid. Thus, the amino acid sequences of the *B. thuringiensis* δ-endotoxins and peptides can be prepared by equivalent nucleotide sequences encoding the same amino acid sequence of the protein or peptide. Accordingly, the subject invention includes such equivalent nucleotide sequences. Also, inverse or complement sequences are an aspect of the subject invention and can be readily used by a person skilled in this art. In addition it has been shown that proteins of identified structure and function may be constructed by changing the amino acid sequence if such changes do not alter the protein secondary structure (Kaiser and Kezdy, 1984). Thus, the subject invention includes mutants of the amino acid sequence depicted herein which do not alter the protein secondary structure, or if the structure is altered, the biological activity is substantially retained. Further, the invention also includes mutants of organisms hosting all or part of a δ-endotoxin encoding a gene of the invention. Such mutants can be made by techniques well known to persons skilled in the art. For example, UV irradiation can be used to prepare mutants of host organisms. Likewise, such mutants may include asporogenous host cells which also can be prepared by procedures well known in the art.

5.0 EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

Preparation of Templates for Random Mutagenesis

Structural maps for the cry1C plasmids pEG315 and pEG916 are shown in FIG. 2. The cry1C gene contained on these plasmids was isolated from the *B. thuringiensis* strain EG6346 subsp. *aizawai*, first described by Chambers et al. (1991). An ~4 kb SalI-BamHI fragment containing the intact cry1C gene from EG6346 was cloned into the unique XhoI and BamHI sites of the shuttle vector pEG854, described by Baum et al. (1990) to yield pEG315. pEG916 is a pEG853 derivative (also described by Baum et al., 1990) containing the same cry1C gene fragment and a 3' transcription terminator region derived from the cry1F gene described by Chambers et al. (1991).

pEG345 (FIG. 3) is a pEG597 derivative (also described by Baum et al., 1990) that contains the cry1C gene from *B. thuringiensis* subsp. *aizawai* strain 7.29, described by Sanchis et al. (1989) and disclosed in the European Pat. Appl. No. EP 295156A1 and Intl. Pat. Appl. Publ. No. WO 88/09812. Both genes are nearly identical to the holotype cry1C gene described by Honee et al. (1988).

The recombinant DNA techniques employed are familiar to those skilled in the art of manipulating and cloning DNA fragments and employed pursuant to the teachings of Maniatis et al. (1982) and Sambrook et al. (1989).

A frame-shift mutation was introduced into the cry1C gene of pEG916 at codon 118. By analogy to the published crystal structures for Cry1Aa and Cry3A, the glutamic acid residue (E) at this position is predicted to lie within or immediately adjacent to the loop region between α helices 3 and 4 of Cry1C domain 1, the target site for random mutagenesis. This mutated gene can be used as a template for oligonucleotide-directed mutagenesis using a mutagenic primer that corrects the frame-shift mutation, thus ensuring that the majority of clones recovered encoding full-length protoxin molecules will have incorporated the mutagenic oligonucleotide.

The frame-shift mutation was introduced by a PCR™-mediated mutagenesis protocol using the oligonucleotide primers A, B, and C and pEG916 (FIG. 2) as the DNA template. The mutagenesis protocol, described by (Michael, 1994) relies on the use of a thermostable ligase to incorporate a phosphorylated mutagenic oligonucleotide into an amplified DNA fragment. The DNA sequence of these primers is shown below:

Primer A: (SEQ ID NO:15)
5'-CCCGATCGGCCGCATGC-3'

Primer B: (SEQ ID NO:16)
5'-GCATTTAAAGAATGGGAAGGGATCCTAGGAATC CAGCAACCAGGACCAGAG-3'

Primer C: (SEQ ID NO:17)
5'-GAGCTCTTGTTAAAAAAGGTGTTCCAGATC-3'

The mutagenic oligonucleotide, primer B, was designed to incorporate a BamHI and BlnI restriction site in addition to the frame-shift mutation at codon 118 (FIG. 4). The product obtained from the PCR™ was resolved by electrophoresis of an agarose-TAE gel and purified using the Geneclean II® Kit (Bio 101, Inc., La Jolla, Calif.) following the manufacturer's suggested protocol. The purified DNA fragment was digested with the restriction enzymes AgeI and BbuI. pEG916 was also digested with the restriction enzymes AgeI and BbuI and the restricted DNA fragments resolved by agarose gel electrophoresis and the vector fragment purified as described above. The amplified DNA fragment and the pEG916 vector fragment were ligated together with T4 ligase, and the ligation reaction used to transform the acrystalliferous *B. thuringiensis* strain EG10368 (described in U.S. Pat. No. 5,322,687) to Cml resistance, using the electroporation procedure described by Mettus and Macaluso (1990). Individual transformants were selected and many were determined to be acrystalliferous by phase-contrast microscopy of the sporulated cultures. Recombinant plasmids were isolated from *B. thuringiensis* transfonmants using the alkaline lysis procedure described by Maniatis et al. (1982). Incorporation of the frame-shift mutation into cry1C was also indicated by the presence of the BamHI and BlnI sites, determined by restriction enzyme analysis of the recombinant plasmids isolated from the EG10368 transformants. The recombinant plasmid incorporating the frame-shift mutation and the BamHI and BlnI sites was designated pEG359 (FIG. 2 and FIG. 4).

pEG359 was introduced into the *E. coli* host strain DH5α by transformation using frozen competent cells and procedures obtained from GIBCO BRL (Gaithersburg, Md.). pEG359, purified from *E. coli* using the alkaline lysis procedure (Maniatis et al., 1982), was further modified by digestion with the restriction enzyme BglII and religation of the vector fragment with T4 ligase. The ligation reaction was used to transform the *E. coli* host strain DH5α as before. The resulting plasmid, designated p154 (FIG. 2), contains a deletion of the cry1C gene sequences downstream of the unique BglII site in cry1C

5.2 Example 2

Random Mytagesesis of Nucleotides 352–372 in Cry1C

Mutagenesis of nucleotides 352–372, encoding the putative loop region between a helices 3 and 4 of Cry1C domain 1, was performed according to the PCR™-mediated "Megaprimer" method as described (Upender et al, 1995), using the oligonucleotide primers A (SEQ ID NO:15), C (SEQ ID NO:17), and D (SEQ ID NO:18).

Primer D: (SEQ ID NO:18)

5'-GCATTTAAAGAATGGGAANNNNNNNNNNNNNNN NNNNNNACCAGGACCAGAGTAATTGATCGC-3'

N (20,21,23,28,29,31,32, and 39)=82% A; 6% G, C, T,

N (25, 26, 34, 35, and 38)=82% C; 6% G, T, A

N (19, 22, and 37)=82% G; 6% C, T, A

N (24, 27, 30, 33, and 36)=82% T; 6% G, C, A. Numbers in parentheses correspond to the positions above in SEQ ID NO:18, wherein the first G is position number 1.

The mutagenic primer D corrects the frame-shift mutation and eliminates the BamHI and BlnI sites introduced into pEG359. To accomplish this mutagenesis, the Megaprimer was first synthesized by PCR™ amplification of pEG315 DNA (FIG. 2) using the mutagenic primer D and the opposing primer C (FIG. 5). The resulting amplified DNA fragment was purified by gel electrophoresis as described above and used in a second PCR™ using primers A and C and p154 as the template. Because the p154 template contains a deletion of the region complementary to primer C (FIG. 5), initiation of the PCR™ first requires extension of the Megaprimer to allow annealing of primer A to the mutagenic strand, thus ensuring that most of the amplified product obtain from the PCR™ incorporates the mutagenic DNA. The resulting PCR™ product was isolated and purified following gel electrophoresis in agarose and 1× TAE as described above.

The amplified DNA fragment was digested with the restriction enzymes AgeI and BbuI, to provide sticky ends suitable for cloning, and with the enzymes BamHI and BlnI to eliminate any residual p154 template DNA. pEG359 was digested with AgeI and BbuI and the vector fragment ligated to the restricted amplified DNA preparation. The ligation reaction was used to transform the *E. coli* Sure™ (Stratagene Cloning Systems, La Jolla, Calif.) strain to ampicillin (Amp) resistance (Amp®) using a standard transformation procedure. Amp® colonies were scraped from plates and growth for 1–2 hr at 37° C. in Luria Broth with 50 μg/ml of Amp. Plasmid DNA was isolated from this culture using the alkaline lysis procedure described above and used to transform *B. thuringiensis* EG10368 to Cml resistance (Cml®) by electroporation. Transformants were plated on starch agar plates containing 5 μg/ml Cml and incubated at 25–30° C. Restriction enzyme analysis of plasmid DNAs isolated from crystal-forming transformants indicated that 75% of the transformants had incorporated the mutagenic oligonucleotide at the target site (nt 352–372). That is, ~75% of the crystal-forming transformants had lost the BamHI and BlnI sites at the target site on cry1C.

5.3 Example 3

Mutagenesis of Arg Residuea in Cry1C Domain 1

Arginine residues within potential loop regions of Cry1C domain 1 were replaced by alanine residues using oligonucleotide-directed mutagenesis. The elimination of these arginine residues may reduce the proteolysis of toxin protein by trypsin-like proteases in the lepidopteran midgut since trypsin is known to cleave peptide bonds immediately C-terminal to arginine and lysine. The arginine residues at amino acid positions 148 and 180 in the Cry1C amino acid sequence were replaced with alanine residues. The PCR™-mediated mutagenesis protocol used, described by Michael (1994) relies on the use of a thermostable ligase to incorporate a phosphorylated mutagenic oligonucleotide into an amplified DNA fragment. The mutagenesis of R148 employed the mutagenic primer E (SEQ ID NO:19) and the flanking primers A (SEQ ID NO:15) and primer F (SEQ ID NO:20). The mutagenesis of R180 employed the mutagenic primer G (SEQ ID NO:21) and the flanking primers A (SEQ ID NO:15) and F (SEQ ID NO:20). Both PCR™ studies employed pEG315 (FIG. 2) DNA as the cry1C template. Primer E was designed to eliminate an AsuII site within the wild-type cry1C nucleotide sequence. Primer G was designed to introduce a HincII site within the cry1C nucleotide sequence.

Primer E: (SEQ ID NO:19)

5'-GGGCTACTTGAAAGGGACATTCCTTCGTTTGCA ATTTCTGGATTTGAAGTACCCC-3'

Primer F: (SEQ ID NO:20)

5'-CCAAGAAAATACTAGAGCTCTTGTTAAAAAAGG TGTTCC-3'

Primer G: (SEQ ID NO:21)

5'-GAGATTCTGTAATTTTTGGAGAAGCATGGGGGT TGACAACGATAAATGTC-3'

The products obtained from the PCR™ were purified following agarose gel electrophoresis using the Geneclean II® procedure and reamplified using the opposing primers A and F and standard PCR™ procedures. The resultant PCR™ products were digested with the restriction enzymes BbuI and AgeI. pEG315, containing the intact cry1C gene of EG6346, was digested with the restriction enzymes BbuI and AgeI. The restricted fragments were resolved by agarose gel electrophoresis in 1× TAE, the pEG315 vector fragment purified using the Geneclean II® procedure and, subsequently ligated to the amplified DNA fragments obtained from the mutagenesis using T4 ligase. The ligation reactions were used to transform the *E. coli* DH5α™ to Amp resistance using standard transformation methods. Transformants were selected on Luria plates containing 50 μg/ml Amp. Plasmid DNAs isolated from the *E. coli* transformants generated by the R148 mutagenesis were used to transform *B. thuringiensis* EG10368 to Cml®, using the electroporation procedure described by Mettus and Macaluso (1990). Transformants were selected on Luria plates containing 3 μg/ml Cml. Approximately 75% of the EG10368 transformants generated by the R148 mutagenesis had lost the AsuII site, indicating that the mutagenic oligonucleotide primer E had been incorporated into the cry1C gene. One transformant, designated EG11811, was chosen for further study. Approximately 25% of the *E. coli* transformants generated by the R180 mutagenesis contained the new HincII site introduced by the mutagenic oligonucleotide primer G, indicating that the mutagenic oligonucleotide had been incorporated into the cry1C gene. Plasmid DNA from one such transformant was used to transform the *B. thuringiensis* host strain EG10368 to Cml® by electroporation as before. One of the resulting transformants was designated EG11815.

The mutagenesis of R148 was repeated using the cry1C gene contained in plasmid pEG345. Plasmid pEG345 (FIG. 2) contains the cry1C gene from *B. thuringiensis* subsp. *aizawai* strain 7.29 (Sanchis et al., 1989; Eur. Pat. Application EP 295156A1; Intl. Pat. Appl. Publ. No. WO 88/09812). The mutagenesis of R148 employed the mutagenic primer E (SEQ ID No:19), the flanking primers H (SEQ ID NO:52) and F (SEQ ID NO:20), and plasmid pEG345 as the source of the cry1C DNA template. Primer E was designed to eliminate an AsuII site within the wild-type cry1C sequence.

Primer H:

5'-GGATCCCTCGAGCTGCAGGAGC-3' (SEQ ID NO:52) cry1C template DNA was obtained from a PCR™ using the opposing primers H and F and plasmid pEG345 as a template. This DNA was then used as the template for a PCR™-mediated mutagenesis reaction that employed the flanking primers H and F and the mutagenic oligonucleotide E, using the procedure described by Michael (1994). The resultant PCR™ products were digested with the restriction enzymes BbuI and AgeI. The restricted DNA fragments were resolved by agarose gel electrophoresis in 1× TAE and the amplified cry1C fragment was purified using the Geneclean II® procedure. Similarly, plasmid pEG345 was digested with the restriction enzymes BbuI and AgeI, resolved by agarose gel electrophoresis in 1× TAE and the pEG345 vector fragment purified using the Geneclean II® procedure. The purified DNA fragments were ligated together using T4 ligase and used to transform *E. coli* DH5α using a standard transformation procedure. Transformants were selected on Luria plates containing 50 μg/ml Amp. Approximately 50% of the DH5α transformants generated by the R148 mutagenesis had lost the AsuII site, indicating that the mutagenic oligonucleotide primer E had been incorporated into the cry1C gene. Plasmid DNA from one transformant was used to transform *B. thuringiensis* EG10368 to Cml®, using the electroporation procedure described by Mettus and Macaluso (1990). Transformants were selected on Luria plates containing 3 μg/ml chloramphenicol. One of the transformants was designated EG11822.

The arginine residue at amino acid position 148 was also replaced with random amino acids. This mutagenesis of R148 employed the mutagenic primer I (SEQ ID No: 53), the flanking primers H (SEQ ID NO:52) and F (SEQ ID NO:20), and plasmid pEG345 as the source of the cry1C DNA template. Primer I was also designed to eliminate an AsuII site within the wild-type cry1C sequence:

Primer I: (SEQ ID NO:53)

5'-GGGCTACTTGAAAGGGACATTCCTTCGTTTNNN ATTTCTGGATTTGAAGTACCCC-3'

N (31, 32, 33)=25% A, 25% C, 25% G, 25% T cry1C template DNA was obtained from a PCR™ using the opposing primers H and F and plasmid pEG345 as a template. This DNA was then used as the template for a PCR™-mediated mutagenesis reaction that employed the flanking primers H and F and the mutagenic oligonucleotide I, using the procedure described by Michael (1994). The resultant PCR™ products were digested with the restriction enzymes BbuI and AgeI. The restricted DNA fragments were resolved by agarose gel electrophoresis in 1× TAE and the amplified cry1C fragment was purified using the Geneclean II® procedure. Similarly, plasmid pEG345 was digested with the restriction enzymes BbuI and AgeI, resolved by agarose gel electroph resisrin 1× TAE and the pEG345 vector fragment purified using the Geneclean II® procedure. The purified DNA fragments were ligated together using T4 ligase and used to transform *E. coli* DH5α to ampicillin resistance using a standard transformation procedure. Transformants were selected on Luria plates containing 50 ug/ml arnpicillin. The DH5α transformants were pooled together and plasmid DNA was prepared using the alkaline lysis procedure. Plasmid DNA from the DH5α transformants was used to transform *B. thuringiensis* EG10368 to Cml®, using the electroporation procedure described by Mettus and Macaluso (1990). Transformants were selected that exhibited an opaque phenotype on starch agar plates containing 3 ug/ml chloramphenicol, indicating crystal protein production. Approximately 90% of the opaque EG10368 transformants generated by the R148 mutagenesis had lost the AsuII site, indicating that the mutagenic oligonucleotide primer I had been incorporated into the cry1C gene.

5.4 Example 4

Bioassay Evaluation of Cry1C* Toxins

EG10368 transformants containing mutant cry1C genes were grown in C2 medium, described by Donovan et al. (1988), for 3 days at 25° C. or until fully sporulated and lysed. The spore-Cry1C crystal suspensions recovered from the spent C2 cultures were used for bioassay evaluation against neonate larvae of *Spodoptera exigua* and 3rd instar larvae of *Plutella xylostella.*

EG10368 transformants harboring Cry1C mutants generated by random mutagenesis were grown in 2 ml of C2 medium and evaluated in one-dose bioassay screens. Each culture was diluted with 10 ml of 0.005% Triton X-100® and 25 μl of these dilutions were seeded into an additional 4 ml of 0.005% Triton X-100® to achieve the appropriate dilution for the bioassay screens. Fifty μl of this dilution were topically applied to 32 wells containing 1.0 ml artificial diet per well (surface area of 175 $mm^2$). A single neonate larvae (*S. exigua*) or 3rd instar larvae (*P. xylostella*) was placed in each of the treated wells and the tray was covered by a clear perforated mylar strand. Larval mortality was scored after 7 days of feeding at 28–30° C. and percent mortality expressed as ratio of the number of dead larvae to the total number of larvae treated.

Three EG10368 transformants, designated EG11740, EG11746, and EG11747, were identified as showing increased insecticidal activity against *Spodoptera exigua* in replicated bioassay screens. The putative Cry1C variants in strains EG11740, EG11746, and EG11747 were designated Cry1C.563, Cry1C.579, and Cry1C.499, respectively. These three variants contain amino acid substitutions within the loop region between α helices 3 and 4 of Cry1C. EG11740, EG11746, and EG11747, as well as EG11726 (which contains the wild-type cry1C gene from strain EG6346) were grown in C2 medium for 3 days at 25° C. The cultures were centrifuged and the spore/crystal pellets were washed three times in 2× volumes of distilled-deionized water. The final pellet was suspended in an original volume of 0.005% TritonX-100 and crystal protein quantified by SDS-PAGE as described by Brussock and Currier (1990). The procedure was modified to eliminate the neutralization step with 3M HEPES. Eight δ-endotoxin concentrations of the spore/crystal preparations were prepared by serial dilution in 0.005% Triton X-100 and each concentration was topically applied to wells containing 1.0 ml of artificial diet. Larval mortality was scored after 7 days of feeding at 23–30° C. (32 larvae for each δ-endotoxin concentration). Mortality data was expressed as $LC_{50}$ and $LC_{95}$ values, in accordance with the technique of Daum (1970), the concentration of Cry1C protein (ng/well) causing 50% and 95% mortality, respectively (Table 5, Table 6, and Table 7). Strains EG11740 (Cry1C.563) and EG11746 (Cry1C.579) exhibited 3-fold lower $LC_{95}$ values than the control strain EG11726 (Cry1C) against *S. exigua*, while retaining a comparable level of activity against *P. xylostella*. EG11740 and EG11746 also exhibited significantly lower $LC_{50}$ values against *S. exigua*.

TABLE 5

BIOASSAY OF CRY1C LOOP α 3–4 MUTANTS USING *SPODOPTERA EXIGUA* LARVAE

| Strain | Toxin | $LC_{50}$[1] (95% C.I.)[3] | $LC_{95}$[2] (95% C.I.) |
|---|---|---|---|
| EG11726 | Cry1C | 116(104–131) | 1601(1253–2131) |
| EG11740 | Cry1C.563 | 50(42–59) | 583(433–844) |
| EG11747 | Cry1C.499 | 67(58–78) | 596(455–834) |
| EG11746 | Cry1C.579 | 68(58–79) | 554(427–766) |

[1]Concentration of Cry1C protein that causes 50% mortality expressed in ng crystal protein per 175 $mm^2$ well. Results of 3–7 sets of replicated bioassays.
[2]Concentration of Cry1C protein that causes 95% mortality expressed in ng crystal protein per 175 $mm^2$ well. Results of 3–7 sets of replicated bioassays.
[3]95% confidence intervals.

TABLE 6

BIOASSAYS USING *PLUTELLA XYLOSTELLA* LARVAE

| Strain | Toxin | $LC_{50}$[1] (95% C.I.)[3] | $LC_{95}$[2] (95% C.I.) |
|---|---|---|---|
| EG11726 | Cry1C | 92(83–102) | 444(371–549) |
| EG11740 | Cry1C.563 | 106(95–119) | 579(478–728) |
| EG11811 | Cry1C R148A | 61(45–85) | 400(241–908) |

[1]Concentration of Cry1C protein that causes 50% mortality expressed in ng crystal protein per 175 $mm^2$ well. Results of two sets of replicated bioassays.
[2]Concentration of Cry1C protein that causes 95% mortality expressed in ng crystal protein per 175 $mm^2$ well. Results of two sets of replicated bioassays.
[3]95% confidence intervals.

The Cry1C mutant strains EG11811 (Cry1C R148A) and EG11815 (Cry1C R180A) were grown in C2 medium and evaluated using the same quantitative eight-dose bioassay procedure. The insecticidal activities of Cry1C and Cry1C R180A against *S. exigua* and *P. xylostella* were not significantly different, however, Cry1C R148A exhibited a 3.6-fold lower $LC_{50}$ and a 3.7-fold lower $LC_{95}$ against *S. exigua* when compared to the original Cry1C-endotoxin (Table 7). Cry1C R148A and Cry1C exhibited comparable insecticidal activity against *P. xylostella* (Table 6).

TABLE 7

BIOASSAYS OF CRY1C R148A USING *SPODOPTERA EXIGUA* LARVAE

| Strain | Toxin | $LC_{50}$[1] (95% C.I.)[3] | $LC_{95}$[2] (95% C.I.) |
|---|---|---|---|
| EG11726 | Cry1C | 141(122–164) | 1747(1279–2563) |
| EG11811 | Cry1C R148A | 41(33–52) | 481(314–864) |

[1]Concentration of Cry1C protein that causes 50% mortality expressed in ng crystal protein per 175 $mm^2$ well. Results of two sets of replicated bioassays.
[2]Concentration of Cry1C protein that causes 95% mortality expressed in ng crystal protein per 175 $mm^2$ well. Results of two sets of replicated bioassays.
[3]95% confidence intervals.

The Cry1C mutant strains EG11811 (Cry1C R148A), EG11740 (Cry1C.563), and EG11726 (producing wildtype Cry1C) were similarly cultured and evaluated in bioassays using neonate larvae of *Trichoplusia ni*. The insecticidal activities of Cry1C R148A and Cry1C.563 against *T. ni* exhibited a lower $LC_{50}$ and $LC_{95}$ against *T. ni* when compared to EG11726 (Table 8).

TABLE 8

BIOASSAYS USING *TRICHOPLUSIA NI* LARVAE

| Strain | Toxin | $LC_{50}$[1] | $LC_{95}$[2] |
|---|---|---|---|
| EG11726 | Cry1C | 40(31–56)[3] | 330 |
| BG11740 | Cry1C.563 | 20(17–24) | 104 |
| EG11811 | Cry1C-R148A | 19(16–23) | 115 |

[1]Concentration of Cry1C protein that causes 50% mortality expressed in ng crystal protein per 175 $mm^2$ well. Results of one set of replicated bioassays.
[2]Concentration of Cry1C protein that causes 95% mortality expressed in ng crystal protein per 175 $mm^2$ well. Results of one set of replicated bioassays.
[3]95% confidence intervals.

Bioassay comparisons with other lepidopteran insects revealed additional improvements in the properties of Cry1C.563 and Cry1C-R148A, particularly in toxicity towards the fall armyworm *Spodoptera frugiperda* (Table 9) The doses reported in Table 8 are as follows: 10,000 ng/well *A. epsilon, H. virescens, H. zea, O. nubilalis*, and *S. frugiperda*.

TABLE 9

BIOASSAY COMPARISONS WITH OTHER LEPIDOPTERAN INSECTS

| | Mortality | | | | 
|---|---|---|---|---|
| Insect | Control | Cry1C.563 | Cry1C-R148A | Native Cry1C |
| *A. ipsilon* | – | – | – | – |
| *H. virescens* | – | + | +++ | + |
| *H. zea* | – | – | – | – |
| *O. nubilalis* | – | +++ | +++ | ++ |
| *S. frugiperda* | – | +++ | +++ | + |

+ = 20–49% mortality
++ = 50–74% mortality
+++ = 75–100% mortality

EG10368 transformants harboring random mutants at position R148 of Cry1C were evaluated in bioassay in a one-dose screen against *S. exigua* as described above. Five Cry1C mutants were identified with improved activity over wild-type Cry1C. The mutants were then evaluated in eight-dose bioassay against *S. exigua* as described above. All five Cry1C mutants gave a significantly lower $LC_{50}$ than wild-type Cry1C (Table 10), comparable to EG11822 (R148A). One mutant, designated EG11832 (Cry1C-R148D) gave a significantly lower $LC_{50}$ and $LC_{95}$ than EG11822, indicating further improved toxicity towards *S. exigua*.

TABLE 10

BIOASSAYS USING *SPODOPTERA EXIGUA* LARVAE

| Strain | Mutation | $LC_{50}$[1] (95% C.I.)[3] | $LC_{95}$[2] (95% C.I.) |
|---|---|---|---|
| EG11822 | R148A | 37(32–43)[4] | 493(375–686)[4] |
| EG11832 | R148D | 22(19–25)[4] | 211(167–282)[4] |
| Wild-type | None | 145(117–182) | 1685(1072–3152) |
| Mutant #1 | R148L | 47(39–57) | 523(367–831) |
| Mutant #12 | R148G | 65(46–93) | 549(316–1367) |
| Mutant #43 | R148L | 31(16–54) | 311(144–1680) |
| Mutant #45 | R148M | 36(29–45) | 469(324–762) |

[1]Concentration of Cry1C protein that causes 50% mortality expressed in ng crystal protein per 175 $mm^2$ well. Results of one set of replicated bioassays.
[2]Concentration of Cry1C protein that causes 95% mortality expressed in ng crystal protein per 175 $mm^2$ well. Results of one set of replicated bioassays.
[3]95% confidence intervals.
[4]Results of two sets of replicated bioassays.

5.5 Example 5

Sequence Analysis of Cry1C Mutations

Recombinant plasmids from the EG10368 transformants were isolated using the alkaline lysis method (Maniatis et al., 1982). Plasmids obtained from the transformants were introduced into the *E. coli* host strain DH5α™ by competent cell transformation and used as templates for DNA sequencing using the Sequenase® v2.0 DNA sequencing kit (U.S. Biochemical Corp., Cleveland, Ohio).

Sequence analysis of plasmid pEG359 (FIG. 4; SEQ ID NO:24) revealed the expected frameshift mutation at codon 118 and the BamHI and BlnI restriction sites introduced by the mutagenic oligonucleotide primer B (SEQ ID NO:16).

Sequence analysis of the cry1C.563 gene on plasmid pEG370 (FIG. 4; SEQ ID NO:25) revealed nucleotide substitutions at positions 354, 361, 369, and 370, resulting in point mutations A to T, A to C, A to C, and G to A, respectively. These mutations resulted in amino acid substitutions in Cry1C.563 (FIG. 4; SEQ ID NO:26) at positions 118 (E to D), 121 (N to H), and 124 (A to T).

Sequence analysis of the cry1C.579 gene on plasmid pEG373 (FIG. 4; SEQ ID NO:54) revealed nucleotide substitutions at positions 353, 369, and 371, resulting in point mutations A to T, A to T, and C to G, respectively. These mutations resulted in amino acid substitutions in Cry1C.579 (FIG. 4; SEQ ID NO:55) at positions 118 (E to V) and 124 (A to G).

Sequence analysis of the cry1C.499 gene on plasmid pEG374 (FIG. 4; SEQ ID NO:56) revealed nucleotide substitutions at positions 360 and 361, resulting in point mutations T to C and A to C, respectively. These mutations resulted in an amino acid substitution in Cry1C.499 (FIG. 4; SEQ ID NO:57) at position 121 (N to H).

Sequence analysis of the cry1C genes in EG11811 and EG11822 confirmed the substitution of alanine for arginine at position 148 (SEQ ID NO:1, SEQ ID NO:2). Nucleotide substitutions C442G and G443C yield the codon GCA, encoding alanine.

Sequence analysis of the random R148 mutants indicate changes of R148 to aspartic acid, methionine, leucine, and glycine. Thus, a variety of amino acid substitutions for the positively-charged arginine residue at position 148 in Cry1C result in improved toxicity. None of these substitutions can be regarded as conservative changes. Alanine, leucine, and methionine are non-polar amino acids, aspartic acid is a negatively-charged amino acid, and glycine is an uncharged amino acid, all possessing side chains smaller than that of arginine. All of these amino acids, with the exception of aspartic acid, differ significantly (±2 units) from arginine using the hydropathic and hydrophilicity indices described above.

The strain harboring the cry1C-R148D gene was designated EG11832. The nucleotide sequence of the cry1C-R148D gene is shown in SEQ ID NO:3, and the amino acid sequence is shown in SEQ ID NO:4. The nucleotide substitutions C442G, G443A, and A444C yield the codon GAC, encoding aspartic acid. The Cry1C-R148D mutant EG11832 exhibits a ~6.5-fold lower $LC_{50}$ and a ~8-fold lower $LC_{95}$ in bioassay against *S. exigua when compared to the wild-type Cry*1C strain.

5.6 Example 6

Summary of Cry1C* Mutants

The cry1C mutants of the present invention are summarized in Table 11.

TABLE 11

SUMMARY OF CRY1C* STRAINS

| Cry1C Designation | Strain | Plasmid Name | Parental Plasmid |
|---|---|---|---|
| Cry1C.563 | EG11740 | pEG370 | pEG916 |
| Cry1C.579 | EG11746 | pEG373 | pEG916 |
| Cry1C.499 | EG11747 | pEG374 | pEG916 |
| Cry1CR148A | EG11811 | pEG1635 | pEG315 |
| Cry1CR180A | EG11815 | pEG1636 | pEG315 |
| Cry1CR148A | EG11822 | pEG1639 | pEG345 |
| Cry1CR148D | EG11832 | pEG1642 | pEG345 |
| Cry1CR148G | EG11833 | pEG1643 | pEG345 |
| Cry1CR148L | EG11834 | pEG1644 | pEG345 |
| Cry1C-R148A-K219A | EG12111 | pEG1639 | pEG1639 |
| Cry1C-R148D-K219A | EG12121 | pEG943 | pEG1642 |
| Cry1CR148M | EG11835 | pEG1645 | pEG345 |

5.7 Example 7

Construction of *B. Thuringiensis* Strains Containing Multiple Cry Genes in Addition to Cry1C and Cry1C R148A The *B. thuringiensis* host strain EG4923-4 may be used as a host strain for the native and mutant cry1C genes of the present invention. Strain EG4923-4 contains three cry1Ac genes and one cry2A gene on native plasmids and exhibits excellent insecticidal activity against a variety of lepidopteran pests. Recombinant plasmids containing the cry1C and cry1C-R148A crystal protein genes, originally derived from *aizawai* strain 7.29, were introduced into the strain EG4923-4 background using the electroporation procedure described by Mettus and Macaluso (1990). The recombinant plasmids containing cry1C and cry1C-R148A were designated pEG348 (FIG. 7) and pEG1641 (FIG. 8), respectively, and were similar in structure to the cry1 plasmids described in U.S. Pat. No. 5,441,884 (specifically incorporated herein by reference).

Strain EG4923-4 transformants containing plasmids pEG348 and pEG1641 were isolated on Luria plates containing 10 μg/ml tetracycline. Recombinant plasmid DNAs from the transformants were isolated by the alkaline lysis procedure described by Baum (1995) and confirmed by restriction enzyme analysis. The plasmid arrays of the transformants were further confirmed by the Eckhardt agarose gel analysis procedure described by Gonzalez Jr. et al., (1982). The EG4923-4 recombinant derivatives were designated EG4923-4/pEG348 and EG4923-4/pEG1641.

5.8 Example 8

Modification of EG4923-4/PEG348 and EG4923-4/PEG1641 to Remove Forfien DNA Elements pEG348 and pEG1641 contain duplicate copies of a site-specific recombination site or internal resolution site (IRS) that serves as a substrate for an in vivo site-specific recombination reaction mediated by the TnpI recombinase of transposon Tn5401 (described in Baum, 1995). This site-specific recombination reaction, described in U.S. Pat. No. 5,441,884, results in the deletion of non-*B. thuringiensis* DNA or foreign DNA elements from the crystal protein-encoding recombinant plasmids. The resulting recombinant *B. thuringiensis* strains are free of foreign DNA elements, a desirable feature for genetically engineered strains destined for use as bioinsecticides for spray-on application. Strains EG4923-4/pEG348 and EG4923-4/pEG1641 were modified using this in vivo site-specific recombination (SSR) system to generate two new strains (Table 12), designated EG7841-1 (alias EG11730) and EG7841-2 (alias EG11831). The recombinant plasmids in strains EG7841-1 and EG7841-2 were designated pEG348Δ and pEG1641Δ, respectively.

TABLE 12

RECOMBINANT *B. THURINGIENSIS* STRAINS

| Strain | Alias | Recombinant plasmid | Progenitor strain |
|---|---|---|---|
| EG7841-1 | EG11730 | pEG348Δ | EG4923-4/pEG348 |
| EG7841-2 | EG11831 | pEG1641Δ | EG4923-4/pEG1641 |

Example 9

Cry1C Combinatorial Mutants at AA Positions 148 and 219

The cry1C-R148A gene on pEG1639 and the cry1C-R148D gene on pEG1642 were used as templates for additional mutagenesis studies aimed at achieving further improvements in insecticidal activity.

In one example, the lysine residue at position 219 (K219) was replaced with an alanine residue, using the PCR™-based mutagenesis protocol described by Michael (1994) and the mutagenic oligonucleotide primer J:

Primer J: (SEQ ID NO:62)

5'-CGGGGATTAAATAATTTACCG <u>GCTAGC</u>ACGTATCAAGATTGGATAAC-3'

Primer J also incorporates a unique NheI site (underlined above) that can be used to distinguish the original gene from the mutant gene by restriction enzyme analysis. The PCR™-mediated mutagenesis reactions employed the flanking primers H (SEQ ID NO:52) and F (SEQ ID NO:20), the mutagenic oligonucleotide primer J (SEQ ID NO:62), and pEG1639 (cry1C-R148A) as a template. In these reactions, 5 units of Taq Extender™ (Stratagene) were included to improve the efficiency of amplification with Taq polymerase. The amplified products from the mutagenesis reaction were resolved by agarose gel electrophoresis and the amplified DNA fragment incorporating the mutagenic oligonucleotide primer J was excised from the gel and purified using the Geneclean II® procedure. This DNA fragment was cleaved with the restriction endonucleases BbuI and AgeI.

In order to subclone the BbuI-AgeI cry1C restriction fragment and express the mutant cry1C gene in *B. thuringiensis*, the cry1C plasmid pEG345 (FIG. 3) was cleaved with BbuI and AgeI, treated with calf intestinal alkaline phosphatase (Boehringer Mannheim Corp.), and the resulting DNA fragments resolved by agarose gel electrophoresis. The larger vector fragment was excised from the gel and purified using the Geneclean II® procedure. The pEG345 vector fragment was subsequently ligated to the amplified cry1C fragment recovered from the mutagenesis reaction and the ligation products used to transform *E. coli* Sure™ cells (Stratagene) to arnpicillin resistance using electroporation. Individual colonies recovered from Luria plates containing 50 μg/ml ampicillin were isolated and inoculated into 3 ml cultures containing 1× brain heart infusion, 0.5% glycerol (BHIG), and 50 μg/ml ampicillin.

Plasmid DNAs were prepared from the broth cultures using the alkaline lysis method, digested with the restriction enzyme NheI, and resolved by agarose gel electrophoresis to distinguish clones incorporating the mutagenic sequence of primer J and therefore encoding the alanine substitution at position 219. Incorporation of the mutant sequence into cry1C-R148A was confirmed by DNA sequence analysis. Plasmid DNAs from four recombinant *E. coli* clones were used to transform the acrystalliferous *B. thuringiensis* strain EG10368 to chloramphenicol resistance using electroporation. Transfer of the recombinant plasmid to EG10368 was confirmed by restriction enzyme analysis of plasmid DNAs recovered from the EG10368 transformants. One chloramphenicol resistant colony was selected and designated EG12111. The cry1C gene in EG12111 was designated cry1C-R148A K219A (SEQ ID NO:58) and the encoded crystal protein designated Cry1C-R148A K219A (SEQ ID NO:59).

The same substitution was made in Cry1C-R148D using the same procedures but using pEG1642 (cry1C-R148D) as the template for the PCR™-mediated mutagenesis reaction. The ligation products were used to transform *E. coli* DH5α cells to ampicillin resistance using standard transformation procedures. Plasmid DNAs were prepared from broth cultures of selected ampicillin resistant clones using the alkaline lysis method, digested with the restriction enzyme NheI, and resolved by agarose gel electrophoresis to distinguish clones incorporating the mutagenic sequence of primer J and therefore encoding the alanine substitution at position 219. Incorporation of the mutant sequence into cry1C-R148D was confirmed by DNA sequence analysis. Recombinant plasmids from three mutant clones were used to transform the acrystalliferous *B. thuringiensis* strain EG10368 to chloramphenicol resistance using electroporation. Transfer of the recombinant plasmid to EG10368 was confirmed by restriction enzyme analysis of plasmid DNAs recovered from the EG10368 transformants. One chloramphenicol resistant colony was selected and designated EG12121. The cry1C gene in EG12121 was designated cry1C-R148D K219A (SEQ ID NO:60) and the encoded crystal protein designated Cry1C-R148D K219A (SEQ ID NO:61). The recombinant cry1C plasmid in EG12121 was designated pEG943 (FIG. 9).

Strains EG12115 (Cry1C wild-type), EG11822 (Cry1C-R148A), EG12111 (Cry1C-R148A K219A), EG11832 (Cry1C-R148D), and EG12121 (Cry1C-R148D K219A) were grown in C2 medium as described in Example 4. The spore-Cry1C crystal suspensions recovered from the spent C2 cultures were used for bioassay evaluation against neonate larvae of *Spodoptera exigua* and *Trichoplusia ni* as described in Example 4. In two sets of replicated eight-dose bioassays against *S. exigua*, the EG12111 and EG12121 Cry1C proteins were indistinguishable from the EG11822 and EG11832 Cry1C proteins, respectively. In bioassays against *T. ni*, however, further improvements in toxicity were observed for the combinatorial mutants (Tables 12 and 13).

TABLE 13

BIOASSAY EVALUATION OF THE COMBINATORIAL MUTANT CRY1C-R148A K219A AGAINST NEONATE LARVAE OF *TRICHOPLUSIA NI*

| Strain | Toxin | $LC_{50}$[1] (95% C.I.)[2] |
|---|---|---|
| EG12115 | Cry1C | 52(32–97) |
| EG11822 | Cry1C-R148A | 24(21–29) |
| EG12111 | Cry1C-R148A K219A | 18(16–21) |

[1]Concentration of Cry1C protein that causes 50% mortality expressed in ng crystal protein per 175 $mm^2$ well.
[2]95% confidence intervals.

TABLE 14

BIOASSAY EVALUATION OF THE COMBINATORIAL MUTANT CRY1C-R148D K219A AGAINST NEONATE LARVAE OF *TRICHOPLUSIA NI*

| Strain | Toxin | $LC_{50}$[1] (95% C.I.)[2] |
|---|---|---|
| EG12115 | Cry1C | 40(34–48) |
| BG11832 | Cry1C-R148D | 35(29–43) |
| EG12121 | Cry1C-R148D K219A | 23(19–28) |

[1]Concentration of Cry1C protein that causes 50% mortality expressed in ng crystal protein per 175 $mm^2$ well.
[2]95% confidence intervals.

Example 10

Cry1C-R148D Combinatorial Mutants Containing Other Substitutions in Loop α 6–7

Additional combinatorial mutants were constructed using cry1C-R148D K219A, contained on pEG943, as a template for PCR™-mediated mutagenesis. A modification of the overlap extension PCR™ procedure (Horton et al., 1989) was used to generate these combinatorial mutants (FIG. 10). Briefly, a PCR™ was performed using pEG943 as a template and the opposing primers H (SEQ ID NO:52) and F (SEQ ID NO:20). The amplified DNA fragment contained the R148D mutation as well as the unique NheI restriction site marking the nucleotide substitutions encoding the K219A mutation in loop α 6–7. This PCR was performed using Taq polymerase and Taq Extender™ and following the protocol recommended by Stratagene. A second DNA fragment was amplified by the PCR™ using pEG943 as a template and the mutagenic oligonucleotide primer K (SEQ ID NO:63) and the opposing primer L (SEQ ID NO:64). In this instance, the PCR™ was performed using the thermostable polymerase Deep Vent™ and following the protocol recommended by New England Biolabs, Inc.

Primer K: (SEQ ID NO:63)

5'-CGGGGATTAAATAATTTACCGAAANNAACGTATCAAGATTGGATAAC-3'

N (25)=50% C; 50% G

N (26)=33.3% C; 33.3% G, 33.3% A

Primer L: (SEQ ID NO:64)

5'-GGATAGCACTCATCAAAGGTACC-3'

The mutagenic primer K incorporated mutations in the codon for serine (S) at position 220 of Cry1C. Six different amino acid substitutions are predicted from the mutagenesis procedure: arginine (R), alanine (A), glutamic acid (E), glutamine (Q), glycine (G), and proline (P). The mutagenic primer K also eliminates the unique NheI site in pEG943 and restores the lysine residue at position 219. Thus, cry1C clones incorporating this primer and containing substitutions at S220 can be distinguished from the template cry1C-R148A K219A gene by the loss of the NheI site.

The amplified DNA fragments were purified following agarose gel electrophoresis using the Geneclean II® procedure. To perform the overlap extension PCR™, approximately equimolar amounts of the two DNA fragments were mixed together and amplified using the flanking primers H (SEQ ID NO:52) and L (SEQ ID NO:64). Annealing of complementary strands from the two DNA fragments allows for extension from their 3' ends (FIG. 10). Fully extended strands can then serve as templates for amplification using the flanking primers. The resulting amplified DNA fragment was purified following agarose gel electrophoresis using the Geneclean II® procedure and digested with the restriction endonucleases BbuI and AgeI. The BbuI-AgeI restriction fragment containing the 5' portion of the cry1C gene was purified following agarose gel electrophoresis using the Geneclean II® procedure. In order to subclone this restriction fragment and express the mutant cry1C genes in *B. thuringiensis*, the cry1C plasmid, pEG943, (FIG. 9) was cleaved with BbuI, NheI, and AgeI, treated with calf intestinal alkaline phosphatase, and the resulting DNA fragments resolved by agarose gel electrophoresis. The vector fragment was excised from the gel and purified using the Geneclean II® procedure. The pEG943 vector fragment was subsequently ligated to the amplified cry1C fragments recovered from the overlap extension PCR™ and the ligation products used to transform *E. coli* Sure™ cells (Stratagene) to ampicillin resistance using electroporation. Several hundred ampicillin resistant colonies were harvested from Luria plates containing 50 μg/ml ampicillin, suspended in 10 ml of Luria broth containing 50 μg/ml ampicillin, and allowed to grow at 37° C. for 1 hour with agitation. Recombinant plasmids from the culture were isolated using the alkaline lysis procedure.

Approximately 0.1–1.0 microgram of the cry1C plasmid preparation was digested with NheI to linearize plasmid molecules harboring the NheI site of pEG943. The plasmid preparation was then used to transform the acrystalliferous *B. thuringiensis* strain EG10650 to chloramphenicol resistance using electroporation. Because linear DNAs do not transform *B. thuringiensis* efficiently, this NheI cleavage step ensures that virtually all of the clones recovered from the transformation encode substitutions at position 220 and lysine at position 219. Individual chloramphenicol resistant colonies were transferred to starch agar or Luria plates containing 3 pg/ml chloramphenicol. To confirm transfer of the cry1C plasmids to EG10650, individual clones were inoculated into 3 ml of BHIG containing 3 μg/ml chloramphenicol and grown at 30° C. until the cultures were turbid. Plasmid DNAs were isolated from the broth cultures using the alkaline lysis method and the plasmid identities confirmed by restriction enzyme analysis. Cry1C-R148D mutants containing substitutions at S220 were designated Cry1C pr66-1, -2, -3, etc.

Amino acid substitutions were also generated at amino acid positions 217, 218, 219, 221, and 222 in Cry1C using this procedure and the following mutagenic oligonucleotide primers:

Position 217: PrimerM (SEQ ID NO:65)

5'-CGGGGATTAAATAATNNACCGAAAAGCACGTATCAAGATTGGATAAC-3'

N (16)=50% C; 50% G

N (17)=33.3% C; 33.3% G; 33.3% A

Position 218: Primer N (SEQ ID NO:66)

5'-CGGGGATTAAATAATTTANNAAAAAGCACGTATCAAGATTGGATAAC-3'

N (19)=50% C; 50% G

N (20)=33.3% C; 33.3% G; 33.3% A

Position 219: Primer O (SEQ ID NO:67)

5'-CGGGGATTAAATAATTTACCGNNAAGCACGTATCAAGATTGGATAAC-3'

N (22)=50% C; 50% G

N (23)=33.3% C; 33.3% G; 33.3% A

Position 221: Primer P (SEQ ID NO:68)

5'-GGATTAAATAATTTACCGAAAAGCNNATATCAAGATTGGATAACATATAATCG-3'

N (25)=50% C; 50% G

N (26)=33.3% C; 33.3% G; 33.3% A

Position 222: Primer Q (SEQ ID NO:69)

5'-GGATTAAATAATTTACCGAAAAGCACGNNACAAGATTGGATAACATATAATCG-3'

N (28)=50% C; 50% G

N (29)=33.3% C; 33.3% G; 33.3% A

Table 15 lists the Cry1C mutants expected from the mutagenesis procedure.

TABLE 15

SUMMARY OF CRY1C-R148D LOOP α 6–7 MUTANTS

| Amino acid Position | Wild-type amino acid | Primer | Predicted amino acid substitutions | Mutant designation |
|---|---|---|---|---|
| 217 | leucine | M | R, E, Q, A, G, P | Cry1C pr67 −1, −2, −3, etc. |
| 218 | proline | N | R, E, Q, A, G, P | Cry1C pr65 −1, −2, −3, etc. |
| 219 | lysine | O | R, E, Q, A, G, P | Cry1C pr70 −1, −2, −3, etc. |
| 221 | threonine | P | R, E, Q, A, G, P | Cry1C pr68 −1, −2, −3, etc. |
| 222 | tyrosine | Q | R, E, Q, A, G, P | Cry1C pr69 −1, −2, −3, etc. |

Example 11

Cry1C-R148D Loop α 5–6 Combinational Mutants

A similar overlap extension PCR™ procedure was used to generate Cry1C R148D mutants containing amino acid substitutions in loop α 5–6, including amino acid positions 178–184. The mutagenic oligonucleotide primers used to generate mutations encoding substitutions in loop α 5–6 are listed below.

Position 178: Primer R (SEQ ID NO:70)

5'-GATTCTGTAATTTTTNNAGAAAGATGGGGATTG ACAACGATAAATGTCAATG -3'

N(16) 50% C; 50% G

N (17) 33.3% C; 33.3% G; 33.3% A

Position 179: Primer S (SEQ ID NO:71)

5'-GATTCTGTAATTTTTGGANNAAGATGGGGATTG ACAACGATAAATGTCAATG -3'

N (19)=50% C; 50% G

N (20)=33.3% C; 33.3% G; 33.3% A

Position 180: Primer T (SEQ ID NO:72)

5'-GATTCTGTAATTTTTGGAGAANNATGGGGATTG ACAACGATAAATGTCAATG -3'

N (22)=50% C; 50% G

N (23)=33.3% C; 33.3% G; 33.3% A

Position 181: Primer U (SEQ ID NO:73)

5'-TCTGTAATTTTTGGAGAAAGANNAGGATTGACAA CGATAAATGTCAATGAAAAC-3'

N (22)=50% C; 50% G

N (23)=33.3% C; 33.3% G; 33.3% A

Position 182: Primer V (SEQ ID NO:74)

5'-TAATTTTTGGAGAAAGATGGNNATTGACAACGA TAAATGTCAATGAAAAC-3'

N (22)=50% C; 50% G

N (23)=25% C; 25% G; 25% A; 25% T

Position 183: Primer W (SEQ ID NO:75)

5'-GTAATTTTTGGAGAAAGATGGGGANNAACAACG ATAAATGTCAATGAAAAC-3'

N (25)=50% C; 50% G

N (26)=25% C; 25% G; 25% A; 25% T

Position 184: Primer X (SEQ ID NO:76)

5'-GTAATTTTTGGAGAAAGATGGGGATTGNNAACG ATAAATGTCAATGAAAAC-3'

N (28)=50% C; 50% G

N (29)=25% C; 25% G; 25% A; 25% T

A PCR™ using the opposing primers H (SEQ ID NO:52) and F (SEQ ID NO:20) and plasmid pEG943 as a template was first performed to generate a DNA fragment containing the R148D and K219A mutations as well as the unique NheI restriction site marking the K219A mutation (FIG. 10). In order to generate cry1C fragments harboring loop α 5–6 mutations, PCRs were run using a mutagenic primer (e.g., primer R) and the opposing primer L (SEQ ID NO:64) (FIG. 11). The amplified DNA fragments were purified following agarose gel electrophoresis using the Geneclean II® procedure. For the overlap extension PCR™, approximately equimolar amounts of the two DNA fragments were mixed and amplified using the flanking primers H (SEQ ID NO:52) and L (SEQ ID NO:64). The amplification products were digested with the restriction enzymes BbuI and AgeI, the resulting BbuI-AgeI cry1C fragments subcloned into a cry1C expression vector, and the *B. thuringiensis* EG10650 transformants constructed as described in Example 10. Table 16 summarizes the Cry1C mutants predicted from the mutagenesis procedure.

TABLE 16

SUMMARY OF CRY1C-R148D LOOP α5–6 MUTANTS

| Amino Acid Position | Wild-Type Amino Acid | Primer | Predicted Amino Acid Substitutions | Mutant Designation |
|---|---|---|---|---|
| 178 | glycine | R | R, E, Q, A, G, P | Cry1C 1 -1, -2, -3, etc. |
| 179 | glutamic acid | S | R, E, Q, A, G, P | Cry1C 2 -1, -2, -3, etc. |
| 180 | arginine | T | R, E, Q, A, G, P | Cry1C 3 -1, -2, -3, etc. |
| 181 | tryptophan | U | R, E, Q, A, G, P | Cry1C 4 -1, -2, -3, etc. |
| 182 | glycine | V | R, E, Q, A, G, P, L, V | Cry1C 5 -1, -2, -3, etc. |
| 183 | leucine | W | R, E, Q, A, G, P, L, V | Cry1C 6 -1, -2, -3, etc. |
| 184 | threonine | X | R, E, Q, A, G, P, L, V | Cry1C 7 -1, -2, -3, etc. |

Example 12

Bioassay Evaluation of Cry1C-R148D Combinational Mutants

EG10650 transformants containing mutant cry1C genes were grown in C2 medium, the spore-crystal protein suspensions recovered, and one-dose bioassays performed against neonate larvae of *S. exigua* and *T. ni* as described in Example 4. Strain EG11832 (Cry1C-R148D) was used as the control strain in these bioassays. Dilutions of the spore-crystal suspensions were typically adjusted to obtain 20–40% mortality with strain EG11832. Replicated one-dose screens of the Cry1C-R148D combinatorial mutants identified several mutants with increased mortality. Sixteen of these mutants were grown again in C2 medium and their Cry1C crystal proteins quantified as described in Example 4. One-dose bioassays were performed against *S. exigua* using 50 ng Cry1C protein per diet well. One dose bioassays were performed against *T. ni* using 25 ng Cry1C protein per diet well. The results of those bioassays are shown in Table 17. Triplicate samples of the control strain EG11832 (Cry1C-R148D) were also tested. Several Cry1C-R148D combinatorial mutants show increased (approximately two-fold) toxicity towards *S. exigua* when compared to EG11832 (Cry1C-R148D). Several of these mutants, including Cry1C 7-3, Cry1C 66-19, and Cry1C 69-24 also showed excellent toxicity towards *T. ni*.

TABLE 17

TOXICITY OF CRY1C R148D COMBINATORIAL MUTANTS TOWARDS *TRICHOPLUSIA NI* AND *SPODOPTERA EXIGUA*

| Mutant | *T. ni* % mortality[1] | *S. exigua* % mortality[2] |
|---|---|---|
| 1C 2-7 | 53.1 | 11.29 |
| 1C 2-17 | 12.5 | 4.84 |
| 1C 3-13 | 51.6 | 29.03 |
| 1C 5-1 | 28.1 | 17.74 |
| 1C 5-3 | 57.8 | 17.74 |
| 1C 5-5 | 54.7 | 25.81 |
| 1C 6-21 | 14.1 | 19.35 |
| 1C 7-3 | 81.2 | 32.26 |
| 1C 7-16 | 48.44 | 14.52 |
| 1C 7-21 | 50 | 12.9 |
| 1C 66-14 | 37.5 | 16.13 |
| 1C 66-19 | 60.9 | 35.48 |
| 1C 66-21 | 78.1 | 29.03 |
| 1C 69-9 | 68.7 | 20.97 |
| 1C 69-15 | 62.5 | 24.19 |
| 1C 69-24 | 71.88 | 40.32 |
| 11832#1 (Cry1C-R148D) | 53 | 16.13 |
| 11832#2 (Cry1C-R148D) | 50 | 20.97 |
| 11832#3 (Cry1C-R148D) | 51.6 | 17.74 |

[1]Percent mortality obtained using 25 ng Cry1C protein per 175 $mm^2$ diet well, 64 larvae per assay.
[2]Percent mortality obtained using 50 ng Cry1C protein per 175 $mm^2$ diet well, 64 larvae per assay.

5.13 Example 13

Amino Acid Sequences of the Modified Crystal Proteins

5.13.1 Amino Acid Sequence of Cry1C-R148A (SEQ ID NO:2)

Met Glu Glu Asn Asn Gln Asn Gln Cys Ile Pro Tyr Asn Cys Leu Ser
Asn Pro Glu Glu Val Leu Leu Asp Gly Glu Arg Ile Ser Thr Gly Asn
Ser Ser Ile Asp Ile Ser Leu Ser Leu Val Gln Phe Leu Val Ser Asn
Phe Val Pro Gly Gly Gly Phe Leu Val Gly Leu Ile Asp Phe Val Trp
Gly Ile Val Gly Pro Ser Gln Trp Asp Ala Phe Leu Val Gln Ile Glu
Gln Leu Ile Asn Glu Arg Ile Ala Glu Phe Ala Arg Asn Ala Ala Ile
Ala Asn Leu Glu Gly Leu Gly Asn Asn Phe Asn Ile Tyr Val Glu Ala
Phe Lys Glu Trp Glu Glu Asp Pro Asn Asn Pro Ala Thr Arg Thr Arg
Val Ile Asp Arg Phe Arg Ile Leu Asp Gly Leu Leu Glu Arg Asp Ile
Pro Ser Phe Ala Ile Ser Gly Phe Glu Val Pro Leu Leu Ser Val Tyr
Ala Gln Ala Ala Asn Leu His Leu Ala Ile Leu Arg Asp Ser Val Ile
Phe Gly Glu Arg Trp Gly Leu Thr Thr Ile Asn Val Asn Glu Asn Tyr
Asn Arg Leu Ile Arg His Ile Asp Glu Tyr Ala Asp His Cys Ala Asn
Thr Tyr Asn Arg Gly Leu Asn Asn Leu Pro Lys Ser Thr Tyr Gln Asp
Trp Ile Thr Tyr Asn Arg Leu Arg Arg Asp Leu Thr Leu Thr Val Leu
Asp Ile Ala Ala Phe Phe Pro Asn Tyr Asp Asn Arg Arg Tyr Pro Ile
Gln Pro Val Gly Gln Leu Thr Arg Glu Val Tyr Thr Asp Pro Leu Ile
Asn Phe Asn Pro Gln Leu Gln Ser Val Ala Gln Leu Pro Thr Phe Asn
Val Met Glu Ser Ser Ala Ile Arg Asn Pro His Leu Phe Asp Ile Leu
Asn Asn Leu Thr Ile Phe Thr Asp Trp Phe Ser Val Gly Arg Asn Phe
Tyr Trp Gly Gly His Arg Val Ile Ser Ser Leu Ile Gly Gly Gly Asn
Ile Thr Ser Pro Ile Tyr Gly Arg Glu Ala Asn Gln Glu Pro Pro Arg
Ser Phe Thr Phe Asn Gly Pro Val Phe Arg Thr Leu Ser Asn Pro Thr
Leu Arg Leu Leu Gln Gln Pro Trp Pro Ala Pro Pro Phe Asn Leu Arg
Gly Val Glu Gly Val Glu Phe Ser Thr Pro Thr Asn Ser Phe Thr Tyr
Arg Gly Arg Gly Thr Val Asp Ser Leu Thr Glu Leu Pro Pro Glu Asp
Asn Ser Val Pro Pro Arg Glu Gly Tyr Ser His Arg Leu Cys His Ala
Thr Phe Val Gln Arg Ser Gly Thr Pro Phe Leu Thr Thr Gly Val Val
Phe Ser Trp Thr His Arg Ser Ala Thr Leu Thr Asn Thr Ile Asp Pro
Glu Arg Ile Asn Gln Ile Pro Leu Val Lys Gly Phe Arg Val Trp Gly
Gly Thr Ser Val Ile Thr Gly Pro Gly Phe Thr Gly Gly Asp Ile Leu
Arg Arg Asn Thr Phe Gly Asp Phe Val Ser Leu Gln Val Asn Ile Asn
Ser Pro Ile Thr Gln Arg Tyr Arg Leu Arg Phe Arg Tyr Ala Ser Ser
Arg Asp Ala Arg Val Ile Val Leu Thr Gly Ala Ala Ser Thr Gly Val
Gly Gly Gln Val Ser Val Asn Met Pro Leu Gln Lys Thr Met Glu Ile
Gly Glu Asn Leu Thr Ser Arg Thr Phe Arg Tyr Thr Asp Phe Ser Asn
Pro Phe Ser Phe Arg Ala Asn Pro Asp Ile Ile Gly Ile Ser Glu Gln
Pro Leu Phe Gly Ala Gly Ser Ile Ser Ser Gly Glu Leu Tyr Ile Asp
Lys Ile Glu Ile Ile Leu Ala Asp Ala Thr Phe Glu Ala Glu Ser Asp
Leu Glu Arg Ala Gln Lys Ala Val Asn Ala Leu Phe Thr Ser Ser Asn
Gln Ile Gly Leu Lys Thr Asp Val Thr Asp Tyr His Ile Asp Gln Val
Ser Asn Leu Val Asp Cys Leu Ser Asp Glu Phe Cys Leu Asp Glu Lys

Arg Glu Leu Ser Glu Lys Val Lys His Ala Lys Arg Leu Ser Asp Glu
Arg Asn Leu Leu Gln Asp Pro Asn Phe Arg Gly Ile Asn Arg Gln Pro
Asp Arg Gly Trp Arg Gly Ser Thr Asp Ile Thr Ile Gln Gly Gly Asp
Asp Val Phe Lys Glu Asn Tyr Val Thr Leu Pro Gly Thr Val Asp Glu
Cys Tyr Pro Thr Tyr Leu Tyr Gln Lys Ile Asp Glu Ser Lys Leu Lys
Ala Tyr Thr Arg Tyr Glu Leu Arg Gly Tyr Ile Glu Asp Ser Gln Asp
Leu Glu Ile Tyr Leu Ile Arg Tyr Asn Ala Lys His Glu Ile Val Asn
Val Pro Gly Thr Gly Ser Leu Trp Pro Leu Ser Ala Gln Ser Pro Ile
Gly Lys Cys Gly Glu Pro Asn Arg Cys Ala Pro His Leu Glu Trp Asn
Pro Asp Leu Asp Cys Ser Cys Arg Asp Gly Glu Lys Cys Ala His His
Ser His His Phe Thr Leu Asp Ile Asp Val Gly Cys Thr Asp Leu Asn
Glu Asp Leu Gly Val Trp Val Ile Phe Lys Ile Lys Thr Gln Asp Gly
His Ala Arg Leu Gly Asn Leu Glu Phe Leu Glu Glu Lys Pro Leu Leu
Gly Glu Ala Leu Ala Arg Val Lys Arg Ala Glu Lys Lys Trp Arg Asp
Lys Arg Glu Lys Leu Gln Leu Glu Thr Asn Ile Val Tyr Lys Glu Ala
Lys Glu Ser Val Asp Ala Leu Phe Val Asn Ser Gln Tyr Asp Arg Leu
Gln Val Asp Thr Asn Ile Ala Met Ile His Ala Ala Asp Lys Arg Val
His Arg Ile Arg Glu Ala Tyr Leu Pro Glu Leu Ser Val Ile Pro Gly
Val Asn Ala Ala Ile Phe Glu Glu Leu Glu Gly Arg Ile Phe Thr Ala
Tyr Ser Leu Tyr Asp Ala Arg Asn Val Ile Lys Asn Gly Asp Phe Asn
Asn Gly Leu Leu Cys Trp Asn Val Lys Gly His Val Asp Val Glu Glu
Gln Asn Asn His Arg Ser Val Leu Val Ile Pro Glu Trp Glu Ala Glu
Val Ser Gln Glu Val Arg Val Cys Pro Gly Arg Gly Tyr Ile Leu Arg
Val Thr Ala Tyr Lys Glu Gly Tyr Gly Glu Gly Cys Val Thr Ile His
Glu Ile Glu Asp Asn Thr Asp Glu Leu Lys Phe Ser Asn Cys Val Glu
Glu Glu Val Tyr Pro Asn Asn Thr Val Thr Cys Asn Asn Tyr Thr Gly
Thr Gln Glu Glu Tyr Glu Gly Thr Tyr Thr Ser Arg Asn Gln Gly Tyr
Asp Glu Ala Tyr Gly Asn Asn Pro Ser Val Pro Ala Asp Tyr Ala Ser
Val Tyr Glu Glu Lys Ser Tyr Thr Asp Gly Arg Arg Glu Asn Pro Cys
Glu Ser Asn Arg Gly Tyr Gly Asp Tyr Thr Pro Leu Pro Ala Gly Tyr
Val Thr Lys Asp Leu Glu Tyr Phe Pro Glu Thr Asp Lys Val Trp Ile
Glu Ile Gly Glu Thr Glu Gly Thr Phe Ile Val Asp Ser Val Glu Leu
Leu Leu Met Glu Glu 5.13.2 Amino Acid Sequence of Cry1C-R148D (SEQ ID NO:4)

Met Glu Glu Asn Asn Gln Asn Gln Cys Ile Pro Tyr Asn Cys Leu Ser
Asn Pro Glu Glu Val Leu Leu Asp Gly Glu Arg Ile Ser Thr Gly Asn
Ser Ser Ile Asp Ile Ser Leu Ser Leu Val Gln Phe Leu Val Ser Asn
Phe Val Pro Gly Gly Gly Phe Leu Val Gly Leu Ile Asp Phe Val Trp
Gly Ile Val Gly Pro Ser Gln Trp Asp Ala Phe Leu Val Gln Ile Glu
Gln Leu Ile Asn Glu Arg Ile Ala Glu Phe Ala Arg Asn Ala Ala Ile
Ala Asn Leu Glu Gly Leu Gly Asn Asn Phe Asn Ile Tyr Val Glu Ala
Phe Lys Glu Trp Glu Glu Asp Pro Asn Asn Pro Ala Thr Arg Thr Arg
Val Ile Asp Arg Phe Arg Ile Leu Asp Gly Leu Leu Glu Arg Asp Ile
Pro Ser Phe Asp Ile Ser Gly Phe Glu Val Pro Leu Leu Ser Val Tyr
Ala Gln Ala Ala Asn Leu His Leu Ala Ile Leu Arg Asp Ser Val Ile
Phe Gly Glu Arg Trp Gly Leu Thr Thr Ile Asn Val Asn Glu Asn Tyr
Asn Arg Leu Ile Arg His Ile Asp Glu Tyr Ala Asp His Cys Ala Asn
Thr Tyr Asn Arg Gly Leu Asn Asn Leu Pro Lys Ser Thr Tyr Gln Asp
Trp Ile Thr Tyr Asn Arg Leu Arg Arg Asp Leu Thr Leu Thr Val Leu
Asp Ile Ala Ala Phe Phe Pro Asn Tyr Asp Asn Arg Arg Tyr Pro Ile
Gln Pro Val Gly Gln Leu Thr Arg Glu Val Tyr Thr Asp Pro Leu Ile
Asn Phe Asn Pro Gln Leu Gln Ser Val Ala Gln Leu Pro Thr Phe Asn
Val Met Glu Ser Ser Ala Ile Arg Asn Pro His Leu Phe Asp Ile Leu
Asn Asn Leu Thr Ile Phe Thr Asp Trp Phe Ser Val Gly Arg Asn Phe
Tyr Trp Gly Gly His Arg Val Ile Ser Ser Leu Ile Gly Gly Gly Asn
Ile Thr Ser Pro Ile Tyr Gly Arg Glu Ala Asn Gln Glu Pro Pro Arg
Ser Phe Thr Phe Asn Gly Pro Val Phe Arg Thr Leu Ser Asn Pro Thr
Leu Arg Leu Leu Gln Gln Pro Trp Pro Ala Pro Pro Phe Asn Leu Arg
Gly Val Glu Gly Val Glu Phe Ser Thr Pro Thr Asn Ser Phe Thr Tyr
Arg Gly Arg Gly Thr Val Asp Ser Leu Thr Glu Leu Pro Pro Glu Asp
Asn Ser Val Pro Pro Arg Glu Gly Tyr Ser His Arg Leu Cys His Ala
Thr Phe Val Gln Arg Ser Gly Thr Pro Phe Leu Thr Thr Gly Val Val
Phe Ser Trp Thr His Arg Ser Ala Thr Leu Thr Asn Thr Ile Asp Pro
Glu Arg Ile Asn Gln Ile Pro Leu Val Lys Gly Phe Arg Val Trp Gly
Gly Thr Ser Val Ile Thr Gly Pro Gly Phe Thr Gly Gly Asp Ile Leu
Arg Arg Asn Thr Phe Gly Asp Phe Val Ser Leu Gln Val Asn Ile Asn
Ser Pro Ile Thr Gln Arg Tyr Arg Leu Arg Phe Arg Tyr Ala Ser Ser
Arg Asp Ala Arg Val Ile Val Leu Thr Gly Ala Ala Ser Thr Gly Val

Gly Gly Gln Val Ser Val Asn Met Pro Leu Gln Lys Thr Met Glu Ile

Gly Glu Asn Leu Thr Ser Arg Thr Phe Arg Tyr Thr Asp Phe Ser Asn

Pro Phe Ser Phe Arg Ala Asn Pro Asp Ile Ile Gly Ile Ser Glu Gln

Pro Leu Phe Gly Ala Gly Ser Ile Ser Ser Gly Glu Leu Tyr Ile Asp

Lys Ile Glu Ile Ile Leu Ala Asp Ala Thr Phe Glu Ala Glu Ser Asp

Leu Glu Arg Ala Gln Lys Ala Val Asn Ala Leu Phe Thr Ser Ser Asn

Gln Ile Gly Leu Lys Thr Asp Val Thr Asp Tyr His Ile Asp Gln Val

Ser Asn Leu Val Asp Cys Leu Ser Asp Glu Phe Cys Leu Asp Glu Lys

Arg Glu Leu Ser Glu Lys Val Lys His Ala Lys Arg Leu Ser Asp Glu

Arg Asn Leu Leu Gln Asp Pro Asn Phe Arg Gly Ile Asn Arg Gln Pro

Asp Arg Gly Trp Arg Gly Ser Thr Asp Ile Thr Ile Gln Gly Gly Asp

Asp Val Phe Lys Glu Asn Tyr Val Thr Leu Pro Gly Thr Val Asp Glu

Cys Tyr Pro Thr Tyr Leu Tyr Gln Lys Ile Asp Glu Ser Lys Leu Lys

Ala Tyr Thr Arg Tyr Glu Leu Arg Gly Tyr Ile Glu Asp Ser Gln Asp

Leu Glu Ile Tyr Leu Ile Arg Tyr Asn Ala Lys His Glu Ile Val Asn

Val Pro Gly Thr Gly Ser Leu Trp Pro Leu Ser Ala Gln Ser Pro Ile

Gly Lys Cys Gly Glu Pro Asn Arg Cys Ala Pro His Leu Glu Trp Asn

Pro Asp Leu Asp Cys Ser Cys Arg Asp Gly Glu Lys Cys Ala His His

Ser His His Phe Thr Leu Asp Ile Asp Val Gly Cys Thr Asp Leu Asn

Glu Asp Leu Gly Val Trp Val Ile Phe Lys Ile Lys Thr Gln Asp Gly

His Ala Arg Leu Gly Asn Leu Glu Phe Leu Glu Glu Lys Pro Leu Leu

Gly Glu Ala Leu Ala Arg Val Lys Arg Ala Glu Lys Lys Trp Arg Asp

Lys Arg Glu Lys Leu Gln Leu Glu Thr Asn Ile Val Tyr Lys Glu Ala

Lys Glu Ser Val Asp Ala Leu Phe Val Asn Ser Gln Tyr Asp Arg Leu

Gln Val Asp Thr Asn Ile Ala Met Ile His Ala Ala Asp Lys Arg Val

His Arg Ile Arg Glu Ala Tyr Leu Pro Glu Leu Ser Val Ile Pro Gly

Val Asn Ala Ala Ile Phe Glu Glu Leu Glu Gly Arg Ile Phe Thr Ala

Tyr Ser Leu Tyr Asp Ala Arg Asn Val Ile Lys Asn Gly Asp Phe Asn

Asn Gly Leu Leu Cys Trp Asn Val Lys Gly His Val Asp Val Glu Glu

Gln Asn Asn His Arg Ser Val Leu Val Ile Pro Glu Trp Glu Ala Glu

Val Ser Gln Glu Val Arg Val Cys Pro Gly Arg Gly Tyr Ile Leu Arg

Val Thr Ala Tyr Lys Glu Gly Tyr Gly Glu Gly Cys Val Thr Ile His

Glu Ile Glu Asp Asn Thr Asp Glu Leu Lys Phe Ser Asn Cys Val Glu

Glu Glu Val Tyr Pro Asn Asn Thr Val Thr Cys Asn Asn Tyr Thr Gly

Thr Gln Glu Glu Tyr Glu Gly Thr Tyr Thr Ser Arg Asn Gln Gly Tyr

Asp Glu Ala Tyr Gly Asn Asn Pro Ser Val Pro Ala Asp Tyr Ala Ser

Val Tyr Glu Glu Lys Ser Tyr Thr Asp Gly Arg Arg Glu Asn Pro Cys

Glu Ser Asn Arg Gly Tyr Gly Asp Tyr Thr Pro Leu Pro Ala Gly Tyr

Val Thr Lys Asp Leu Glu Tyr Phe Pro Glu Thr Asp Lys Val Trp Ile

Glu Ile Gly Glu Thr Glu Gly Thr Phe Ile Val Asp Ser Val Glu Leu

Leu Leu Met Glu Glu 5.13.3 Amino Acid Sequence of Cry1C-R180A (SEQ ID NO:6)

Met Glu Glu Asn Asn Gln Asn Gln Cys Ile Pro Tyr Asn Cys Leu Ser

Asn Pro Glu Glu Val Leu Leu Asp Gly Glu Arg Ile Ser Thr Gly Asn

Ser Ser Ile Asp Ile Ser Leu Ser Leu Val Gln Phe Leu Val Ser Asn

Phe Val Pro Gly Gly Gly Phe Leu Val Gly Leu Ile Asp Phe Val Trp

Gly Ile Val Gly Pro Ser Gln Trp Asp Ala Phe Leu Val Gln Ile Glu

Gln Leu Ile Asn Glu Arg Ile Ala Glu Phe Ala Arg Asn Ala Ala Ile

Ala Asn Leu Glu Gly Leu Gly Asn Asn Phe Asn Ile Tyr Val Glu Ala

Phe Lys Glu Trp Glu Glu Asp Pro Asn Asn Pro Ala Thr Arg Thr Arg

Val Ile Asp Arg Phe Arg Ile Leu Asp Gly Leu Leu Glu Arg Asp Ile

Pro Ser Phe Arg Ile Ser Gly Phe Glu Val Pro Leu Leu Ser Val Tyr

Ala Gln Ala Ala Asn Leu His Leu Ala Ile Leu Arg Asp Ser Val Ile

Phe Gly Glu Ala Trp Gly Leu Thr Thr Ile Asn Val Asn Glu Asn Tyr

Asn Arg Leu Ile Arg His Ile Asp Glu Tyr Ala Asp His Cys Ala Asn

Thr Tyr Asn Arg Gly Leu Asn Asn Leu Pro Lys Ser Thr Tyr Gln Asp

Trp Ile Thr Tyr Asn Arg Leu Arg Arg Asp Leu Thr Leu Thr Val Leu

Asp Ile Ala Ala Phe Phe Pro Asn Tyr Asp Asn Arg Arg Tyr Pro Ile

Gln Pro Val Gly Gln Leu Thr Arg Glu Val Tyr Thr Asp Pro Leu Ile

Asn Phe Asn Pro Gln Leu Gln Ser Val Ala Gln Leu Pro Thr Phe Asn

Val Met Glu Ser Ser Ala Ile Arg Asn Pro His Leu Phe Asp Ile Leu

Asn Asn Leu Thr Ile Phe Thr Asp Trp Phe Ser Val Gly Arg Asn Phe

Tyr Trp Gly Gly His Arg Val Ile Ser Ser Leu Ile Gly Gly Gly Asn

Ile Thr Ser Pro Ile Tyr Gly Arg Glu Ala Asn Gln Glu Pro Pro Arg

Ser Phe Thr Phe Asn Gly Pro Val Phe Arg Thr Leu Ser Asn Pro Thr

Leu Arg Leu Leu Gln Gln Pro Trp Pro Ala Pro Pro Phe Asn Leu Arg

Gly Val Glu Gly Val Glu Phe Ser Thr Pro Thr Asn Ser Phe Thr Tyr

Arg Gly Arg Gly Thr Val Asp Ser Leu Thr Glu Leu Pro Pro Glu Asp

Asn Ser Val Pro Pro Arg Glu Gly Tyr Ser His Arg Leu Cys His Ala
Thr Phe Val Gln Arg Ser Gly Thr Pro Phe Leu Thr Thr Gly Val Val
Phe Ser Trp Thr His Arg Ser Ala Thr Leu Thr Asn Thr Ile Asp Pro
Glu Arg Ile Asn Gln Ile Pro Leu Val Lys Gly Phe Arg Val Trp Gly
Gly Thr Ser Val Ile Thr Gly Pro Gly Phe Thr Gly Gly Asp Ile Leu
Arg Arg Asn Thr Phe Gly Asp Phe Val Ser Leu Gln Val Asn Ile Asn
Ser Pro Ile Thr Gln Arg Tyr Arg Leu Arg Phe Arg Tyr Ala Ser Ser
Arg Asp Ala Arg Val Ile Val Leu Thr Gly Ala Ala Ser Thr Gly Val
Gly Gly Gln Val Ser Val Asn Met Pro Leu Gln Lys Thr Met Glu Ile
Gly Glu Asn Leu Thr Ser Arg Thr Phe Arg Tyr Thr Asp Phe Ser Asn
Pro Phe Ser Phe Arg Ala Asn Pro Asp Ile Ile Gly Ile Ser Glu Gln
Pro Leu Phe Gly Ala Gly Ser Ile Ser Ser Gly Glu Leu Tyr Ile Asp
Lys Ile Glu Ile Ile Leu Ala Asp Ala Thr Phe Glu Ala Glu Ser Asp
Leu Glu Arg Ala Gln Lys Ala Val Asn Ala Leu Phe Thr Ser Ser Asn
Gln Ile Gly Leu Lys Thr Asp Val Thr Asp Tyr His Ile Asp Gln Val
Ser Asn Leu Val Asp Cys Leu Ser Asp Glu Phe Cys Leu Asp Glu Lys
Arg Glu Leu Ser Glu Lys Val Lys His Ala Lys Arg Leu Ser Asp Glu
Arg Asn Leu Leu Gln Asp Pro Asn Phe Arg Gly Ile Asn Arg Gln Pro
Asp Arg Gly Trp Arg Gly Ser Thr Asp Ile Thr Ile Gln Gly Gly Asp
Asp Val Phe Lys Glu Asn Tyr Val Thr Leu Pro Gly Thr Val Asp Glu
Cys Tyr Pro Thr Tyr Leu Tyr Gln Lys Ile Asp Glu Ser Lys Leu Lys
Ala Tyr Thr Arg Tyr Glu Leu Arg Gly Tyr Ile Glu Asp Ser Gln Asp
Leu Glu Ile Tyr Leu Ile Arg Tyr Asn Ala Lys His Glu Ile Val Asn
Val Pro Gly Thr Gly Ser Leu Trp Pro Leu Ser Ala Gln Ser Pro Ile
Gly Lys Cys Gly Glu Pro Asn Arg Cys Ala Pro His Leu Glu Trp Asn
Pro Asp Leu Asp Cys Ser Cys Arg Asp Gly Glu Lys Cys Ala His His
Ser His His Phe Thr Leu Asp Ile Asp Val Gly Cys Thr Asp Leu Asn
Glu Asp Leu Gly Val Trp Val Ile Phe Lys Ile Lys Thr Gln Asp Gly
His Ala Arg Leu Gly Asn Leu Glu Phe Leu Glu Glu Lys Pro Leu Leu
Gly Glu Ala Leu Ala Arg Val Lys Arg Ala Glu Lys Lys Trp Arg Asp
Lys Arg Glu Lys Leu Gln Leu Glu Thr Asn Ile Val Tyr Lys Glu Ala
Lys Glu Ser Val Asp Ala Leu Phe Val Asn Ser Gln Tyr Asp Arg Leu
Gln Val Asp Thr Asn Ile Ala Met Ile His Ala Ala Asp Lys Arg Val
His Arg Ile Arg Glu Ala Tyr Leu Pro Glu Leu Ser Val Ile Pro Gly
Val Asn Ala Ala Ile Phe Glu Glu Leu Glu Gly Arg Ile Phe Thr Ala
Tyr Ser Leu Tyr Asp Ala Arg Asn Val Ile Lys Asn Gly Asp Phe Asn
Asn Gly Leu Leu Cys Trp Asn Val Lys Gly His Val Asp Val Glu Glu
Gln Asn Asn His Arg Ser Val Leu Val Ile Pro Glu Trp Glu Ala Glu
Val Ser Gln Glu Val Arg Val Cys Pro Gly Arg Gly Tyr Ile Leu Arg
Val Thr Ala Tyr Lys Glu Gly Tyr Gly Glu Gly Cys Val Thr Ile His
Glu Ile Glu Asp Asn Thr Asp Glu Leu Lys Phe Ser Asn Cys Val Glu
Glu Glu Val Tyr Pro Asn Asn Thr Val Thr Cys Asn Asn Tyr Thr Gly
Thr Gln Glu Glu Tyr Glu Gly Thr Tyr Thr Ser Arg Asn Gln Gly Tyr
Asp Glu Ala Tyr Gly Asn Asn Pro Ser Val Pro Ala Asp Tyr Ala Ser
Val Tyr Glu Glu Lys Ser Tyr Thr Asp Gly Arg Arg Glu Asn Pro Cys
Glu Ser Asn Arg Gly Tyr Gly Asp Tyr Thr Pro Leu Pro Ala Gly Tyr
Val Thr Lys Asp Leu Glu Tyr Phe Pro Glu Thr Asp Lys Val Trp Ile
Glu Ile Gly Glu Thr Glu Gly Thr Phe Ile Val Asp Ser Val Glu Leu
Leu Leu Met Glu Glu 5.13.4 Amino Acid Sequence of Cry1C.563 (SEQ ID NO:8)

Met Glu Glu Asn Asn Gln Asn Gln Cys Ile Pro Tyr Asn Cys Leu Ser
Asn Pro Glu Glu Val Leu Leu Asp Gly Glu Arg Ile Ser Thr Gly Asn
Ser Ser Ile Asp Ile Ser Leu Ser Leu Val Gln Phe Leu Val Ser Asn
Phe Val Pro Gly Gly Gly Phe Leu Val Gly Leu Ile Asp Phe Val Trp
Gly Ile Val Gly Pro Ser Gln Trp Asp Ala Phe Leu Val Gln Ile Glu
Gln Leu Ile Asn Glu Arg Ile Ala Glu Phe Ala Arg Asn Ala Ala Ile
Ala Asn Leu Glu Gly Leu Gly Asn Asn Phe Asn Ile Tyr Val Glu Ala
Phe Lys Glu Trp Glu Asp Asp Pro His Asn Pro Thr Thr Arg Thr Arg
Val Ile Asp Arg Phe Arg Ile Leu Asp Gly Leu Leu Glu Arg Asp Ile
Pro Ser Phe Arg Ile Ser Gly Phe Glu Val Pro Leu Leu Ser Val Tyr
Ala Gln Ala Ala Asn Leu His Leu Ala Ile Leu Arg Asp Ser Val Ile
Phe Gly Glu Arg Trp Gly Leu Thr Thr Ile Asn Val Asn Glu Asn Tyr
Asn Arg Leu Ile Arg His Ile Asp Glu Tyr Ala Asp His Cys Ala Asn
Thr Tyr Asn Arg Gly Leu Asn Asn Leu Pro Lys Ser Thr Tyr Gln Asp
Trp Ile Thr Tyr Asn Arg Leu Arg Arg Asp Leu Thr Leu Thr Val Leu
Asp Ile Ala Ala Phe Phe Pro Asn Tyr Asp Asn Arg Arg Tyr Pro Ile
Gln Pro Val Gly Gln Leu Thr Arg Glu Val Tyr Thr Asp Pro Leu Ile
Asn Phe Asn Pro Gln Leu Gln Ser Val Ala Gln Leu Pro Thr Phe Asn
Val Met Glu Ser Ser Ala Ile Arg Asn Pro His Leu Phe Asp Ile Leu

Asn Asn Leu Thr Ile Phe Thr Asp Trp Phe Ser Val Gly Arg Asn Phe
Tyr Trp Gly Gly His Arg Val Ile Ser Ser Leu Ile Gly Gly Gly Asn
Ile Thr Ser Pro Ile Tyr Gly Arg Glu Ala Asn Gln Glu Pro Pro Arg
Ser Phe Thr Phe Asn Gly Pro Val Phe Arg Thr Leu Ser Asn Pro Thr
Leu Arg Leu Leu Gln Gln Pro Trp Pro Ala Pro Pro Phe Asn Leu Arg
Gly Val Glu Gly Val Glu Phe Ser Thr Pro Thr Asn Ser Phe Thr Tyr
Arg Gly Arg Gly Thr Val Asp Ser Leu Thr Glu Leu Pro Pro Glu Asp
Asn Ser Val Pro Pro Arg Glu Gly Tyr Ser His Arg Leu Cys His Ala
Thr Phe Val Gln Arg Ser Gly Thr Pro Phe Leu Thr Thr Gly Val Val
Phe Ser Trp Thr His Arg Ser Ala Thr Leu Thr Asn Thr Ile Asp Pro
Glu Arg Ile Asn Gln Ile Pro Leu Val Lys Gly Phe Arg Val Trp Gly
Gly Thr Ser Val Ile Thr Gly Pro Gly Phe Thr Gly Gly Asp Ile Leu
Arg Arg Asn Thr Phe Gly Asp Phe Val Ser Leu Gln Val Asn Ile Asn
Ser Pro Ile Thr Gln Arg Tyr Arg Leu Arg Phe Arg Tyr Ala Ser Ser
Arg Asp Ala Arg Val Ile Val Leu Thr Gly Ala Ala Ser Thr Gly Val
Gly Gly Gln Val Ser Val Asn Met Pro Leu Gln Lys Thr Met Glu Ile
Gly Glu Asn Leu Thr Ser Arg Thr Phe Arg Tyr Thr Asp Phe Ser Asn
Pro Phe Ser Phe Arg Ala Asn Pro Asp Ile Ile Gly Ile Ser Glu Gln
Pro Leu Phe Gly Ala Gly Ser Ile Ser Ser Gly Glu Leu Tyr Ile Asp
Lys Ile Glu Ile Ile Leu Ala Asp Ala Thr Phe Glu Ala Glu Ser Asp
Leu Glu Arg Ala Gln Lys Ala Val Asn Ala Leu Phe Thr Ser Ser Asn
Gln Ile Gly Leu Lys Thr. Asp Val Thr Asp Tyr His Ile Asp Gln Val
Ser Asn Leu Val Asp Cys Leu Ser Asp Glu Phe Cys Leu Asp Glu Lys
Arg Glu Leu Ser Glu Lys Val Lys His Ala Lys Arg Leu Ser Asp Glu
Arg Asn Leu Leu Gln Asp Pro Asn Phe Arg Gly Ile Asn Arg Gln Pro
Asp Arg Gly Trp Arg Gly Ser Thr Asp Ile Thr Ile Gln Gly Gly Asp
Asp Val Phe Lys Glu Asn Tyr Val Thr Leu Pro Gly Thr Val Asp Glu
Cys Tyr Pro Thr Tyr Leu Tyr Gln Lys Ile Asp Glu Ser Lys Leu Lys
Ala Tyr Thr Arg Tyr Glu Leu Arg Gly Tyr Ile Glu Asp Ser Gln Asp
Leu Glu Ile Tyr Leu Ile Arg Tyr Asn Ala Lys His Glu Ile Val Asn
Val Pro Gly Thr Gly Ser Leu Trp Pro Leu Ser Ala Gln Ser Pro Ile
Gly Lys Cys Gly Glu Pro Asn Arg Cys Ala Pro His Leu Glu Trp Asn
Pro Asp Leu Asp Cys Ser Cys Arg Asp Gly Glu Lys Cys Ala His His
Ser His His Phe Thr Leu Asp Ile Asp Val Gly Cys Thr Asp Leu Asn

Glu Asp Leu Gly Val Trp Val Ile Phe Lys Ile Lys Thr Gln Asp Gly
His Ala Arg Leu Gly Asn Leu Glu Phe Leu Glu Glu Lys Pro Leu Leu
Gly Glu Ala Leu Ala Arg Val Lys Arg Ala Glu Lys Lys Trp Arg Asp
Lys Arg Glu Lys Leu Gln Leu Glu Thr Asn Ile Val Tyr Lys Glu Ala
Lys Glu Ser Val Asp Ala Leu Phe Val Asn Ser Gln Tyr Asp Arg Leu
Gln Val Asp Thr Asn Ile Ala Met Ile His Ala Ala Asp Lys Arg Val
His Arg Ile Arg Glu Ala Tyr Leu Pro Glu Leu Ser Val Ile Pro Gly
Val Asn Ala Ala Ile Phe Glu Glu Leu Glu Gly Arg Ile Phe Thr Ala
Tyr Ser Leu Tyr Asp Ala Arg Asn Val Ile Lys Asn Gly Asp Phe Asn
Asn Gly Leu Leu Cys Trp Asn Val Lys Gly His Val Asp Val Glu Glu
Gln Asn Asn His Arg Ser Val Leu Val Ile Pro Glu Trp Glu Ala Glu
Val Ser Gln Glu Val Arg Val Cys Pro Gly Arg Gly Tyr Ile Leu Arg
Val Thr Ala Tyr Lys Glu Gly Tyr Gly Glu Gly Cys Val Thr Ile His
Glu Ile Glu Asp Asn Thr Asp Glu Leu Lys Phe Ser Asn Cys Val Glu
Glu Glu Val Tyr Pro Asn Asn Thr Val Thr Cys Asn Asn Tyr Thr Gly
Thr Gln Glu Glu Tyr Glu Gly Thr Tyr Thr Ser Arg Asn Gln Gly Tyr
Asp Glu Ala Tyr Gly Asn Asn Pro Ser Val Pro Ala Asp Tyr Ala Ser
Val Tyr Glu Glu Lys Ser Tyr Thr Asp Gly Arg Arg Glu Asn Pro Cys
Glu Ser Asn Arg Gly Tyr Gly Asp Tyr Thr Pro Leu Pro Ala Gly Tyr
Val Thr Lys Asp Leu Glu Tyr Phe Pro Glu Thr Asp Lys Val Trp Ile
Glu Ile Gly Glu Thr Glu Gly Thr Phe Ile Val Asp Ser Val Glu Leu
Leu Leu Met Glu Glu 5.13.5 Amino Acid Sequence of Cry1C.579 (SEQ ID NO:10)

Met Glu Glu Asn Asn Gln Asn Gln Cys Ile Pro Tyr Asn Cys Leu Ser
Asn Pro Glu Glu Val Leu Leu Asp Gly Glu Arg Ile Ser Thr Gly Asn
Ser Ser Ile Asp Ile Ser Leu Ser Leu Val Gln Phe Leu Val Ser Asn
Phe Val Pro Gly Gly Gly Phe Leu Val Gly Leu Ile Asp Phe Val Trp
Gly Ile Val Gly Pro Ser Gln Trp Asp Ala Phe Leu Val Gln Ile Glu
Gln Leu Ile Asn Glu Arg Ile Ala Glu Phe Ala Arg Asn Ala Ala Ile
Ala Asn Leu Glu Gly Leu Gly Asn Asn Phe Asn Ile Tyr Val Glu Ala
Phe Lys Glu Trp Glu Val Asp Pro Asn Asn Pro Gly Thr Arg Thr Arg
Val Ile Asp Arg Phe Arg Ile Leu Asp Gly Leu Leu Glu Arg Asp Ile
Pro Ser Phe Arg Ile Ser Gly Phe Glu Val Pro Leu Leu Ser Val Tyr
Ala Gln Ala Ala Asn Leu His Leu Ala Ile Leu Arg Asp Ser Val Ile

Phe Gly Glu Arg Trp Gly Leu Thr Thr Ile Asn Val Asn Glu Asn Tyr
Asn Arg Leu Ile Arg His Ile Asp Glu Tyr Ala Asp His Cys Ala Asn
Thr Tyr Asn Arg Gly Leu Asn Asn Leu Pro Lys Ser Thr Tyr Gln Asp
Trp Ile Thr Tyr Asn Arg Leu Arg Arg Asp Leu Thr Leu Thr Val Leu
Asp Ile Ala Ala Phe Phe Pro Asn Tyr Asp Asn Arg Arg Tyr Pro Ile
Gln Pro Val Gly Gln Leu Thr Arg Glu Val Tyr Thr Asp Pro Leu Ile
Asn Phe Asn Pro Gln Leu Gln Ser Val Ala Gln Leu Pro Thr Phe Asn
Val Met Glu Ser Ser Ala Ile Arg Asn Pro His Leu Phe Asp Ile Leu
Asn Asn Leu Thr Ile Phe Thr Asp Trp Phe Ser Val Gly Arg Asn Phe
Tyr Trp Gly Gly His Arg Val Ile Ser Ser Leu Ile Gly Gly Gly Asn
Ile Thr Ser Pro Ile Tyr Gly Arg Glu Ala Asn Gln Glu Pro Pro Arg
Ser Phe Thr Phe Asn Gly Pro Val Phe Arg Thr Leu Ser Asn Pro Thr
Leu Arg Leu Leu Gln Gln Pro Trp Pro Ala Pro Pro Phe Asn Leu Arg
Gly Val Glu Gly Val Glu Phe Ser Thr Pro Thr Asn Ser Phe Thr Tyr
Arg Gly Arg Gly Thr Val Asp Ser Leu Thr Glu Leu Pro Pro Glu Asp
Asn Ser Val Pro Pro Arg Glu Gly Tyr Ser His Arg Leu Cys His Ala
Thr Phe Val Gln Arg Ser Gly Thr Pro Phe Leu Thr Thr Gly Val Val
Phe Ser Trp Thr His Arg Ser Ala Thr Leu Thr Asn Thr Ile Asp Pro
Glu Arg Ile Asn Gln Ile Pro Leu Val Lys Gly Phe Arg Val Trp Gly
Gly Thr Ser Val Ile Thr Gly Pro Gly Phe Thr Gly Gly Asp Ile Leu
Arg Arg Asn Thr Phe Gly Asp Phe Val Ser Leu Gln Val Asn Ile Asn
Ser Pro Ile Thr Gln Arg Tyr Arg Leu Arg Phe Arg Tyr Ala Ser Ser
Arg Asp Ala Arg Val Ile Val Leu Thr Gly Ala Ala Ser Thr Gly Val
Gly Gly Gln Val Ser Val Asn Met Pro Leu Gln Lys Thr Met Glu Ile
Gly Glu Asn Leu Thr Ser Arg Thr Phe Arg Tyr Thr Asp Phe Ser Asn
Pro Phe Ser Phe Arg Ala Asn Pro Asp Ile Ile Gly Ile Ser Glu Gln
Pro Leu Phe Gly Ala Gly Ser Ile Ser Ser Gly Glu Leu Tyr Ile Asp
Lys Ile Glu Ile Ile Leu Ala Asp Ala Thr Phe Glu Ala Glu Ser Asp
Leu Glu Arg Ala Gln Lys Ala Val Asn Ala Leu Phe Thr Ser Ser Asn
Gln Ile Gly Leu Lys Thr Asp Val Thr Asp Tyr His Ile Asp Gln Val
Ser Asn Leu Val Asp Cys Leu Ser Asp Glu Phe Cys Leu Asp Glu Lys
Arg Glu Leu Ser Glu Lys Val Lys His Ala Lys Arg Leu Ser Asp Glu
Arg Asn Leu Leu Gln Asp Pro Asn Phe Arg Gly Ile Asn Arg Gln Pro
Asp Arg Gly Trp Arg Gly Ser Thr Asp Ile Thr Ile Gln Gly Gly Asp
Asp Val Phe Lys Glu Asn Tyr Val Thr Leu Pro Gly Thr Val Asp Glu
Cys Tyr Pro Thr Tyr Leu Tyr Gln Lys Ile Asp Glu Ser Lys Leu Lys
Ala Tyr Thr Arg Tyr Glu Leu Arg Gly Tyr Ile Glu Asp Ser Gln Asp
Leu Glu Ile Tyr Leu Ile Arg Tyr Asn Ala Lys His Glu Ile Val Asn
Val Pro Gly Thr Gly Ser Leu Trp Pro Leu Ser Ala Gln Ser Pro Ile
Gly Lys Cys Gly Glu Pro Asn Arg Cys Ala Pro His Leu Glu Trp Asn
Pro Asp Leu Asp Cys Ser Cys Arg Asp Gly Glu Lys Cys Ala His His
Ser His His Phe Thr Leu Asp Ile Asp Val Gly Cys Thr Asp Leu Asn
Glu Asp Leu Gly Val Trp Val Ile Phe Lys Ile Lys Thr Gln Asp Gly
His Ala Arg Leu Gly Asn Leu Glu Phe Leu Glu Glu Lys Pro Leu Leu
Gly Glu Ala Leu Ala Arg Val Lys Arg Ala Glu Lys Lys Trp Arg Asp
Lys Arg Glu Lys Leu Gln Leu Glu Thr Asn Ile Val Tyr Lys Glu Ala
Lys Glu Ser Val Asp Ala Leu Phe Val Asn Ser Gln Tyr Asp Arg Leu
Gln Val Asp Thr Asn Ile Ala Met Ile His Ala Ala Asp Lys Arg Val
His Arg Ile Arg Glu Ala Tyr Leu Pro Glu Leu Ser Val Ile Pro Gly
Val Asn Ala Ala Ile Phe Glu Glu Leu Glu Gly Arg Ile Phe Thr Ala
Tyr Ser Leu Tyr Asp Ala Arg Asn Val Ile Lys Asn Gly Asp Phe Asn
Asn Gly Leu Leu Cys Trp Asn Val Lys Gly His Val Asp Val Glu Glu
Gln Asn Asn His Arg Ser Val Leu Val Ile Pro Glu Trp Glu Ala Glu
Val Ser Gln Glu Val Arg Val Cys Pro Gly Arg Gly Tyr Ile Leu Arg
Val Thr Ala Tyr Lys Glu Gly Tyr Gly Glu Gly Cys Val Thr Ile His
Glu Ile Glu Asp Asn Thr Asp Glu Leu Lys Phe Ser Asn Cys Val Glu
Glu Glu Val Tyr Pro Asn Asn Thr Val Thr Cys Asn Asn Tyr Thr Gly
Thr Gln Glu Glu Tyr Glu Gly Thr Tyr Thr Ser Arg Asn Gln Gly Tyr
Asp Glu Ala Tyr Gly Asn Asn Pro Ser Val Pro Ala Asp Tyr Ala Ser
Val Tyr Glu Glu Lys Ser Tyr Thr Asp Gly Arg Arg Glu Asn Pro Cys
Glu Ser Asn Arg Gly Tyr Gly Asp Tyr Thr Pro Leu Pro Ala Gly Tyr
Val Thr Lys Asp Leu Glu Tyr Phe Pro Glu Thr Asp Lys Val Trp Ile
Glu Ile Gly Glu Thr Glu Gly Thr Phe Ile Val Asp Ser Val Glu Leu
Leu Leu Met Glu Glu 5.13.6 Amino Acid Sequence of Cry1C.499 (SEQ ID NO:12)

Met Glu Glu Asn Asn Gln Asn Gln Cys Ile Pro Tyr Asn Cys Leu Ser
Asn Pro Glu Glu Val Leu Leu Asp Gly Glu Arg Ile Ser Thr Gly Asn
Ser Ser Ile Asp Ile Ser Leu Ser Leu Val Gln Phe Leu Val Ser Asn

Phe Val Pro Gly Gly Gly Phe Leu Val Gly Leu Ile Asp Phe Val Trp

Gly Ile Val Gly Pro Ser Gln Trp Asp Ala Phe Leu Val Gln Ile Glu

Gln Leu Ile Asn Glu Arg Ile Ala Glu Phe Ala Arg Asn Ala Ala Ile

Ala Asn Leu Glu Gly Leu Gly Asn Asn Phe Asn Ile Tyr Val Glu Ala

Phe Lys Glu Trp Glu Glu Asp Pro His Asn Pro Ala Thr Arg Thr Arg

Val Ile Asp Arg Phe Arg Ile Leu Asp Gly Leu Leu Glu Arg Asp Ile

Pro Ser Phe Arg Ile Ser Gly Phe Glu Val Pro Leu Leu Ser Val Tyr

Ala Gln Ala Ala Asn Leu His Leu Ala Ile Leu Arg Asp Ser Val Ile

Phe Gly Glu Arg Trp Gly Leu Thr Thr Ile Asn Val Asn Glu Asn Tyr

Asn Arg Leu Ile Arg His Ile Asp Glu Tyr Ala Asp His Cys Ala Asn

Thr Tyr Asn Arg Gly Leu Asn Asn Leu Pro Lys Ser Thr Tyr Gln Asp

Trp Ile Thr Tyr Asn Arg Leu Arg Arg Asp Leu Thr Leu Thr Val Leu

Asp Ile Ala Ala Phe Phe Pro Asn Tyr Asp Asn Arg Arg Tyr Pro Ile

Gln Pro Val Gly Gln Leu Thr Arg Glu Val Tyr Thr Asp Pro Leu Ile

Asn Phe Asn Pro Gln Leu Gln Ser Val Ala Gln Leu Pro Thr Phe Asn

Val Met Glu Ser Ser Ala Ile Arg Asn Pro His Leu Phe Asp Ile Leu

Asn Asn Leu Thr Ile Phe Thr Asp Trp Phe Ser Val Gly Arg Asn Phe

Tyr Trp Gly Gly His Arg Val Ile Ser Ser Leu Ile Gly Gly Gly Asn

Ile Thr Ser Pro Ile Tyr Gly Arg Glu Ala Asn Gln Glu Pro Pro Arg

Ser Phe Thr Phe Asn Gly Pro Val Phe Arg Thr Leu Ser Asn Pro Thr

Leu Arg Leu Leu Gln Gln Pro Trp Pro Ala Pro Pro Phe Asn Leu Arg

Gly Val Glu Gly Val Glu Phe Ser Thr Pro Thr Asn Ser Phe Thr Tyr

Arg Gly Arg Gly Thr Val Asp Ser Leu Thr Glu Leu Pro Pro Glu Asp

Asn Ser Val Pro Pro Arg Glu Gly Tyr Ser His Arg Leu Cys His Ala

Thr Phe Val Gln Arg Ser Gly Thr Pro Phe Leu Thr Thr Gly Val Val

Phe Ser Trp Thr His Arg Ser Ala Thr Leu Thr Asn Thr Ile Asp Pro

Glu Arg Ile Asn Gln Ile Pro Leu Val Lys Gly Phe Arg Val Trp Gly

Gly Thr Ser Val Ile Thr Gly Pro Gly Phe Thr Gly Gly Asp Ile Leu

Arg Arg Asn Thr Phe Gly Asp Phe Val Ser Leu Gln Val Asn Ile Asn

Ser Pro Ile Thr Gln Arg Tyr Arg Leu Arg Phe Arg Tyr Ala Ser Ser

Arg Asp Ala Arg Val Ile Val Leu Thr Gly Ala Ala Ser Thr Gly Val

Gly Gly Gln Val Ser Val Asn Met Pro Leu Gln Lys Thr Met Glu Ile

Gly Glu Asn Leu Thr Ser Arg Thr Phe Arg Tyr Thr Asp Phe Ser Asn

Pro Phe Ser Phe Arg Ala Asn Pro Asp Ile Ile Gly Ile Ser Glu Gln

Pro Leu Phe Gly Ala Gly Ser Ile Ser Ser Gly Glu Leu Tyr Ile Asp

Lys Ile Glu Ile Ile Leu Ala Asp Ala Thr Phe Glu Ala Glu Ser Asp

Leu Glu Arg Ala Gln Lys Ala Val Asn Ala Leu Phe Thr Ser Ser Asn

Gln Ile Gly Leu Lys Thr Asp Val Thr Asp Tyr His Ile Asp Gln Val

Ser Asn Leu Val Asp Cys Leu Ser Asp Glu Phe Cys Leu Asp Glu Lys

Arg Glu Leu Ser Glu Lys Val Lys His Ala Lys Arg Leu Ser Asp Glu

Arg Asn Leu Leu Gln Asp Pro Asn Phe Arg Gly Ile Asn Arg Gln Pro

Asp Arg Gly Trp Arg Gly Ser Thr Asp Ile Thr Ile Gln Gly Gly Asp

Asp Val Phe Lys Glu Asn Tyr Val Thr Leu Pro Gly Thr Val Asp Glu

Cys Tyr Pro Thr Tyr Leu Tyr Gln Lys Ile Asp Glu Ser Lys Leu Lys

Ala Tyr Thr Arg Tyr Glu Leu Arg Gly Tyr Ile Glu Asp Ser Gln Asp

Leu Glu Ile Tyr Leu Ile Arg Tyr Asn Ala Lys His Glu Ile Val Asn

Val Pro Gly Thr Gly Ser Leu Trp Pro Leu Ser Ala Gln Ser Pro Ile

Gly Lys Cys Gly Glu Pro Asn Arg Cys Ala Pro His Leu Glu Trp Asn

Pro Asp Leu Asp Cys Ser Cys Arg Asp Gly Glu Lys Cys Ala His His

Ser His His Phe Thr Leu Asp Ile Asp Val Gly Cys Thr Asp Leu Asn

Glu Asp Leu Gly Val Trp Val Ile Phe Lys Ile Lys Thr Gln Asp Gly

His Ala Arg Leu Gly Asn Leu Glu Phe Leu Glu Glu Lys Pro Leu Leu

Gly Glu Ala Leu Ala Arg Val Lys Arg Ala Glu Lys Lys Trp Arg Asp

Lys Arg Glu Lys Leu Gln Leu Glu Thr Asn Ile Val Tyr Lys Glu Ala

Lys Glu Ser Val Asp Ala Leu Phe Val Asn Ser Gln Tyr Asp Arg Leu

Gln Val Asp Thr Asn Ile Ala Met Ile His Ala Ala Asp Lys Arg Val

His Arg Ile Arg Glu Ala Tyr Leu Pro Glu Leu Ser Val Ile Pro Gly

Val Asn Ala Ala Ile Phe Glu Glu Leu Glu Gly Arg Ile Phe Thr Ala

Tyr Ser Leu Tyr Asp Ala Arg Asn Val Ile Lys Asn Gly Asp Phe Asn

Asn Gly Leu Leu Cys Trp Asn Val Lys Gly His Val Asp Val Glu Glu

Gln Asn Asn His Arg Ser Val Leu Val Ile Pro Glu Trp Glu Ala Glu

Val Ser Gln Glu Val Arg Val Cys Pro Gly Arg Gly Tyr Ile Leu Arg

Val Thr Ala Tyr Lys Glu Gly Tyr Gly Glu Gly Cys Val Thr Ile His

Glu Ile Glu Asp Asn Thr Asp Glu Leu Lys Phe Ser Asn Cys Val Glu

Glu Glu Val Tyr Pro Asn Asn Thr Val Thr Cys Asn Asn Tyr Thr Gly

Thr Gln Glu Glu Tyr Glu Gly Thr Tyr Thr Ser Arg Asn Gln Gly Tyr

Asp Glu Ala Tyr Gly Asn Asn Pro Ser Val Pro Ala Asp Tyr Ala Ser

Val Tyr Glu Glu Lys Ser Tyr Thr Asp Gly Arg Arg Glu Asn Pro Cys

Glu Ser Asn Arg Gly Tyr Gly Asp Tyr Thr Pro Leu Pro Ala Gly Tyr

Val Thr Lys Asp Leu Glu Tyr Phe Pro Glu Thr Asp Lys Val Trp Ile

Glu Ile Gly Glu Thr Glu Gly Thr Phe Ile Val Asp Ser Val Glu Leu

Leu Leu Met Glu Glu

5.14 Example 14

Nucleic Acid Sequences of the Genes Encoding Modified Cry1C* Crystal Proteins

5.14.1 Nucleic Acid Sequence of Cry1C-R148A (SEQ ID NO:1)

ATGGAGGAAAATAATCAAAATCAATGCATACCTTACAATTGTTTAAGTAATCCTGAAGAAGTACTTTTGGAT

GGAGAACGGATATCAACTGGTAATTCATCAATTGATATTTCTCTGTCACTTGTTCAGTTTCTGGTATCTAAC

TTTGTACCAGGGGGAGGATTTTTAGTTGGATTAATAGATTTTGTATGGGGAATAGTTGGCCCTTCTCAATGG

GATGCATTTCTAGTACAAATTGAACAATTAATTAATGAAAGAATAGCTGAATTTGCTAGGAATGCTGCTATT

GCTAATTTAGAAGGATTAGGAAACAATTTCAATATATATGTGGAAGCATTTAAAGAATGGGAAGAAGATCCT

AATAATCCAGCAACCAGGACCAGAGTAATTGATCGCTTTCGTATACTTGATGGGCTACTTGAAAGGGACATT

CCTTCGTTTGCAATTTCTGGATTTGAAGTACCCCTTTTATCCGTTTATGCTCAAGCGGCCAATCTGCATCTA

GCTATATTAAGAGATTCTGTAATTTTTGGAGAAAGATGGGGATTGACAACGATAAATGTCAATGAAAACTAT

AATAGACTAATTAGGCATATTGATGAATATGCTGATCACTGTGCAAATACGTATAATCGGGGATTAAATAAT

TTACCGAAATCTACGTATCAAGATTGGATAACATATAATCGATTACGGAGAGACTTAACATTGACTGTATTA

GATATCGCCGCTTTCTTTCCAAACTATGACAATAGGAGATATCCAATTCAGCCAGTTGGTCAACTAACAAGG

GAAGTTTATACGGACCCATTAATTAATTTTAATCCACAGTTACAGTCTGTAGCTCAATTACCTACTTTTAAC

GTTATGGAGAGCAGCGCAATTAGAAATCCTCATTTATTTGATATATTGAATAATCTTACAATCTTTACGGAT

TGGTTTAGTGTTGGACGCAATTTTTATTGGGGAGGACATCGAGTAATATCTAGCCTTATAGGAGGTGGTAAC

ATAACATCTCCTATATATGGAAGAGAGGCGAACCAGGAGCCTCCAAGATCCTTTACTTTTAATGGACCGGTA

TTTAGGACTTTATCAAATCCTACTTTACGATTATTACAGCAACCTTGGCCAGCGCCACCATTTAATTTACGT

GGTGTTGAAGGAGTAGAATTTTCTACACCTACAAATAGCTTTACGTATCGAGGAAGAGGTACGGTTGATTCT

TTAACTGAATTACCGCCTGAGGATAATAGTGTGCCACCTCGCGAAGGATATAGTCATCGTTTATGTCATGCA

ACTTTTGTTCAAAGATCTGGAACACCTTTTTTAACAACTGGTGTAGTATTTTCTTGGACGCATCGTAGTGCA

ACTCTTACAAATACAATTGATCCAGAGAGAATTAATCAAATACCTTTAGTGAAAGGATTTAGAGTTTGGGGG

GGCACCTCTGTCATTACAGGACCAGGATTTACAGGAGGGGATATCCTTCGAAGAAATACCTTTGGTGATTTT

GTATCTCTACAAGTCAATATTAATTCACCAATTACCCAAAGATACCGTTTAAGATTTCGTTACGCTTCCAGT

AGGGATGCACGAGTTATAGTATTAACAGGAGCGGCATCCACAGGAGTGGGAGGCCAAGTTAGTGTAAATATG

CCTCTTCAGAAAACTATGGAAATAGGGGAGAACTTAACATCTAGAACATTTAGATATACCGATTTTAGTAAT

CCTTTTTCATTTAGAGCTAATCCAGATATAATTGGGATAAGTGAACAACCTCTATTTGGTGCAGGTTCTATT

AGTAGCGGTGAACTTTATATAGATAAAATTGAAATTATTCTAGCAGATGCAACATTTGAAGCAGAATCTGAT

TTAGAAAGAGCACAAAAGGCGGTGAATGCCCTGTTTACTTCTTCCAATCAnATCGGGTTAAAAACCGATGTG

ACGGATTATCATATTGATCAAGTATCCAATTTAGTGGATTGTTTATCAGATGAATTTTGTCTGGATGAAAAG

CGAGAATTGTCCGAGAAAGTCAAACATGCGAAGCGACTCAGTGATGAGCGGAATTTACTTCAAGATCCAAAC

TTCAGAGGGATCAATAGACAACCAGACCGTGGCTGGAGAGGAAGTACAGATATTACCATCCAAGGAGGAGAT

GACGTATTCAAAGAGAATTACGTCACACTACCGGGTACCGTTGATGAGTGCTATCCAACGTATTTATATCAG

AAAATAGATGAGTCGAAATTAAAAGCTTATACCCGTTATGAATTAAGAGGGTATATCGAAGATAGTCAAGAC

TTAGAAATCTATTTGATCCGTTACAATGCAAAACACGAAATAGTAAATGTGCCAGGCACGGGTTCCTTATGG

CCGCTTTCAGCCCAAAGTCCAATCGGAAAGTGTGGAGAACCGAATCGATGCGCGCCACACCTTGAATGGAAT

CCTGATCTAGATTGTTCCTGCAGAGACGGGGAAAAATGTGCACATCATTCCCATCATTTCACCTTGGATATT

GATGTTGGATGTACAGACTTAAATGAGGACTTAGGTGTATGGGTGATATTCAAGATTAAGACGCAAGATGGC

CATGCAAGACTAGGGAATCTAGAGTTTCTCGAAGAGAAACCATTATTAGGGGAAGCACTAGCTCGTGTGAAA

AGAGCGGAGAAGAAGTGGAGAGACAAACGAGAGAAACTGCAGTTGGAAACAAATATTGTTTATAAAGAGGCA

AAAGAATCTGTAGATGCTTTATTTGTAAACTCTCAATATGATAGATTACAAGTGGATACGAACATCGCAATG

ATTCATGCGGCAGATAAACGCGTTCATAGAATCCGGGAAGCGTATCTGCCAGAGTTGTCTGTGATTCCAGGT

GTCAATGCGGCCATTTTCGAAGAATTAGAGGGACGTATTTTTACAGCGTATTCCTTATATGATGCGAGAAAT

GTCATTAAAAATGGCGATTTCAATAATG-
GCTTATTATGCTGGAACGTGAAAGGT-
CATGTAGATGTAGAAGAG

CAAAACAACCACCGTTCGGTCCTTGT-
TATCCCAGAATGGGAGGCAGAAGTGTCA-
CAAGAGGTTCGTGTCTGT

CCAGGTCGTGGCTATATCCTTCGTGTCA-
CAGCATATAAAGAGGGATATG-
GAGAGGGCTGCGTAACGATCCAT

GAGATCGAAGACAATACAGACGAACT-
GAAATTCAGCAACTGTGTAGAAGAG-
GAAGTATATCCAAACAACACA

GTAACGTGTAATAATTATACTGGGACT-
CAAGAAGAATATGAGGGTACGTACACT-
TCTCGTAATCAAGGATAT

GACGAAGCCTATGGTAATAACCCTTCCG-
TACCAGCTGATTACGCTTCAGTCTAT-
GAAGAAAAATCGTATACA

GATGGACGAAGAGAGAATCCTTGT-
GAATCTAACAGAGGCTATGGGGATTACA-
CACCACTACCGGCTGGTTAT

GTAACAAAGGATTTAGAGTACTTCCCA-
GAGACCGATAAGGTATGGATTGAGATCG-
GAGAAACAGAAGGAACA

TTCATCGTGGATAGCGTGGAATTACTC-
CTTATGGAGGAA 5.14.2 Nucleic Acid Sequence of Cry1C-R148D (SEQ ID NO:3)

ATGGAGGAAAATAATCAAAATCAATG-
CATACCTTACAATTGTTTAAGTAATCCT-
GAAGAAGTACTTTTGGAT

GGAGAACGGATATCAACTGGTAATTCAT-
CAATTGATATTTCTCTGTCACTTGT-
TCAGTTTCTGGTATCTAAC

TTTGTACCAGGGGGAGGATTTTTAGTTG-
GATTAATAGATTTTGTATGGGGAATAGT-
TGGCCCTTCTCAATGG

GATGCATTTCTAGTACAAATTGAACAAT-
TAATTAATGAAAGAATAGCT-
GAATTTGCTAGGAATGCTGCTATT

GCTAATTTAGAAGGATTAGGAAA-
CAATTTCAATATATATGTGGAAGCATT-
TAAAGAATGGGAAGAAGATCCT

AATAATCCAGCAACCAGGACCAGAG-
TAATTGATCGCTTTCGTATACT-
TGATGGGCTACTTGAAAGGGACATT

CCTTCGTTTGACATTTCTGGATTTGAAG-
TACCCCTTTTATCCGTTTATGCT-
CAAGCGGCCAATCTGCATCTA

GCTATATTAAGAGATTCTGTAATTTTTG-
GAGAAAGATGGGGATTGACAAC-
GATAAATGTCAATGAAAACTAT

AATAGACTAATTAGGCATATTGAT-
GAATATGCTGATCACTGTGCAAATACG-
TATAATCGGGGATTAAATAAT

TTACCGAAATCTACGTATCAAGATTG-
GATAACATATAATCGATTACG-
GAGAGACTTAACATTGACTGTATTA

GATATCGCCGCTTTCTTTCCAnACTAT-
GACAATAGGAGATATCCAATTCAGC-
CAGTTGGTCAACTAACAAGG

GAAGTTTATACGGACCCATTAAT-
TAATTTTAATCCACAGTTACAGTCTG-
TAGCTCAATTACCTACTTTTAAC

GTTATGGAGAGCAGCGCAATTAGAAATC-
CTCATTTATTTGATATATTGAATAATCT-
TACAATCTTTACGGAT

TGGTTTAGTGTTGGACGCAATTTTTAT-
TGGGGAGGACATCGAGTAATATCTAGC-
CTTATAGGAGGTGGTAAC

ATAACATCTCCTATATATGGAAGAGAG-
GCGAACCAGGAGCCTCCAAGATCCTT-
TACTTTTAATGGACCGGTA

TTTAGGACTTTATCAAATCCTACTTTAC-
GATTATTACAGCAACCTTGGCCAGCGC-
CACCATTTAATTTACGT

GGTGTTGAAGGAGTAGAATTTTCTACAC-
CTACAAATAGCTTTACGTATCGAGGAA-
GAGGTACGGTTGATTCT

TTAACTGAATTACCGCCTGAGGATAAT-
AGTGTGCCACCTCGCGAAGGATATAGT-
CATCGTTTATGTCATGCA

ACTTTTGTTCAAAGATCTGGAACAC-
CTTTTTTAACAACTGGTGTAG-
TATTTTCTTGGACGCATCGTAGTGCA

ACTCTTACAAATACAATTGATCCA-
GAGAGAATTAATCAAATACCTTTAGT-
GAAAGGATTTAGAGTTTGGGGG

GGCACCTCTGTCATTACAGGACCAG-
GATTTACAGGAGGGGATATCCTTCGAA-
GAAATACCTTTGGTGATTTT

GTATCTCTACAAGTCAATATTAATTCAC-
CAATTACCCAAAGATACCGTTTAA-
GATTTCGTTACGCTTCCAGT

AGGGATGCACGAGTTATAGTATTAACAG-
GAGCGGCATCCACAGGAGTGGGAGGC-
CAAGTTAGTGTAAATATG

CCTCTTCAGAAAACTATGGAAATAGGG-
GAGAACTTAACATCTAGAACATTTA-
GATATACCGATTTTAGTAAT

CCTTTTTCATTTAGAGCTAATCCA-
GATATAATTGGGATAAGTGAACAACCTC-
TATTTGGTGCAGGTTCTATT

AGTAGCGGTGAACTTTATATA-
GATAAAATTGAAATTATTCTAGCAGATG-
CAACATTTGAAGCAGAATCTGAT

TTAGAAAGAGCACAAAAGGCGGTGAAT-
GCCCTGTTTACTTCTTCCAAT-
CAAATCGGGTTAAAAACCGATGTG

ACGGATTATCATATTGATCAAGTATC-
CAATTTAGTGGATTGTTTATCAGAT-
GAATTTTGTCTGGATGAAAAG

CGAGAATTGTCCGAGAAAGTCAAACAT-
GCGAAGCGACTCAGTGATGAGCGGAATT-
TACTTCAAGATCCAAAC

TTCAGAGGGATCAATAGACAACCAGAC-
CGTGGCTGGAGAGGAAGTACAGATAT-
TACCATCCAAGGAGGAGAT

GACGTATTCAAAGAGAATTACGTCACAC-
TACCGGGTACCGTTGATGAGTGCTATC-
CAACGTATTTATATCAG

AAAATAGATGAGTCGAAATTAAAAGCT-
TATACCCGTTATGAATTAAGAGGG-
TATATCGAAGATAGTCAAGAC

TTAGAAATCTATTTGATCCGTTACAATG-
CAAAACACGAAATAGTAAATGTGCCAG-
GCACGGGTTCCTTATGG

CCGCTTTCAGCCCAAAGTCCAATCG-
GAAAGTGTGGAGAACCGAATCGAT-
GCGCGCCACACCTTGAATGGAAT

CCTGATCTAGATTGTTCCTGCA-
GAGACGGGGAAAAATGTGCACATCATTC-
CCATCATTTCACCTTGGATATT

GATGTTGGATGTACAGACTTAAATGAG-
GACTTAGGTGTATGGGTGATATTCAA-
GATTAAGACGCAAGATGGC

CATGCAAGACTAGGGAATCTA-
GAGTTTCTCGAAGAGAAACCATTATT-
AGGGGAAGCACTAGCTCGTGTGAAA

AGAGCGGAGAAGAAGTGGAGAGACAAAC-
GAGAGAAACTGCAGTTGGAAACAAATAT-
TGTTTATAAAGAGGCA

AAAGAATCTGTAGATGCTTTATTTG-
TAAACTCTCAATATGATAGATTA-
CAAGTGGATACGAACATCGCAATG

ATTCATGCGGCAGATAAACGCGTTCATA-
GAATCCGGGAAGCGTATCTGCCAGAGT-
TGTCTGTGATTCCAGGT

GTCAATGCGGCCATTTTCGAAGAATTA-
GAGGGACGTATTTTTACAGCGTATTCCT-
TATATGATGCGAGAAAT

GTCATTAAAAATGGCGATTTCAATAATG-
GCTTATTATGCTGGAACGTGAAAGGT-
CATGTAGATGTAGAAGAG

CAAAACAACCACCGTTCGGTCCTTGT-
TATCCCAGAATGGGAGGCAGAAGTGTCA-
CAAGAGGTTCGTGTCTGT

CCAGGTCGTGGCTATATCCTTCGTGTCA-
CAGCATATAAAGAGGGATATG-
GAGAGGGCTGCGTAACGATCCAT

GAGATCGAAGACAATACAGACGAACT-
GAAATTCAGCAACTGTGTAGAAGAG-
GAAGTATATCCAAACAACACA

GTAACGTGTAATAATTATACTGGGACT-
CAAGAAGAATATGAGGGTACGTACACT-
TCTCGTAATCAAGGATAT

GACGAAGCCTATGGTAATAACCCTTCCG-
TACCAGCTGATTACGCTTCAGTCTAT-
GAAGAARAATCGTATACA

GATGGACGAAGAGAGAATCCTTGT-
GAATCTAACAGAGGCTATGGGGATTACA-
CACCACTACCGGCTGGTTAT

GTAACAAAGGATTTAGAGTACTTCCCA-
GAGACCGATAAGGTATGGATTGAGATCG-
GAGAAACAGAAGGAACA

TTCATCGTGGATAGCGTGGAATTACTC-
CTTATGGAGGAA 5.14.3 Nucleic Acid Sequence of Cry1C-R180A (SEQ ID NO:5)

ATGGAGGAAAATAATCAAAATCAATG-
CATACCTTACAATTGTTTAAGTAATCCT-
GAAGAAGTACTTTTGGAT

GGAGAACGGATATCAACTGGTAATTCAT-
CAATTGATATTTCTCTGTCACTTGT-
TCAGTTTCTGGTATCTAAC

TTTGTACCAGGGGGAGGATTTTTAGTTG-
GATTAATAGATTTTGTATGGGGAATAGT-
TGGCCCTTCTCAATGG

GATGCATTTCTAGTACAAATTGAACAAT-
TAATTAATGAAAGAATAGCT-
GAATTTGCTAGGAATGCTGCTATT

GCTAATTTAGAAGGATTAGGAAA-
CAATTTCAATATATATGTGGAAGCATT-
TAAAGAATGGGAAGAAGATCCT

AATAATCCAGCAACCAGGACCAGAG-
TAATTGATCGCTTTCGTATACT-
TGATGGGCTACTTGAAAGGGACATT

CCTTCGTTTCGAATTTCTGGATTTGAAG-
TACCCCTTTTATCCGTTTATGCT-
CAAGCGGCCAATCTGCATCTA

GCTATATTAAGAGATTCTGTAATTTTTG-
GAGAAGCATGGGGGTTGACAAC-
GATAAATGTCAATGAAAACTAT

AATAGACTAATTAGGCATATTGAT-
GAATATGCTGATCACTGTGCAAATACG-
TATAATCGGGGATTAAATAAT

TTACCGAAATCTACGTATCAAGATTG-
GATAACATATAATCGATTACG-
GAGAGACTTAACATTGACTGTATTA

GATATCGCCGCTTTCTTTCCAAACTAT-
GACAATAGGAGATATCCAATTCAGC-
CAGTTGGTCAACTAACAAGG

GAAGTTTATACGGACCCATTAAT-
TAATTTTAATCCACAGTTACAGTCTG-
TAGCTCAATTACCTACTTTTAAC

GTTATGGAGAGCAGCGCAATTAGAAATC-
CTCATTTATTTGATATATTGAATAATCT-
TACAATCTTTACGGAT

TGGTTTAGTGTTGGACGCAATTTTTAT-
TGGGGAGGACATCGAGTAATATCTAGC-
CTTATAGGAGGTGGTAAC

ATAACATCTCCTATATATGGAAGAGAG-
GCGAACCAGGAGCCTCCAAGATCCTT-
TACTTTTAATGGACCGGTA

TTTAGGACTTTATCAAATCCTACTTTAC-
GATTATTACAGCAACCTTGGCCAGCGC-
CACCATTTAATTTACGT

GGTGTTGAAGGAGTAGAATTTTCTACAC-
CTACAAATAGCTTTACGTATCGAGGAA-
GAGGTACGGTTGATTCT

TTAACTGAATTACCGCCTGAGGATAAT-
AGTGTGCCACCTCGCGAAGGATATAGT-
CATCGTTTATGTCATGCA

ACTTTTGTTCAAAGATCTGGAACAC-
CTTTTTTAACAACTGGTGTAG-
TATTTTCTTGGACGCATCGTAGTGCA

ACTCTTACAAATACAATTGATCCA-
GAGAGAATTAATCAAATACCTTTAGT-
GAAAGGATTTAGAGTTTGGGGG

GGCACCTCTGTCATTACAGGACCAG-
GATTTACAGGAGGGGATATCCTTCGAA-
GAAATACCTTTGGTGATTTT

GTATCTCTACAAGTCAATATTAATTCAC-
CAATTACCCAAAGATACCGTTTAA-
GATTTCGTTACGCTTCCAGT

AGGGATGCACGAGTTATAGTATTAACAG-
GAGCGGCATCCACAGGAGTGGGAGGC-
CAAGTTAGTGTAAATATG

CCTCTTCAGAAAACTATGGAAATAGGG-
GAGAACTTAACATCTAGAACATTTA-
GATATACCGATTTTAGTAAT

CCTTTTTCATTTAGAGCTAATCCA-
GATATAATTGGGATAAGTGAACAACCTC-
TATTTGGTGCAGGTTCTATT

AGTAGCGGTGAACTTTATATA-
GATAAAATTGAAATTATTCTAGCAGATG-
CAACATTTGAAGCAGAATCTGAT

TTAGAAAGAGCACAAAAGGCGGTGAAT-
GCCCTGTTTACTTCTTCCAAT-
CAAATCGGGTTAAAAACCGATGTG

ACGGATTATCATATTGATCAAGTATC-
CAATTTAGTGGATTGTTTATCAGAT-
GAATTTTGTCTGGATGAAAAG

CGAGAATTGTCCGAGAAAGTCAAACAT-
GCGAAGCGACTCAGTGATGAGCGGAATT-
TACTTCAAGATCCAAAC

TTCAGAGGGATCAATAGACAACCAGAC-
CGTGGCTGGAGAGGAAGTACAGATAT-
TACCATCCAAGGAGGAGAT

GACGTATTCAAAGAGAATTACGTCACAC-
TACCGGGTACCGTTGATGAGTGCTATC-
CAACGTATTTATATCAG

AAAATAGATGAGTCGAAATTAAAAGCTTATACCCGTTATGAATTAAGAGGGTATATCGAAGATAGTCAAGAC

TTAGAAATCTATTTGATCCGTTACAATGCAAAACACGAAATAGTAAATGTGCCAGGCACGGGTTCCTTATGG

CCGCTTTCAGCCCAAAGTCCAATCGGAAAGTGTGGAGAACCGAATCGATGCGCGCCACACCTTGAATGGAAT

CCTGATCTAGATTGTTCCTGCAGAGACGGGGAAAAATGTGCACATCATTCCCATCATTTCACCTTGGATATT

GATGTTGGATGTACAGACTTAAATGAGGACTTAGGTGTATGGGTGATATTCAAGATTAAGACGCAAGATGGC

CATGCAAGACTAGGGAATCTAGAGTTTCTCGAAGAGAAACCATTATTAGGGGAAGCACTAGCTCGTGTGAAA

AGAGCGGAGAAGAAGTGGAGAGACAAACGAGAGAAACTGCAGTTGGAAACAAATATTGTTTATAAAGAGGCA

AAAGAATCTGTAGATGCTTTATTTGTAAACTCTCAATATGATAGATTACAAGTGGATACGAACATCGCAATG

ATTCATGCGGCAGATAAACGCGTTCATAGAATCCGGGAAGCGTATCTGCCAGAGTTGTCTGTGATTCCAGGT

GTCAATGCGGCCATTTTCGAAGAATTAGAGGGACGTATTTTTACAGCGTATTCCTTATATGATGCGAGAAAT

GTCATTAAAAATGGCGATTTCAATAATGGCTTATTATGCTGGAACGTGAAAGGTCATGTAGATGTAGAAGAG

CAAAACAACCACCGTTCGGTCCTTGTTATCCCAGAATGGGAGGCAGAAGTGTCACAAGAGGTTCGTGTCTGT

CCAGGTCGTGGCTATATCCTTCGTGTCACAGCATATAAAGAGGGATATGGAGAGGGCTGCGTAACGATCCAT

GAGATCGAAGACAATACAGACGAACTGAAATTCAGCAACTGTGTAGAAGAGGAAGTATATCCAAACAACACA

GTAACGTGTAATAATTATACTGGGACTCAAGAAGAATATGAGGGTACGTACACTTCTCGTAATCAAGGATAT

GACGAAGCCTATGGTAATAACCCTTCCGTACCAGCTGATTACGCTTCAGTCTATGAAGAAAAATCGTATACA

GATGGACGAAGAGAGAATCCTTGTGAATCTAACAGAGGCTATGGGGATTACACACCACTACCGGCTGGTTAT

GTAACAAAGGATTTAGAGTACTTCCCAGAGACCGATAAGGTATGGATTGAGATCGGAGAAACAGAAGGAACA

TTCATCGTGGATAGCGTGGAATTACTCCTTATGGAGGAA 5.14.4 Nucleic Acid Sequence of Cry1C.563 (SEQ ID NO:7)

ATGGAGGAAAATAATCAAAATCAATGCATACCTTACAATTGTTTAAGTAATCCTGAAGAAGTACTTTTGGAT

GGAGAACGGATATCAACTGGTAATTCATCAATTGATATTTCTCTGTCACTTGTTCAGTTTCTGGTATCTAAC

TTTGTACCAGGGGGAGGATTTTTAGTTGGATTAATAGATTTTGTATGGGGAATAGTTGGCCCTTCTCAATGG

GATGCATTTCTAGTACAAATTGAACAATTAATTAATGAAAGAATAGCTGAATTTGCTAGGAATGCTGCTATT

GCTAATTTAGAAGGATTAGGAAACAATTTCAATATATATGTGGAAGCATTTAAAGAATGGGAAGATGATCCT

CATAATCCCACAACCAGGACCAGAGTAATTGATCGCTTTCGTATACTTGATGGGCTACTTGAAAGGGACATT

CCTTCGTTTCGAATTTCTGGATTTGAAGTACCCCTTTTATCCGTTTATGCTCAAGCGGCCAATCTGCATCTA

GCTATATTAAGAGATTCTGTAATTTTTGGAGAAAGATGGGGATTGACAACGATAAATGTCAATGAAAACTAT

AATAGACTAATTAGGCATATTGATGAATATGCTGATCACTGTGCAAATACGTATAATCGGGGATTAAATAAT

TTACCGAAATCTACGTATCAAGATTGGATAACATATAATCGATTACGGAGAGACTTAACATTGACTGTATTA

GATATCGCCGCTTTCTTTCCAAACTATGACAATAGGAGATATCCAATTCAGCCAGTTGGTCAACTAACAAGG

GAAGTTTATACGGACCCATTAATTAATTTTAATCCACAGTTACAGTCTGTAGCTCAATTACCTACTTTTAAC

GTTATGGAGAGCAGCGCAATTAGAAATCCTCATTTATTTGATATATTGAATAATCTTACAATCTTTACGGAT

TGGTTTAGTGTTGGACGCAATTTTTATTGGGGAGGACATCGAGTAATATCTAGCCTTATAGGAGGTGGTAAC

ATAACATCTCCTATATATGGAAGAGAGGCGAACCAGGAGCCTCCAAGATCCTTTACTTTTAATGGACCGGTA

TTTAGGACTTTATCAAATCCTACTTTACGATTATTACAGCAACCTTGGCCAGCGCCACCATTTAATTTACGT

GGTGTTGAAGGAGTAGAATTTTCTACACCTACAAATAGCTTTACGTATCGAGGAAGAGGTACGGTTGATTCT

TTAACTGAATTACCGCCTGAGGATAATAGTGTGCCACCTCGCGAAGGATATAGTCATCGTTTATGTCATGCA

ACTTTTGTTCAAAGATCTGGAACACCTTTTTTAACAACTGGTGTAGTATTTTCTTGGACGCATCGTAGTGCA

ACTCTTACAAATACAATTGATCCAGAGAGAATTAATCAAATACCTTTAGTGAAAGGATTTAGAGTTTGGGGG

GGCACCTCTGTCATTACAGGACCAGGATTTACAGGAGGGGATATCCTTCGAAGAAATACCTTTGGTGATTTT

GTATCTCTACAAGTCAATATTAATTCACCAATTACCCAAAGATACCGTTTAAGATTTCGTTACGCTTCCAGT

AGGGATGCACGAGTTATAGTATTAACAGGAGCGGCATCCACAGGAGTGGGAGGCCAAGTTAGTGTAAATATG

CCTCTTCAGAAAACTATGGAAATAGGGGAGAACTTAACATCTAGAACATTTAGATATACCGATTTTAGTAAT

CCTTTTTCATTTAGAGCTAATCCAGATATAATTGGGATAAGTGAACAACCTCTATTTGGTGCAGGTTCTATT

AGTAGCGGTGAACTTTATATAGATAAAATTGAAATTATTCTAGCAGATGCAACATTTGAAGCAGAATCTGAT

TTAGAAAGAGCACAAAAGGCGGTGAAT-GCCCTGTTTACTTCTTCCAAT-CAAATCGGGTTAAAAACCGATGTG

ACGGATTATCATATTGATCAAGTATC-CAATTTAGTGGATTGTTTATCAGAT-GAATTTTGTCTGGATGAAAAG

CGAGAATTGTCCGAGAAAGTCAAACAT-GCGAAGCGACTCAGTGATGAGCGGAATT-TACTTCAAGATCCAAAC

TTCAGAGGGATCAATAGACAACCAGAC-CGTGGCTGGAGAGGAAGTACAGATAT-TACCATCCAAGGAGGAGAT

GACGTATTCAAAGAGAATTACGTCACAC-TACCGGGTACCGTTGATGAGTGCTATC-CAACGTATTTATATCAG

AAAATAGATGAGTCGAAATTAAAAGCT-TATACCCGTTATGAATTAAGAGGG-TATATCGAAGATAGTCAAGAC

TTAGAAATCTATTTGATCCGTTACAATG-CAAAACACGAAATAGTAAATGTGCCAG-GCACGGGTTCCTTATGG

CCGCTTTCAGCCCAAAGTCCAATCG-GAAAGTGTGGAGAACCGAATCGAT-GCGCGCCACACCTTGAATGGAAT

CCTGATCTAGATTGTTCCTGCA-GAGACGGGGAAAAATGTGCACATCATTC-CCATCATTTCACCTTGGATATT

GATGTTGGATGTACAGACTTAAATGAG-GACTTAGGTGTATGGGTGATATTCAA-GATTAAGACGCAAGATGGC

CATGCAAGACTAGGGAATCTA-GAGTTTCTCGAAGAGAAACCATTATT-AGGGGAAGCACTAGCTCGTGTGAAA

AGAGCGGAGAAGAAGTGGAGAGACAAAC-GAGAGAAACTGCAGTTGGAAACAAATAT-TGTTTATAAAGAGGCA

AAAGAATCTGTAGATGCTTTATTTG-TAAACTCTCAATATGATAGATTA-CAAGTGGATACGAACATCGCAATG

ATTCATGCGGCAGATAAACGCGTTCATA-GAATCCGGGAAGCGTATCTGCCAGAGT-TGTCTGTGATTCCAGGT

GTCAATGCGGCCATTTTCGAAGAATTA-GAGGGACGTATTTTTACAGCGTATTCCT-TATATGATGCGAGAAAT

GTCATTAAAAATGGCGATTTCAATAATG-GCTTATTATGCTGGAACGTGAAAGGT-CATGTAGATGTAGAAGAG

CAAAACAACCACCGTTCGGTCCTTGT-TATCCCAGAATGGGAGGCAGAAGTGTCA-CAAGAGGTTCGTGTCTGT

CCAGGTCGTGGCTATATCCTTCGTGTCA-CAGCATATAAAGAGGGATATG-GAGAGGGCTGCGTAACGATCCAT

GAGATCGAAGACAATACAGACGAACT-GAAATTCAGCAACTGTGTAGAAGAG-GAAGTATATCCAAACAACACA

GTAACGTGTAATAATTATACTGGGACT-CAAGAAGAATATGAGGGTACGTACACT-TCTCGTAATCAAGGATAT

GACGAAGCCTATGGTAATAACCCTTCCG-TACCAGCTGATTACGCTTCAGTCTAT-GAAGAAAAATCGTATACA

GATGGACGAAGAGAGAATCCTTGT-GAATCTAACAGAGGCTATGGGGATTACA-CACCACTACCGGCTGGTTAT

GTAACAAAGGATTTAGAGTACTTCCCA-GAGACCGATAAGGTATGGATTGAGATCG-GAGAAACAGAAGGAACA

TTCATCGTGGATAGCGTGGAATTACTC-CTTATGGAGGAA 5.14.5 Nucleic Acid Sequence of Cry1C.579 (SEQ ID NO:9)

ATGGAGGAAAATAATCAAAATCAATG-CATACCTTACAATTGTTTAAGTAATCCT-GAAGAAGTACTTTTGGAT

GGAGAACGGATATCAACTGGTAATTCAT-CAATTGATATTTCTCTGTCACTTGT-TCAGTTTCTGGTATCTAAC

TTTGTACCAGGGGGAGGATTTTTAGTTG-GATTAATAGATTTTGTATGGGGAATAGT-TGGCCCTTCTCAATGG

GATGCATTTCTAGTACAAATTGAACAAT-TAATTAATGAAAGAATAGCT-GAATTTGCTAGGAATGCTGCTATT

GCTAATTTAGAAGGATTAGGAAA-CAATTTCAATATATATGTGGAAGCATT-TAAAGAATGGGAAGTAGATCCT

AATAATCCTGGAACCAGGACCAGAG-TAATTGATCGCTTTCGTATACT-TGATGGGCTACTTGAAAGGGACATT

CCTTCGTTTCGAATTTCTGGATTTGAAG-TACCCCTTTTATCCGTTTATGCT-CAAGCGGCCAATCTGCATCTA

GCTATATTAAGAGATTCTGTAATTTTTG-GAGAAAGATGGGGATTGACAAC-GATAAATGTCAATGAAAACTAT

AATAGACTAATTAGGCATATTGAT-GAATATGCTGATCACTGTGCAAATACG-TATAATCGGGGATTAAATAAT

TTACCGAAATCTACGTATCAAGATTG-GATAACATATAATCGATTACG-GAGAGACTTAACATTGACTGTATTA

GATATCGCCGCTTTCTTTCCAAACTAT-GACAATAGGAGATATCCAATTCAGC-CAGTTGGTCAACTAACAAGG

GAAGTTTATACGGACCCATTAAT-TAATTTTAATCCACAGTTACAGTCTG-TAGCTCAATTACCTACTTTTAAC

GTTATGGAGAGCAGCGCAATTAGAAATC-CTCATTTATTTGATATATTGAATAATCT-TACAATCTTTACGGAT

TGGTTTAGTGTTGGACGCAATTTTTAT-TGGGGAGGACATCGAGTAATATCTAGC-CTTATAGGAGGTGGTAAC

ATAACATCTCCTATATATGGAAGAGAG-GCGAACCAGGAGCCTCCAAGATCCTT-TACTTTTAATGGACCGGTA

TTTAGGACTTTATCAAATCCTACTTTAC-GATTATTACAGCAACCTTGGCCAGCGC-CACCATTTAATTTACGT

GGTGTTGAAGGAGTAGAATTTTCTACAC-CTACAAATAGCTTTACGTATCGAGGAA-GAGGTACGGTTGATTCT

TTAACTGAATTACCGCCTGAGGATAAT-AGTGTGCCACCTCGCGAAGGATATAGT-CATCGTTTATGTCATGCA

ACTTTTGTTCAAAGATCTGGAACAC-CTTTTTTAACAACTGGTGTAG-TATTTTCTTGGACGCATCGTAGTGCA

ACTCTTACAAATACAATTGATCCA-GAGAGAATTAATCAAATACCTTTAGT-GAAAGGATTTAGAGTTTGGGGG

GGCACCTCTGTCATTACAGGACCAG-GATTTACAGGAGGGGATATCCTTCGAA-GAAATACCTTTGGTGATTTT

GTATCTCTACAAGTCAATATTAATTCAC-
CAATTACCCAAAGATACCGTTTAA-
GATTTCGTTACGCTTCCAGT
AGGGATGCACGAGTTATAGTATTAACAG-
GAGCGGCATCCACAGGAGTGGGAGGC-
CAAGTTAGTGTAAATATG
CCTCTTCAGAAAACTATGGAAATAGGG-
GAGAACTTAACATCTAGAACATTTA-
GATATACCGATTTTAGTAAT
CCTTTTTCATTTAGAGCTAATCCA-
GATATAATTGGGATAAGTGAACAACCTC-
TATTTGGTGCAGGTTCTATT
AGTAGCGGTGAACTTTATATA-
GATAAAATTGAAATTATTCTAGCAGATG-
CAACATTTGAAGCAGAATCTGAT
TTAGAAAGAGCACAAAAGGCGGTGAAT-
GCCCTGTTTACTTCTTCCAAT-
CAAATCGGGTTAAAAACCGATGTG
ACGGATTATCATATTGATCAAGTATC-
CAATTTAGTGGATTGTTTATCAGAT-
GAATTTTGTCTGGATGAAAAG
CGAGAATTGTCCGAGAAAGTCAAACAT-
GCGAAGCGACTCAGTGATGAGCGGAATT-
TACTTCAAGATCCAAAC
TTCAGAGGGATCAATAGACAACCAGAC-
CGTGGCTGGAGAGGAAGTACAGATAT-
TACCATCCAAGGAGGAGAT
GACGTATTCAAAGAGAATTACGTCACAC-
TACCGGGTACCGTTGATGAGTGCTATC-
CAACGTATTTATATCAG
AAAATAGATGAGTCGAAATTAAAAGCT-
TATACCCGTTATGAATTAAGAGGG-
TATATCGAAGATAGTCAAGAC
TTAGAAATCTATTTGATCCGTTACAATG-
CAAAACACGAAATAGTAAATGTGCCAG-
GCACGGGTTCCTTATGG
CCGCTTTCAGCCCAAAGTCCAATCG-
GAAAGTGTGGAGAACCGAATCGAT-
GCGCGCCACACCTTGAATGGAAT
CCTGATCTAGATTGTTCCTGCA-
GAGACGGGGAAAAATGTGCACATCATTC-
CCATCATTTCACCTTGGATATT
GATGTTGGATGTACAGACTTAAATGAG-GACTTAGGTGTATGGGTGATATTCAA-GATTAAGACGCAAGATGGC
CATGCAAGACTAGGGAATCTA-GAGTTTCTCGAAGAGAAACCATTATT-AGGGGAAGCACTAGCTCGTGTGAAA
AGAGCGGAGAAGAAGTGGAGAGACAAAC-GAGAGAAACTGCAGTTGGAAACAAATAT-TGTTTATAAAGAGGCA
AAAGAATCTGTAGATGCTTTATTTG-TAAACTCTCAATATGATAGATTA-CAAGTGGATACGAACATCGCAATG
ATTCATGCGGCAGATAAACGCGTTCATA-GAATCCGGGAAGCGTATCTGCCAGAGT-TGTCTGTGATTCCAGGT
GTCAATGCGGCCATTTTCGAAGAATTA-GAGGGACGTATTTTTACAGCGTATTCCT-TATATGATGCGAGAAAT
GTCATTAAAAATGGCGATTTCAATAATG-GCTTATTATGCTGGAACGTGAAAGGT-CATGTAGATGTAGAAGAG
CAAAACAACCACCGTTCGGTCCTTGT-TATCCCAGAATGGGAGGCAGAAGTGTCA-CAAGAGGTTCGTGTCTGT
CCAGGTCGTGGCTATATCCTTCGTGTCA-CAGCATATAAAGAGGGATATG-GAGAGGGCTGCGTAACGATCCAT

GAGATCGAAGACAATACAGACGAACT-GAAATTCAGCAACTGTGTAGAAGAG-GAAGTATATCCAAACAACACA
GTAACGTGTAATAATTATACTGGGACT-CAAGAAGAATATGAGGGTACGTACACT-TCTCGTAATCAAGGATAT
GACGAAGCCTATGGTAATAACCCTTCCG-TACCAGCTGATTACGCTTCAGTCTAT-GAAGAAAAATCGTATACA
GATGGACGAAGAGAGAATCCTTGT-GAATCTAACAGAGGCTATGGGGATTACA-CACCACTACCGGCTGGTTAT
GTAACAAAGGATTTAGAGTACTTCCCA-GAGACCGATAAGGTATGGATTGAGATCG-GAGAnACAGAAGGAACA
TTCATCGTGGATAGCGTGGAATTACTC-CTTATGGAGGAA 5.14.6 Nucleic Acid Sequence of Cry1C.499 (SEQ ID NO:11)

ATGGAGGAAAATAATCAAAATCAATG-CATACCTTACAATTGTTTAAGTAATCCT-GAAGAAGTACT
TTTGGATGGAGAACGGATATCAACTGG-TAATTCATCAATTGATATTTCTCTGT-CACTTGTTCAGT
TTCTGGTATCTAACTTTGTACCAGGGG-GAGGATTTTTAGTTGGATTAATA-GATTTTGTATGGGGA
ATAGTTGGCCCTTCTCAATGGGATG-CATTTCTAGTACAAATTGAACAATTAAT-TAATGAAAGAAT
AGCTGAATTTGCTAGGAATGCTGCTAT-TGCTAATTTAGAAGGATTAGGAAA-CAATTTCAATATAT
ATGTGGAAGCATTTAAAGAATGGGAA-GAAGATCCCCATAATCCAGCAACCAG-GACCAGAGTAATT
GATCGCTTTCGTATACTTGATGGGC-TACTTGAAAGGGACATTCCTTCGTTTC-GAATTTCTGGATT
TGAAGTACCCCTTTTATCCGTTTATGCT-CAAGCGGCCAATCTGCATCTAGCTATAT-TAAGAGATT
CTGTAATTTTTGGAGAAAGATGGGGAT-TGACAACGATAAATGTCAATGAAAAC-TATAATAGACTA
ATTAGGCATATTGATGAATATGCTGAT-CACTGTGCAAATACGTATAATCGGGGAT-TAAATAATTT
ACCGAAATCTACGTATCAAGATTG-GATAACATATAATCGATTACG-GAGAGACTTAACATTGACTG
TATTAGATATCGCCGCTTTCTTTC-CAAACTATGACAATAGGAGATATCCAAT-TCAGCCAGTTGGT
CAACTAACAAGGGAAGTTTATACGGAC-CCATTAATTAATTTTAATCCACAGTTA-CAGTCTGTAGC
TCAATTACCTACTTTTAACGTTATG-GAGAGCAGCGCAATTAGAAATCCTCATT-TATTTGATATAT
TGAATAATCTTACAATCTTTACGGATTG-GTTTAGTGTTGGACGCAATTTTTAT-TGGGGAGGACAT
CGAGTAATATCTAGCCTTATAGGAGGTG-GTAACATAACATCTCCTATATATGGAA-GAGAGGCGAA

CCAGGAGCCTCCAAGATCCTTTACTTT-
TAATGGACCGGTATTTAGGACTTTAT-
CAAATCCTACTT

TACGATTATTACAGCAACCTTGGC-
CAGCGCCACCATTTAATTTACGTGGTGT-
TGAAGGAGTAGAA

TTTTCTACACCTACAAATAGCTTTACG-
TATCGAGGAAGAGGTACGGTTGATTCTT-
TAACTGAATT

ACCGCCTGAGGATAATAGTGTGCCAC-
CTCGCGAAGGATATAGTCATCGTTTAT-
GTCATGCAACTT

TTGTTCAAAGATCTGGAACACCTTTTT-
TAACAACTGGTGTAGTATTTTCTTG-
GACGCATCGTAGT

GCAACTCTTACAAATACAATTGATCCA-
GAGAGAATTAATCAAATACCTTTAGT-
GAAAGGATTTAG

AGTTTGGGGGGGCACCTCTGTCATTA-
CAGGACCAGGATTTACAGGAGGG-
GATATCCTTCGAAGAA

ATACCTTTGGTGATTTTGTATCTCTA-
CAAGTCAATATTAATTCACCAATTAC-
CCAAAGATACCGT

TTAAGATTTCGTTACGCTTCCAGTAGG-
GATGCACGAGTTATAGTATTAACAG-
GAGCGGCATCCAC

AGGAGTGGGAGGCCAAGTTAGTG-
TAAATATGCCTCTTCAGAAAACTATG-
GAAATAGGGGAGAACT

TAACATCTAGAACATTTAGATATAC-
CGATTTTAGTAATCCTTTTTCATTTA-
GAGCTAATCCAGAT

ATAATTGGGATAAGTGAACAACCTC-
TATTTGGTGCAGGTTCTATTAGTAGCG-
GTGAACTTTATAT

AGATAAAATTGAAATTATTCTAGCAGAT-
GCAACATTTGAAGCAGAATCTGATTTA-
GAAAGAGCAC

AAAAGGCGGTGAATGCCCTGTTTACT-
TCTTCCAATCAAATCGGGTTAAAAAC-
CGATGTGACGGAT

TATCATATTGATCAAGTATCCAATT-
TAGTGGATTGTTTATCAGAT-
GAATTTTGTCTGGATGAAAA

GCGAGAATTGTCCGAGAAAGTCAAACAT-
GCGAAGCGACTCAGTGATGAGCGGAATT-
TACTTCAAG

ATCCAAACTTCAGAGGGATCAATAGA-
CAACCAGACCGTGGCTGGAGAGGAAGTA-
CAGATATTACC

ATCCAAGGAGGAGATGACGTATTCAAA-
GAGAATTACGTCACACTACCGGGTAC-
CGTTGATGAGTG

CTATCCAACGTATTTATATCAGAAAATA-
GATGAGTCGAAATTAAAAGCTTATAC-
CCGTTATGAAT

TAAGAGGGTATATCGAAGATAGTCAA-
GACTTAGAAATCTATTTGATCCGTTA-
CAATGCAAAACAC

GAAATAGTAAATGTGCCAGGCACGGGT-
TCCTTATGGCCGCTTTCAGCCCAAAGTC-
CAATCGGAAA

GTGTGGAGAACCGAATCGATGCGCGCCA-
CACCTTGAATGGAATCCTGATCTAGAT-
TGTTCCTGCA

GAGACGGGGAAAAATGTGCACATCATTC-
CCATCATTTCACCTTGGATATTGATGT-
TGGATGTACA

GACTTAAATGAGGACTTAGGTG-
TATGGGTGATATTCAAGATTAAGACG-
CAAGATGGCCATGCAAG

ACTAGGGAATCTAGAGTTTCTCGAA-
GAGAAACCATTATTAGGGGAAGCAC-
TAGCTCGTGTGAAAA

GAGCGGAGAAGAAGTGGAGAGACAAAC-
GAGAGAAACTGCAGTTGGAAACAAATAT-
TGTTTATAAA

GAGGCAAAAGAATCTGTAGATGCTT-
TATTTGTAAACTCTCAATATGATAGAT-
TACAAGTGGATAC

GAACATCGCAATGATTCATGCGGCA-
GATAAACGCGTTCATAGAATCCGG-
GAAGCGTATCTGCCAG

AGTTGTCTGTGATTCCAGGTGTCAAT-
GCGGCCATTTTCGAAGAATTAGAGG-
GACGTATTTTTACA

GCGTATTCCTTATATGATGCGAGAAAT-
GTCATTAAAAATGGCGATTTCAATAATG-
GCTTATTATG

CTGGAACGTGAAAGGTCATGTAGATGTA-
GAAGAGCAAAACAACCACCGTTCGGTC-
CTTGTTATCC

CAGAATGGGAGGCAGAAGTGTCACAA-
GAGGTTCGTGTCTGTCCAGGTCGTGGC-
TATATCCTTCGT

GTCACAGCATATAAAGAGGGATATG-
GAGAGGGCTGCGTAACGATCCAT-
GAGATCGAAGACAATAC

AGACGAACTGAAATTCAGCAACTGTGTA-
GAAGAGGAAGTATATCCAAACAACACAG-
TAACGTGTA

ATAATTATACTGGGACTCAAGAA-
GAATATGAGGGTACGTACACTTCTCG-
TAATCAAGGATATGAC

GAAGCCTATGGTAATAACCCTTCCGTAC-
CAGCTGATTACGCTTCAGTCTATGAA-
GAAAAATCGTA

TACAGATGGACGAAGAGAGAATCCTTGT-
GAATCTAACAGAGGCTATGGGGATTACA-
CACCACTAC

CGGCTGGTTATGTAACAAAGGATTTA-
GAGTACTTCCCAGAGACCGATAAGG-
TATGGATTGAGATC

GGAGAAACAGAAGGAACATTCATCGTG-
GATAGCGTGGAATTACTCCTTATGGAGGAA

5.15 Example 15

Isolation of Transgenic Plants Resistant to Cry* Variants

5.15.1 Plant Gene Construction

The expression of a plant gene which exists in double-stranded DNA form involves transcription of messenger RNA (mRNA) from one strand of the DNA by RNA polymerase enzyme, and the subsequent processing of the mRNA primary transcript inside the nucleus. This processing involves a 3' non-translated region which adds polyadenylate nucleotides to the 3' end of the RNA. Transcription of DNA into mRNA is regulated by a region of DNA usually referred to as the "promoter". The promoter region contains a sequence of bases that signals RNA polymerase to associate with the DNA and to initiate the transcription of mRNA using one of the DNA strands as a template to make a corresponding strand of RNA.

A number of promoters which are active in plant cells have been described in the literature. Such promoters may be obtained from plants or plant viruses and include, but are not limited to, the nopaline synthase (NOS) and octopine synthase (OCS) promoters (which are carried on tumor-inducing plasmids of *Agrobacterium tumefaciens*), the cauliflower mosaic virus (CaMV) 19S and 35S promoters, the light-inducible promoter from the small subunit of ribulose 1,5-bisphosphate carboxylase (ssRUBISCO, a very abundant plant polypeptide), and the Figwort Mosaic Virus (FMV) 35S promoter. All of these promoters have been used to create various types of DNA constructs which have been expressed in plants (see e.g., U.S. Pat. No. 5,463,175, specifically incorporated herein by reference).

The particular promoter selected should be capable of causing sufficient expression of the enzyme coding sequence to result in the production of an effective amount of protein. One set of preferred promoters are constitutive promoters such as the CaMV35S or FMV35S promoters that yield high levels of expression in most plant organs (U.S. Pat. No. 5,378,619, specifically incorporated herein by reference). Another set of preferred promoters are root enhanced or specific promoters such as the CaMV derived 4 as-1 promoter or the wheat POX1 promoter (U.S. Pat. No. 5,023,179, specifically incorporated herein by reference; Hertig et al., 1991). The root enhanced or specific promoters would be particularly preferred for the control of corn rootworm (Diabroticus spp.) in transgenic corn plants.

The promoters used in the DNA constructs (i.e. chimeric plant genes) of the present invention may be modified, if desired, to affect their control characteristics. For example, the CaMV35S promoter may be ligated to the portion of the ssRUBISCO gene that represses the expression of ssRUBISCO in the absence of light, to create a promoter which is active in leaves but not in roots. The resulting chimeric promoter may be used as described herein. For purposes of this description, the phrase "CaMV35S" promoter thus includes variations of CaMV35S promoter, e.g., promoters derived by means of ligation with operator regions, random or controlled mutagenesis, etc. Furthermore, the promoters may be altered to contain multiple "enhancer sequences" to assist in elevating gene expression.

The RNA produced by a DNA construct of the present invention also contains a 5' non-translated leader sequence. This sequence can be derived from the promoter selected to express the gene, and can be specifically modified so as to increase translation of the mRNA. The 5' non-translated regions can also be obtained from viral RNA's, from suitable eucaryotic genes, or from a synthetic gene sequence. The present invention is not limited to constructs wherein the non-translated region is derived from the 5' nontranslated sequence that accompanies the promoter sequence.

For optimized expression in monocotyledenous plants such as maize, an intron should also be included in the DNA expression construct. This intron would typically be placed near the 5' end of the mRNA in untranslated sequence. This intron could be obtained from, but not limited to, a set of introns consisting of the maize hsp70 intron (U.S. Pat. No. 5,424,412; specifically incorporated herein by reference) or the rice Act1 intron (McElroy et al., 1990). As shown below, the maize hsp70 intron is useful in the present invention.

As noted above, the 3' non-translated region of the chimeric plant genes of the present invention contains a polyadenylation signal which functions in plants to cause the addition of adenylate nucleotides to the 3' end of the RNA. Examples of preferred 3' regions are (1) the 3' transcribed, non-translated regions containing the polyadenylate signal of Agrobacterium tumor-inducing (Ti) plasmid genes, such as the nopaline synthase (NOS) gene and (2) plant genes such as the pea ssRUBISCO E9 gene (Fischhoff etal., 1987).

5.15.2 Plant Transformation and Expression

A chimeric transgene containing a structural coding sequence of the present invention can be inserted into the genome of a plant by any suitable method such as those detailed herein. Suitable plant transformation vectors include those derived from a Ti plasmid of *Agrobacterium tumefaciens*, as well as those disclosed, e.g., by Herrera-Estrella (1983), Bevan (1983), Klee (1985) and Eur. Pat. Appl. Publ. No. EP0120516. In addition to plant transformation vectors derived from the Ti or root-inducing (Ri) plasmids of Agrobacterium, alternative methods can be used to insert the DNA constructs of this invention into plant cells. Such methods may involve, for example, the use of liposomes, electroporation, chemicals that increase free DNA uptake, free DNA delivery via microprojectile bombardment, and transformation using viruses or pollen (Fromm et al., 1986; Armstrong et al., 1990; Fromm et al., 1990).

5.15.3 Construction of Plant Expression Vectors for Cry* Transgenes

For efficient expression of the cry* variants disclosed herein in transgenic plants, the gene encoding the variants must have a suitable sequence composition (Diehn et al., 1996).

To place a cry* gene in a vector suitable for expression in monocotyledonous plants (i.e. under control of the enhanced Cauliflower Mosaic Virus 35S promoter and link to the hsp70 intron followed by a nopaline synthase polyadenylation site as in U.S. Pat. No. 5,424,412, specifically incorporated herein by reference), the vector is digested with appropriate enzymes such as NcoI and EcoRI. The larger vector band of approximately 4.6 kb is then electrophoresed, purified, and ligated with T4 DNA ligase to the appropriate restriction fragment containing the plantized cry* gene. The ligation mix is then transformed into *E. coli*, carbenicillin resistant colonies recovered and plasmid DNA recovered by DNA miniprep procedures. The DNA may then be subjected to restriction endonuclease analysis with enzymes such as NcoI and EcoRI (together), NotI, and PstI to identify clones containing the cry* gene coding sequence fused to the hsp70 intron under control of the enhanced CaMV35S promoter).

To place the gene in a vector suitable for recovery of stably transformed and insect resistant plants, the restriction fragment from pMON33708 containing the lysine oxidase coding sequence fused to the hsp70 intron under control of the enhanced CaMV35S promoter may be isolated by gel electrophoresis and purification. This fragment can then be ligated with a vector such as pMON30460 treated with NotI and calf intestinal alkaline phosphatase (pMON30460 contains the neomycin phosphotransferase coding sequence under control of the CaMV35S promoter). Kanamycin resistant colonies may then be obtained by transformation of this ligation mix into *E. coli* and colonies containing the resulting plasmid can be identified by restriction endonuclease digestion of plasmid miniprep DNAs. Restriction enzymes such as NotI, EcoRV, HindIII, NcoI, EcoRI, and BglII can be used to identify the appropriate clones containing the restriction fragment properly inserted in the corresponding site of pMON30460, in the orientation such that both genes are in tandem (ie. the 3' end of the cry* gene expression cassette is linked to the 5' end of the nptII expression cassette). Expression of the Cry* protein by the resulting vector is then confirmed in plant protoplasts by electroporation of the vector into protoplasts followed by protein blot and ELISA analysis. This vector can be introduced into the genomic DNA of plant embryos such as maize by particle gun bombardment followed by paromomycin selection to obtain corn plants expressing the cry* gene essentially as described in U.S. Pat. No. 5,424,412, specifically incorporated herein by reference. In this example, the vector was introduced via cobombardment with a hygromycin resistance conferring plasmid into immature embryo scutella (IES) of maize, followed by hygromycin selection, and regeneration. Transgenic plant lines expressing the Cry* protein are then identified by ELISA analysis. Progeny seed from these events are then subsequently tested for protection from susceptible insect feeding.

6.0 REFERENCES

The following references, to the extent that they provide exemplary procedural or other details supplementary to those set forth herein, are specifically incorporated herein by reference.

U.S. Pat. No. 4,237,224, issued Dec. 2, 1980.
U.S. Pat. No. 4,332,898, issued Jun. 1, 1982.
U.S. Pat. No. 4,342,832, issued Aug. 3, 1982.
U.S. Pat. No. 4,356,270, issued Oct. 26, 1982.
U.S. Pat. No. 4,362,817, issued Dec. 7, 1982.
U.S. Pat. No. 4,371,625, issued Feb. 1, 1983.
U.S. Pat. No. 4,448,885, issued May 15, 1984.
U.S. Pat. No. 4,467,036, issued Aug. 21, 1984.
U.S. Pat. No. 4,554,101, issued Nov. 19, 1985.
U.S. Pat. No. 4,683,195, issued Jul. 28, 1987.
U.S. Pat. No. 4,683,202, issued Jul. 28, 1987.
U.S. Pat. No. 4,757,011, issued Jul. 12, 1988.
U.S. Pat. No. 4,766,203, issued Aug. 23, 1988.
U.S. Pat. No. 4,769,061, issued Sep. 6, 1988.
U.S. Pat. No. 4,797,279, issued Jan. 10, 1989.
U.S. Pat. No. 4,800,159, issued Jan. 24, 1989.
U.S. Pat. No. 4,883,750, issued Nov. 28, 1989.
U.S. Pat. No. 4,910,016, issued Mar. 20, 1990.
U.S. Pat. No. 4,940,835, issued Feb. 23, 1990.
U.S. Pat. No. 4,965,188, issued Oct. 23, 1990.
U.S. Pat. No. 4,971,908, issued Nov. 20, 1990.
U.S. Pat. No. 4,987,071, issued Jan. 22, 1991.
U.S. Pat. No. 5,023,179, issued Jun. 11, 1991.
U.S. Pat. No. 5,024,837, issued Jun. 18, 1991.
U.S. Pat. No. 5,126,133, issued Jun. 30, 1992.
U.S. Pat. No. 5,176,995, issued Oct. 15, 1991.
U.S. Pat. No. 5,322,687, issued Jun. 21, 1994.
U.S. Pat. No. 5,334,711, issued Aug. 2, 1994.
U.S. Pat. No. 5,380,831, issued Jan. 10, 1995.
U.S. Pat. No. 5,424,412, issued Jun. 13, 1995.
U.S. Pat. No. 5,441,884, issued Aug. 15, 1995.
U.S. Pat. No. 5,463,175, issued Oct. 31, 1995.
U.S. Pat. No. 5,500,365, issued Mar. 19, 1996.
Intl. Pat. Appl. Publ. No. PCT/US87/00880.
Intl. Pat. Appl. Publ. No. PCT/US89/01025.
Intl. Pat. Appl. Publ. No. WO 88/09812.
Intl. Pat. Appl. Publ. No. WO 88/10315.
Intl. Pat. Appl. Publ. No. WO 89/06700.
Intl. Pat. Appl. Publ. No. WO 91/03162.
Intl. Pat. Appl. Publ. No. WO 92/07065.
Intl. Pat. Appl. Publ. No. WO 92/110298.4.
Intl. Pat. Appl. Publ. No. WO 93/07278.
Intl. Pat. Appl. Publ. No. WO 93/15187.
Intl. Pat. Appl. Publ. No. WO 93/23569.
Intl. Pat. Appl. Publ. No. WO 94/02595.
Intl. Pat. Appl. Publ. No. WO 94/13688.
Eur. Pat. Appl. Publ. No. EP 0120516.
Eur. Pat. Appl. Publ. No. 295156A1.
Eur. Pat. Appl. Publ. No. 320,308.
Eur. Pat. Appl. Publ. No. 329,822.
Great Britain Pat. Appl. No. 2202328.
Abdullah et al., *Biotechnology*, 4:1087, 1986.
Adami and Nevins, In: *RNA Processing*, Cold Spring Harbor Laboratory, p. 26, 1988.
Adang, et al., In: *Molecular Strategies for Crop Protection*, Alan R. Liss, Inc., pp. 345353, 1987.
Almond and Dean, *Biochemistry*, 32:1040–1046, 1993.
Angsuthanasamnbat et al., *FEMS Microbiol. Lett.*, 111:255–262, 1993.
Aronson, Wu, and Zhang, "Mutagenesis of specificity and toxicity regions of a *Bacillus thuringiensis* protoxin gene", *J: Bacteriol*, 177:4059–4065, 1995.
Bagdasarian et al., *Gene*, 16:237, 1981.
Barton, etal, *Plant Physiol.*, 85:1103–1109, 1987.
Baum et al, *Appl. Environ. Microbiol.*, 56:3420–3428, 1990.
Baum, *J Bacteriol.*, 177:4036–4042, 1995.
Benbrook et al., In: *Proceedings Bio Expo* 1986, Butterworth, Stoneham, Mass., pp. 27–54, 1986.
Bevan, M. et al., *Nature*, 304:184, 1983.
Bolivar et al., *Gene*, 2:95, 1977.
Brady and Wold, In: *RNA Processing*, Cold Spring Harbor Laboratory, p. 224, 1988.
Brown, *Nuc. Acids Res.*, 14(24):9549, 1986.
Brussock and Currier, "Use of sodium dodecyl sulfate-polyacrylamide gel electrophoresis to quantify *Bacillus thuringiensis* δ-endotoxins," In: Analytical Chemistry of *Bacillus thuringiensis*, eds., Hickle and Fitch, The American Chemical Society, pp. 78–87, 1990.
Bytebier et al., *Proc. Natl. Acad. Sci. USA*, 84:5345, 1987.
Callis and Walbot, *Genes and Develop.*, 1:1183–1200,1987.
Capecchi, "High efficiency transformation by direct microinjection of DNA into cultured mammalian cells," *Cell*, 22(2):479–488, 1980.
Caramori, Albertini, Galizzi, In vivo generation of hybrids between two *Bacillus thuringiensis* insect-toxin-encoding genes, *Gene*, 98:37–44, 1991.
Cashmore et al., In: *Gen. Eng. of Plants, Plenum Press*, New York, 29–38, 1983.
Chambers et al., *Appl Environ. Microbiol*, 173:3966–3976, 1991.
Chau et al., *Science*, 244:174–181, 1989.
Chen et al., *Nucl. Acids Res.*, 20:4581–9, 1992.
Chen, Curtiss, Alcantara, Dean., "Mutations in domain I of *Bacillus thuringiensis* δ-endotoxin CryIAb reduce the irreversible binding of toxin to *Manduca sexta* brush border membrane vesicles," *J Biol Chem.*, 270:6412–6419, 1995.
Chen, Lee, Dean, "Site-directed mutations in a highly conserved region of *Bacillus thuringiensis* δ-endotoxin affect inhibition of short circuit current across *Bombyx mori* midguts," *Proc. Natl. Acad. Sci. USA*, 90:9041–9045, 1993.
Chowrira and Burke, *Nucl. Acids Res.*, 20:2835–2840, 1992
Clapp, "Somatic gene therapy into hematopoietic cells. Current status and future implications," *Clin. Perinatol.*, 20(1):155–168, 1993.
Conway and Wickens, In: *RNA Processing*, Cold Spring Harbor Laboratory, p. 40, 1988.
Comellssenetal., *EMBOJ.*, 5(1):37–40, 1986.
Cristou et al, *Plant Physiol*, 87:671–674, 1988.
Curiel, Agarwal, Wagner, Cotten, "Adenovirus enhancement of transferrin-polylysine-mediated gene delivery," *Proc. Natl. Acad. Sci. USA*, 88(19):8850–8854, 1991.
Curiel, Wagner, Cotten, Birmstiel, Agarwal, Li, Loechel, Hu, "High-efficiency gene transfer mediated by adenovirus coupled to DNA-polylysine complexes," *Hum. Gen. Ther.*, 3(2):147–154, 1992.
Daar et al., In: *RNA Processing*, Cold Spring Harbor Laboratory, p. 45, 1988.
de Maagd, Kwa, van der Klei, Yamamoto, Schipper, Vlak, Stiekema, Bosch, "Domain III substitution in *Bacillus thuringiensis* delta-endotoxin CryIA(b) results in superior toxicity for *Spodoptera exigua* and altered membrane protein recognition," *Appl. Environ. Microbiol.*, 62:1537–1543, 1996.
Dean et al., *Nuc. Acids Res.*, 14(5):2229, 1986.
Dedrick et al., *J Biol Chem.*, 262(19):9098–1106, 1987.
Dhir et al., *Plant Cell Reports*, 10:97, 1991.
Diehn, De Rocher, Green, "Problems that can limit the expression of foreign genes in plants: Lessons to be learned from B.t. toxin genes," In: *Genetic Engineering*, ed. Setlow, Plenum Press, N.Y., Vol. 18, 1996.
Donovan et al., *J Biol. Chem.*, 263(1):561–567, 1988.
Doyle et al, *J Biol. Chem.*, 261(20): 9228–9236, 1986.
Dropulic et al, *J Virol.*, 66:1432–41, 1992.
Earp and Ellar, *Nucl Acids Res.*, 15:3619, 1987.
Eglitis and Anderso, "Retroviral vectors for introduction of genes into mammalian cells," *Biotechniques* 6(7) :608–614, 1988.
Eglitis, Kantoff, Kohn, Karson, Moen, Lothrop, Blaese, Anderson, "Retroviral-mediated gene transfer into hemopoietic cells," *Adv. Exp. Med. Biol.*, 241:19–27, 1988a.
Elionor et al, *Mol. Gen. Genet.*, 218:78–86, 1989.
Elroy-Stein and Moss, *Proc. Natl. Acad. Sci. USA*, 87:6743–7, 1990.
English and Slatin, *Insect Biochem. Mol. Biol.*, 22:1–7, 1992.
Fischhoffet al, *Bio/Technology*, 5:807, 1987.
Fraley et al, *Biotechnology*, 3:629, 1985.
Fraley et al, *Proc. Natl. Acad. Sci. USA*, 80:4803, 1983.
Fraley et al, *Bio/Technology*, 3:629–635, 1985.
Frohman, In: *PCR Protocols, A Guide to Methods and Applications*, Academic Press, XVIII Ed., 1990.
Fromm, Taylor, Walbot, *Nature*, 319:791–793, 1986.
Fromm, Taylor, Walbot, "Expression of genes transferred into monocot and dicot plant cells by electroporation," *Proc. Natl. Acad. Sci USA*, 82(17):5824–5828, 1985.
Fujimura et al, *Plant Tissue Culture Letters*, 2:74, 1985.
Fuitterer and Hohn, "Translation in plants—rules and exceptions," *Plant Mol. Biol.*, 32:159–189, 1996.
Fynan, Webster, Fuller, Haynes, Santoro, Robinson, "DNA vaccines: protective immunizations by parenteral, mucosal, and gene gun inoculations," *Proc. Natl. Acad. Sci USA* 90(24):11478–11482, 1993.
Gallego and Nadal-Ginard, In: *RNA Processing*, Cold Spring Harbor Laboratory, p. 61, 1988.
Gao and Huang, *Nucl. Acids Res.*, 21:2867–72, 1993.
Gazit and Shai, "The assembly and organization of the α5 and α7 helices from the poreforming domain of *Bacillus thuringiensis* δ-endotoxin," *J Biol. Chem.*, 270:2571–2578, 1995.
Gazit and Shai, "Structural and functional characterization of the α5 segment of *Bacillus thuringiensis* δ-endotoxin," *Biochemistry*, 32:3429–3436, 1993.
Ge, Rivers, Milne, Dean, "Functional domains of *Bacillus thuringiensis* insecticidal crystal proteins: refinement of *Heliothis virescens* and *Trichoplusia ni* specificity domains on CryIA(c)," *J Biol. Chem.*, 266:17954–17958, 1991.
Genovese and Milcarek, In: *RNA Processing*, Cold Spring Harbor Laboratory, p. 62, 1988.
Gil and Proudfoot, *Nature*, 312:473, 1984.
Gonzalez Jr. et al., *Proc. Natl. Acad. Sci USA*, 79:6951–6955, 1982.
Goodall et al., In: *RNA Processing*, Cold Spring Harbor Laboratory, p. 63, 1988.
Graham and van der Eb, "Transformation of rat cells by DNA of human adenovirus 5," *Virology* 54(2):536–539, 1973.
Grochulski, Masson, Borisova, Pusztai-Carey, Schwartz, Brousseau, Cygler, "*Bacillus thuringiensis* CryIA(a) insecticidal toxin: crystal structure and channel formation," *J Mol. Biol.*, 254:447–464, 1995.
Gross et al., In: *RNA Processing*, Cold Spring Harbor Laboratory, p. 128, 1988.
Hampson and Rottmnan, In: *RNA Processing*, Cold Spring Harbor Laboratory, p. 68, 1988.
Hanley and Schuler, *Nucl. Acids Res.*, 16(14):7159, 1988.
Harlow and Lane, In: *Antibodies: A Laboratory Manual*, Cold Spring Harbor Laboratory, Cold Spring Harbor, N.Y., 1988.
Helfinan and Ricci, In: *RNA Processing*, Cold Spring Harbor Laboratory, p. 219, 1988.
Herrera-Estrella et al., *Nature*, 303:209, 1983.
Hertig et al., "Sequence and tissue-specific expression of a putative peroxidase gene from wheat (*Triticum aestivum L.*)," *Plant Mol. Biol.*, 16(1):171–174, 1991.
Hess, *Intern Rev. Cytol.*, 107:367, 1987.
Hoekema et al., *Molecular and Cellular Biology*, 7:2914–2924, 1987.
Höfte and Whiteley, *Microbiol. Rev.*, 53:242–255, 1989.
Holland et al., *Biochemistry*, 17:4900, 1978.
Honee et al., *Nuc. Acids Res.*, 16(13), 1988.
Honee, van der Salm, Visser, *Nuc. Acids Res.*, 16:6240, 1988.
Horsch et al., *Science*, 227:1229–1231, 1985.
Horton et al., *Gene*, 77:61–68, 1989.
Humason, In: *Animal Tissue Techniques*, W. H. Freeman and Co., 1967. lannacone, Grieco, Cellini, "Specific sequence modifications of a cry3B endotoxin gene results in high levels of expression and insect resistance," *Plant, Mol. Biol.*, 34:485–496, 1997.
Jaeger et al., *Proc. Natl. Acad. Sci. USA*, 86: 7706–7710, 1989.
Jarret et al., *In Vitro*, 17:825, 1981.
Jarret et al., *Physiol. Plant*, 49:177, 1980.
Johnston and Tang, "Gene gun transfection of animal cells and genetic immunization," *Methods Cell. Biol.*, 43(A):353–365, 1994.
Jorgensen et al., *Mol. Gen. Genet.*, 207:471, 1987.
Kaiser et al., "Amphiphilic secondary structure: design of peptide hormones," *Science*, 223(4633):249–255, 1984.
Kashani-Saber et al, *Antisense Res. Dev.*, 2:3–15, 1992.
Kay et al., *Science*, 236:1299–1302, 1987.
Keller et al, *EMBO J.*, 8:1309–14, 1989.
Kessler et al., In: *RNA Processing*, Cold Spring Harbor Laboratory, p. 85, 1988.
Klee et al., *Bio/Technology*, 3:637, 1985.
Klee et al., *Bio/Technology*, 3:637–642, 1985.
Klein et al., *Nature*, 327:70, 1987.
Klein et al., *Proc. Natl. Acad. Sci. USA*, 85:8502–8505, 1988.
Kozak, *Nature*, 308:241–246, 1984.
Krebbers et al., *Plant Molecular Biology*, 11:745–759, 1988.
Krieg et al., *Anzeiger fur Schadlingskunde Pflanzenschutz Umweltschutz*, 57:145–150, 1984.
Krieg et al, *Z. ang Ent.*, 96:500–508, 1983.
Kuby, In: *Immunology 2nd Edition*, W. H. Freeman & Company, N.Y., 1994.

Kunkel et al., *Methods Enzymol.*, 154:367–382, 1987.
Kunkel, *Proc. Natl. Acad. Sci. USA*, 82:488–492, 1985.
Kwak, Lu, Dean, "Exploration of receptor binding of *Bacillus thuringiensis* toxins," *Mem. Inst. Oswaldo*, 90:75–79, 1995.
Kwoh et al., *Proc. Natl. Acad. Sci, USA*, 86(4):1173–1177, 1989.
Kyte and Doolittle, *J Mol. Biol.*, 157:105–132, 1982.
Lambert, Buysse, Decock, Jansens, Piens, Saey, Seurinck, Van Audenhove, Van Rie, Van Vliet, Peferoen, "A *Bacillus thuringiensis* insecticidal crystal protein with a high activity against members of the family Noctuidae," *Appl. Environ. Microbiol.*, 62:80–86, 1996.
Langridge et al, *Proc. Natl. Acad Sci. USA*, 86:3219–3223, 1989.
Lee, Young, Dean, "Domain III exchanges of *Bacillus thuringiensis* CryIA toxins affect binding to different gypsy moth midgut receptors," *Biochem. Biophys. Res. Commun.*, 216:306–312,1995.
Lee, Milne, Ge, Dean, "Location of a *Bombyx mori* receptor binding region on a *Bacillus thuringiensis* δ-endotoxin," *J Biol. Chem.*, 267:3115–3121, 1992.
L'Huillier et al., *EMBO J.*, 11:4411–8, 1992.
Li et al., *Nature*, 353:815–821, 1991.
Lieber et al., *Methods Enzymol.*, 217:47–66, 1993.
Lindstrom et al., *Developmental Genetics*, 11:160, 1990.
Lisziewicz et al., *Proc. Natl. Acad. Sci. U.S.A.*, 90:8000–4, 1993.
Lorz et al., *Mol. Gen. Genet.*, 199:178, 1985.
Lu, Rajamnohan, Dean, "Identification of amino acid residues of *Bacillus thuringiensis* δ-endotoxin CryIAa associated with membrane binding and toxicity to *Bombyx mori.,*" *J. Bacteriol.*, 176:5554–5559, 1994.
Lu, Xiao, Clapp, Li, Broxmeyer, "High efficiency retroviral mediated gene transduction into single isolated immature and replatable CD34(3+) hematopoietic stern/progenitor cells from human umbilical cord blood," *J Exp. Med.*, 178(6):2089–2096, 1993.
Macaluso and Mettus, *J Bacteriol.*, 173:1353–1356, 1991.
Maddock et al., *Third International Congress of plant Molecular Biology*, Abstract 372, 1991.
Maloy et al., In: *Microbial Genetics*, 2nd Edition, Jones and Bartlett Publishers, Boston, Mass., 1994.
Maloy, In: *Experimental Techniques in Bacterial Genetics*, Jones and Bartlett Publishers, Boston, Mass., 1990.
Maniatis et al., In: *Molecular Cloning: a Laboratory Manual*, Cold Spring Harbor Laboratory, Cold Spring Harbor, N.Y., 1982.
Marcotte et al., *Nature*, 335:454, 1988.
Marrone et al., *J. Econ. Entomol.*, 78–290–293, 1985.
Marzluff and Pandey, In: *RNA Processing*, Cold Spring Harbor Laboratory, p. 244, 19 88.
McCabe et al., *Biotechnology*, 6:923, 1988.
McCormick et al., *Plant Cell Reports*, 5:81–84, 1986.
McDevitt et al., *Cell*, 37:993–999, 1984.
Mettus and Macaluso, *Appl. Environ. Microbiol.*, 56:1128–1134, 1990.
Michael, *Biotechniques*, 16:410–412, 1994.
Murashige and Skoog, *Physiol. Plant*, 15:473, 1962.
Murray, Lotzer, Eberle, "Codon usage in plant genes," *Nucl. Acids Res.*, 17:(2)477–498, 1989.
Neuhaus et al., *Theor. Appl. Genet.*, 75:30, 1987.
Odell et al., *Nature*, 313:810, 1985.
Odell et al., *Nature*, 313:810, 1985.
Ohara et al., *Proc. Natl. Acad. Sci. USA*, 86(15):5673–5677, 1989.
Ohkawa et al., *Nucl. Acids Symp. Ser.*, 27:15–6, 1992.
Ojwang et al., *Proc. Natl. Acad. Sci. USA*, 89:10802–6, 1992.
Olson et al., *J. Bacteriol.*, 150:6069, 1982.
Omirulleh et al., *Plant Molecular Biology*, 21:415–428, 1993.
Pandey and Marzluff, In: *RNA Processing*, Cold Spring Harbor Laboratory, p. 133, 1987.
Pena et al., *Nature*, 325:274, 1987.
Perrault et al, *Nature*, 344:565, 1990.
Pieken et al., *Science*, 253:314, 1991.
Poszkowski et al., *EMBO J.*, 3:2719, 1989.
Potrykus et al, *Mol. Gen. Genet.*, 199:183, 1985.
Poulsen et al., *Mol. Gen. Genet.*, 205:193–200, 1986.
Prokop and Bajpai, "Recombinant DNA Technology I," *Ann. N.Y. Acad. Sci.*, Vol. 646, 1991.
Proudfoot et al., In: *RNA Processing*, Cold Spring Harbor Laboratory, p. 17, 1987.
Rajamohan, Alcantara, Lee, Chen, Curtiss, Dean, "Single amino acid changes in domain II of *Bacillus thuringiensis* CryIAb δ-endotoxin affect irreversible binding to *Manduca sexta* midgut membrane vesicles," *J. Bacteriol.*, 177:2276–2282, 1995.
Rajatnohan, Cotrill, Gould, Dean, "Role of domain II, loop 2 residues of *Bacillus thuringiensis* CryIAb δ-endotoxin in reversible and irreversible binding to *Manduca sexta* and *Heliothis virescens,* " *J Biol. Chem.*, 271:2390–2397, 1996.
Reines et al., *J Mol. Biol.*, 196:299–312, 1987.
Rogers et al., In: *Methods For Plant Molecular Biology*, A. Weissbach and H. Weissbach, eds., Academic Press Inc., San Diego, Calif., 1988.
Rogers et al., *Methods Enzymol.*, 153:253–277, 1987.
Rouwendal, Mendes, Wolbert, De Boer, "Enhanced expression in tobaccoo of the gene encoding green fluorescent protein by modification of its codon usage," *Plant Mol. Biol.*, 33:989–999, 1997.
Sadofsky and Alwine, *Molecular and Cellular Biology*, 4(8):1460–1468, 1984.
Sambrook et al., In: *Molecular Cloning: A Laboratory Manual*, Cold Spring Harbor Laboratory, Cold Spring Harbor, N.Y., 1989.
Sanchis, Lereclus, Menou, Chaufaux, Lecadet, *Mol. Microbiol.*, 2:393–404, 1988.
Sanchis, Lereclus, Menou, Chaufaux, Guo, Lecadet, *Mol. Microbiol.*, 3:229–238, 1989.
Sanders et al., *Nucl. Acids Res.*, 15(4):1543, 1987.
Sarver et al., "Ribozymes as potential anti-HIV-1 therapeutic agents," *Science*, 247:1222–1225, 1990.
Scanlon et al., *Proc. NatlAcad. Sci. USA*, 88:10591–5, 1991.
Scaringe et al., *Nucl Acids Res.*, 18:5433–5441, 1990.
Schnepf and Whitely, *Proc. Natl. Acad. Sci. USA*, 78:2893–2897, 1981.
Schnepfet al., *J. Biol. Chem.*, 260:6264–6272, 1985.
Schuler et al., *Nucl Acids Res.*, 10(24):8225–8244, 1982.
Segal, In: *Biochemical Calculations*, 2nd Edition, John Wiley & Sons, New York, 1976.
Shaw and Kamen, *Cell*, 46:659–667, 1986.
Shaw and Kamen, In: *RNA Processing*, Cold Spring Harbor Laboratory, p. 220, 1987.
Simpson, *Science*, 233:34, 1986.
Smedley and Ellar, "Mutagenesis of three surface-exposed loops of a *Bacillus thuringiensis* insecticidal toxin reveals residues important for toxicity, receptor recognition and possibly membrane insertion," *Microbiology*, 142:1617–1624, 1996.
Smith and Ellar, "Mutagenesis of two surface-exposed loops of the *Bacillus thuringiensis* Cry1C δ-endotoxin affects insecticidal specificity," *Biochem. J.*, 302:611–616, 1994.

Smith, Merrick, Bone, Ellar, *Appl. Environ. Microbiol.*, 62:680–684, 1996.

Spielmann et al., *Mol. Gen. Genet.*, 205:34, 1986.

Stemmer, "DNA shuffling by random fragmentation and reassembly: in vitro recombination for molecular evolution," *Proc. Natl. Acad. Sci. U.S.A.*, 91(22):10747–10751, 1994.

Taira et al., *Nucl. Acids Res.*, 19:5125–30, 1991.

Tomic et al., *Nucl. Acids Res.*, 12:1656, 1990.

Toriyama et al., *Theor. Appl. Genet.*, 73:16, 1986.

Trolinder and Goodin, *Plant Cell Reports*, 6:231–234, 1987.

Tsurushita and Kom, In: *RNA Processing*, Cold Spring Harbor Laboratory, p. 215, 1987.

Turner et al., *Nucleic Acids Reg.*, 14:8, 3325, 1986.

Uchimiya et al., *Mol Gen. Genet.*, 204:204, 1986.

Upender et al., *Biotechniques*, 18:29–31, 1995.

Usman and Cedergren, *Trends in Biochem. Sci.*, 17:334, 1992.

Vaeck et al., *Nature*, 328:33, 1987.

Van Tunen et al., *EMBO J.*, 7:1257, 1988.

Vasil et al., "Herbicide-resistant fertile transgenic wheat plants obtained by microprojectile bombardment of regenerable embryogenic callus," *Biotechnology*, 10:667–674, 1992.

Vasil, *Biotechnology*, 6:397, 1988.

Velten and Schell, *Nucl. Acids Res.*, 13:6981–6998, 1985.

Velten et al., *EMBO. J.*, 3:2723–2730, 1984.

Ventura et al., *Nucl. Acids Res.*, 21:3249–55, 1993.

Visser et al., *Mol. Gen. Genet.*, 212:219–224, 1988.

Vodkin et al., *Cell*, 34:1023, 1983.

Vogel etal., *J. Cell Biochem., Suppl.*, 13D:312, 1989.

Von Tersch et al., *Appl. Environ. Microbiol.*, 60:3711–3717, 1994.

Wagner, Zatloukal, Cotten, Kirlappos, Mechtler, Curiel, Birnstiel, "Coupling of adenovirus to transferrin-polylysine/DNA complexes greatly enhances receptormediated gene delivery and expression of transfected genes," *Proc. Natl. Acad. Sci. USA*, 89(13):6099–6103, 1992.

Walker et al., *Proc. Natl. Acad. Sci. USA*, 89(1):392–396, 1992.

Walters et al., *Biochem. Biophys. Res. Commun.*, 196:921–926, 1993.

Watson et al., In: *Molecular Biology of the Gene*, 4th Ed., W. A. Benjamin, Inc., Menlo Park, Calif., 1987.

Webb et al., *Plant Sci. Letters*, 30:1, 1983.

Weerasinghe et al., *J. Virol.*, 65:5531–4, 1991.

Weissbach and Weissbach, In: *Methods for Plant Molecular Biology*, Academic Press, Inc., San Diego, Calif., 1988.

Wenzler et al., *Plant Mol. Biol.*, 12:41–50, 1989.

Wickens and Stephenson, *Science*, 226:1045, 1984.

Wickens et al., In: *RNA Processing*, Cold Spring Harbor Laboratory, p. 9, 1987.

Wiebauer et al., *Molecular and Cellular Biology*, 8(5):2042–2051, 1988.

Wolfersberger et al., *Appl. Environ. Microbiol.*, 62:279–282, 1996.

Wong and Neumann, "Electric field mediated gene transfer," *Biochim. Biophys. Res. Commun.* 107(2):584–587, 1982.

Wu and Aronson, "Localized mutagenesis defines regions of the *Bacillus thuringiensis* δ-endotoxin involved in toxicity and specificity," *J. Biol. Chem.*, 267:2311–2317, 1992.

Wu and Dean, "Functional significance of loops in the receptor binding domain of *Bacillus thuringiensis* CryIIIA δ-endotoxin.," *J. Mol. Biol.*, 255:628–640, 1996.

Yamada et al., *Plant Cell Rep.*, 4:85, 1986.

Yamamoto and Iizuka, *Arch. Biochem. Biophys.*, 227(1):233–241, 1983.

Yang et al., *Proc. Natl. Acad. Sci. USA*, 87:4144–48, 1990.

Yu et al., *Proc. Natl. Acad. Sci. USA*, 90:6340–4, 1993.

Zatloukal, Wagner, Cotten, Phillips, Plank, Steinlein, Curiel, Birnstiel, "Transferrinfection: a highly efficient way to express gene constructs in eukaryotic cells," *Ann. N.Y. Acad. Sci.*, 660:136–153, 1992.

Zhou et al., *Methods Enzymol.*, 101:433, 1983.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A composition comprising an isolated polypeptide that comprises the amino acid sequence of SEQ ID NO:59 or SEQ ID NO:61.

2. The composition of claim 1, wherein said polypeptide is insecticidally-active against Lepidopterans.

3. The composition of claim 1, wherein said polypeptide is isolatable from *Bacillus thuringiensis*.

4. The composition of claim 1, wherein said polypeptide comprises from about 0.5% to about 99% by weight of said composition.

5. The composition of claim 4, wherein said polypeptide comprises from about 50% to about 99% by weight of said composition.

6. A composition comprising a polypeptide preparable by a process comprising the steps of:

(a) culturing a *B. thuringiensis* EG12111 or EG12121 cell under conditions effective to produce a composition comprising a *B. thuringiensis* polypeptide; and (b) obtaining said composition from said cell.

7. The composition according to claim 6, wherein said composition is toxic to an insect cell.

8. The composition according to claim 6, wherein said composition is comprised within an insecticidal formulation.

9. The composition of claim 8, wherein said insecticidal formulation is a plant protective spray.

* * * * *